(12) United States Patent
Long et al.

(10) Patent No.: US 10,710,996 B2
(45) Date of Patent: Jul. 14, 2020

(54) PYRIDO-AZAHETERECYDIC COMPOUND AND PREPARATION METHOD AND USE THEREOF

(71) Applicant: SHANGHAI INSTITUTE OF MATERIA MEDICA, CHINESE ACADEMY OF SCIENCES, Pudong, Shanghai (CN)

(72) Inventors: Yaqiu Long, Shanghai (CN); Meiyu Geng, Shanghai (CN); Zhongliang Xu, Shanghai (CN); Jing Ai, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 104 days.

(21) Appl. No.: 15/575,903

(22) PCT Filed: May 23, 2016

(86) PCT No.: PCT/CN2016/083011
§ 371 (c)(1),
(2) Date: Apr. 12, 2018

(87) PCT Pub. No.: WO2016/184434
PCT Pub. Date: Nov. 24, 2016

(65) Prior Publication Data
US 2018/0244667 A1   Aug. 30, 2018

(30) Foreign Application Priority Data

May 21, 2015 (CN) .......................... 2015 1 0264585

(51) Int. Cl.
| | | |
|---|---|---|
| C07D 471/04 | (2006.01) |
| A61K 31/501 | (2006.01) |
| A61K 31/4985 | (2006.01) |
| A61K 31/4375 | (2006.01) |
| A61K 31/496 | (2006.01) |
| A61K 31/4545 | (2006.01) |
| A61K 31/444 | (2006.01) |
| A61K 31/5377 | (2006.01) |
| A61P 35/00 | (2006.01) |

(52) U.S. Cl.
CPC ........ *C07D 471/04* (2013.01); *A61K 31/4375* (2013.01); *A61K 31/444* (2013.01); *A61K 31/4545* (2013.01); *A61K 31/496* (2013.01); *A61K 31/4985* (2013.01); *A61K 31/501* (2013.01); *A61K 31/5377* (2013.01); *A61P 35/00* (2018.01)

(58) Field of Classification Search
CPC .................................................. C07D 471/04
See application file for complete search history.

(56) References Cited

U.S. PATENT DOCUMENTS

| | | | | |
|---|---|---|---|---|
| 8,198,279 B2* | 6/2012 | Springer | ............ | A61K 31/4985 514/249 |
| 2012/0196872 A1* | 8/2012 | Dreyer | ................ | C07D 471/04 514/253.04 |
| 2014/0018365 A1* | 1/2014 | Schultz-Fademrecht | .................... | C07D 401/12 514/235.2 |

FOREIGN PATENT DOCUMENTS

| | | |
|---|---|---|
| CN | 101437820 | 5/2009 |
| CN | 101945869 | 1/2011 |
| CN | 102827186 | 12/2012 |
| CN | 102942530 | 2/2013 |
| CN | 104507930 | 4/2015 |
| WO | 2006108059 | 10/2006 |
| WO | 2006116713 | 11/2006 |

(Continued)

OTHER PUBLICATIONS

Chemical Abstracts Registry No. 1203509-61-8, indexed in the Registry file on STN CAS Online on Jan. 25, 2010. (Year: 2010).*

(Continued)

*Primary Examiner* — Laura L Stockton
(74) *Attorney, Agent, or Firm* — Ping Wang; Morris, Manning & Martin LLP

(57) ABSTRACT

The present invention discloses a pyrido-azacyclic compound represented by formula I, an isomer thereof, a pharmaceutically acceptable salt or a pharmaceutically acceptable solvate thereof, a preparation process thereof and a composition comprising the compound, and a use thereof as a multi-target protein kinase inhibitor in the preparation of a medicament for the treatment of diseases that are associated with protein kinase, especially c-Met, such as cancer and the like. The compound represented by formula I has potent inhibitory activity on tumor cells with overexpression of c-Met kinase, can effectively target c-Met-mediated signaling pathway, and can be used in the treatment of diseases such as cancer and the like that is caused by the overexpression of c-Met kinase.

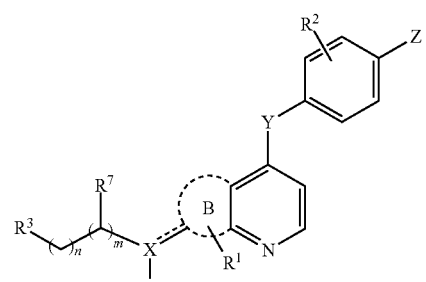

7 Claims, 1 Drawing Sheet

(56) References Cited

FOREIGN PATENT DOCUMENTS

WO      2011017142      2/2011
WO      2014000713      1/2014

OTHER PUBLICATIONS

Grant, R., Grant, C. (1987). Grant & Hackh's Chemical Dictionary (5th ed.). New York, NY: McGraw-Hill, p. 313. (Year: 1987).*
Moore, http://butane.chem.uiuc.edu/jsmoore/chem232/notes_current/Stereochemistry/NOTES-Stereoisomers.pdf, Dec. 2009 (Year: 2009).*
International Search Report of International Application No. PCT/CN2016/083011 dated Aug. 26, 2016.
Extended European Search Report of International Application No. 16795921 2 dated Apr. 3, 2018.
Zhang, W. et al., "Discovery of Novel c-Met Inhibitors Bearing a 3-Carboxyl Piperidin-2-one Scaffold," Molecules, 2014, vol. 19(2), pp. 2655-2673.
Raeppel, S. et al., "N -(3-fluoro-4-(2-arylthieno(3.2- b )pyridin-7-yloxy)phenyl)-2-oxo-3-phenylimidazolidine-1-carboxamides: A novel series of dual c-Met/VEGFR2 receptor tyrosine kinase inhibitors," Bioorganic & Medicinal Chemistry Letters . vol. 19 (5), 2009, pp. 1323-1326.

* cited by examiner

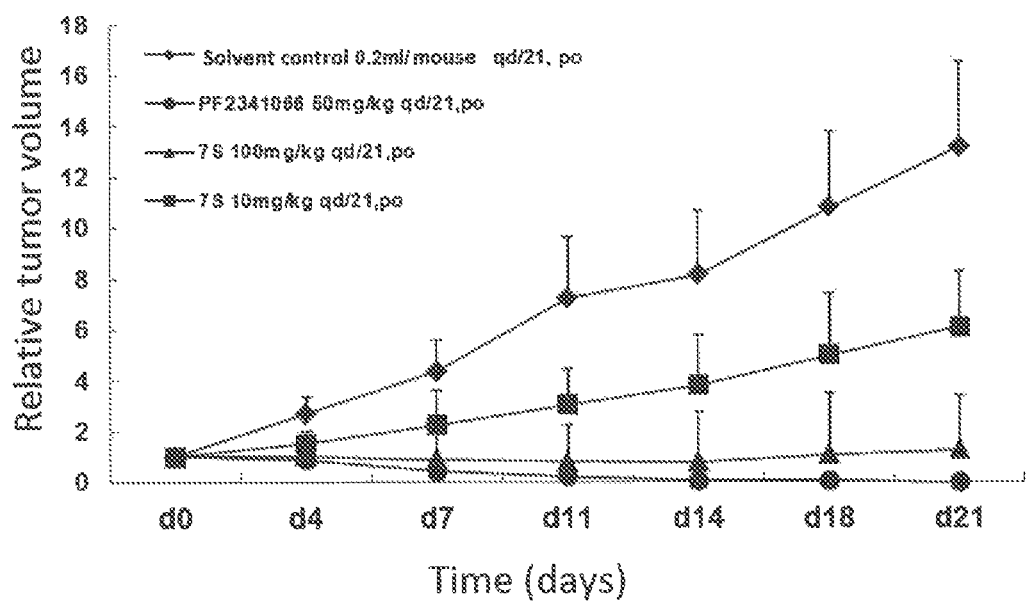

PYRIDO-AZAHETERECYDIC COMPOUND AND PREPARATION METHOD AND USE THEREOF

TECHNICAL FIELD

The present invention relates to pharmaceutical chemistry field, particularly to a pyrido-azacyclic compound, an isomer thereof and a pharmaceutically acceptable salt or a pharmaceutically acceptable solvate thereof, preparation process thereof and a composition comprising the same. The present invention also relates to a use of the compound, the isomer thereof and pharmaceutically acceptable salt and pharmaceutical composition thereof as a multi-target protein kinase inhibitor in the preparation of a medicament for the treatment of diseases associated with protein kinases, particularly c-Met, such as tumor diseases.

BACKGROUND

In "World Cancer Report 2014", the World Health Organization (WHO) reported that in 2012, there were already 14 million cancer patients worldwide, and it was estimated that the number of cancer patients would increase to 19 million by 2025, to 24 million by 2035. In 2012, there were 3.07 million cancer patients added in China, causing about 2.2 million deaths, accounting for 21.9% and 26.8% of the global amounts, respectively. In China, one in five deaths dies from cancer. Cancer becomes a second biggest killer next only to cardiovascular disease, seriously threatening human health. In recent years, as the development of the study on tumor biology, receptor tyrosine kinase has become a target for the research and development of antitumor drugs due to its important role in tumorigenesis, development and drug resistance.

c-Met, an important member of the receptor tyrosine kinase family, is highly expressed in most cancers and partial sarcomas, and is closely related to poor prognosis, such as lung cancer, breast cancer, colon cancer, prostate cancer, pancreatic cancer, stomach cancer, liver cancer, ovarian cancer, kidney cancer, glioma, melanoma and the like. c-Met induces cell proliferation, invasion, migration, and inhibits apoptosis as well as promotes angiogenesis by activating intracellular tyrosine kinases through interacting with its ligand HGF/SF or other pathways, thus playing an important role in the process of tumorigenesis and tumor development. Unlike other kinases, c-Met, a key node in tumor signaling network pathways, may interact with other tumor-associated molecules on cell surface to crosslinkingly activate and amplify tumor-associated effects, greatly promoting tumorigenesis, development and metastasis. The results show that 20% of acquired resistance of epidermal growth factor inhibitor (EGFR-TKIs) is closely related to the amplification of Met gene; combination of Met inhibitor and EGFR inhibitor can delay acquired drug resistance of EGFR-TKIs, and extend its clinical life. Therefore, targeting c-Met/HGF pathway has become a new and notable strategy for the treatment of cancer, and thus the research on chemical blocking c-Met signaling pathway, especially on anticancer drugs like small molecule c-Met kinase inhibitor, has currently become a hot spot in the field of cancer treatment. To date, 17 small molecule c-Met inhibitors have been or are in clinical trials, among them, PF-2341066 (Crizotinib), a dual kinase inhibitor of ALK/c-Met with high selectivity, had been approved by FDA for the treatment of non-small cell lung with positive ALK fusion gene in 2011; XL184/BMS907351, a multi-kinase inhibitor for Met, VEGFR-2, RET and the like, had been approved for the treatment of medullary thyroid carcinoma by the end of 2012. Although these kinase inhibitors have shown clinically superior targeting effect during the treatment, the occurrence of tumor resistance mutations has greatly diminished the effectiveness of these drugs during long-term treatment. The similarity of chemical structures also aggravates the cross-resistance of kinase inhibitors. On the other hand, although there is no direct evidence that specific kinase inhibitors are superior to multiple kinase inhibitors, the selectivity of kinases is closely related to off-target effects. Therefore, the discovery of pilot compounds with new structure and new mechanism currently becomes a new trend in the development of anti-tumor drugs targeting c-Met kinase.

SUMMARY OF THE INVENTION

In order to solve the above technical problem, it is one object of the present invention to provide a pyrido-azacyclic compound, an isomer thereof, a pharmaceutically acceptable salt or a pharmaceutically acceptable solvate thereof, and a pharmaceutical composition containing the same.

It is another object of the present invention to provide a preparation process for the above compound.

It is yet another object of the present invention to provide a use of the above compound in the preparation of a medicament for inhibiting the activity of tyrosine kinase c-Met, in the preparation of a medicament for the prevention or treatment of diseases associated with in vivo hepatocyte growth factor and its receptor (c-Met)-related cell abnormal proliferation, morphological changes and hyperkinesia, and diseases associated with angiogenesis or cancer metastasis, especially for the preparation of a medicament for preventing or treating tumor growth and metastasis.

In order to achieve the above object of the invention, the present invention discloses the following technical solutions:

In one aspect of the present invention, it provides a pyrido-azacyclic compound, an isomer thereof and a pharmaceutically acceptable salt or a pharmaceutically acceptable solvate thereof, the compound has a structure represented by the following formula I:

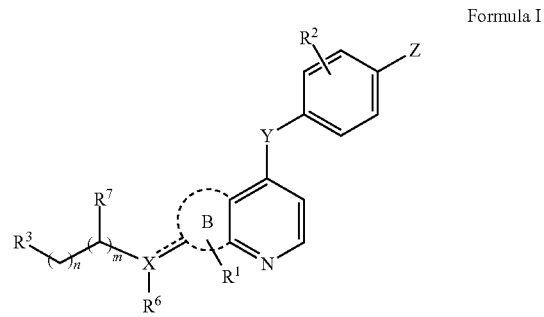

Formula I

Wherein,

⎓ represents a single bond or a double bond;

$R^1$ and $R^2$ are each independently selected from hydrogen and halogen; preferably $R^1$ and $R^2$ are each independently selected from hydrogen, F, Cl and Br; more preferably, $R^1$ is selected from hydrogen, Cl and Br; $R^2$ is selected from hydrogen, F and Cl; further preferably, $R^1$ is hydrogen, Cl or Br; $R^2$ is hydrogen or F;

X is absent (is a direct bond), or X and Y are each independently selected from C, N, O and S; preferably, X is absent, or X and Y are each independently selected from C, N and O;

n is 0, 1, 2 or 3; preferably n is 0, 1 or 2; m is 0 or 1;

$R^3$ is absent, or is hydrogen, a substituted or unsubstituted $C_1$-$C_6$ alkyl, a substituted or unsubstituted $C_6$-$C_{10}$ aryl, a substituted or unsubstituted 5- or 6-membered saturated or unsaturated heterocyclic group containing 1 to 2 heteroatoms selected from N, O and S, a substituted or unsubstituted 5- or 6-membered saturated or unsaturated heterocyclic carbonyl group containing 1 to 2 heteroatoms selected from N, O and S,

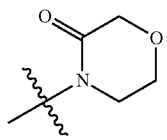

or a substituted or unsubstituted 5- or 6-membered heteroaromatic ring group containing 1 to 2 heteroatoms selected from N, O and S, wherein the number of the substituents may be 1 or 2 and the substituents are each independently selected from halogen, —CN, —CF$_3$, —NO$_2$, hydroxyl, $C_1$-$C_6$ alkyl, amino substituted by $C_1$-$C_6$ alkyl, $C_1$-$C_6$ alkoxy, benzyl, $C_1$-$C_6$ alkoxy substituted by halogen, $C_1$-$C_6$ alkylsulfonyl and an unsubstituted or $C_1$-$C_6$ alkyl-substituted 5- or 6-membered saturated or unsaturated heterocyclic group or heteroaromatic ring group containing 1 to 2 heteroatoms selected from N and O; more preferably, $R^3$ is absent, or is hydrogen, a substituted or unsubstituted $C_1$-$C_6$ alkyl, a substituted or unsubstituted $C_6$-$C_{10}$ aryl, a substituted or unsubstituted 5- or 6-membered saturated or unsaturated heterocyclic group containing 1 to 2 heteroatoms selected from N, O and S, a substituted or unsubstituted 5- or 6-membered saturated or unsaturated heterocyclic carbonyl group containing 1 to 2 heteroatoms selected from N, O and S,

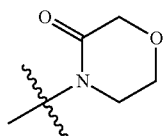

or a substituted or unsubstituted 5- or 6-membered heteroaromatic ring group containing 1 to 2 heteroatoms selected from N and O, wherein the number of the substituents may be 1 or 2 and the substituents are each independently selected from halogen, —CN, benzyl, $C_1$-$C_6$ alkyl, amino substituted by $C_1$-$C_6$ alkyl, $C_1$-$C_6$ alkylsulfonyl and an unsubstituted or $C_1$-$C_6$ alkyl-substituted 5- or 6-membered saturated or unsaturated heterocyclic group containing 1 to 2 heteroatoms selected from N and O; further preferably, $R^3$ is absent, or is hydrogen, a substituted or unsubstituted $C_1$-$C_6$ alkyl, a substituted or unsubstituted $C_6$-$C_{10}$ aryl, a substituted or unsubstituted 5- or 6-membered saturated or unsaturated heterocyclic group containing 1 to 2 heteroatoms selected from N, O and S, a substituted or unsubstituted 5- or 6-membered saturated or unsaturated heterocyclic carbonyl group containing 1 to 2 heteroatoms selected from N, O and S,

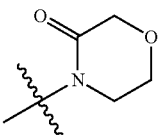 [SMILES: *N1CCOCC1=O]

or a substituted or unsubstituted 5- or 6-membered heteroaromatic ring group containing 1 to 2 heteroatoms selected from N and O, wherein the number of the substituents may be 1 or 2 and the substituents are each independently selected from halogen, benzyl, $C_1$-$C_4$ alkyl, amino substituted by $C_1$-$C_4$ alkyl, $C_1$-$C_4$ alkylsulfonyl and an unsubstituted or $C_1$-$C_6$ alkyl-substituted 5- or 6-membered saturated or unsaturated heterocyclic group containing 1 to 2 heteroatoms selected from N and O; most preferably, $R_3$ is absent, or is $C_1$-$C_3$ alkyl, a substituted or unsubstituted pyridyl, a substituted or unsubstituted morpholinyl, a substituted or unsubstituted morpholinylcarbonyl,

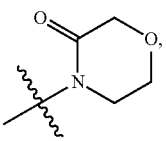 [SMILES: *N1CCOCC1=O]

a substituted or unsubstituted piperidyl, a substituted or unsubstituted imidazolyl, a substituted or unsubstituted piperazinyl, a substituted or unsubstituted oxazolyl, a substituted or unsubstituted isoxazolyl, a substituted or unsubstituted pyrimidinyl, a substituted or unsubstituted thiazolyl, a substituted or unsubstituted isothiazolyl, a substituted or unsubstituted phenyl, or a substituted or unsubstituted pyrazolyl, wherein the number of the substituents may be 1 or 2 and the substituents are each independently selected from F, Cl, Br, —NO$_2$, $C_1$-$C_3$ alkyl, benzyl, $C_1$-$C_3$ alkylsulfonyl, amino substituted by $C_1$-$C_3$ alkyl, unsubstituted or $C_1$-$C_6$ alkyl substituted piperidinyl and morpholinyl;

$R^6$ is absent, or is selected from hydrogen and $C_1$-$C_6$ alkyl; preferably, is absent, or is selected from hydrogen and $C_1$-$C_4$ alkyl; more preferably, is absent, or is selected from hydrogen and $C_1$-$C_2$ alkyl; most preferably, is absent, or is hydrogen or methyl;

$R^7$ is absent, or is selected from hydrogen and $C_1$-$C_6$ alkyl; preferably, is absent, or is hydrogen, methyl, ethyl or propyl; most preferably, is absent, or is methyl;

Z is amino, phenylacetamido or any of the following structures:

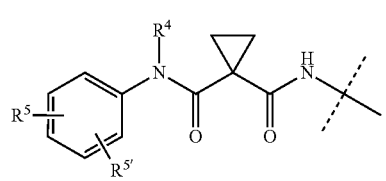

II

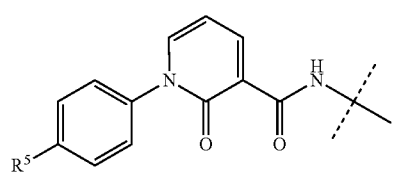

III

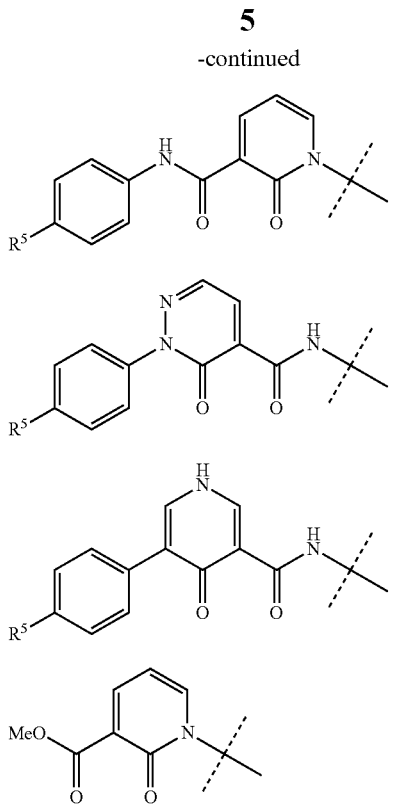

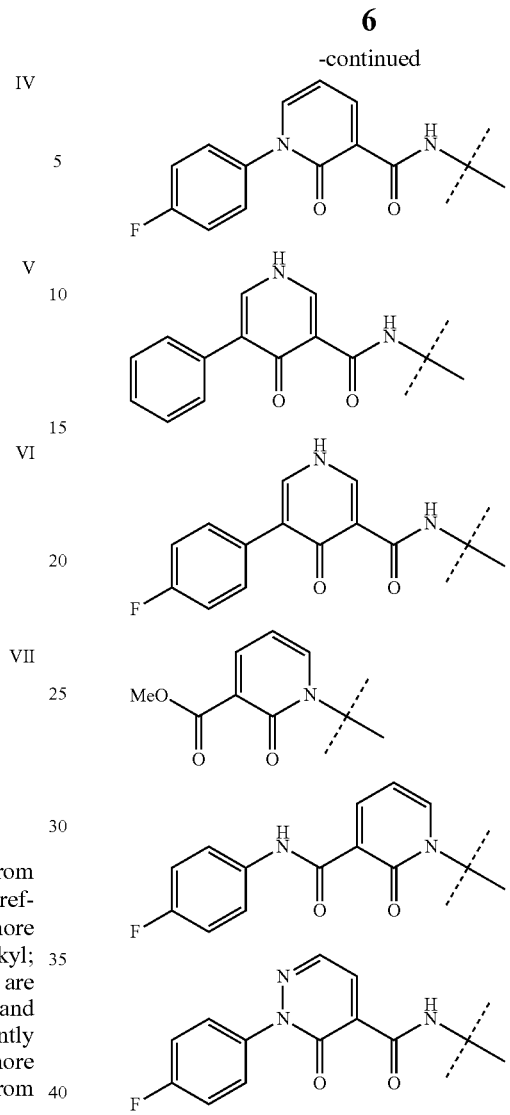

In the above formulas II, III, IV and V, $R^4$ is selected from hydrogen, $C_1$-$C_6$ alkyl and $C_5$-$C_{10}$ aryl or heteroaryl; preferably, $R^4$ is selected from hydrogen and $C_1$-$C_6$ alkyl; more preferably, $R^4$ is selected from hydrogen and $C_1$-$C_3$ alkyl; most preferably, $R^4$ is hydrogen or methyl; $R^5$ and $R^{5'}$ are each independently selected from hydrogen, halogen and $C_1$-$C_6$ alkoxy; preferably, $R^5$ and $R^{5'}$ are each independently selected from hydrogen, F, Cl, Br and $C_1$-$C_4$ alkoxy; more preferably, $R^5$ and $R^{5'}$ are each independently selected from hydrogen, F and $C_1$-$C_2$ alkoxy;

Most preferably, Z is amino, phenylacetamido or any of the following structures:

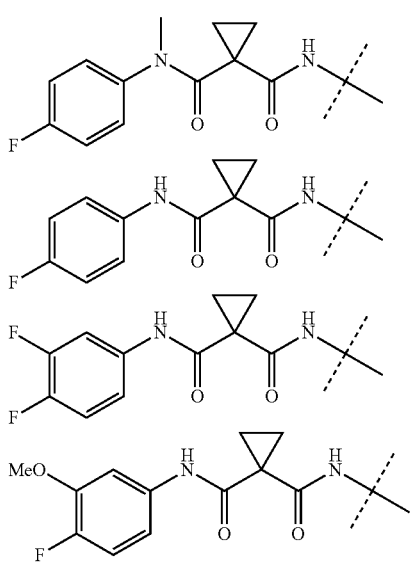

Ring B is a 5- or 6-membered saturated or unsaturated heterocyclic group or heteroaromatic group containing 1 or 2 heteroatoms selected from N, O and S; preferably, ring B is a 5- or 6-membered saturated or unsaturated heterocyclic group or heteroaromatic group containing 1 or 2 heteroatoms selected from N or O; more preferably, ring B is a 5- or 6-membered saturated or unsaturated heterocyclic group or heteroaromatic group containing 1 or 2 nitrogen atoms; most preferably, Ring B forms one structure of the following formulas with pyridine or together with X:

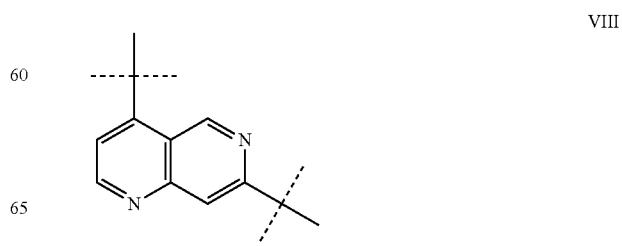

-continued

IX
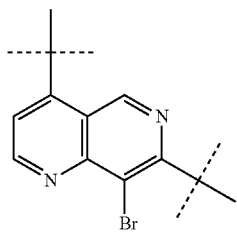

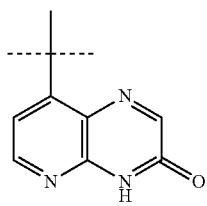

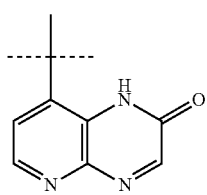

-continued

XII
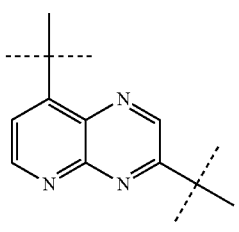

XIII
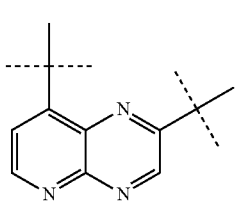

Wherein, the halogen includes F, Cl, Br and I;

Most preferably, the compound is one selected from the following compounds:

| Cpd. No. | Name | Structure |
|---|---|---|
| 1S | N-(4-((7-chloro-1,6-naphthyridin-4-yl)oxy)-3-fluorophenyl)-N-(4-fluorophenyl)cyclopropyl-1,1-dicarboxamide | 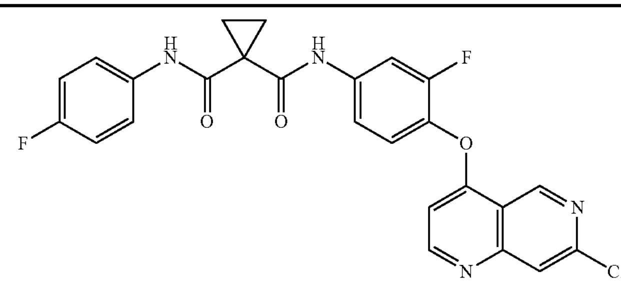 |
| 2S | N-(4-((7-(dimethylamino)-1,6-naphthyridin-4-yl)oxy)-3-fluorophenyl)-N-(4-fluorophenyl)cyclopropyl-1,1-dicarboxamide | 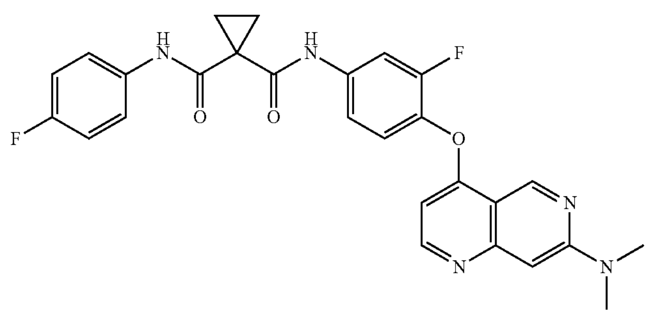 [SMILES: CN(C)c1cc2nccc(Oc3ccc(NC(=O)C4(C(=O)Nc5ccc(F)cc5)CC4)cc3F)c2cn1] |
| 3S | N-(4-((7-methoxy-1,6-naphthyridin-4-yl)oxy)-3-fluorophenyl)-N-(4-fluorophenyl)cyclopropyl-1,1-dicarboxamide | 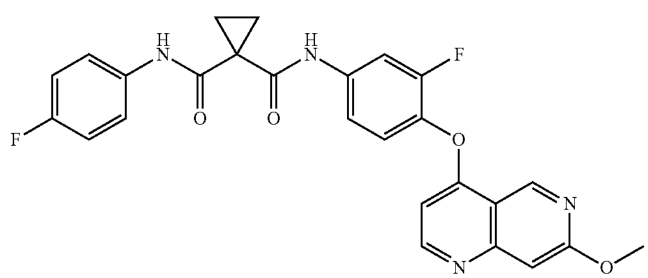 [SMILES: COc1cc2nccc(Oc3ccc(NC(=O)C4(C(=O)Nc5ccc(F)cc5)CC4)cc3F)c2cn1] |

-continued

| Cpd. No. | Name | Structure |
|---|---|---|
| 4S | 4-((8-bromo-7-(2-morpholinoethoxy)-1,6-naphthyridin-4-yl)oxy)-3-fluoroaniline | 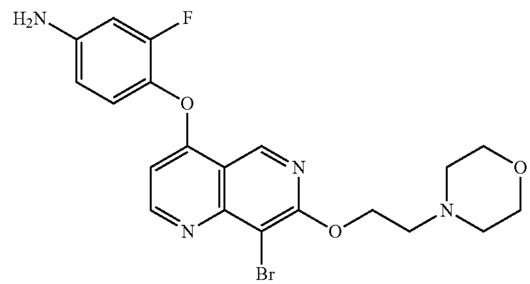 [SMILES: Nc1ccc(Oc2ccnc3c(Br)c(OCCN4CCOCC4)ncc23)c(F)c1] |
| 5S | 2-fluoro-N$^1$-(7-(2-morpholinoethoxy)-1,6-naphthyridin-4-yl)phenyl-1,4-diamine | 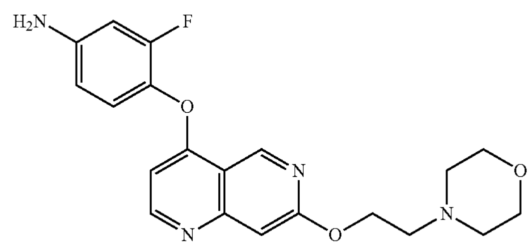 [SMILES: Nc1ccc(Oc2ccnc3cc(OCCN4CCOCC4)ncc23)c(F)c1] |
| 6S | N-(4-((8-bromo-7-(2-morpholinoethoxy)-1,6-naphthyridin-4-yl)oxy)-3-fluorophenyl)-N-(4-fluorophenyl)cyclopropyl-1,1-dicarboxamide | 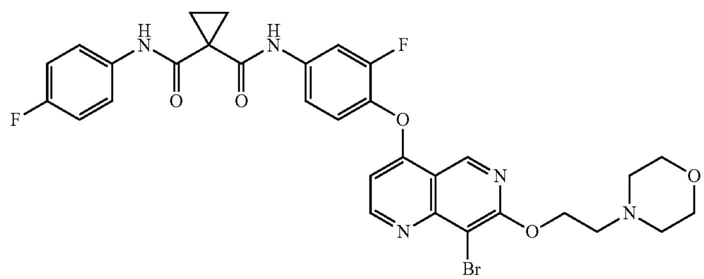 [SMILES: O=C(Nc1ccc(F)cc1)C1(C(=O)Nc2ccc(Oc3ccnc4c(Br)c(OCCN5CCOCC5)ncc34)c(F)c2)CC1] |
| 7S | N-(3-fluoro-4-((7-(2-morpholinoethoxy)-1,6-naphthyridin-4-yl)oxy)phenyl)-N-(4-fluorophenyl)cyclopropyl-1,1-dicarboxamide | 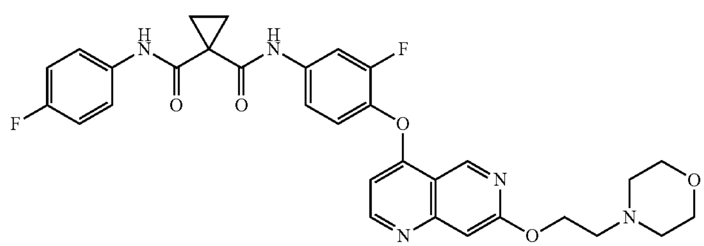 [SMILES: O=C(Nc1ccc(F)cc1)C1(C(=O)Nc2ccc(Oc3ccnc4cc(OCCN5CCOCC5)ncc34)c(F)c2)CC1] |
| 8S | N-(3-fluoro-4-((7-(2-morpholinopropoxy)-1,6-naphthyridin-4-yl)oxy)phenyl)-N-(4-fluorophenyl)cyclopropyl-1,1-dicarboxamide | 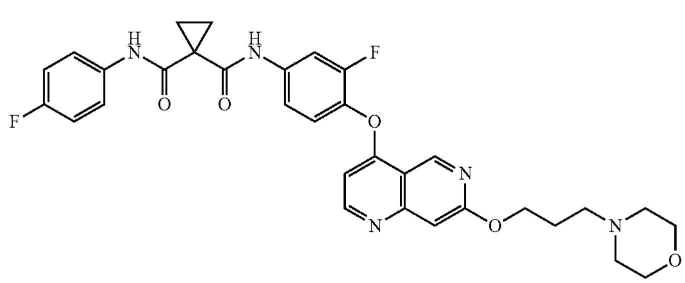 [SMILES: O=C(Nc1ccc(F)cc1)C1(C(=O)Nc2ccc(Oc3ccnc4cc(OCCCN5CCOCC5)ncc34)c(F)c2)CC1] |

-continued

| Cpd. No. | Name | Structure |
|---|---|---|
| 9S | N-(3-fluoro-4-((7-((1-methylpiperidin-4-yl)methoxy)-1,6-naphthyridin-4-yl)oxy)phenyl)-N-(4-fluorophenyl)cyclopropyl-1,1-dicarboxamide | 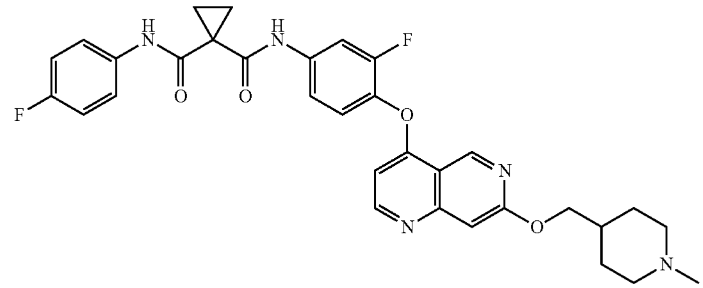 [SMILES: CN1CCC(COc2cc3nccc(Oc4ccc(NC(=O)C5(C(=O)Nc6ccc(F)cc6)CC5)cc4F)c3cn2)CC1] |
| 10S | N-(4-((8-bromo-7-(2-(4-methylpiperazin-1-yl)ethoxy)-1,6-naphthyridin-4-yl)oxy)-3-fluorophenyl)-N-(4-fluorophenyl)cyclopropyl-1,1-dicarboxamide | 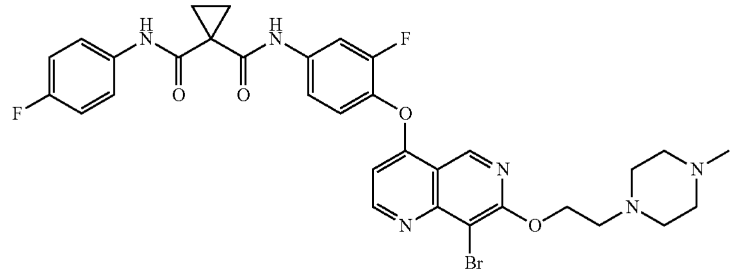 [SMILES: CN1CCN(CCOc2ncc3c(Oc4ccc(NC(=O)C5(C(=O)Nc6ccc(F)cc6)CC5)cc4F)ccnc3c2Br)CC1] |
| 11S | N-(3-fluoro-4-((7-(2-(4-methylpiperazin-1-yl)ethoxy)-1,6-naphthyridin-4-yl)oxy)phenyl)-N-(4-fluorophenyl)cyclopropyl-1,1-dicarboxamide | 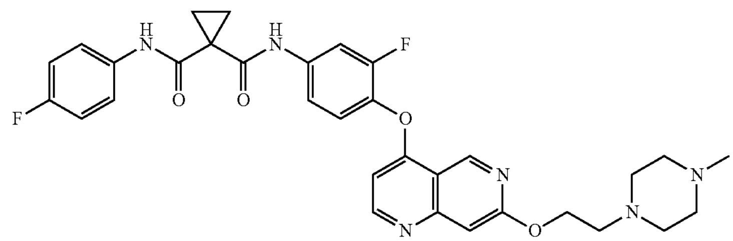 [SMILES: CN1CCN(CCOc2cc3nccc(Oc4ccc(NC(=O)C5(C(=O)Nc6ccc(F)cc6)CC5)cc4F)c3cn2)CC1] |
| 12S | N-(4-fluorophenyl)-N-(4-((7-(2-morpholinoethoxy)-1,6-naphthyridin-4-yl)oxy)phenyl)cyclopropyl-1,1-dicarboxamide | 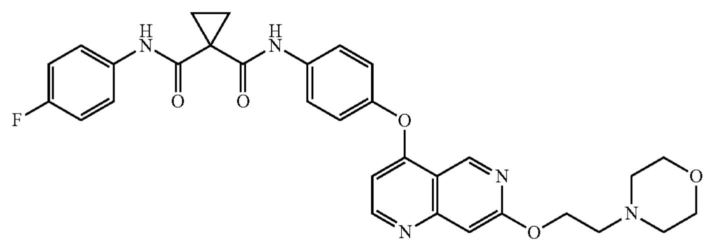 [SMILES: O=C(Nc1ccc(F)cc1)C1(C(=O)Nc2ccc(Oc3ccnc4cc(OCCN5CCOCC5)ncc34)cc2)CC1] |
| 13S | N-(4-fluorophenyl)-N-(4-((7-(2-morpholinoethoxy)-1,6-naphthyridin-4-yl)amino)phenyl)cyclopropyl-1,1-dicarboxamide | 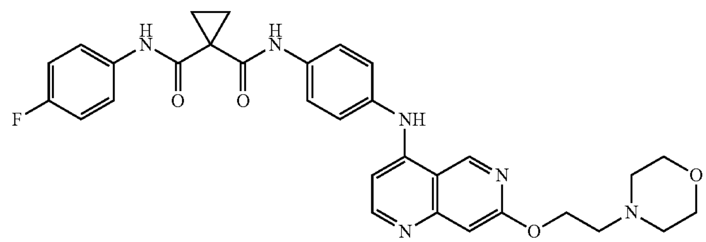 [SMILES: O=C(Nc1ccc(F)cc1)C1(C(=O)Nc2ccc(Nc3ccnc4cc(OCCN5CCOCC5)ncc34)cc2)CC1] |
| 14S | N-(3-fluoro-4-((7-(2-morpholinoethoxy)-1,6-naphthyridin-4-yl)oxy)phenyl)-N-(4-fluorophenyl)-N-methylcyclopropyl-1,1-dicarboxamide | 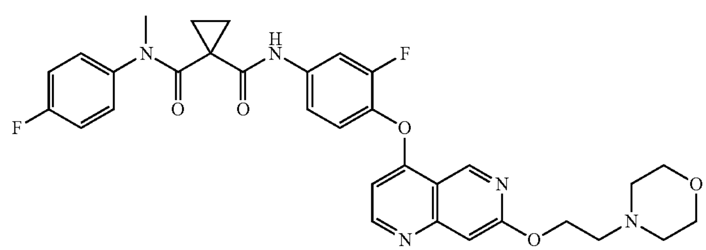 [SMILES: CN(C(=O)C1(C(=O)Nc2ccc(Oc3ccnc4cc(OCCN5CCOCC5)ncc34)c(F)c2)CC1)c1ccc(F)cc1] |

-continued

| Cpd. No. | Name | Structure |
|---|---|---|
| 15S | N-(3-fluoro-4-((7-(2-morpholinoethoxy)-1,6-naphthyridin-4-yl)oxy)phenyl)-1-(4-fluorophenyl)-2-oxo-1,2-dihydropyridine-3-carboxamide | 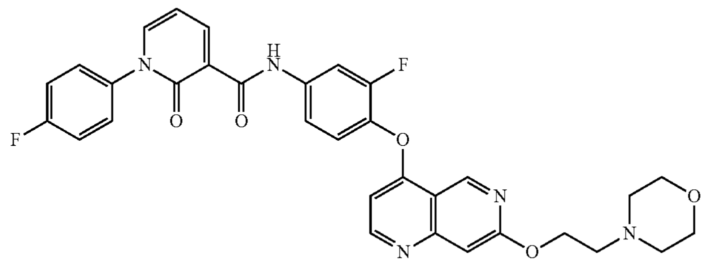 [SMILES: O=C(Nc1ccc(Oc2ccnc3cc(OCCN4CCOCC4)ncc23)c(F)c1)c1cccn(-c2ccc(F)cc2)c1=O] |
| 16S | 1-(3-fluoro-4-((7-(2-morpholinoethoxy)-1,6-naphthyridin-4-yl)oxy)phenyl)-N-(4-fluorophenyl)-2-oxo-1,2-dihydropyridine-3-carboxamide | 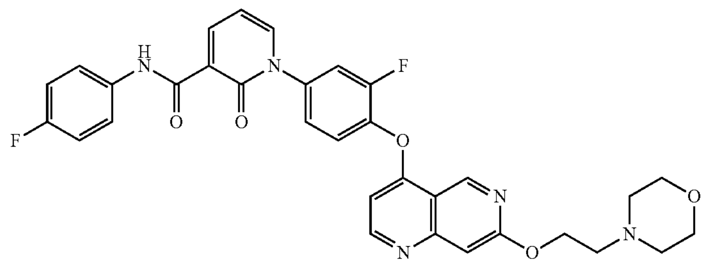 [SMILES: O=C(Nc1ccc(F)cc1)c1cccn(-c2ccc(Oc3ccnc4cc(OCCN5CCOCC5)ncc34)c(F)c2)c1=O] |
| 17S | methyl 1-(3-fluoro-4-((7-(2-morpholinoethoxy)-1,6-naphthyridin-4-yl)oxy)phenyl)-2-oxo-1,2-dihydropyridine-3-carboxylate | 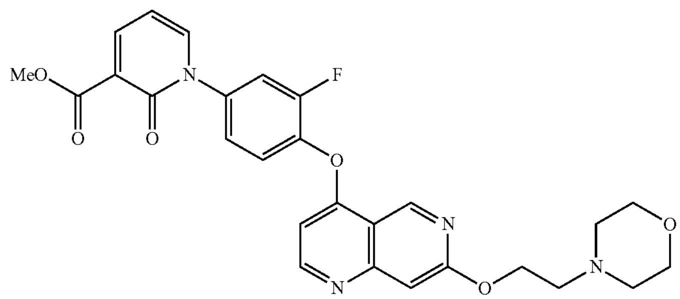 [SMILES: COC(=O)c1cccn(-c2ccc(Oc3ccnc4cc(OCCN5CCOCC5)ncc34)c(F)c2)c1=O] |
| 18S | N-(4-((8-bromo-7-(2-morpholinoethoxy)-1,6-naphthyridin-4-yl)oxy)-3-fluorophenyl)-2-phenylacetamide | 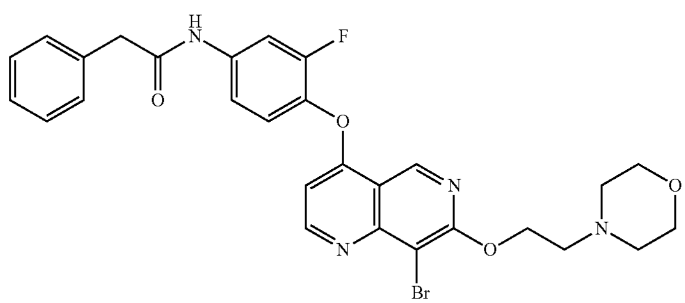 [SMILES: O=C(Cc1ccccc1)Nc1ccc(Oc2ccnc3c(Br)c(OCCN4CCOCC4)ncc23)c(F)c1] |
| 19S | N-(4-((8-bromo-7-(2-morpholinoethoxy)-1,6-naphthyridin-4-yl)oxy)-3-fluorophenyl)-4-oxo-5-phenyl-1,4-dihydropyridine-3-carboxamide | 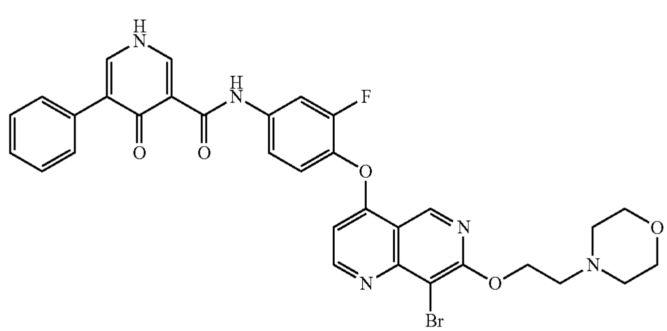 [SMILES: O=C(Nc1ccc(Oc2ccnc3c(Br)c(OCCN4CCOCC4)ncc23)c(F)c1)c1c[nH]cc(-c2ccccc2)c1=O] |

-continued

| Cpd. No. | Name |
|---|---|
| 20S | N-(3-fluoro-4-((7-(2-morpholinoethoxy)-1,6-naphthyridin-4-yl)oxy)phenyl)-4-oxo-5-phenyl-1,4-dihydropyridine-3-carboxamide |
| 21S | N-(4-((8-bromo-7-(2-morpholinoethoxy)-1,6-naphthyridin-4-yl)oxy)-3-fluorophenyl)-5-(4-fluorophenyl)-4-oxo-1,4-dihydropyridine-3-carboxamide |
| 22S | N-(3-fluoro-4-((7-(2-morpholinoethoxy)-1,6-naphthyridin-4-yl)oxy)phenyl)-5-(4-fluorophenyl)-4-oxo-1,4-dihydropyridine-3-carboxamide |
| 23S | N-(3,4-difluorophenyl)-N-(3-fluoro-4-((7-(2-morpholinoethoxy)-1,6-naphthyridin-4-yl)oxy)phenyl)cyclopropyl-1,1-dicarboxamide |
| 24S | N-(4-fluoro-3-methoxyphenyl)-N-(3-fluoro-4-((7-(2-morpholinoethoxy)-1,6-naphthyridin-4-yl)oxy)phenyl)cyclopropyl-1,1-dicarboxamide |

-continued

| Cpd. No. | Name | Structure |
|---|---|---|
| 25S | N-(3-fluoro-4-((7-(2-(pyridin-4-yl)ethoxy)-1,6-naphthyridin-4-yl)oxy)phenyl)-N-(4-fluorophenyl)cyclopropyl-1,1-dicarboxamide | 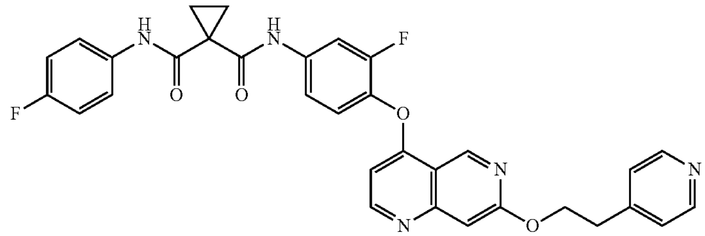 [SMILES: O=C(Nc1ccc(F)cc1)C1(C(=O)Nc2ccc(Oc3ccnc4cc(OCCc5ccncc5)ncc34)c(F)c2)CC1] |
| 26S | N-(3-fluoro-4-((7-((1-morpholinopropan-2-yl)oxy)-1,6-naphthyridin-4-yl)oxy)phenyl)-N-(4-fluorophenyl)cyclopropyl-1,1-dicarboxamide | 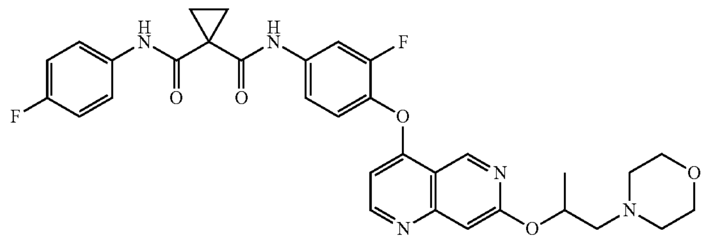 [SMILES: CC(CN1CCOCC1)Oc1cc2nccc(Oc3ccc(NC(=O)C4(C(=O)Nc5ccc(F)cc5)CC4)cc3F)c2cn1] |
| 27S | N-(3-fluoro-4-((7-morpholino-1,6-naphthyridin-4-yl)oxy)phenyl)-N-(4-fluorophenyl)cyclopropyl-1,1-dicarboxamide | 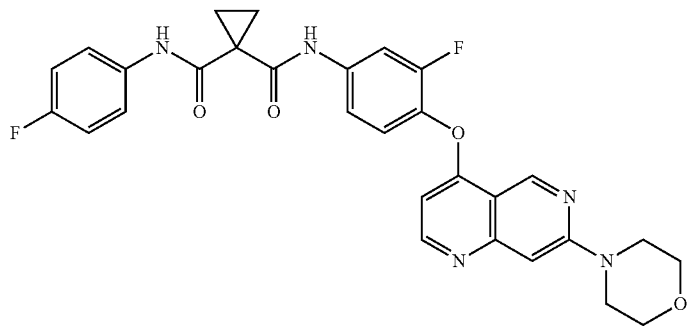 [SMILES: O=C(Nc1ccc(F)cc1)C1(C(=O)Nc2ccc(Oc3ccnc4cc(N5CCOCC5)ncc34)c(F)c2)CC1] |
| 28S | N-(3-fluoro-4-((7-(4-morpholinopiperidin-1-yl)--naphthyridin-4-yl)oxy)phenyl)-N-(4-fluorophenyl)cyclopropyl-1,1-dicarboxamide | 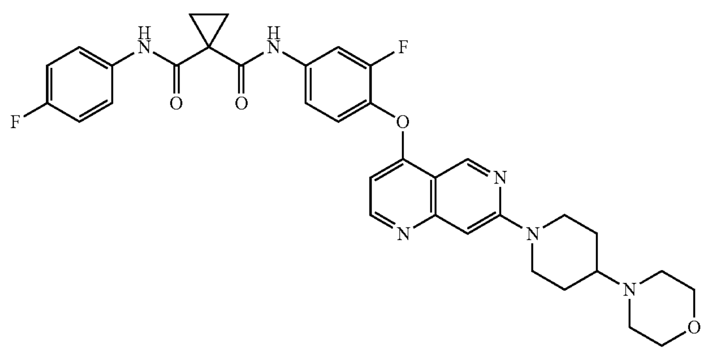 [SMILES: O=C(Nc1ccc(F)cc1)C1(C(=O)Nc2ccc(Oc3ccnc4cc(N5CCC(N6CCOCC6)CC5)ncc34)c(F)c2)CC1] |
| 29S | (S)-N-(3-fluoro-4-((7-(2-(3-methylmorpholino)ethoxy)-naphthyridin-4-yl)oxy)phenyl)-N-(4-fluorophenyl)cyclopropyl-1,1-dicarboxamide | 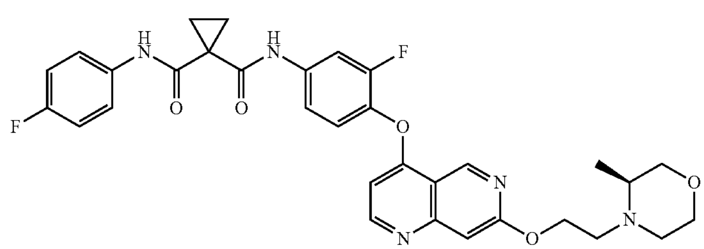 [SMILES: C[C@H]1COCCN1CCOc1cc2nccc(Oc3ccc(NC(=O)C4(C(=O)Nc5ccc(F)cc5)CC4)cc3F)c2cn1] |

| Cpd. No. | Name |
|---|---|
| 30S | (R)-N-(3-fluoro-4-((7-(2-(3-methylmorpholino)ethoxy)-naphthyridin-4-yl)oxy)phenyl)-N-(4-fluorophenyl)cyclopropyl-1,1-dicarboxamide |
| 31S | N-(4-((7-(2-(1H-imidazol-1-yl)ethoxy)-naphthyridin-4-yl)oxy)-3-fluorophenyl)-N-(4-fluorophenyl)cyclopropyl-1,1-dicarboxamide |
| 32S | N-(4-((7-(4-benzylpiperazin-1-yl)-naphthyridin-4-yl)oxy)-3-fluorophenyl)-N-(4-fluorophenyl)cyclopropyl-1,1-dicarboxamide |
| 33S | N-(3-fluoro-4-((3-oxo-3,4-dihydropyrido[2,3-b]pyrazin-8-yl)oxy)phenyl)-N-(4-fluorophenyl)cyclopropyl-1,1-dicarboxamide |
| 34S | N-(3-fluoro-4-((2-oxo-1,2-dihydropyrido[2,3-b]pyrazin-8-yl)oxy)phenyl)-N-(4-fluorophenyl)cyclopropyl-1,1-dicarboxamide |

-continued

| Cpd. No. | Name | Structure |
|---|---|---|
| 35S | N-(4-((7-((1-ethyl-3-fluoropiperidin-4-yl)amino)-1,6-naphthyridin-4-yl)oxy)-3-fluorophenyl)-2-(4-fluorophenyl)-3-oxo-2,3-dihydropyridazine-4-carboxamide | 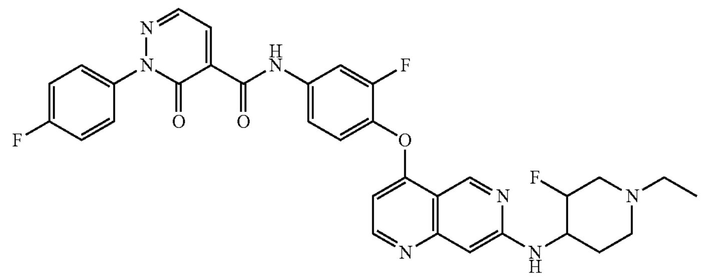 [SMILES: CCN1CCC(Nc2cc3nccc(Oc4ccc(NC(=O)c5ccnn(-c6ccc(F)cc6)c5=O)cc4F)c3cn2)C(F)C1] |
| 36S | N-(3-fluoro-4-((7-(2-morpholino-2-acetoxy)-1,6-naphthyridin-4-yl)oxy)phenyl)-N-(4-fluorophenyl)cyclopropyl-1,1-dicarboxamide | 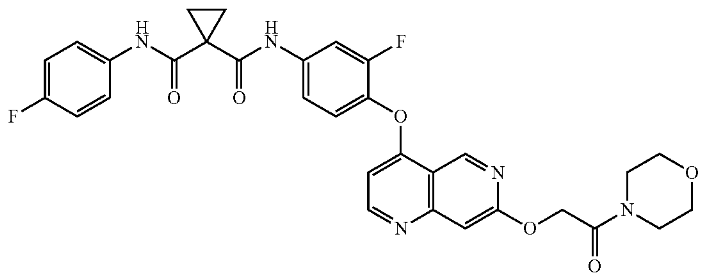 [SMILES: O=C(COc1cc2nccc(Oc3ccc(NC(=O)C4(C(=O)Nc5ccc(F)cc5)CC4)cc3F)c2cn1)N1CCOCC1] |
| 37S | N-(3-fluoro-4-((7-(2-(3-oxomorpholino)ethoxy)-1,6-naphthyridin-4-yl)oxy)phenyl)-N-(4-fluorophenyl)cyclopropyl-1,1-dicarboxamide | 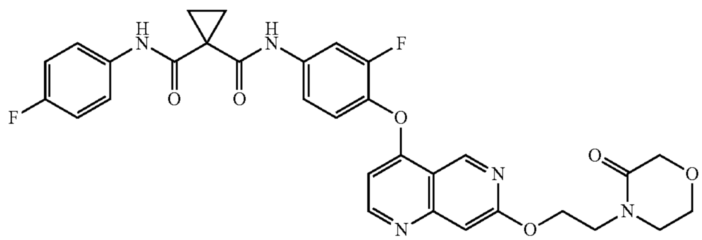 [SMILES: O=C1COCCN1CCOc1cc2nccc(Oc3ccc(NC(=O)C4(C(=O)Nc5ccc(F)cc5)CC4)cc3F)c2cn1] |
| 38S | N-(3-fluoro-4-((7-(1-methyl-1H-pyrazol-4-yl)-1,6-naphthyridin-4-yl)oxy)phenyl)-N-(4-fluorophenyl)cyclopropyl-1,1-dicarboxamide | 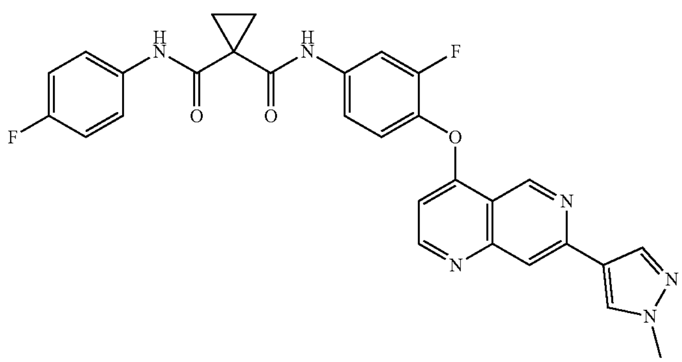 [SMILES: Cn1cc(-c2cc3nccc(Oc4ccc(NC(=O)C5(C(=O)Nc6ccc(F)cc6)CC5)cc4F)c3cn2)cn1] |
| 39S | N-(4-((7-(1H-pyrazol-4-yl)-1,6-naphthyridin-4-yl)oxy)-3-fluorophenyl)-N-(4-fluorophenyl)cyclopropyl-1,1-dicarboxamide | 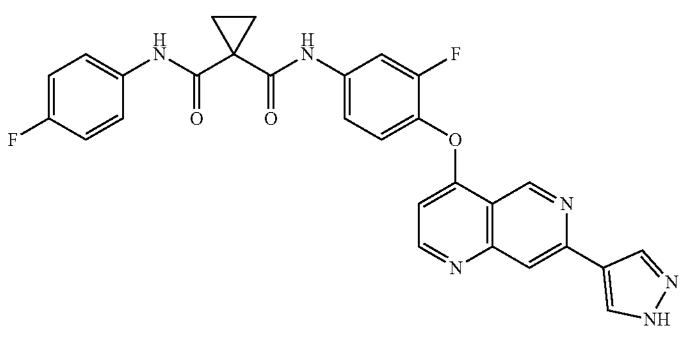 [SMILES: O=C(Nc1ccc(F)cc1)C1(C(=O)Nc2ccc(Oc3ccnc4cc(-c5cn[nH]c5)ncc34)c(F)c2)CC1] |

-continued

| Cpd. No. | Name | Structure |
|---|---|---|
| 40S | N-(3-fluoro-4-((7-(1-(methylsulfonyl)-1H-pyrazol-4-yl)-1,6-naphthyridin-4-yl)oxy)phenyl)-N-(4-fluorophenyl)cyclopropyl-1,1-dicarboxamide | 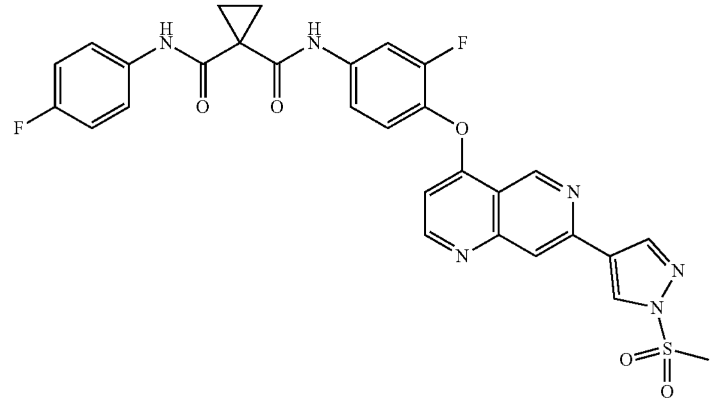 [SMILES: CS(=O)(=O)n1cc(-c2cc3nccc(Oc4ccc(NC(=O)C5(C(=O)Nc6ccc(F)cc6)CC5)cc4F)c3cn2)cn1] |
| 41S | N-(3-fluoro-4-((7-(1-isopropyl-1H-pyrazol-4-yl)-1,6-naphthyridin-4-yl)oxy)phenyl)-N-(4-fluorophenyl)cyclopropyl-1,1-dicarboxamide | 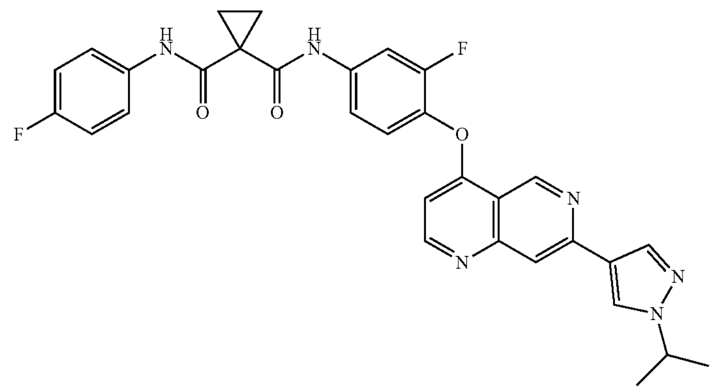 [SMILES: CC(C)n1cc(-c2cc3nccc(Oc4ccc(NC(=O)C5(C(=O)Nc6ccc(F)cc6)CC5)cc4F)c3cn2)cn1] |
| 42S | N-(3-fluoro-4-((7-(1-(piperidin-4-yl)-1H-pyrazol-4-yl)-1,6-naphthyridin-4-yl)oxy)phenyl)-N-(4-fluorophenyl)cyclopropyl-1,1-dicarboxamide | 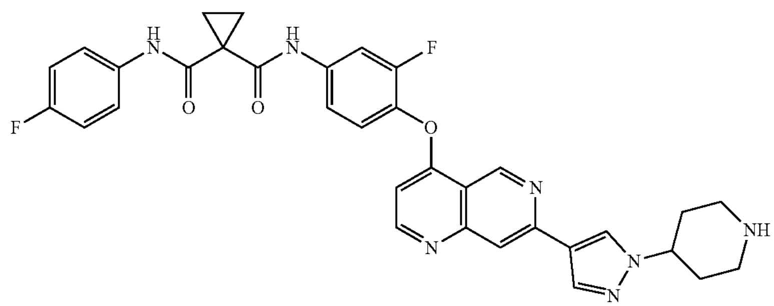 [SMILES: O=C(Nc1ccc(F)cc1)C1(C(=O)Nc2ccc(Oc3ccnc4cc(-c5cnn(C6CCNCC6)c5)ncc34)c(F)c2)CC1] |
| 43S | N-(3-fluoro-4-((7-(1-(1-isopropylpiperidin-4-yl)-1H-pyrazol-4-yl)-1,6-naphthyridin-4-yl)oxy)phenyl)-N-(4-fluorophenyl)cyclopropyl-1,1-dicarboxamide | 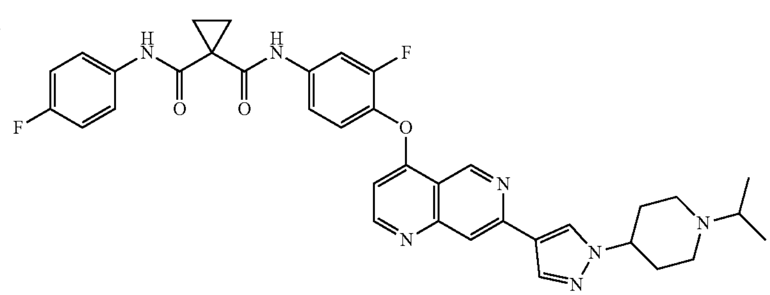 [SMILES: CC(C)N1CCC(n2cc(-c3cc4nccc(Oc5ccc(NC(=O)C6(C(=O)Nc7ccc(F)cc7)CC6)cc5F)c4cn3)cn2)CC1] |

-continued

| Cpd. No. | Name | Structure |
|---|---|---|
| 44S | N-(4-((7-((1H-imidazol-1-yl)methyl)-1,6-naphthyridin-4-yl)oxy)-3-fluorophenyl)-N-(4-fluorophenyl)cyclopropyl-1,1-dicarboxamide | 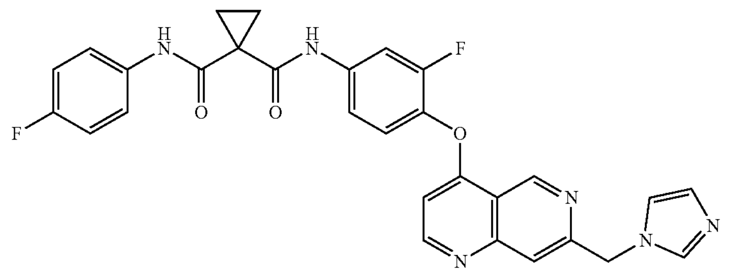 [SMILES: O=C(Nc1ccc(F)cc1)C1(C(=O)Nc2ccc(Oc3ccnc4cc(Cn5ccnc5)ncc34)c(F)c2)CC1] |
| 45S | N-(4-((7-(3,5-dimethylisoxazol-4-yl)-1,6-naphthyridin-4-yl)oxy)-3-fluorophenyl)-N-(4-fluorophenyl)cyclopropyl-1,1-dicarboxamide | 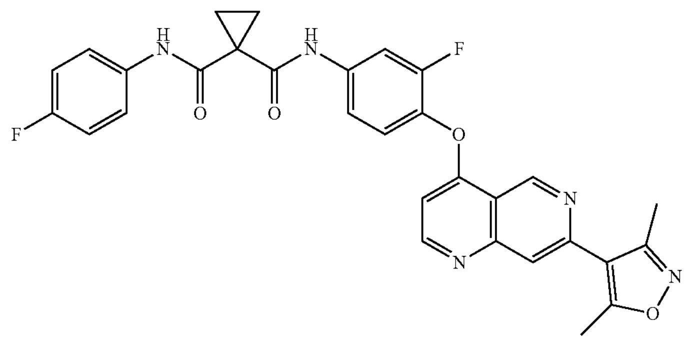 [SMILES: Cc1noc(C)c1-c1cc2nccc(Oc3ccc(NC(=O)C4(C(=O)Nc5ccc(F)cc5)CC4)cc3F)c2cn1] |
| 46S | N-(3-fluoro-4-((7-(pyridin-4-yl)-1,6-naphthyridin-4-yl)oxy)phenyl)-N-(4-fluorophenyl)cyclopropyl-1,1-dicarboxamide | 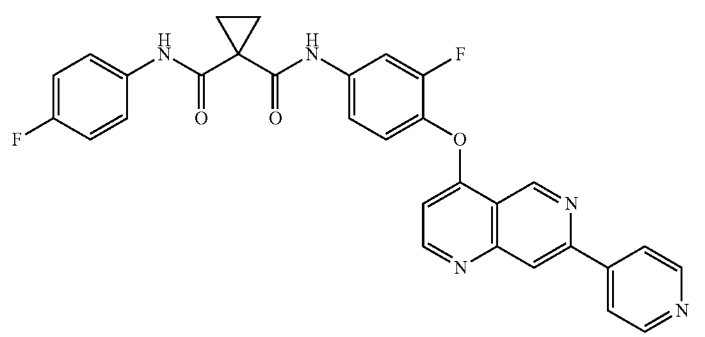 [SMILES: O=C(Nc1ccc(F)cc1)C1(C(=O)Nc2ccc(Oc3ccnc4cc(-c5ccncc5)ncc34)c(F)c2)CC1] |
| 47S | N-(3-fluoro-4-((7-(pyrimidin-5-yl)-1,6-naphthyridin-4-yl)oxy)phenyl)-N-(4-fluorophenyl)cyclopropyl-1,1-dicarboxamide | 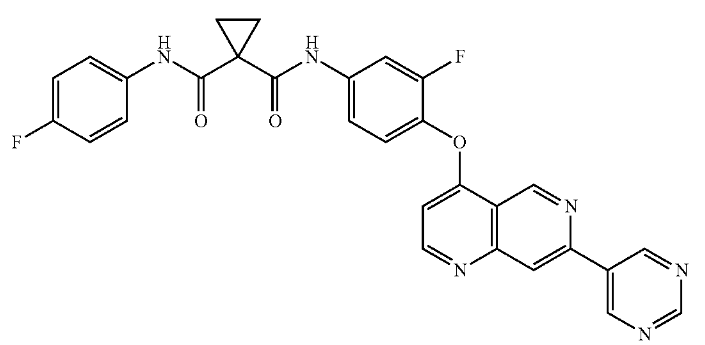 [SMILES: O=C(Nc1ccc(F)cc1)C1(C(=O)Nc2ccc(Oc3ccnc4cc(-c5cncnc5)ncc34)c(F)c2)CC1] |

| Cpd. No. | Name | Structure |
|---|---|---|
| 48S | N-(3-fluoro-4-((7-(4-nitrophenyl)-1,6-naphthyridin-4-yl)oxy)phenyl)-N-(4-fluorophenyl)cyclopropyl-1,1-dicarboxamide | 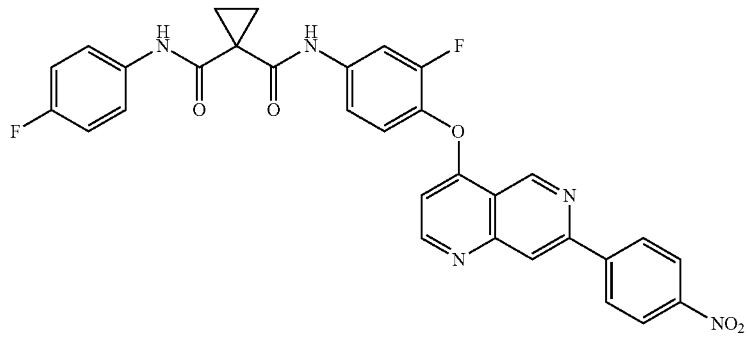 [SMILES: O=C(Nc1ccc(F)cc1)C1(C(=O)Nc2ccc(Oc3ccnc4cc(-c5ccc([N+](=O)[O-])cc5)ncc34)c(F)c2)CC1] |
| 49S | N-(3-fluoro-4-((7-(3,4-difluorophenyl)-1,6-naphthyridin-4-yl)oxy)phenyl)-N-(4-fluorophenyl)cyclopropyl-1,1-dicarboxamide | 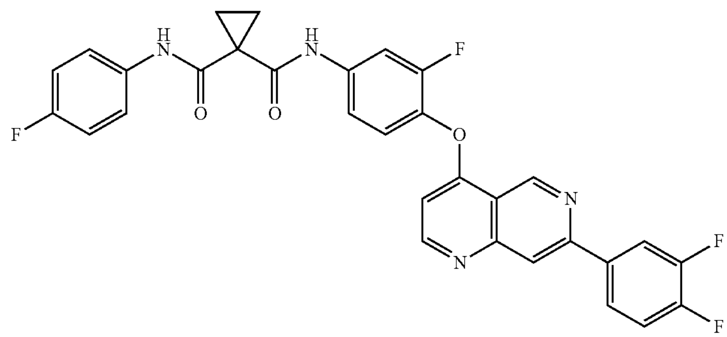 [SMILES: O=C(Nc1ccc(F)cc1)C1(C(=O)Nc2ccc(Oc3ccnc4cc(-c5ccc(F)c(F)c5)ncc34)c(F)c2)CC1] |
| 50S | N-(3-fluoro-4-((7-(4-morpholinophenyl)-1,6-naphthyridin-4-yl)oxy)phenyl)-N-(4-fluorophenyl)cyclopropyl-1,1-dicarboxamide | 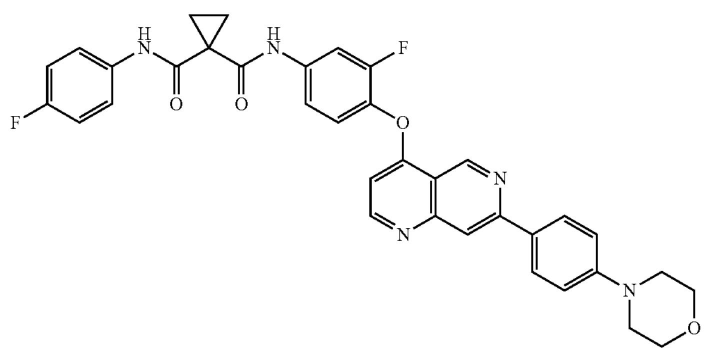 [SMILES: O=C(Nc1ccc(F)cc1)C1(C(=O)Nc2ccc(Oc3ccnc4cc(-c5ccc(N6CCOCC6)cc5)ncc34)c(F)c2)CC1] |
| 51S | N-4-((7-(isoxazol-4-yl)-1,6-naphthyridin-4-yl)oxy)-3-fluorophenyl)-N-(4-fluorophenyl)cyclopropyl-1,1-dicarboxamide | 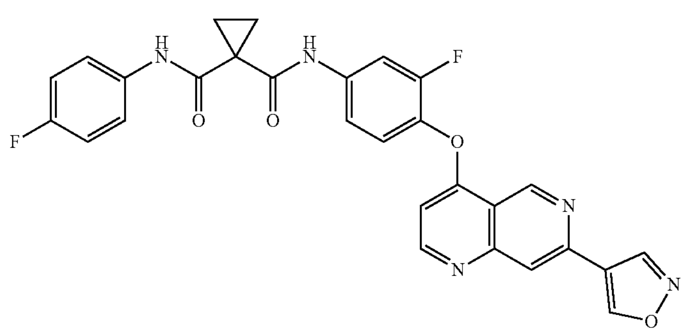 [SMILES: O=C(Nc1ccc(F)cc1)C1(C(=O)Nc2ccc(Oc3ccnc4cc(-c5cnoc5)ncc34)c(F)c2)CC1] |

-continued

| Cpd. No. | Name | Structure |
|---|---|---|
| 52S | N-4-((7-(isothiazol-3-yl)-1,6-naphthyridin-4-yl)oxy)-3-fluorophenyl)-N-(4-fluorophenyl)cyclopropyl-1,1-dicarboxamide | 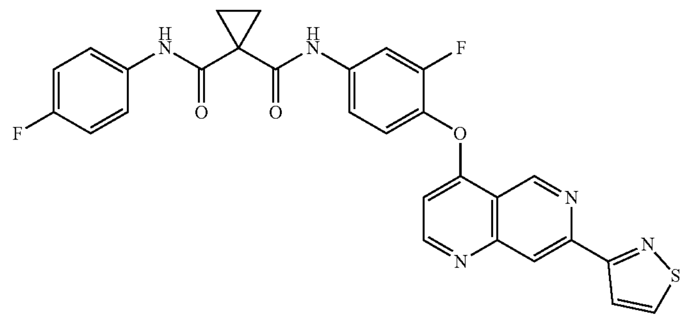 [SMILES: O=C(Nc1ccc(F)cc1)C1(C(=O)Nc2ccc(Oc3ccnc4cc(-c5ccsn5)ncc34)c(F)c2)CC1] |
| 53S | N-(3-fluoro-4-((7-(1-methyl-1H-pyrazol-4-yl)-1,6-naphthyridin-4-yl)oxy)phenyl)-1-(4-fluorophenyl)-2-oxo-1,2-dihydropyridine-3-carboxamide | 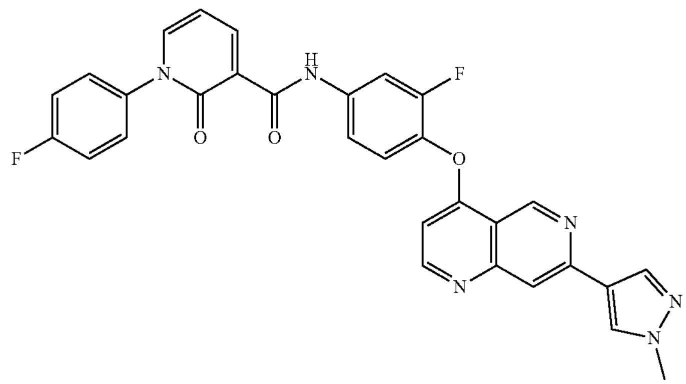 [SMILES: Cn1cc(-c2cc3nccc(Oc4ccc(NC(=O)c5cccn(-c6ccc(F)cc6)c5=O)cc4F)c3cn2)cn1] |
| 54S | N-(3-fluoro-4-((7-(1-methyl-1H-pyrazol-4-yl)-1,6-naphthyridin-4-yl)oxy)phenyl)-5-(4-fluorophenyl)-4-oxo-1,4-dihydropyridine-3-carboxamide | 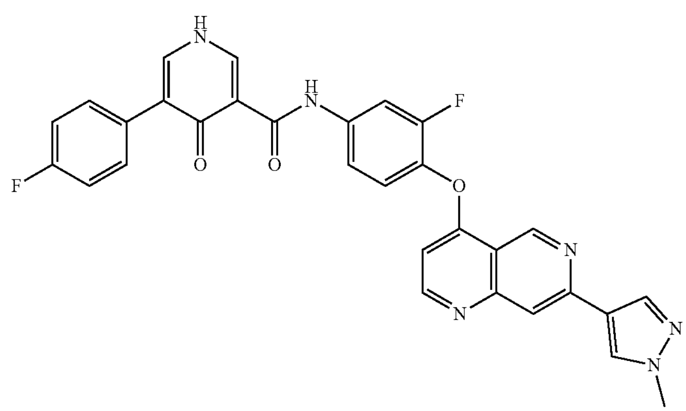 [SMILES: Cn1cc(-c2cc3nccc(Oc4ccc(NC(=O)c5c[nH]cc(-c6ccc(F)cc6)c5=O)cc4F)c3cn2)cn1] |
| 55S | N-(4-((3-chloropyrido[2,3-b]pyrazin-8-yl)oxy)-3-fluorophenyl)-N-(4-fluorophenyl)cyclopropyl-1,1-dicarboxamide | 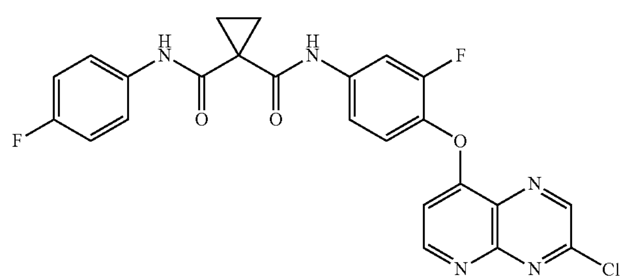 [SMILES: O=C(Nc1ccc(F)cc1)C1(C(=O)Nc2ccc(Oc3ccnc4nc(Cl)cnc34)c(F)c2)CC1] |

-continued

| Cpd. No. | Name | Structure |
|---|---|---|
| 56S | N-(4-(2-chloropyrido[2,3-b]pyrazin-8-yl)oxy)-3-fluorophenyl)-N-(4-fluorophenyl)cyclopropyl-1,1-dicarboxamide | 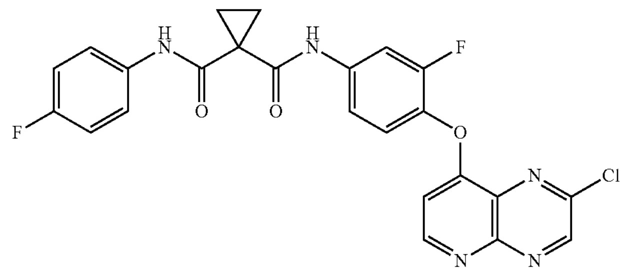 [SMILES: O=C(Nc1ccc(F)cc1)C1(C(=O)Nc2ccc(Oc3ccnc4ncc(Cl)nc34)c(F)c2)CC1] |
| 57S | N-4-((3-morpholinopyrido[2,3-b]pyrazin-8-yl)oxy)-3-fluorophenyl)-N-(4-fluorophenyl)cyclopropyl-1,1-dicarboxamide | 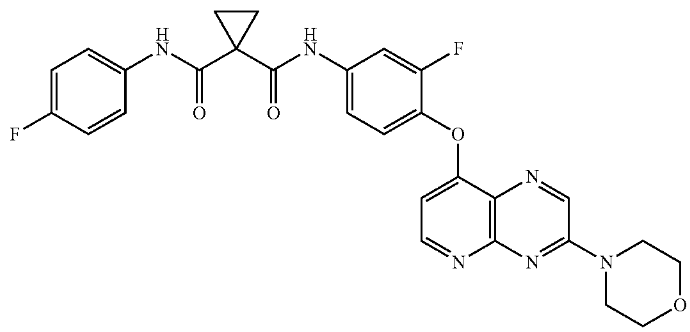 [SMILES: O=C(Nc1ccc(F)cc1)C1(C(=O)Nc2ccc(Oc3ccnc4nc(N5CCOCC5)cnc34)c(F)c2)CC1] |
| 58S | N-4-((2-morpholinopyrido[2,3-b]pyrazin-8-yl)oxy)-3-fluorophenyl)-N-(4-fluorophenyl)cyclopropyl-1,1-dicarboxamide | 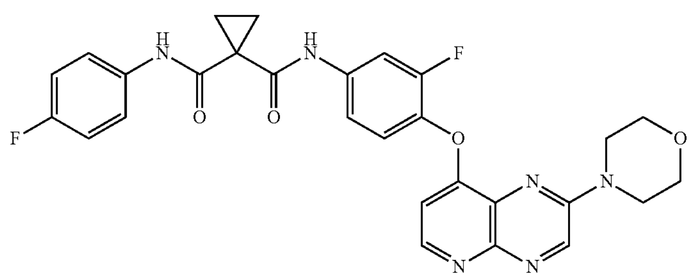 [SMILES: O=C(Nc1ccc(F)cc1)C1(C(=O)Nc2ccc(Oc3ccnc4ncc(N5CCOCC5)nc34)c(F)c2)CC1] |
| 59S | N-(3-fluoro-4-((3-(4-methylpiperazin-1-yl)pyrido[2,3-b]pyrazin-8-yl)oxy)phenyl)-N-(4-fluorophenyl)cyclopropyl-1,1-dicarboxamide | 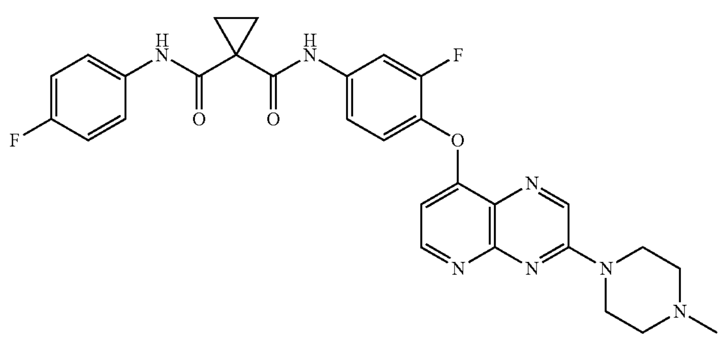 [SMILES: CN1CCN(c2cnc3c(Oc4ccc(NC(=O)C5(C(=O)Nc6ccc(F)cc6)CC5)cc4F)ccnc3n2)CC1] |
| 60S | N-(3-fluoro-4-((3-(2-morpholinoethoxy)pyrido[2,3-b]pyrazin-8-yl)oxy)phenyl)-N-(4-fluorophenyl)cyclopropyl-1,1-dicarboxamide | 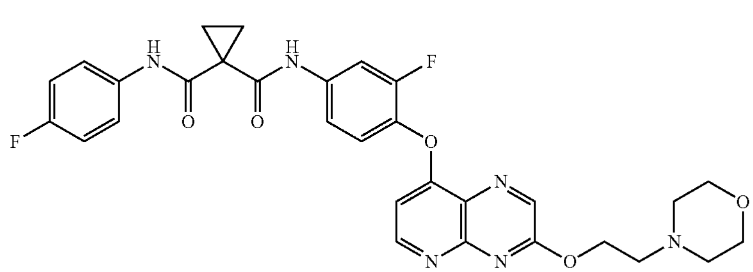 [SMILES: O=C(Nc1ccc(F)cc1)C1(C(=O)Nc2ccc(Oc3ccnc4nc(OCCN5CCOCC5)cnc34)c(F)c2)CC1] |

-continued

| Cpd. No. | Name | Structure |
|---|---|---|
| 61S | N-(3-fluoro-4-((3-(3-morpholinopropoxy) pyrido[2,3-b]pyrazin-8-yl)oxy) phenyl)-N-(4-fluorophenyl)cyclopropyl-1,1-dicarboxamide | 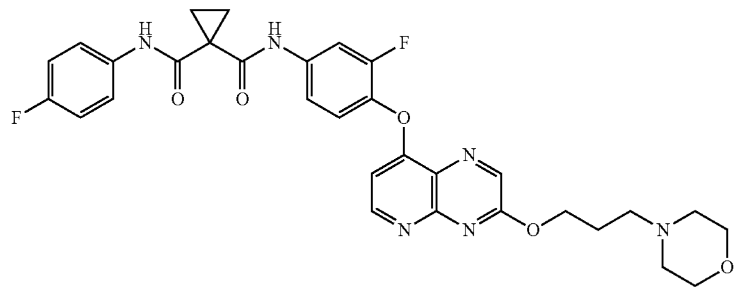 [SMILES: O=C(Nc1ccc(F)cc1)C1(C(=O)Nc2ccc(Oc3ccnc4nc(OCCCN5CCOCC5)cnc34)c(F)c2)CC1] |
| 62S | N-(3-fluoro-4-((3-((3-morpholinopropyl) amino)pyrido[2,3-b]pyrazin-8-yl) oxy)phenyl)-N-(4-fluorophenyl) cyclopropyl-1,1-dicarboxamide | 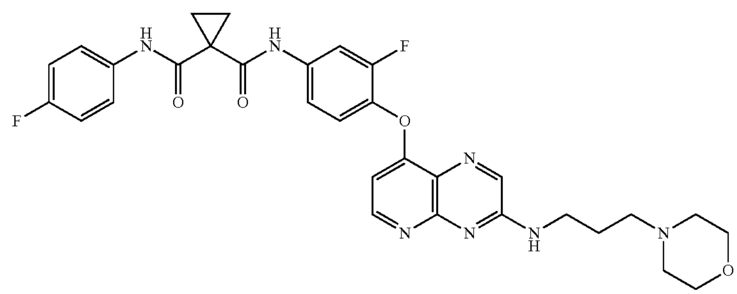 |
| 63S | N-(3-fluoro-4-((2-((3-morpholinopropyl) amino)pyrido[2,3-b]pyrazin-8-yl) oxy)phenyl)-N-(4-fluorophenyl) cyclopropyl-1,1-dicarboxamide | 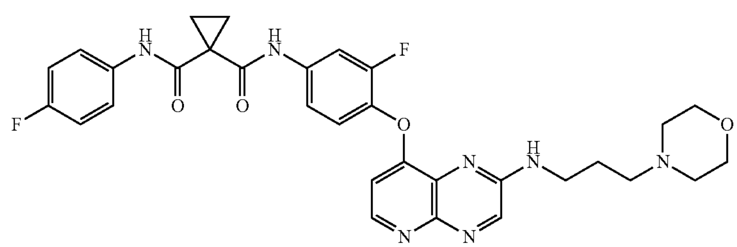 [SMILES: O=C(Nc1ccc(F)cc1)C1(C(=O)Nc2ccc(Oc3ccnc4ncc(NCCCN5CCOCC5)nc34)c(F)c2)CC1] |
| 64S | N-(4-((3-piperazinyl-pyrido[2,3-b] pyrazin-8-yl)oxy)-3-fluorophenyl)-N-(4-fluorophenyl)cyclopropyl-1,1-dicarboxamide | 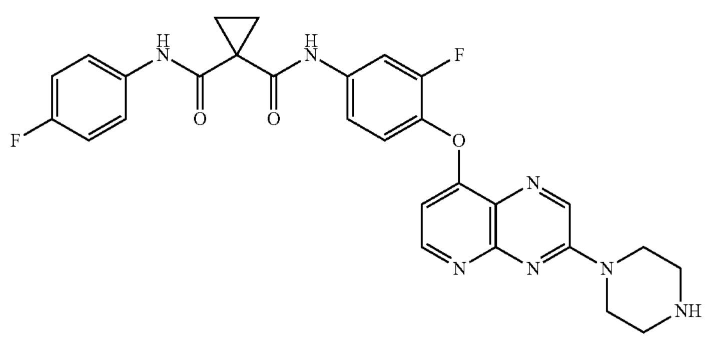 [SMILES: O=C(Nc1ccc(F)cc1)C1(C(=O)Nc2ccc(Oc3ccnc4nc(N5CCNCC5)cnc34)c(F)c2)CC1] |
| 65S | N-(4-((2-piperazinyl-pyrido[2,3-b] pyrazin-8-yl)oxy)-3-fluorophenyl)-N-(4-fluorophenyl)cyclopropyl-1,1-dicarboxamide | 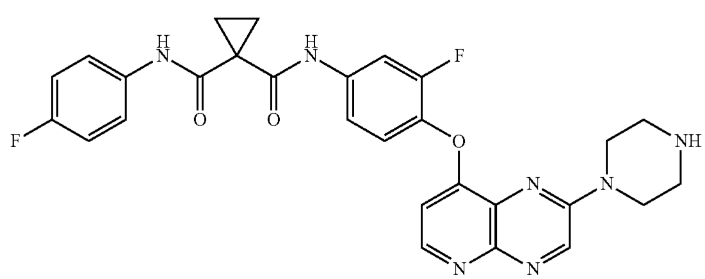 [SMILES: O=C(Nc1ccc(F)cc1)C1(C(=O)Nc2ccc(Oc3ccnc4ncc(N5CCNCC5)nc34)c(F)c2)CC1] |

| Cpd. No. | Name | Structure |
|---|---|---|
| 66S | N-(3-fluoro-4-((2-(2-(4-methylpiperazin-1-yl)ethoxy)pyrido[2,3-b]pyrazin-8-yl)oxy)phenyl)-N-(4-fluorophenyl) cyclopropyl-1,1-dicarboxamide | 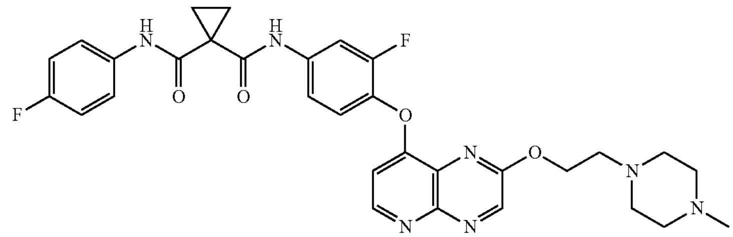 [SMILES: CN1CCN(CCOc2cnc3nccc(Oc4ccc(NC(=O)C5(C(=O)Nc6ccc(F)cc6)CC5)cc4F)c3n2)CC1] |
| 67S | N-(3-fluoro-4-((2-(2-morpholinoethoxy) pyrido[2,3-b]pyrazin-8-yl)oxy) phenyl)-N-(4-fluorophenyl)cyclopropyl-1,1-dicarboxamide | 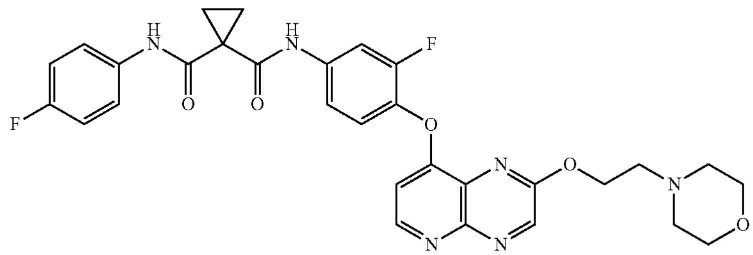 [SMILES: O=C(Nc1ccc(F)cc1)C1(C(=O)Nc2ccc(Oc3ccnc4ncc(OCCN5CCOCC5)nc34)c(F)c2)CC1] |
| 68S | N-(3-fluoro-4-((2-(3-morpholinopropoxy) pyrido[2,3-b]pyrazin-8-yl)oxy) phenyl)-N-(4-fluorophenyl)cyclopropyl-1,1-dicarboxamide | 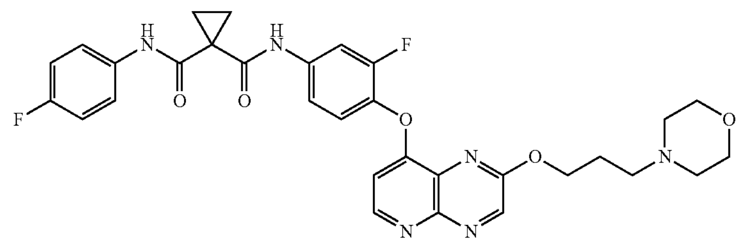 [SMILES: O=C(Nc1ccc(F)cc1)C1(C(=O)Nc2ccc(Oc3ccnc4ncc(OCCCN5CCOCC5)nc34)c(F)c2)CC1] |

In another aspect, the present invention provides a process for preparing the pyrido-azacyclic compound represented by the above formula I, the isomer thereof, the pharmaceutically acceptable salt thereof or the pharmaceutically acceptable solvate thereof, the process may be carried out by one of the following reaction schemes:

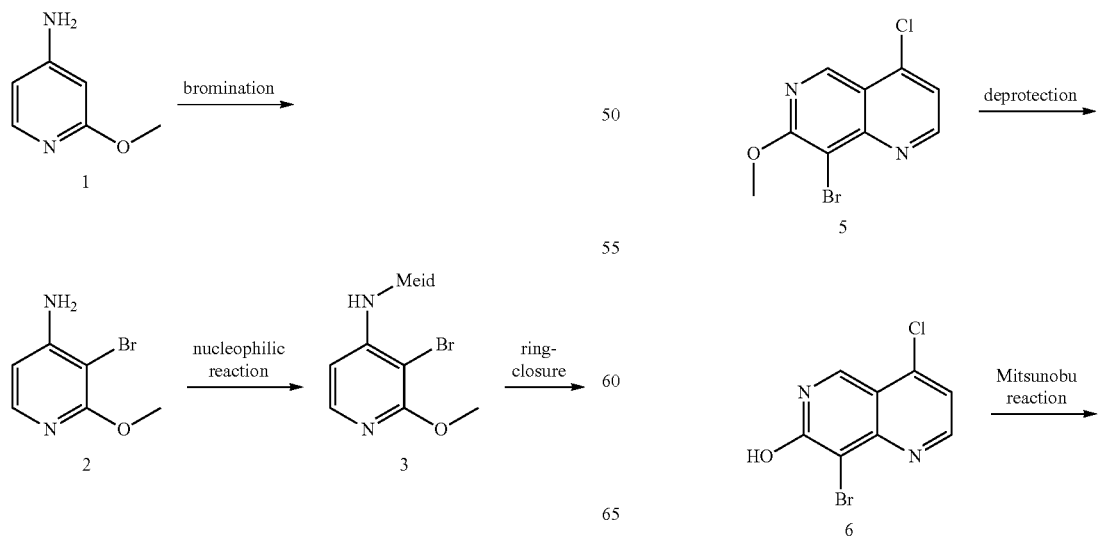

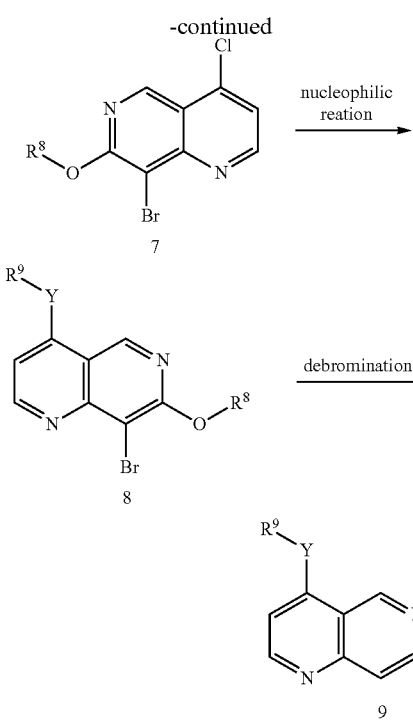

Wherein $R^8$ is

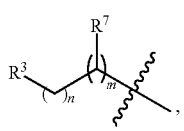

$R^9$ is

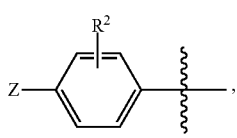

the definitions of Y, $R^2$, $R^3$, $R^7$, Z, m and n are the same as those defined in the above formula I;

(1) Compound 5 is obtained by the chlorination reaction of compound 4. The reagent for chlorination may be sulfoxide chloride ($SOCl_2$)/N,N-dimethylformamide (DMF), phosphorus oxychloride ($POCl_3$)/DMF or $POCl_3$/N, N-diisopropylethylamine (DIEA)/acetonitrile (MeCN) and the like, and $POCl_3$/DMF is preferred.

(2) Compound 6 is obtained by the deprotection of compound 5. The reagent for deprotection may be: boron tribromide ($BBr_3$)/dichloromethane (DCM), 40% aqueous hydrogen bromide (HBr), pyridine hydrochloride, hydrochloric acid or sulfuric acid, hydrochloric acid-aluminum chloride, aluminum chloride-ethanethiol, trimethylchlorosilane (TMSCl)/sodium iodide (NaI), trifluoromethanesulfonic acid, and trifluoromethanesulfonic acid is preferred.

(3) Compound 7 is produced from compound 6 via the Mitsunobu reaction. The selected reagents may be diethyl azodicarboxylate (DEAD)/triphenylphosphine ($PPh_3$), N',N'-tetraisopropylazodicarboxamide (TIPA)-tributylphosphine TBP, 1,1'-(azodicarboxylic acid)dipiperidine (ADDP)-TBP, tetramethylazodicarboxamide (TMAD)-TBP, 4,7-dimethyl-3,4,5,6,7,8-hexahydro-1,2,4,7-tetraazocin-3,8-dione (DHTD)-TBP, cyanomethylene tri n-butylphosphine (CMBP) or cyanomethylene trimethylphosphine (CMMP). DEAD/$PPh_3$ is preferred.

(4) Compound 8 is produced from compound 7 via the nucleophilic substitution reaction, and the selected reagent may be a common organic or inorganic base, such as anhydrous potassium carbonate, cesium carbonate, triethylamine (TEA), DIEA, potassium tert-butoxide, sodium hydride, sodium methoxide, sodium ethoxide; and anhydrous potassium carbonate, cesium carbonate, TEA, DIEA and potassium tert-butoxide are preferred.

(5) Compound 9 is obtained by the debromination of compound 8, preferably, the reaction condition may be palladium on carbon Pd/C-ammonium formate, Pd/C-acetamide, Pd/C-hydrogen; and Pd/C-ammonium formate is preferred.

Reaction Scheme 2:

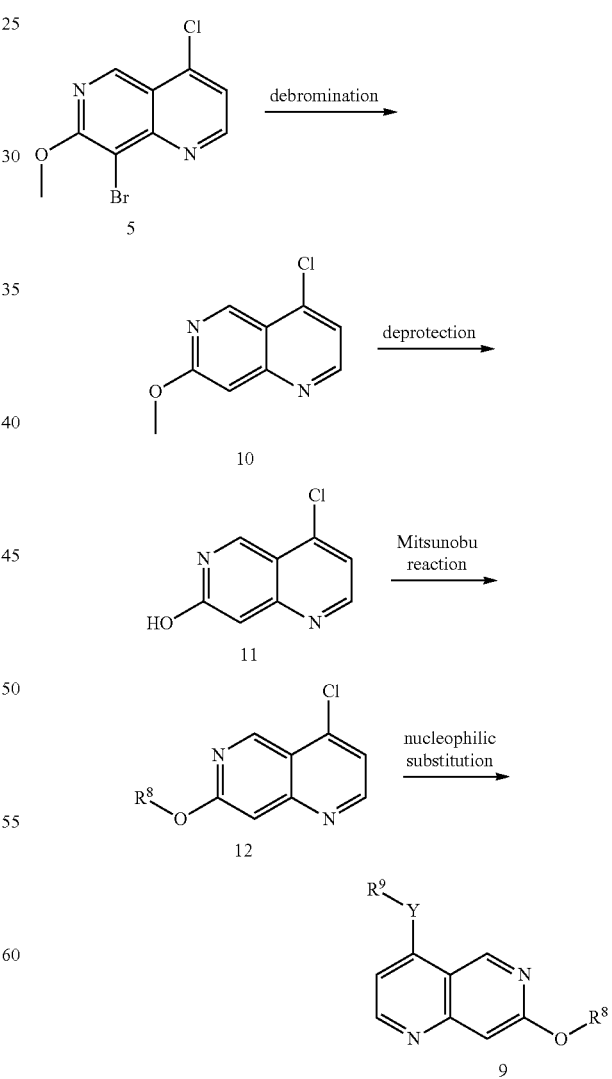

Wherein R⁸ is

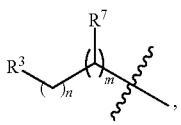

R⁹ is

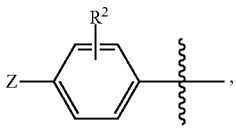

the definitions of Y, R², R³, R⁷, Z, m and n are the same as those defined in the above formula I;

(1) Compound 10 is obtained by the debromination of compound 5, preferably, the reaction condition may be Pd/C-ammonium formate, Pd/C-acetamide, Pd/C-hydrogen; and Pd/C-ammonium formate is preferred.

(2) Compound 11 is obtained by the deprotection of compound 10. The reagent for deprotection may be: BBr₃/DCM, 40% aqueous HBr, pyridine hydrochloride, hydrochloric acid or sulfuric acid, hydrochloric acid-aluminum chloride, aluminum chloride-ethanethiol, TMSCl/NaI, trifluoromethanesulfonic acid. Trifluoromethanesulfonic acid is preferred.

(3) Compound 12 is produced from compound 11 via the Mitsunobu reaction, and the selected reagents may be DEAD/PPh₃, TIPA-TBP, ADDP-TBP, TMAD-TBP, DHTD-TBP, CMBP or CMMP. DEAD/PPh₃ is preferred.

(4) Compound 9 is produced from compound 12 via the nucleophilic substitution reaction, and the selected reagent may be a common organic or inorganic base, such as anhydrous potassium carbonate, cesium carbonate, TEA, DIEA, potassium tert-butoxide, sodium hydride, sodium methoxide, sodium ethoxide; and anhydrous potassium carbonate, cesium carbonate, TEA, DIEA and potassium tert-butoxide are preferred.

Reaction scheme 3:

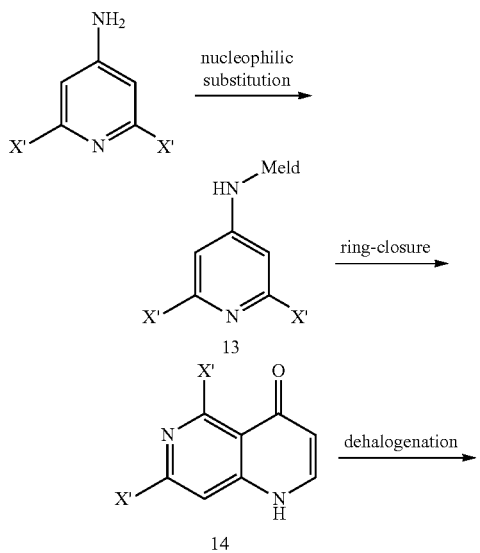

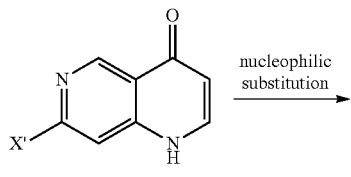

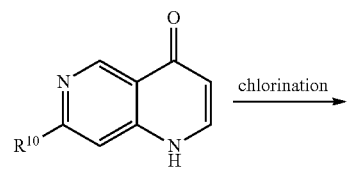

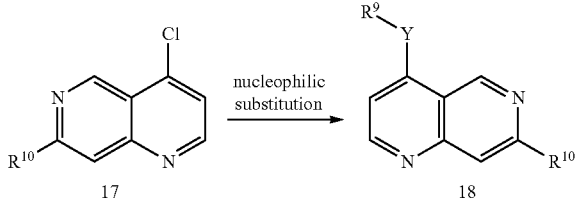

Wherein R¹⁰ is

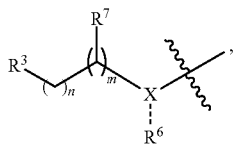

R⁹ is

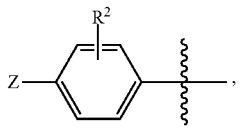

and the definitions of X, Y, R², R³, R⁶, R⁷, Z, m and n are the same as those defined in claims 1 to 5, respectively; X' is Cl or Br;

(1) Compound 15 is obtained by the dechloridation of compound 14, the reaction reagent is zinc (Zn)/acetic acid (MeCOOH);

(2) Compound 17 is obtained by the chlorination of compound 16, and the reagent for chlorination may be SOCl₂/DMF, POCl₃/DMF, POCl₃/DIEA/MeCN and the like, and POCl₃/DIEA/MeCN is preferred;

(3) Compound 18 is produced from compound 17 via the nucleophilic substitution reaction, and the selected reagent may be a common organic or inorganic base, such as anhydrous potassium carbonate, cesium carbonate, TEA, DIEA, potassium tert-butoxide, sodium hydride, sodium methoxide, sodium ethoxide; and anhydrous potassium carbonate, cesium carbonate, TEA, DIEA and potassium tert-butoxide are preferred;

Reaction scheme 4:

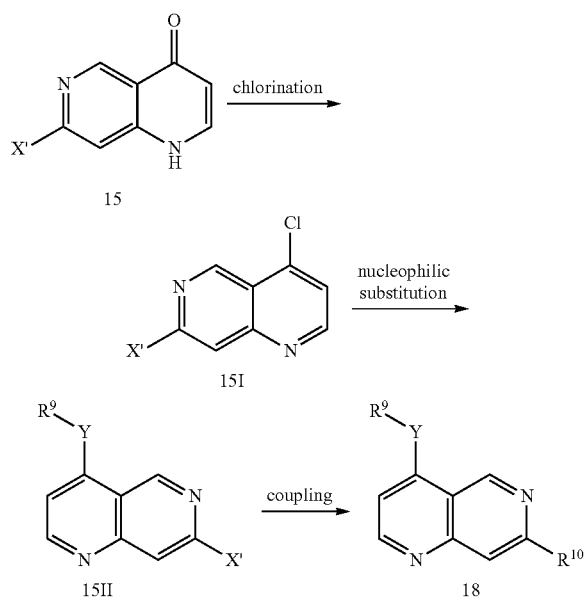

and the definitions of X, Y, $R^2$, $R^3$, $R^6$, $R^7$, Z, m and n are the same as those defined in claims 1 to 5, respectively; X' is Cl or Br;

(1) Compound 15I is obtained by the chlorination of compound 15, and the reagent for chlorination may be $SOCl_2$/DMF, $POCl_3$/DMF, $POCl_3$/DIEA/MeCN and the like, and $POCl_3$/DIEA/MeCN is preferred;

(2) Compound 15II is produced from compound 15I via the nucleophilic substitution reaction, and the selected reagent may be a common organic or inorganic base, such as anhydrous potassium carbonate, cesium carbonate, TEA, DIEA, potassium tert-butoxide, sodium hydride, sodium methoxide, sodium ethoxide; and anhydrous potassium carbonate, cesium carbonate, TEA, DIEA and potassium tert-butoxide are preferred;

(3) Compound 18 is produced from compound 15II via the Suzuki coupling reaction, the base being used may be potassium acetate, potassium phosphate or potassium carbonate; the solvent being used may be dimethylsulfoxide, DMF, dioxane or toluene, and an appropriate amount of water is added; The catalyst being used may be tetrakis(triphenylphosphine)palladium, [1,1'-Bis(diphenylphosphino)ferrocene]dichloropalladium $PdCl_2$(dppf);

Reaction scheme 5:

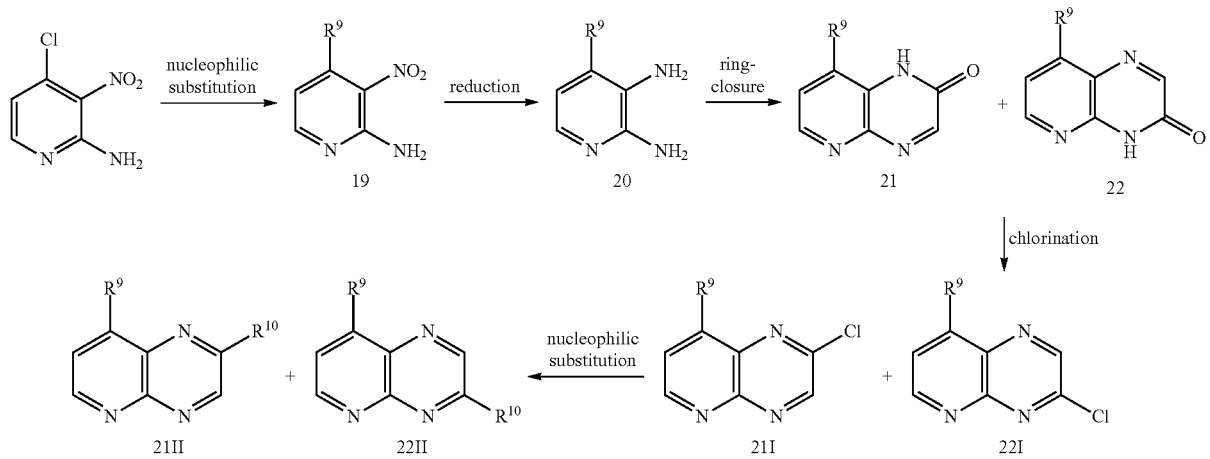

Wherein $R^{10}$ is

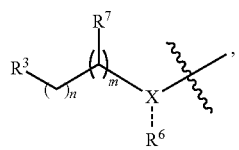

$R^9$ is

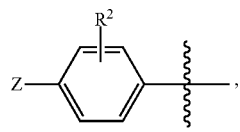

Wherein $R^{10}$ is

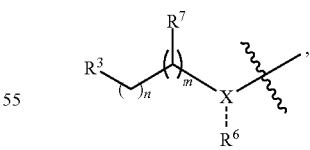

$R^9$ is

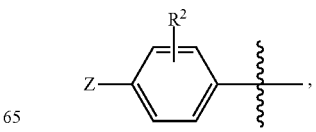

and the definitions of X, Y, $R^2$, $R^3$, $R^6$, $R^7$, Z, m and n are the same as those defined in claims 1 to 5, respectively;

(1) Compound 19 is produced via a substitution reaction, the selected reagent may be a common organic or inorganic base, such as anhydrous potassium carbonate, cesium carbonate, TEA, DIEA, potassium tert-butoxide, sodium hydride, sodium methoxide, sodium ethoxide; and anhydrous potassium carbonate, cesium carbonate, TEA, DIEA and potassium tert-butoxide are preferred;

(2) Compound 20 is obtained by reducing compound 19, and the reducing agents being used may be nickel chloride ($NiCl_2$)/sodium borohydride ($NaBH_4$), Zn/AcOH, Pd/C—$H_2$, Fe/hydrogen chloride (HCl) and sodium sulfide ($Na_2S$)/ethanol (EtOH), ammonium hydrogen sulfide ($NH_4HS$), lithium aluminum hydride ($LiAlH_4$); and $NiCl_2$/$NaBH_4$ and Pd/C—$H_2$ are preferred;

(3) Compounds 21 and 22 are obtained by the ring-closure reaction of compound 20, the condition for the ring-closure reaction may be ethyl formyl acetate, the solvent may be various common solvents, such as methanol (MeOH), EtOH, acetonitrile (MeCN), dioxane and the like;

(4) a chlorination reaction, the reagent for chlorination may be $SOCl_2$/DMF, $POCl_3$/DMF, $POCl_3$/DIEA/MeCN and the like, and $POCl_3$/DIEA/MeCN is preferred;

(5) a nucleophilic substitution reaction, the selected reagent may be a common organic or inorganic base, such as anhydrous potassium carbonate, cesium carbonate, TEA, DIEA, potassium tert-butoxide, sodium hydride, sodium methoxide, sodium ethoxide; and anhydrous potassium carbonate, cesium carbonate, TEA, DIEA and potassium tert-butoxide are preferred.

In another aspect, the present invention further provides a composition comprising a therapeutically effective amount of one or more selected from a compound of formula I, an isomer, a pharmaceutically acceptable salt or a pharmaceutically acceptable solvate thereof.

In another aspect, the present invention also provides a use of a compound of formula I, an isomer thereof, a pharmaceutically acceptable salt, a pharmaceutically acceptable solvate, and a composition thereof in the preparation of a medicament as a multi-target protein kinase inhibitor, in the preparation of a medicament for inhibiting the activity of tyrosine kinase c-Met, in the preparation of a medicament for the prevention or treatment of diseases associated with in vivo hepatocyte growth factor receptor (c-Met)-related cell abnormal proliferation, morphological changes and hyperkinesia, and diseases associated with angiogenesis or tumor metastasis, especially for the preparation of a medicament for preventing or treating tumor growth and metastasis.

The kinase includes c-Met, Flt-1, PDGFR-α, PDGFR-β, RET, c-Src, EPH-A2, FGFR, Abl, Lck, KDR, IGF-1α and ALK.

The medicament is used in the treatment and/or prevention of diseases associated with protein kinases (particularly c-Met), such as tumors.

In the present invention, the tumor may be lung cancer, medullary thyroid tumor, glioblastoma, stomach cancer, renal cell cancer, breast cancer, ovarian cancer, prostate cancer or colorectal cancer.

The present invention has the following advantageous effects:

After screening the activity on c-Met kinase, the inventors found that the compounds represented by the above formula I showed high inhibitory activity on c-Met kinase at 10 nM; and showed high inhibitory activity on tumor cells in which c-Met kinase was highly expressed at 100 nM. The representative compound 7S showed good pharmacokinetic properties: bioavailability F=51.8%, mean retention time MRT=2.6 h, half-life $t_{1/2}$=1.66 h, and the area under the curve of the drug concentration vs. time AUC=16652 h*ng/ml. In addition, the small molecule inhibitor showed a good curative effect in vivo, e.g., in the 100 mg/kg treatment group (oral administration once a day, continuous administrating for 21 days), the relative tumor growth rate T/C of human lung cancer EBC-1 xenograft tumor in nude mice was 9.5%, tumor volume growth inhibition rate GI was 96.5%, tumor weight inhibition rate was 86.9%, and it was safe and non-toxic within effective dose. Therefore, the compounds represented by formula I can effectively target the c-Met-mediated signaling pathway, and can be used for the treatment of diseases such as tumor and the like that are caused by the overexpression of c-Met kinase. The pharmaceutical composition comprising the pharmaceutically acceptable compound of formula I is also effective in targeting the c-Met-mediated signaling pathway, and is useful in the treatment of diseases such as tumors and the like that are caused by the overexpression of c-Met kinase.

DESCRIPTION OF DRAWINGS

FIG. 1 shows the therapeutic effect of Compound 7S on human lung cancer EBC-1 xenograft tumor in nude mice in the experiment.

DETAILED EMBODIMENT

Examples

The present invention will be further described with reference to the following examples, but these examples are not intended to limit the protection scope of the present invention.

The compounds were determined as follows: $^1$H-NMR spectral data was recorded on a Varian Mercury-300 MHz or Varian Mercury-400 MHz nuclear magnetic resonance spectrometer, mass spectrometry EI-MS was recorded on a Finnigan MAT 95 mass spectrometer, and ESI-MS was measured by using a Finnigan LCQ Deca mass spectrometer. Flash column chromatography was performed on silica gel H (10-40 μM). Reagent purification is referred to Purification of laboratory Chemicals; D. D. Perrin; W. L. F. Armarego and D. R. Perrin Eds., Pergamon Press: Oxiford, 1980.

Unless otherwise specified, reagents, processes and the like used in the present invention are well-known reagents and processes in the art.

Example 1 Synthesis of Fragment II Series

This fragment was synthesized with reference to WO2011/137342 A1

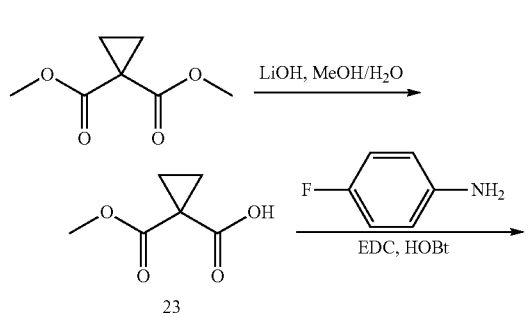

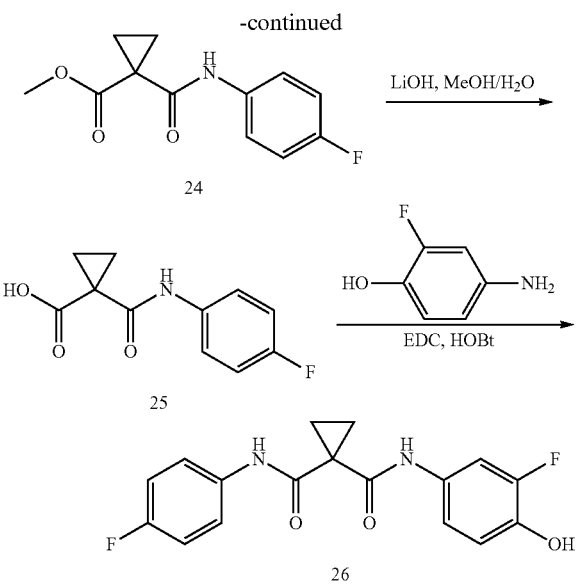

1-(methoxycarbonyl) Cyclopropane Monocarboxylic Acid (23)

Dimethyl cyclopropane dicarboxylate (10.12 g, 63.99 mmol) was dissolved in 100 mL (1:1 V:V) $CH_3OH/H_2O$ and stirred at room temperature. Lithium hydroxide (2.68 g, 63.99 mmol) dissolved in 20 ml $H_2O$ was slowly added to the above solution for three times at room temperature, and then the mixture was allowed to react for 1 h with stirring. After the reaction was completed, the resultant was adjusted to pH3 with dilute hydrochloric acid, extracted with DCM, and dried over anhydrous sodium sulfate. The product without purification was to be used in the next step.

1-((4-fluorophenyl) carbamoyl) Cyclopropane Monocarboxylic Acid (25)

Compound 23 (9.21 g, 63.99 mmol) and p-fluoroaniline (12.15 ml, 127.98 mmol) were dissolved in 150 ml of DCM, and the resulted solution was added with HOBt (hydroxybenzotriazole) (12.97 g, 95.98 mmol) and 1-(3-dimethylaminopropyl)-3-ethylcarbodiimide (EDC) (14.90 g, 95.98 mmol) at room temperature. The mixture was stirred at room temperature and the reaction was monitored by TLC. After the reaction was completed, the resultant was evaporated to remove most DCM, extracted with EA, then washed with saturated $NaHCO_3$, water (pH=3) and saturated brine, dried over anhydrous $Na_2SO_4$ and concentrated to give a crude compound 24. The resulting crude product was directly dissolved in 100 mL (1:1 V:V) $MeOH/H_2O$, and the solution was stirred at room temperature and then added with lithium hydroxide (3.06 g, 127.98 mmol), then the mixture was allowed to react for 1 h with stirring, and the reaction was monitored by TLC. After the reaction was completed, the resultant was adjusted to pH3 with dilute hydrochloric acid, then a large amount of solid was precipitated, after being filtrated and dried, an off-white solid 10.56 g was obtained, yield 74.1% in two steps. $^1$H NMR (DMSO, 400 MHz): δ 10.51 (s, 1H), 10.32 (s, 1H), 10.00 (s, 1H), 7.77 (d, J=12.9 Hz, 1H), 7.66-7.61 (m, 2H), 7.41 (d, J=8.7 Hz, 1H), 7.30 (t, J=8.8 Hz, 1H), 7.15 (d, J=9.0 Hz, 2H), 1.61 (m, 2H), 1.44 (m, 2H).

N-(3-fluoro-4-hydroxyphenyl)-N-(4-fluorophenyl) Cyclopropane-1,1-dicarboxamide (26)

Compound 25 (2.00 g, 8.97 mmol) and 4-amino-2-fluorophenol (1.14 g, 8.97 mmol) were dissolved in 10 ml of DCM, and the resulted solution was added with HOBt (1.21 g, 13.46 mmol) and EDC (1.77 g, 13.46 mmol) at room temperature. The mixture was stirred at room temperature and the reaction was monitored by TLC. After the reaction was completed, the resultant was evaporated to remove most DCM, extracted with EA, then washed with saturated $NaHCO_3$, water (pH=3) and saturated brine, dried over anhydrous $Na_2SO_4$ and concentrated to give the crude product, which was crystallized in methanol to give a tan solid, yield 63%. $^1$H NMR (DMSO, 400 MHz): δ 10.51 (s, 1H), 10.32 (s, 1H), 10.00 (s, 1H), 7.77 (d, J=12.9 Hz, 1H), 7.66-7.61 (D, J=8.7 Hz, 1H), 7.30 (t, J=8.8 Hz, 1H), 7.15 (d, J=9.0 Hz, 2H), 1.61 (m, 2H), 1.44).

N-(3-fluoro-4-hydroxyphenyl)-N-(4-fluorophenyl)-N-methylcyclopropane-1,1-dicarboxamide (27)

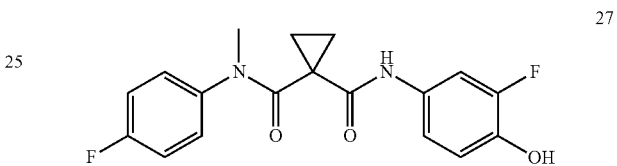

The preparation process of compound 27 was same as that of compound 26, except that the starting material was p-fluoro-N-methylaniline. 1H NMR (DMSO, 300 MHz): δ 9.56 (s, 1H), 9.42 (s, 1H), 7.35-7.23 (m, 2H), 7.19-7.03 (m, 2H), 6.97-6.87 (m, 1H), 6.85-6.75 (m, 1H), 3.22 (s, 3H), 1.38-1.10 (m, 4H).

N-(3,4-difluorophenyl)-N-(3-fluoro-4-hydroxyphenyl) Cyclopropane-1,1-dicarboxamide (28)

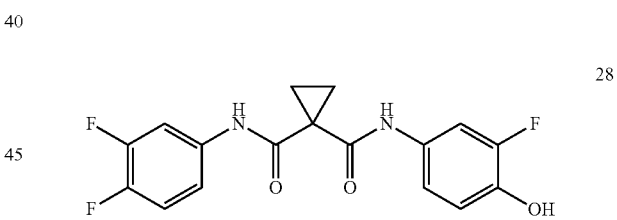

The preparation process of compound 28 was same as that of compound 26, except that the starting material was 3,4-difluoroaniline. 1H NMR ($CDCl_3$, 300 MHz): δ 10.64 (s, 1H), 7.72-7.58 (m, 1H), 7.13-7.00 (m, 2H), 6.83 (t, J=8.5 Hz, 1H), 6.52-6.34 (m, 2H), 1.97 (m, 2H).

N-(4-fluoro-3-methoxy)-N-(3-fluoro-4-hydroxyphenyl) Cyclopropane-1,1-dicarboxamide (29)

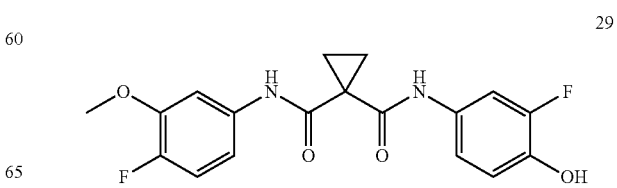

The preparation process of compound 29 was same as that of compound 26, except that the starting material was 4-fluoro-3-methoxyaniline. ¹H NMR (DMSO, 400 MHz): δ 10.08 (s, 1H), 9.87 (s, 1H), 9.62 (s, 1H), 7.57-7.48 (m, 2H), 7.21-7.11 (m, 3H), 6.87 (t, J=9.2 Hz, 1H), 3.80 (s, 3H), 1.50-1.37 (m, 4H)

N-(4-fluorophenyl)-N-(4-hydroxyphenyl) Cyclopropane-1,1-dicarboxamide (31)

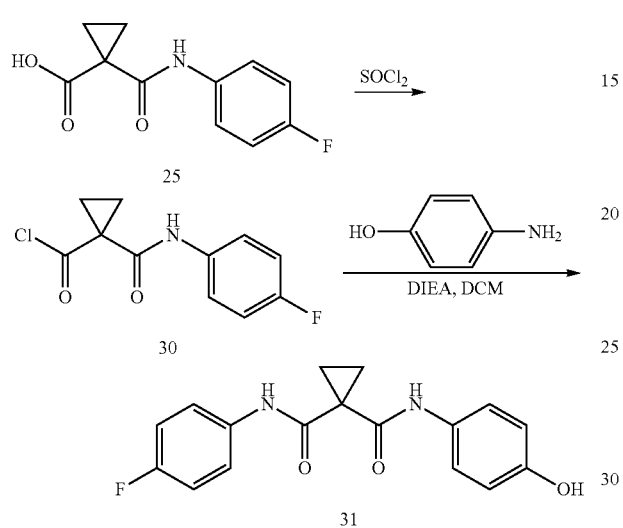

Compound 25 (0.50 g, 2.24 mmol) was added to a round-bottom flask, then 2 mL of SOCl₂ was added therein, and the mixture was allowed to react for 2 h at 80° C., then the resultant was concentrated to give crude compound 30. The concentrate was diluted with 5 mL of DCM; p-hydroxyaniline (366 mg, 3.36 mmol) was dissolved in 30 ml of DCM, then added with DIEA (386 mg, 3.36 mmol). The compound 30 was added dropwise to the reaction solution slowly under ice bath, after the dropping is finished, the mixture was allowed to continuously react for 1 h with stirring at room temperature. After the reaction was completed, the resultant was extracted with EA, then washed with saturated NaHCO₃, water (pH=3) and saturated brine, dried over anhydrous Na₂SO₄ and concentrated to give the crude product, which was purified by column chromatography to give compound 31 as a khaki-colored solid, yield 63% in two steps. ¹H NMR (DMSO, 300 MHz): δ 10.18 (s, 1H), 9.74 (s, 1H), 9.25 (s, 1H), 7.63 (dd, J=8.1, 5.2 Hz, 2H), 7.36 (d, J=8.2 Hz, 2H), 7.15 (t, J=8.4 Hz, 2H), 6.70 (d, J=7.9 Hz, 2H), 1.47-1.41 (m, 2H), 1.14-1.06 (m, 2H).

N-(4-aminophenyl)-N-(4-hydroxyphenyl) Cyclopropane-1,1-dicarboxamide (32)

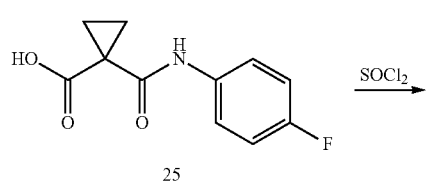

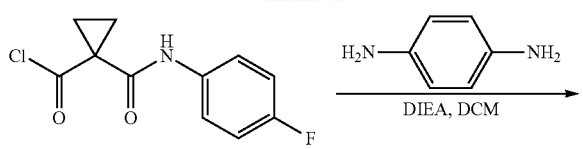

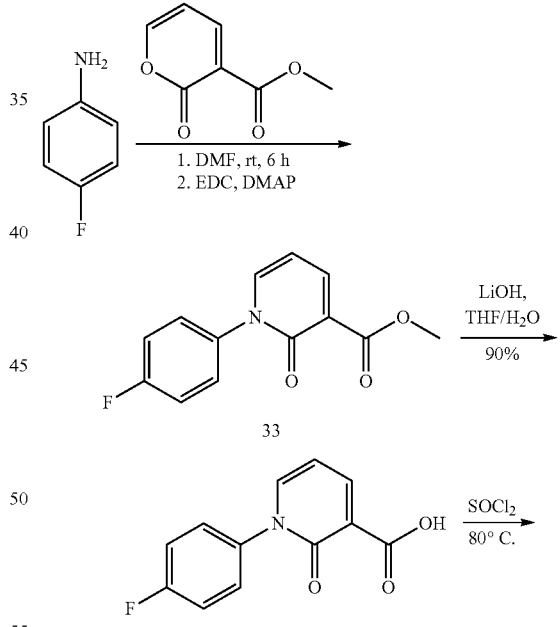

The preparation process of compound 32 was same as that of compound 31, except that the starting material was 1,4-phenylenediamine, yield 56% in two steps. ¹H NMR (DMSO, 300 MHz): δ 10.25 (s, 1H), 9.57 (s, 1H), 7.68-7.60 (m, 2H), 7.30-7.10 (m, 4H), 6.51 (d, J=8.6 Hz, 2H), 4.96 (s, 2H), 1.53-1.37 (m, 4H).

Example 2 Synthesis of Fragment III

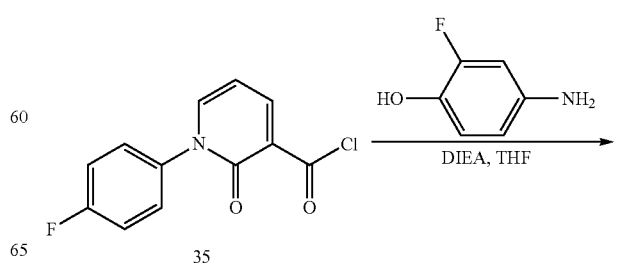

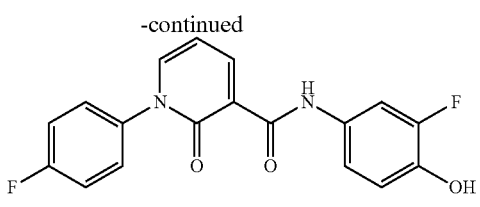

36

1-(4-fluorophenyl)-2-oxo-1,2-dihydropyridine-3-carboxylic Acid (34)

Methyl 2-oxo-2H-pyran-3-carboxylate (300 mg, 1.95 mmol) and p-fluoroaniline (0.19 ml, 1.96 mmol) were dissolved in 5 ml of DMF and reacted for 6 h with stirring at room temperature, then EDC (0.49 g, 2.54 mmol) and DMAP (dimethylaminopyridine) (60 mg, 0.49 mmol) were added to the reaction solution and reacted overnight with stirring at room temperature. After the reaction was completed, the resultant was extracted with EA, then washed with saturated NaHCO$_3$ and saturated brine, dried over anhydrous Na$_2$SO$_4$ and concentrated to give the crude product. The crude product was directly dissolved in 20 mL solution of 2N NaOH in THF/H$_2$O (1:1 V:V) and reacted for 2 h with stirring at 65° C. After the reaction was completed, the pH value was adjusted to 1 with dilute hydrochloric acid then a large amount of solid was precipitated, which was filtered and dried to give compound 34 as a khaki solid. $^1$H NMR (DMSO, 300 MHz): δ 8.47 (dd, J=7.1, 2.2 Hz, 1H), 8.19 (dd, J=6.6, 2.2 Hz, 1H), 7.59-7.63 (m, 2H), 7.39-7.44 (m, 2H), 6.78 (dd, J=6.6, 7.1 Hz, 1H).

N-(3-fluoro-4-hydroxyphenyl)-1-(4-fluorophenyl)-2-oxo-1,2-dihydropyridine-3-carboxamide (36)

Compound 34 (0.52 g, 2.24 mmol) was added to a round-bottom flask, 2 mL of SOCl$_2$ was added therein, and the mixture was allowed to react at 80° C. for 2 h, then the resultant was concentrated to give compound 35. The concentrate was diluted with 5 mL of DCM; p-hydroxy-3-fluoroaniline (427 mg, 3.36 mmol) was dissolved in 30 ml of DCM, then added with DIEA (386 mg, 3.36 mmol). The compound 35 was added dropwise to the reaction solution slowly under ice bath, after the dropping was finished, the mixture was allowed to continuously react for 1 h with stirring at room temperature. After the reaction was completed, the resultant was extracted with EA, then washed with saturated NaHCO$_3$ and saturated brine, dried over anhydrous Na$_2$SO$_4$ and concentrated to give a crude product, which was puritied by column chromatography to give compound 36 as a khaki-colored solid, yield 52% in two steps. $^1$H NMR (DMSO, 300 MHz): δ 11.79 (s, 1H), 9.72 (s, 1H), 8.55 (d, J=7.2 Hz, 1H), 8.11 (dd, J=13.6, 6.3 Hz, 1H), 7.74 (d, J=13.5 Hz, 1H), 7.59 (dt, J=13.0, 6.5 Hz, 2H), 7.41 (dd, J=16.3, 7.6 Hz, 2H), 7.20-7.09 (m, 1H), 6.92 (t, J=9.2 Hz, 1H), 6.72 (dd, J=14.6, 7.3 Hz, 1H).

Example 3 Synthesis of Fragment IV

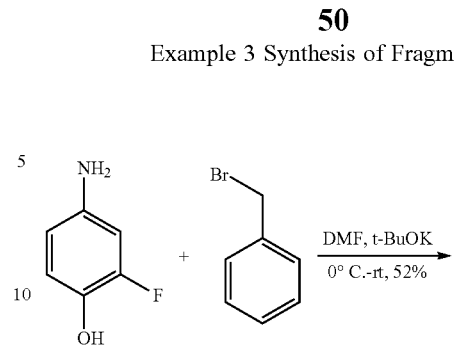

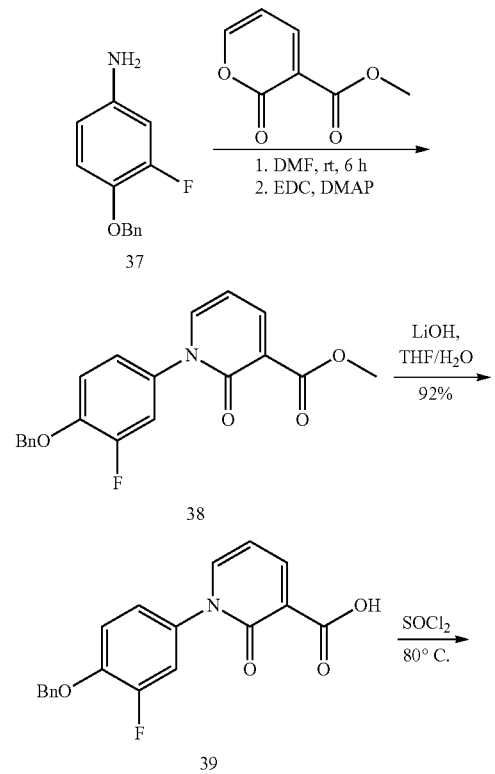

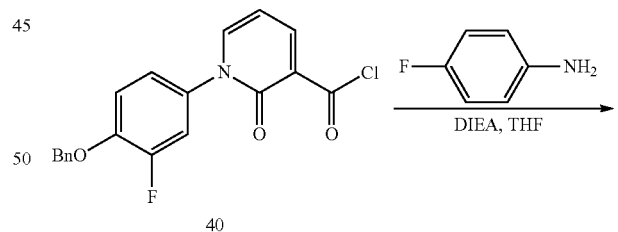

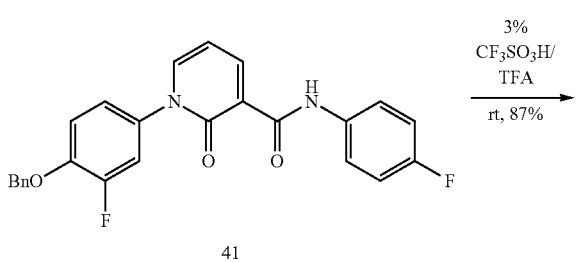

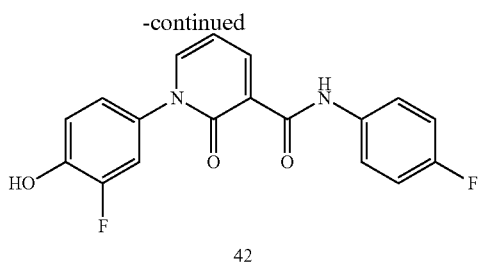

42

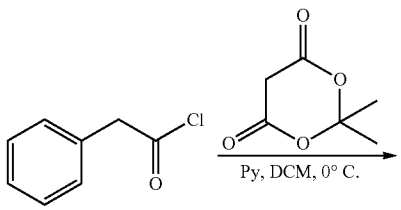

4-(benzyloxy)-3-fluoroaniline (37)

p-hydroxy-3-fluoroaniline (1.0 g, 7.87 mmol) was dissolved in 10 mL of anhydrous DMF, cooled to 0° C., then potassium tert-butoxide (0.88 g, 7.87 mmol) was added thereto, after stirring for 10 min, benzyl bromide (1.35 g, 7.87 mmol) was added therein, and the reaction was monitored by TLC. After the reaction is completed, the resultant was extracted with EA, then washed with saturated $NaHCO_3$ and saturated brine, dried over anhydrous $Na_2SO_4$ and concentrated to give the crude compound 37, which was purified by column chromatography to give a colorless liquid, yield 52%. $^1$H NMR ($CDCl_3$, 300 MHz): δ 7.41-7.28 (m, 5H), 6.91 (dd, 1H), 6.46 (dd, 1H), 6.32 (m, 1H), 4.97 (s, 2H), 4.98 (s, 2H).

1-(4-(benzyloxy)-3-fluorophenyl)-N-(4-fluorophenyl)-2-oxo-1,2-dihydropyridine-3-carboxamide (41)

The synthesis of compound 41 was same as that of compound 36, except that the starting material was 4-(benzyloxy)-3-fluoroaniline (37). $^1$H NMR (DMSO, 300 MHz): δ 11.93 (s, 1H), 8.56 (dd, J=7.2, 1.9 Hz, 1H), 8.10 (dd, J=6.6, 1.9 Hz, 1H), 7.79-7.70 (m, 2H), 7.65-7.37 (m, 7H), 7.37-7.27 (m, 1H), 7.20 (t, J=8.8 Hz, 2H), 6.70 (t, J=7.0 Hz, 1H), 5.30 (s, 2H).

1-(3-fluoro-4-hydroxyphenyl)-N-(4-fluorophenyl)-2-oxo-1,2-dihydropyridine-3-carboxamide (42)

The above compound 41 (432 mg, 1 mmol) was dissolved in 3 ml of trifluoroacetic acid and then 100 μl of trifluoromethanesulfonic acid was added dropwise thereto. The mixture was allowed to react with stirring and the reaction was monitored by TLC. After the reaction was completed, the resultant was diluted with EA and adjusted to pH=6 with 2N NaOH, extracted with EA and washed with saturated brine, dried over anhydrous $Na_2SO_4$ and concentrated to give crude compound 42, which was purified by column chromatography to give a pale yellow solid, yield 87%. $^1$H NMR (DMSO, 300 MHz): δ 11.96 (s, 1H), 10.40 (s, 1H), 8.55 (dd, J=7.3, 2.1 Hz, 1H), 8.08 (dd, J=6.6, 2.1 Hz, 1H), 7.73 (dd, J=8.9, 5.0 Hz, 2H), 7.47 (dd, J=11.8, 2.3 Hz, 1H), 7.26-7.03 (m, 4H), 6.69 (t, J=6.9 Hz, 1H).

Example 4 Synthesis of Fragment V

Fragment V was synthesized with reference to *J Med Chem*, 2008, 51, 5330-5341

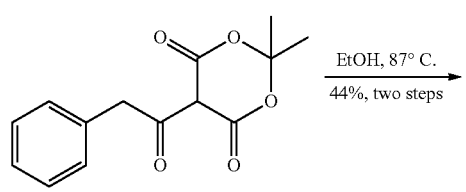

43

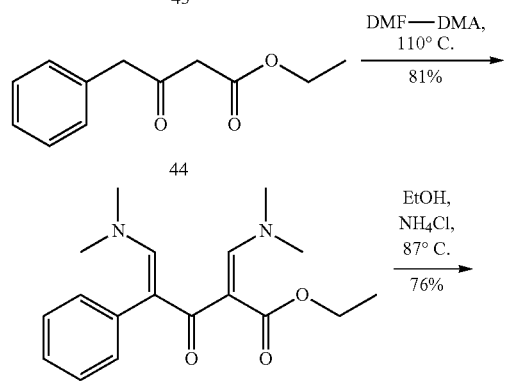

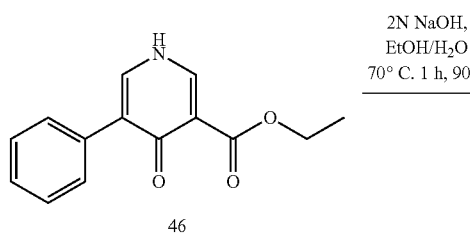

46

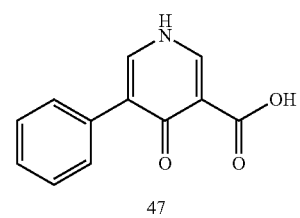

47

Ethyl 3-oxo-4-phenylbutyrate (44)

2,2-dimethyl-1,3-dioxane-4,6-dione (2 g, 13.9 mmol) was dissolved in 40 ml of dichloromethane, and pyridine (1.65 g, 20.9 mmol) was added thereto, then the mixture was cooled to 0° C. and added dropwise with phenylacetyl chloride (2.14 g, 13.9 mmol) slowly, and the mixture was allowed to react for 3 h with stirring at 0° C. After the reaction was completed, the resultant was diluted with 100 mL of DCM, added with 50 mL of 1N HCl. The organic phase was separated after stirring, dried over anhydrous $Na_2SO_4$ and concentrated to give the crude product. The crude product was added directly to 50 ml EtOH and refluxed overnight. After concentrated, the residue was purified by column chromatography to give a pale yellow oil, yield 44% in the two steps. ¹H NMR (CDCl₃, 300 MHz): δ 7.42-7.14 (m, 5H), 4.15 (q, J=7.1 Hz, 2H), 3.81 (s, 2H), 3.43 (s, 2H), 1.24 (t, J=7.2 Hz, 3H).

Ethyl 4-(dimethylamino)-2-((dimethylamino) Methylene)-3-oxo-4-phenylbutyrate (45)

The above liquid was added into DMF-DMA and reacted for 3 h with stirring at 110° C. After the reaction was completed, the resultant was concentrated and stirred in EA to give a white solid, yield 81%. ¹H NMR (DMSO, 300 MHz): δ 7.37-7.14 (m, 5H), 7.06 (s, 1H), 7.04 (s, 1H), 4.07-3.87 (m, 2H), 2.92 (s, 6H), 2.65 (s, 6H), 1.13 (t, J=7.1 Hz, 3H).

Ethyl 4-oxo-5-phenyl-1,4-dihydropyridine-3-carboxylate (46)

The above solid was dissolved in EtOH, and 3 eq of NH₄Cl was added thereto, the mixture was refluxed for 2 h, then cooled to room temperature, and the resultant was filtered and dried to give a pale yellow solid, yield 76%. ¹H NMR (DMSO, 300 MHz): δ 8.22 (s, 1H), 7.86 (s, 1H), 7.64-7.56 (m, 2H), 7.47-7.25 (m, 3H), 4.21 (q, J=7.1 Hz, 2H), 1.27 (t, J=7.1 Hz, 3H).

4-oxo-5-phenyl-1,4-dihydropyridine-3-carboxylic acid (47)

The solid prepared as above was dissolved in ethanol, and 2N NaOH was added thereto, the mixture was allowed to react for 2 h with stirring at 70° C. Thereafter, the resultant was cooled and added with 1.5N HCl to give a solid, which was filtered and dried, yield 90%. ¹H NMR (DMSO, 300 MHz): δ 13.21 (s, 1H), 8.62 (s, 1H), 8.25 (s, 1H), 7.75-7.62 (m, 2H), 7.53-7.36 (m, 3H).

5-(4-fluorophenyl)-4-oxo-1,4-dihydropyridine-3-carboxylic acid (48)

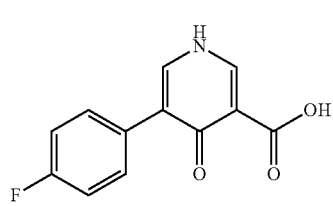

48

The synthesis of compound 48 was same as that of compound 47, except that the starting material was p-fluorophenylacetyl chloride. ¹H NMR (DMSO, 300 MHz): δ 13.21 (s, 1H), 8.63 (s, 1H), 8.27 (s, 1H), 7.73 (dd, J=8.7, 5.7 Hz, 2H), 7.29 (t, J=8.9 Hz, 2H).

Example 5 Synthesis of N-(4-(((7-chloro-1,6-naphthyridin-4-yl) Oxy)-3-fluorophenyl)-N-(4-fluorophenyl) Cyclopropyl-1,1-dicarboxamide (1S)

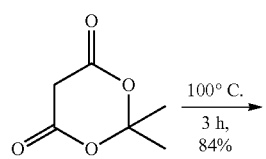

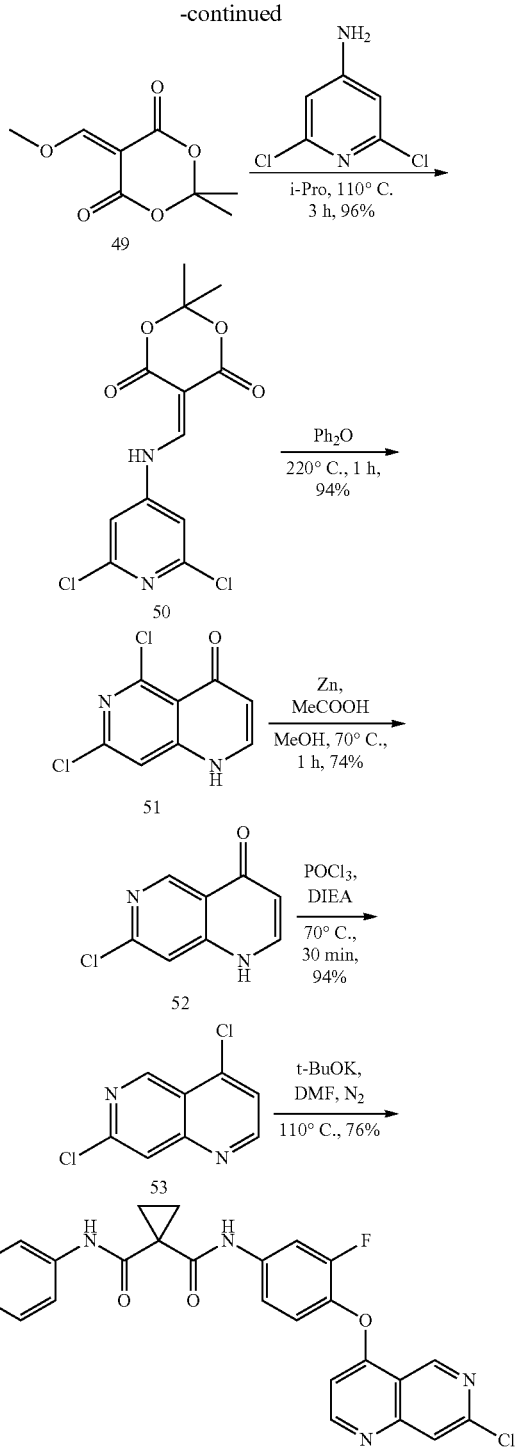

5-(methoxymethylene)-2,2-dimethyl-1,3-dioxane-4,6-dione (49)

10 g of Meldrum's acid was added to 40 ml of trimethyl ortho-carbonate, and the mixture was allowed to react for 3 h with stirring at 100° C. After the reaction was completed, the resultant was cooled and sonicated in petroleum ether to give a large amount of precipitate, which was filtered and washed with PE to yield the product, which was to be used in the next step without purification.

5,7-dichloro-1,6-naphthyridin-4(1H)-one (51)

2,6-dichloro-4-aminopyridine (1 g, 6.13 mmol) was dissolved in isopropanol, then 2 eq of compound 49 was added thereto, and then the mixture was warmed to 110° C. and reacted for 1 h with stirring, then a large amount of solid was precipitated. The reaction was continued for another 2 h with stirring, then the resultant was cooled to room temperature, washed with isopropanol and ether to give the product, yield 96%;

The compound prepared as above was suspended in diphenyl ether at 10 ml/g, warmed to 220° C. and reacted for 1 h with stirring, and then a large amount of solid was precipitated, which was cooled to room temperature, washed with a large amount of PE and filtered to give the product, yield 94%. $^1$H NMR (300 MHz, DMSO) δ 12.11 (s, 1H), 7.93 (dd, J=7.7, 5.5 Hz, 1H), 7.48 (s, 1H), 6.17 (d, J=7.5 Hz, 1H).

7-chloro-1,6-naphthyridin-4 (1H)-one (52)

The treatment of Zinc: a certain amount of zinc powder was added to an amount of dilute hydrochloric acid that would enable the zinc powder bubbling slowly, the oxide layer on the zinc surface was removed by stirring at room temperature for 30 min, then the water was drained, and the residue was washed with water, acetone and ether, each for twice, then evaporated under reduced pressure, the thus prepared zinc powder was for future use.

1 eq of compound 51 was dissolved in dry MeOH solution, then 4 eq of zinc powder was added and 10 eq of acetic acid was added with stirring at room temperature. The mixture was then rapidly warmed to 70° C. and the reaction was monitored by TLC. After the reaction was completed, the resultant was filtered, concentrated, and then sonicated in water to give a solid, which was further filtered and washed with EtOH/Et$_2$O 1:1 to give the title compound, yield 74%; $^1$H NMR (300 MHz, DMSO) δ 8.99 (s, 1H), 8.00 (d, J=7.6 Hz, 1H), 7.49 (s, 1H), 6.17 (d, J=7.6 Hz, 1H).

4,7-dichloro-1,6-naphthyridine (53)

Compound 52 (340 mg, 1.89 mmol) was dissolved in 1,2-dichloroethane. DIEA (653 μl, 3.95 mmol) was added and phosphorus oxychloride (345 μl, 3.78 mmol) was added dropwise with stirring. The mixture was allowed to react for 30 min with stirring at 70° C., then cooled to room temperature, and then poured into ice-water, adjusted to pH 8 with 2N NaOH, extracted with EA, washed with saturated NH$_4$Cl solution and saturated NaCl, dried over anhydrous Na$_2$SO$_4$ and concentrated under reduced pressure, and the residue was purified by column chromatography to give the title compound, yield 94%; $^1$H NMR (300 MHz, DMSO) δ 9.47 (d, J=0.6 Hz, 1H), 9.10 (d, J=4.7 Hz, 1H), 8.18 (s, 1H), 7.94 (d, d, J=4.8 Hz, 1H).

N-(4-((7-chloro-6-naphthyridin-4-yl) Oxy)-3-fluorophenyl)-N-(4-fluorophenyl) Cyclopropyl-1,1-dicarboxamide (1S)

Compound 53 (0.2 g, 1 mmol) was dissolved in anhydrous DMF, 1.1 eq of phenol was added therein followed by the addition of 1.1 eq of potassium tert-butoxide, the atmosphere was then replaced with N$_2$ three times. The mixture was allowed to react at 110° C. with stirring and the reaction was monitored by TLC. After the reaction was completed, the resultant was diluted with EA, washed with saturated NH$_4$Cl solution and saturated NaCl, dried over anhydrous Na$_2$SO$_4$ and concentrated under reduced pressure, and the residue was purified by column chromatography to give the title compound, yield 76%; $^1$H NMR (300 MHz, DMSO) δ 10.77 (s, 1H), 9.92 (s, 1H), 9.57 (d, J=0.7 Hz, 1H), 8.95 (d, J=5.3 Hz, 1H), 8.23-8.04 (m, 2H), 7.62 (dd, J=9.2, 5.1 Hz, 2H), 7.51 (dd, J=11.2, 2.6 Hz, 1H), 7.36-7.13 (m, 3H), 6.82 (d, J=5.3 Hz, 1H), 1.68-1.52 (m, 4H).

Example 6 Synthesis of N-(4-((7-dimethylamino-1,6-naphthyridin-4-yl)oxy)-3-fluorophenyl)-N-(4-fluorophenyl)cyclopropyl-1,1-dicarboxamide (2S)

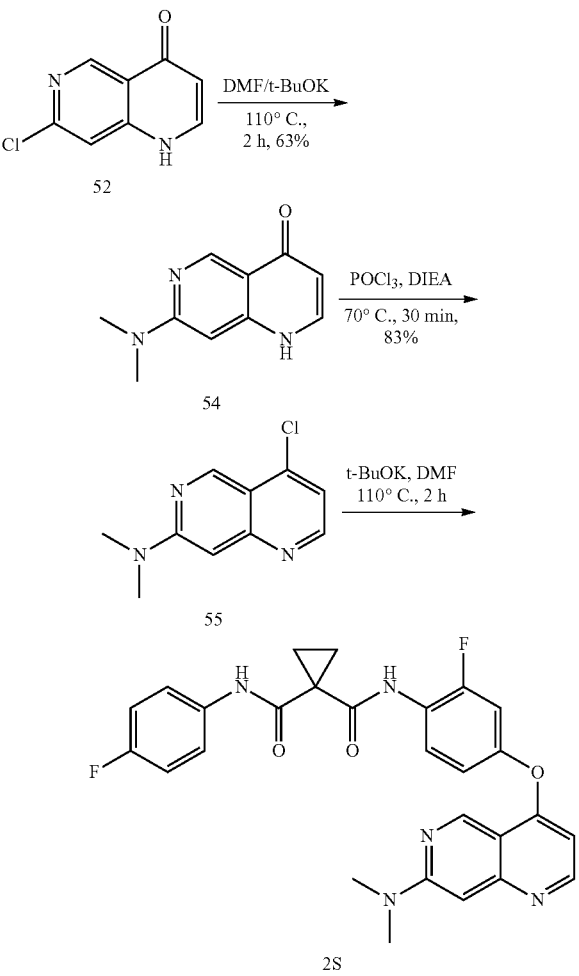

7-(dimethylamino)-1,6-naphthyridin-4(1H)-one (54)

1 eq of compound 52 was dissolved in a dry DMF solution, 2 eq of potassium t-butoxide (t-BuOK) was then added therein and the mixture was warmed to 110° C. and stirred for reaction. Monitored by TLC, when the reaction was completed, the resultant was diluted with EA, washed with saturated NH$_4$Cl solution and saturated NaCl, dried over anhydrous Na$_2$SO$_4$ and concentrated under reduced pressure, and the residue was purified by column chromatography to give the title compound; ¹H NMR (400 MHz, DMSO) δ 11.28 (s, 1H), 8.80 (s, 1H), 7.70 (dd, J=7.5, 5.8 Hz, 1H), 6.22 (s, 1H), 5.82 (d, J=7.6 Hz, 1H), 3.08 (s, 6H).

4-chloro-1,6-naphthyridine-7-dimethylamine (55)

1 eq of compound 54 was dissolved in 1,2-dichloroethane solution, 3 eq of DIEA and 2 eq of phosphorus oxychloride were then added, and the mixture was warmed to 70° C. and stirred for reaction. Monitored by TLC, when the reaction was completed, the resultant was diluted with EA, washed with saturated NH₄Cl solution and saturated NaCl, dried over anhydrous Na₂SO₄ and concentrated under reduced pressure, and the residue was purified by column chromatography to give the title compound; ¹H NMR (300 MHz, CDCl₃) δ 9.23 (s, 1H), 8.63 (d, J=4.7 Hz, 1H), 7.07 (d, J=4.7 Hz, 1H), 6.80 (s, 1H), 3.20 (d, J=0.9 Hz, 6H).

N-(4-((7-dimethylamino-1,6-naphthyridin-4-yl)oxy)-3-fluorophenyl)-N-(4-fluorophenyl)cyclopropyl-1,1-dicarboxamide (2S)

Compound 55 (0.2 g, 0.97 mmol) was dissolved in anhydrous DMF, 1.1 eq of phenol was added therein followed by the addition of 1.1 eq of potassium tert-butoxide, the atmosphere was then replaced with N₂ three times. The mixture was allowed to react with stirring at 110° C. Monitored by TLC, when the reaction was completed, the resultant was diluted with EA, washed with saturated NH₄Cl solution and saturated NaCl, dried over anhydrous Na₂SO₄ and concentrated under reduced pressure, and the residue was purified by column chromatography to give the title compound; yield 81%. ¹H NMR (300 MHz, CDCl₃) δ 7.74-7.61 (m, 1H), 7.43-7.29 (m, 2H), 7.14-7.05 (m, 1H), 7.05-6.95 (m, 1H), 6.95-6.82 (m, 2H), 6.72-6.64 (m, 1H), 6.63-6.53 (m, 1H), 6.38 (d, J=2.4 Hz, 1H), 6.20 (d, J=2.3 Hz, 1H), 3.25 (s, 6H), 1.49 (m, 4H); EI MS m/z 503 [M]+.

Example 7 Synthesis of N-(4-((7-methoxy-1,6-naphthyridin-4-yl)oxy)-3-fluorophenyl)-N-(4-fluorophenyl)cyclopropyl-1,1-dicarboxamide (3S)

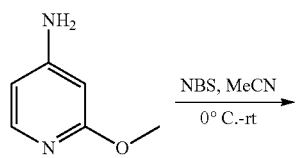

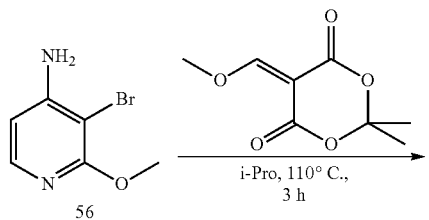

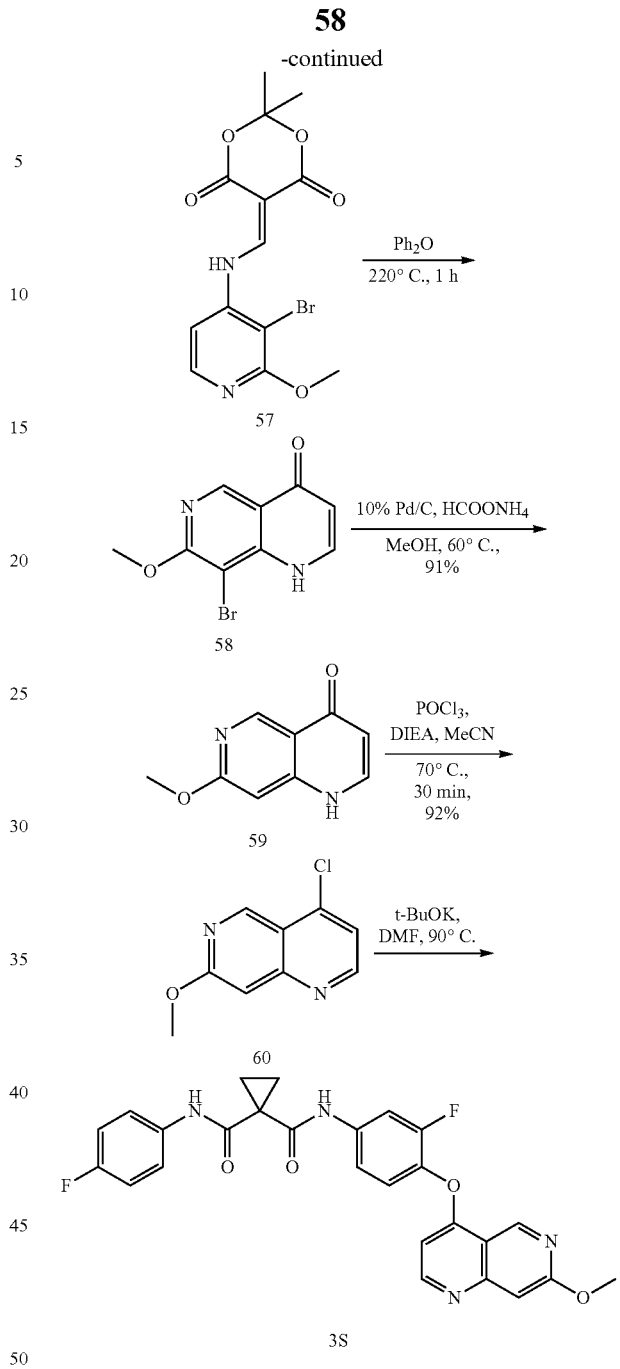

3-bromo-2-methoxy-4-aminopyridine (56)

2-methoxy-4-aminopyridine (5 g, 40.3 mmol) was dissolved in MeCN and NBS (7.18 g, 40.3 mmol) was added therein in portions at 0° C. The mixture was slowly raised to room temperature and was allowed to react with stirring and the reaction was monitored by TLC. After the reaction was completed, the resultant was diluted with EA, washed with saturated NH₄Cl solution, sodium hydrosulfite and saturated NaCl, dried over anhydrous Na₂SO₄ and concentrated under reduced pressure, and the residue was purified by column chromatography to give the title compound, yield 77%. ¹H NMR (300 MHz, CDCl₃) δ 7.57 (d, 1H), 6.36 (d, 1H), 6.20 (s, 2H), 3.7 (s, 3H).

7-methoxy-1,6-naphthyridin-4(1H)-one (59)

1 eq of 3-bromo-2-methoxy-4-aminopyridine was dissolved in isopropanol, then 2 eq of compound 49 was added thereto. After heating to 110° C., the mixture was allowed to react for 1 h with stirring, and then a large amount of solid was precipitated. 2 h later, the solid was cooled to room temperature, washed with isopropanol and ether to give the product compound 57, yield 92%;

The compound obtained above was suspended in diphenyl ether at 10 ml/g, and the mixture was heated to 220° C. and allowed to react for 1 h with stirring, and then a large amount of solid was precipitated, which was cooled to room temperature, washed with a large amount of petroleum ether and filtered to give the compound 58, yield 96%.

The above solid was dissolved in methanol, and 2 eq of ammonium formate was added therein followed by the addition of 10 wt % of 10% Pd/C. The mixture was allowed to react with stirring at 60° C. and the reaction was monitored by TLC. After the reaction was completed, the resultant was cooled and filtered, the filtrate was concentrated and then extracted with EA, washed with saturated NaCl, dried over anhydrous $Na_2SO_4$ and concentrated under reduced pressure to give the compound 59. $^1$H NMR (400 MHz, DMSO) δ 8.89 (s, 1H), 8.46 (s, 1H), 7.87 (d, J=7.6 Hz, 1H), 6.75 (s, 1H), 5.97 (d, J=7.6 Hz, 1H), 3.91 (s, 3H).

4-chloro-7-methoxy-1,6-naphthyridine (60)

Compound 59 (332 mg, 1.89 mmol) was dissolved in 20 mL of acetonitrile, then DIEA (653 μL, 3.95 mmol) was added thereto and phosphorus oxychloride (345 μl, 3.78 mmol) was added dropwise with stirring. The mixture was allowed to react for 30 min with stirring at 70° C., then cooled to room temperature, and then poured into ice-water, adjusted to pH 8 with 2N NaOH, extracted with EA, washed with saturated $NH_4Cl$ solution and saturated NaCl, dried over anhydrous $Na_2SO_4$ and concentrated under reduced pressure, and the residue was purified by column chromatography to give the title compound, yield 92%; $^1$H NMR (300 MHz, CD3OD) δ 9.33 (s, 1H), 8.85 (d, J=4.8 Hz, 1H), 7.55 (d, J=4.8 Hz, 1H), 7.23 (s, 1H), 4.10 (s, 3H).

N-(4-((7-methoxy-1,6-naphthyridin-4-yl)oxy)-3-fluorophenyl)-N-(4-fluorophenyl)cyclopropyl-1,1-dicarboxamide (35)

The synthetic route was same as that of compound 2S, except that the starting material was compound 60. $^1$H NMR (DMSO, 300 MHz): δ 10.43 (s, 1H), 10.02 (s, 1H), 9.48 (s, 1H), 8.79 (d, J=5.2 Hz, 1H), 7.94 (d, J=13.3 Hz, 1H), 7.66 (dd, J=9.2, 5.1 Hz, 2H), 7.58-7.46 (m, 2H), 7.26 (s, 1H), 7.17 (t, J=8.9 Hz, 2H), 6.49 (d, J=5.1 Hz, 1H), 4.04 (s, 3H), 1.55-1.36 (m, 4H).

Example 8 Synthesis of 4-((8-bromo-7-(2-morpholinoethoxy)-1,6-naphthyridin-4-yl)oxy)-3-fluoroaniline (45)

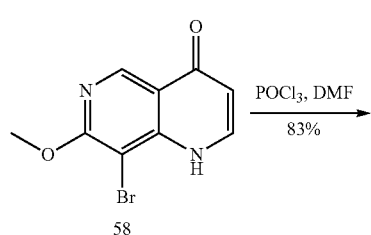

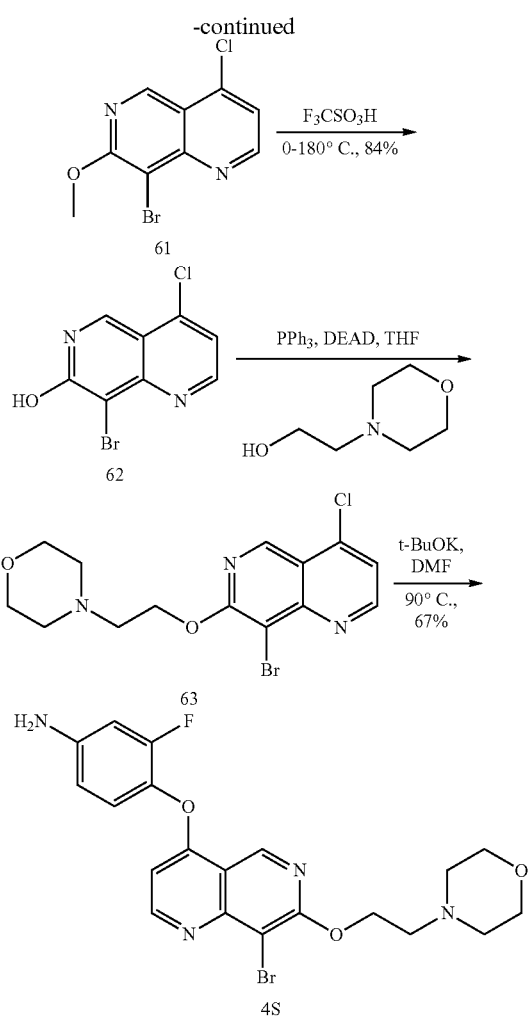

8-bromo-4-chloro-7-methoxy-1,6-naphthyridine (61)

Compound 58 (482 mg, 1.89 mmol) was dissolved in 10 ml of DMF and phosphorus oxychloride (345 μl, 3.78 mmol) was added therein dropwise with stirring. The mixture was allowed to react for 30 min with stirring at room temperature and the reaction was monitored by TLC. After the reaction was completed, the resultant was poured into ice-water, adjusted to pH 8 with 2N NaOH, extracted with EA, washed with saturated $NH_4Cl$ solution and saturated NaCl, dried over anhydrous $Na_2SO_4$ and concentrated under reduced pressure, and the residue was purified by column chromatography to give the title compound, yield 83%; $^1$H NMR (300 MHz, $CDCl_3$) δ 9.25 (s, 1H), 8.94 (d, J=4.7 Hz, 1H), 7.39 (d, J=4.7 Hz, 1H), 4.18 (s, 3H).

8-bromo-4-chloro-7-hydroxy-1,6-naphthyridine (62)

3 ml of trifluoromethanesulfonic acid was placed in a round-bottom flask, compound 61 (516 mg, 1.89 mmol) was added thereto in portions under ice bath, dissolved with stirring, and then transferred to a 180° C. oil bath to allow the reaction for 10 min with stirring, the reaction was monitored by TLC. After the reaction was completed, the resultant was cooled to room temperature and diluted with a small amount of EA, then added with a lot of DCM.

Thereafter, a large amount of solid was obtained after standing, which was then filtered. The filter cake was dissolved with MeCN and the resultant was adjusted to pH 8 with 2N NaOH to give a large amount of yellow solid. After being filtered, the filter cake was dried and purified by flash column chromatography to give the title compound as a yellow solid, yield 84%; $^1$H NMR (300 MHz, DMSO) δ 8.86 (s, 1H), 8.55 (d, J=4.6 Hz, 1H), 7.00 (d, J=4.8 Hz, 1H).

7-(4-morpholinoethoxy)-8-bromo-4-chloro-1,6-naphthyridine (63)

Compound 62 (1.5 g, 5.79 mmol) was dissolved in 40 ml of THF, and 4-hydroxyethylmorpholine (1.14 g, 8.69 mmol), anhydrous magnesium sulfate (1.58 g, 8.69 mmol) were added therein with stirring, after stirring for 10 min at room temperature, triphenylphosphine (2.28 g, 8.69 mmol) was added and DEAD (1.7 ml, 8.69 mmol) was added dropwise slowly. The mixture was stirred for 6 h at room temperature and the reaction was monitored by TLC. After the reaction was completed, the resultant was extracted with EA and washed twice with saturated NaHCO$_3$. The organic phase was washed twice with dilute HCl (pH=3), the inorganic phase was adjusted to pH 8 with 2N NaOH, extracted with EA, washed with saturated NaCl, dried over anhydrous Na$_2$SO$_4$ and concentrated under reduced pressure, and the residue was purified by column chromatography to give the title compound, yield 73%; $^1$H NMR (300 MHz, CDCl$_3$) δ 9.23 (s, 1H), 8.95 (d, J=4.7 Hz, 1H), 7.62 (d, J=4.6 Hz, 1H), 4.72 (t, J=5.7 Hz, 2H), 3.77-3.62 (m, 4H), 2.89 (t, J=5.8 Hz, 2H), 2.70-2.56 (m, 4H).

4-((8-bromo-7-(2-morpholinoethoxy)-1,6-naphthyridin-4-yl)oxy)-3-fluoroaniline (4S)

The synthetic route was same as that of compound 2S, except that the starting materials were compound 63 and p-hydroxy-3-fluoroaniline. $^1$H NMR (DMSO, 300 MHz): δ 9.40 (s, 1H), 8.87 (d, J=5.3 Hz, 1H), 7.15 (t, J=9.0 Hz, 1H), 6.63-6.53 (m, 2H), 6.50 (d, J=8.6 Hz, 1H), 5.58 (s, 2H), 4.67 (t, J=5.7 Hz, 2H), 3.63-3.52 (m, 4H), 2.89-2.75 (m, 2H), 2.63-2.53 (m, 4H).

Example 9 Synthesis of 2-fluoro-N'-(7-(2-morpholinoethoxy)-1,6-naphthyridin-4-yl)phenyl-1,4-diamine (5S)

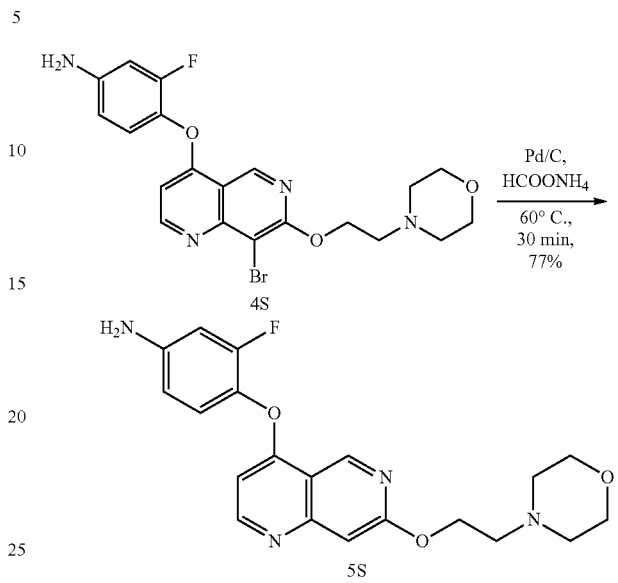

The compound 4S (0.93 g, 2 mmol) was dissolved in 40 ml of methanol and ammonium formate (0.18 g, 4 mmol) was added and 20 mg of 10% Pd/C was then added therein. The mixture was allowed to react for 30 min at 60° C. and the reaction was monitored by TLC. After the reaction was completed, the resultant was cooled and filtered, and the filtrate was concentrated, and the residue was extracted with EA, washed with saturated NaCl, dried over anhydrous Na$_2$SO$_4$ and concentrated under reduced pressure, and the residue was purified by column chromatography to give the product. $^1$H NMR (400 MHz, DMSO) δ 11.15 (s, 1H), 9.38 (s, 1H), 8.84 (d, J=5.1 Hz, 1H), 7.83 (d, J=12.3 Hz, 1H), 7.38-7.30 (m, 1H), 7.29-7.17 (m, 1H), 6.44 (d, J=5.3 Hz, 1H), 4.74 (t, J=5.7 Hz, 2H), 3.74 (d, J=5.2 Hz, 4H), 2.91 (t, J=9.8 Hz, 2H), 2.76-2.62 (m, 4H).

Example 10 Synthesis of N-(4-((8-bromo-7-(2-morpholinoethoxy)-1,6-naphthyridin-4-yl)oxy)-3-fluorophenyl)-N-(4-fluorophenyl)cyclopropyl-1,1-dicarboxamide (65)

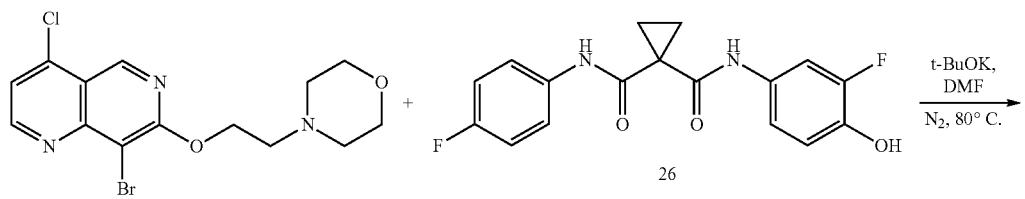

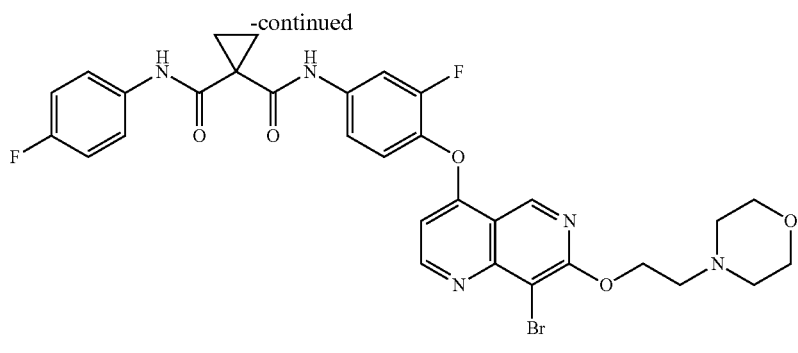

6S

The synthetic route was same as that of compound 2S, except that the starting materials were compound 63 and compound 26. $^1$H NMR (DMSO, 300 MHz): δ 10.43 (s, 1H), 10.02 (s, 1H), 9.45 (s, 1H), 8.77 (d, J=5.4 Hz, 1H), 7.93 (d, J=13.0 Hz, 1H), 7.68-7.59 (m, 2H), 7.57-7.47 (m, 2H), 7.22 (s, 1H), 7.18-7.12 (m, 1H), 6.47 (d, J=5.1 Hz, 1H), 4.49 (t, J=5.8 Hz, 2H), 2.75 (t, J=5.4 Hz, 2H), 2.57-2.51 (m, 4H), 2.41-2.26 (m, 4H), 2.15 (s, 3H), 1.55-1.43 (m, 4H).

Example 11 Synthesis of N-(3-fluoro-4-((7-(2-morpholinoethoxy)-1,6-naphthyridin-4-1)oxy)phenyl)-N-(4-fluorophenol) Cyclopropyl-1,1-dicarboxamide (7S)

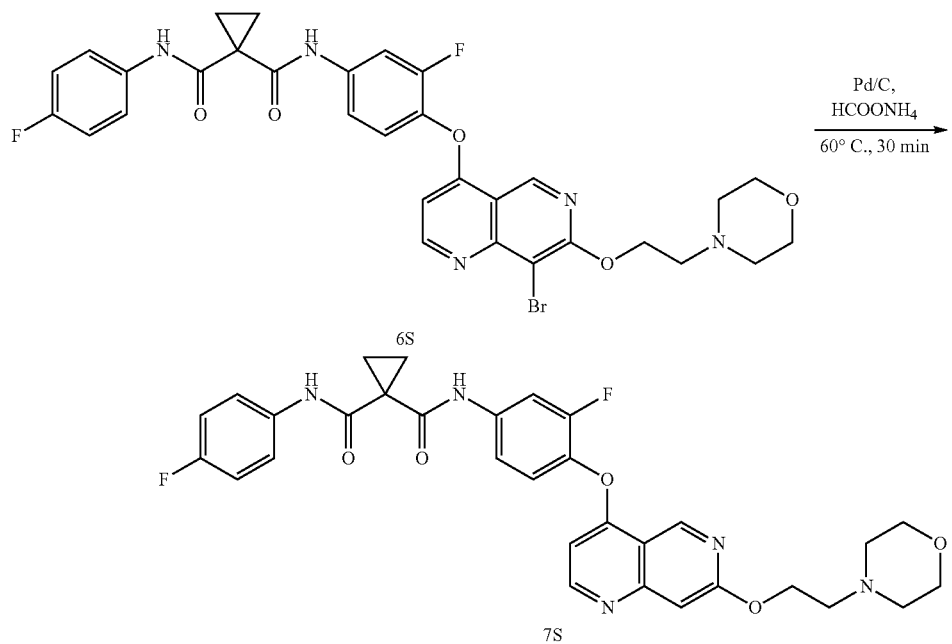

The synthetic route was same as that of compound 5S, except that the starting material was compound 6S. $^1$H NMR (DMSO, 300 MHz): δ 10.43 (s, 1H), 10.01 (s, 1H), 9.45 (s, 1H), 8.78 (d, J=5.2 Hz, 1H), 7.93 (d, J=13.9 Hz, 1H), 7.65 (dd, J=8.7, 5.1 Hz, 2H), 7.60-7.45 (m, 2H), 7.24 (s, 1H), 7.17 (t, J=8.8 Hz, 2H), 6.48 (d, J=5.2 Hz, 1H), 4.52 (t, J=5.6 Hz, 2H), 3.65-3.53 (m, 4H), 2.77 (t, J=5.6 Hz, 2H), 2.56-2.50 (m, 4H), 1.54-1.40 (m, 4H).

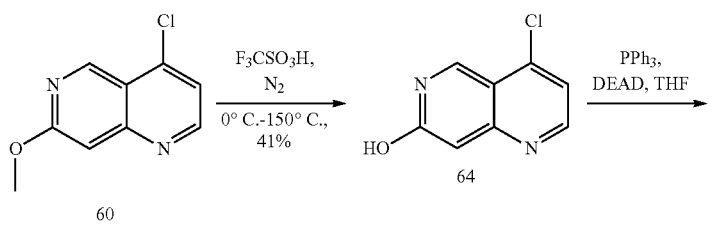

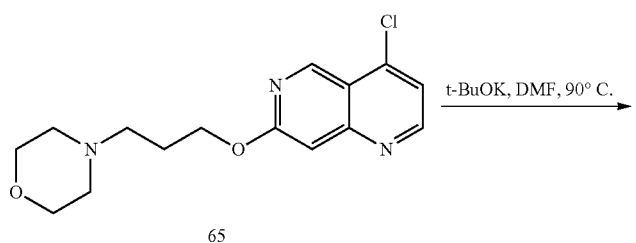

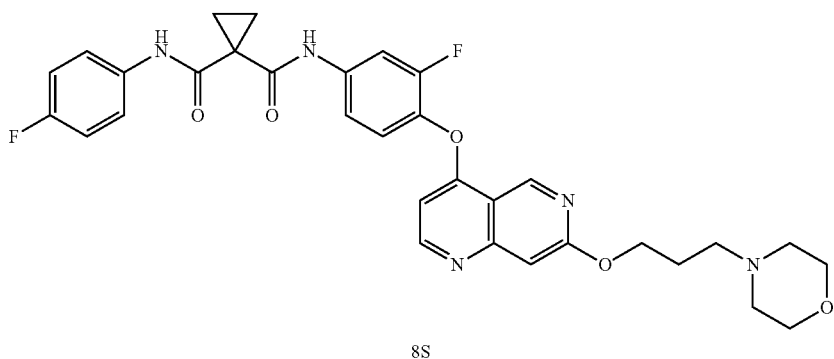

4-chloro-7-hydroxy-1,6-naphthyridine (64)

3 ml of trifluoromethanesulfonic acid was placed in a round-bottom flask, and compound 60 (367 mg, 1.89 mmol) was added in portions under ice bath, after the compound was dissolved with stirring, the resultant was transferred to an oil bath at 150° C. and allowed to react for 2 h with stirring and the reaction was monitored by TLC. After the reaction was completed, the resultant was cooled to room temperature, poured into ice, adjusted to pH 8 with 2N NaOH, extracted several times with EA, and concentrated, and the residue was purified by flash column chromatography to give the title compound as a yellow solid, whose yield is unstable, yield 41%, due to the instability of the compound; $^1$H NMR (300 MHz, DMSO) δ 11.57 (s, 1H), 9.16 (s, 1H), 8.83 (d, J=4.7 Hz, 1H), 7.52 (d, J=4.7 Hz, 1H), 7.01 (s, 1H).

4-(3-((4-chloro-1,6-naphthyridin-7-yl)oxy)propyl) morpholine (65)

The synthesis route was the same as that of compound 63, except that the starting material was N-(3-hydroxypropyl) morpholine. $^1$H NMR (CDCl$_3$, 300 MHz): δ 9.31 (s, 1H), 8.80 (d, J=4.7 Hz, 1H), 7.32 (d, J=4.6 Hz, 1H), 7.25 (s, 1H), 4.45 (t, J=6.3 Hz, 2H), 3.73-3.65 (m, 4H), 2.60-2.53 (m, 2H), 2.52-2.43 (m, 4H), 2.05 (t, J=7.0 Hz, 2H).

N-(3-fluoro-4-((7-(2-morpholinopropoxy)-1,6-naphthyridin-4-yl)oxy)phenyl)-N-(4-fluorophenyl)cyclopropyl-1,1-dicarboxamide (8S)

The synthesis route was the same as that of compound 2S, except that the starting materials were compound 65 and compound 26. $^1$H NMR (DMSO, 300 MHz): δ 10.43 (s, 1H), 10.01 (s, 1H), 9.45 (s, 1H), 8.77 (d, J=5.2 Hz, 1H), 7.94 (d, J=12.3 Hz, 1H), 7.73-7.61 (m, 2H), 7.60-7.44 (m, 2H), 7.27-7.11 (m, 3H), 6.48 (d, J=5.1 Hz, 1H), 4.43 (t, J=6.3 Hz, 2H), 3.72-3.54 (m, 4H), 2.49-2.21 (m, 5H), 2.04-1.90 (m, 2H), 1.55-1.36 (m, 4H).

Example 13 Synthesis of N-(3-fluoro-4-((7-((1-methylpiperidin-4-yl)methoxy)-1,6-naphthyridin-4-yl)oxy)phenyl)-N-(4-fluorophenyl)cyclopropyl-1,1-dicarboxamide (9S)

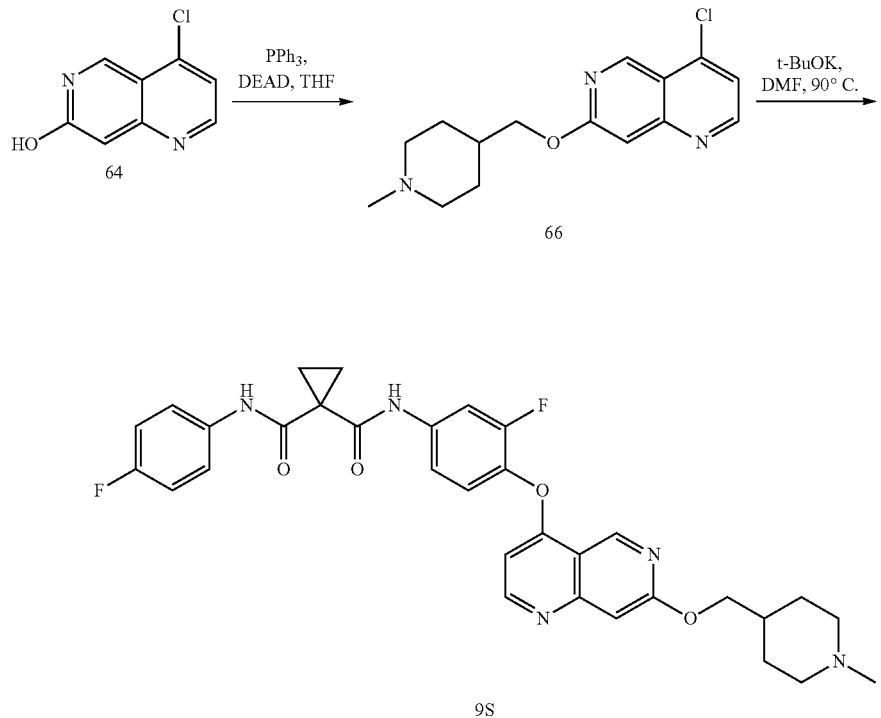

4-chloro-7-((1-methylpiperidin-4-yl)methoxy)-1,6-naphthyridine (66)

Compound 66 was synthesized in the same manner as compound 63, except that the starting material was 4-piperidinemethanol, yield 63%. $^1$H NMR (300 MHz, CDCl$_3$) δ 9.27 (s, 1H), 8.77 (d, J=4.7 Hz, 1H), 7.28 (d, J=4.7 Hz, 1H), 7.20 (s, 1H), 4.21 (d, J=6.2 Hz, 2H), 2.87 (d, J=11.4 Hz, 2H), 2.33-2.21 (s, 3H), 1.95-1.82 (m, 4H), 1.54-1.34 (m, 2H), 1.33-1.16 (m, 1H).

N-(3-fluoro-4-((7-((1-methylpiperidin-4-yl)methoxy)-1,6-naphthyridin-4-yl)oxy)phenyl)-N-(4-fluorophenyl)cyclopropyl-1,1-dicarboxamide (9S)

The synthetic route was the same as that of compound 2S, except that the starting materials were compound 66 and compound 26. $^1$H NMR (DMSO, 300 MHz): δ 10.48 (s, 1H), 10.05 (s, 1H), 9.46 (s, 1H), 8.78 (d, J=5.3 Hz, 1H), 7.95 (d, J=13.1 Hz, 1H), 7.72-7.61 (m, 2H), 7.61-7.43 (m, 2H), 7.25 (s, 1H), 7.16 (t, J=7.9 Hz, 2H), 6.49 (d, J=5.2 Hz, 1H), 4.32 (d, J=6.1 Hz, 2H), 3.01-2.79 (m, 2H), 2.69 (s, 3H), 2.19-1.87 (m, 3H), 1.77-1.57 (m, 2H), 1.56-1.32 (m, 4H).

Example 14 Synthesis of N-(4-((8-bromo-7-(2-(4-methylpiperazin-1-yl)ethoxy)-1,6-naphthyridin-4-yl)oxy)-3-fluorophenyl)-N-(4-fluorophenyl)cyclopropyl-1,1-dicarboxamide (10S)

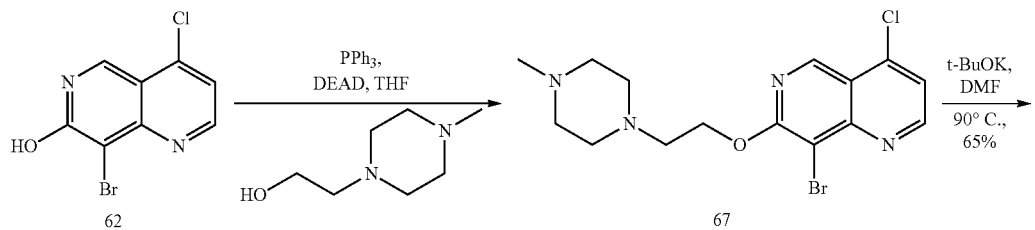

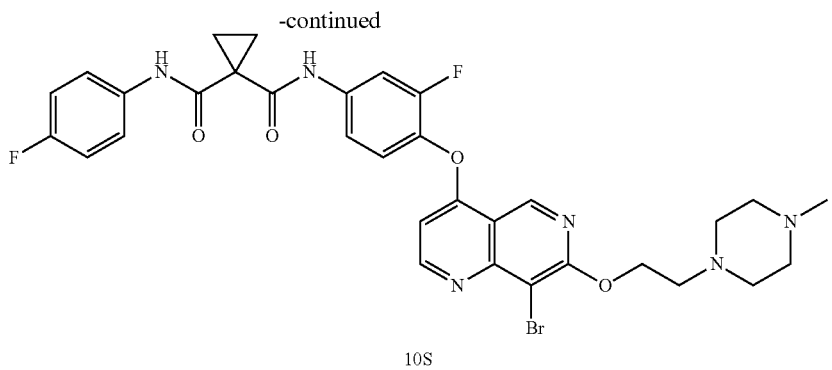

8-bromo-4-chloro-7-(2-(4-methylpiperazin-1-yl)ethoxy)-1,6-naphthyridine (67)

The synthetic route was the same as that of compound 63, except that the starting materials were compound 62 and 1-(2-hydroxyethyl)-4-methylpiperazine. $^1$H NMR (CDCl$_3$, 300 MHz): δ 9.20 (s, 1H), 8.92 (d, J=4.7 Hz, 1H), 7.37 (d, J=4.7 Hz, 1H), 4.69 (t, J=5.9 Hz, 2H), 2.89 (t, J=5.9 Hz, 2H), 2.79-2.61 (m, 4H), 2.54-2.34 (m, 4H), 2.26 (s, 3H).

N-(4-((8-bromo-7-(2-(4-methylpiperazin-1-yl)ethoxy)-1,6-naphthyridin-4-yl)oxy)-3-fluoro phenyl)-N-(4-fluorophenyl)cyclopropyl-1,1-dicarboxamide (10S)

The synthetic route was the same as that of compound 2S, except that the starting materials were compound 67 and compound 26. $^1$H NMR (DMSO, 300 MHz): δ 10.47 (s, 1H), 10.02 (s, 1H), 9.43 (s, 1H), 8.89 (d, J=5.3 Hz, 1H), 7.95 (d, J=12.4 Hz, 1H), 7.77-7.44 (m, 3H), 7.17 (t, J=8.2 Hz, 2H), 6.62 (d, J=5.4 Hz, 1H), 4.66 (t, J=5.1 Hz, 2H), 3.41-3.24 (m, 4H), 2.85 (t, J=5.4 Hz, 2H), 2.78-2.57 (m, 4H), 2.39 (s, 3H), 1.56-1.32 (m, 4H).

Example 15 Synthesis of N-(3-fluoro-4-((7-(2-(4-methylpiperazin-1-yl)ethoxy)-1,6-naphthyridin-4-yl)oxy)phenyl)-N-(4-fluorophenyl)cyclopropyl-1,1-dicarboxamide (11S)

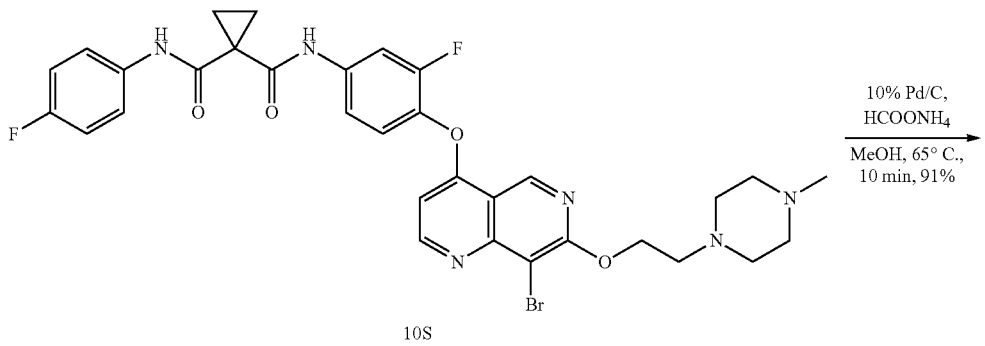

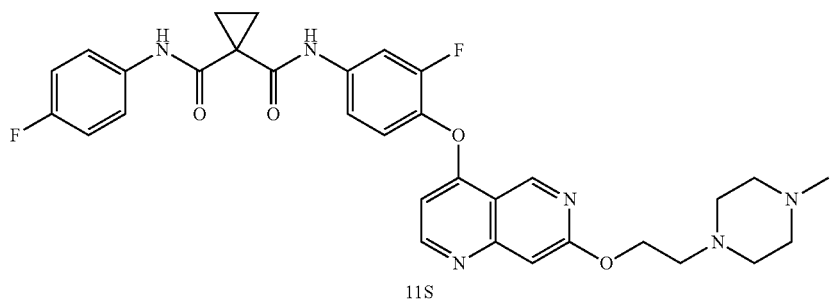

The synthetic route was the same as that of compound 55, except that the starting material was compound 105. ¹H NMR (DMSO, 300 MHz): δ 10.43 (s, 1H), 10.02 (s, 1H), 9.45 (s, 1H), 8.77 (d, J=5.4 Hz, 1H), 7.93 (d, J=13.0 Hz, 1H), 7.68-7.59 (m, 2H), 7.57-7.47 (m, 2H), 7.22 (s, 1H), 7.18-7.12 (m, 1H), 6.47 (d, J=5.1 Hz, 1H), 4.49 (t, J=5.8 Hz, 2H), 2.75 (t, J=5.4 Hz, 2H), 2.57-2.51 (m, 4H), 2.41-2.26 (m, 4H), 2.15 (s, 3H), 1.55-1.43 (m, 4H).

Example 16 Synthesis of N-(4-fluorophenyl)-N-(4-((7-(2-morpholinoethoxy)-1,6-naphthyridin-4-yl)oxy)phenyl)cyclopropyl-1,1-dicarboxamide (12S)

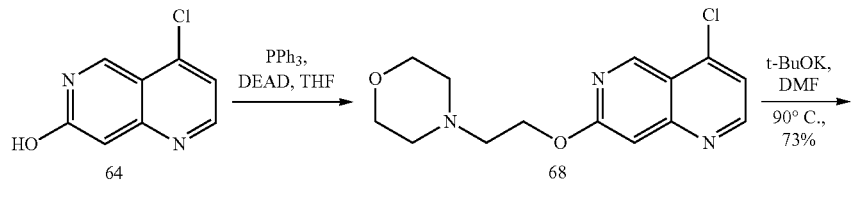

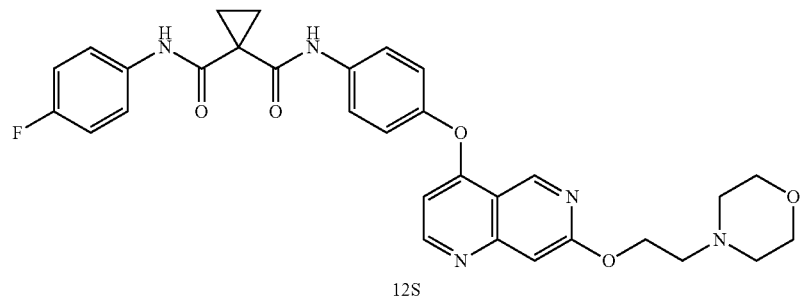

4-(2-((4-chloro-1,6-naphthyridin-7-yl)oxy)ethyl)morpholine (68)

The synthetic route was the same as that of compound 63, except that the starting materials were compound 64 and 4-hydroxyethyl morpholine. ¹H NMR (DMSO, 300 MHz): δ 9.27 (s, 1H), 8.77 (d, J=4.7 Hz, 1H), 7.29 (d, J=4.7 Hz, 1H), 7.24 (s, 1H), 4.54 (t, J=5.8 Hz, 2H), 3.72-3.66 (m, 4H), 2.83 (t, J=5.8 Hz, 2H), 2.61-2.53 (m, 4H).

N-(4-fluorophenyl)-N-(4-((7-(2-morpholinoethoxy)-1,6-naphthyridin-4-yl)oxy)phenyl)cyclopropyl-1,1-dicarboxamide (12S)

The synthetic route was the same as that of compound 2S, except that the starting materials were compound 68 and compound 31. ¹H NMR (DMSO, 300 MHz): δ 10.24 (s, 1H), 10.06 (s, 1H), 9.42 (s, 1H), 8.75 (d, J=5.2 Hz, 1H), 7.80 (d, J=9.1 Hz, 2H), 7.71-7.57 (m, 2H), 7.31 (d, J=9.0 Hz, 2H), 7.23-7.10 (m, 3H), 6.43 (d, J=5.2 Hz, 1H), 4.52 (t, J=7.2 Hz, 2H), 3.58 (d, J=4.9 Hz, 4H), 2.77 (t, J=7.1 Hz, 2H), 2.52 (m, 4H), 1.63-1.38 (m, 2H).

Example 17 Synthesis of N-(4-fluorophenyl)-N-(4-((7-(2-morpholinoethoxy)-1,6-naphthyridin-4-yl)amino)phenyl)cyclopropyl-1,1-dicarboxamide (13S)

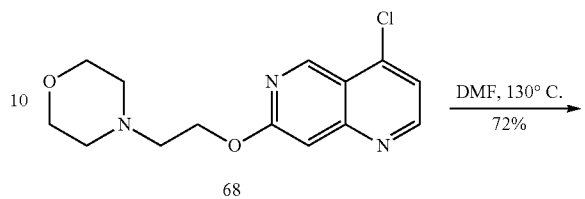

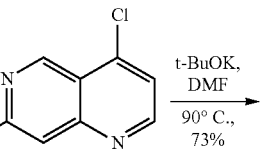

-continued

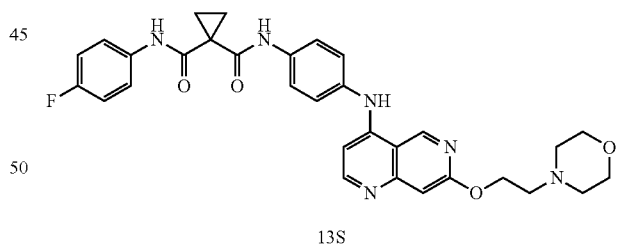

1 eq of compound 68 was dissolved in dry DMF solution, then 1.2 eq of compound 68 was added therein. The mixture was raised to 130° C. and stirred for reaction, the reaction was monitored by TLC. After the reaction was completed, the resultant was diluted with EA, washed with saturated NH₄Cl solution and saturated NaCl, dried over anhydrous Na₂SO₄ and concentrated under reduced pressure, and the residue was purified by column chromatography to give the title compound, yield 72%. ¹H NMR (DMSO, 300 MHz): δ 10.16 (s, 1H), 10.07 (s, 1H), 9.47 (s, 1H), 8.42 (s, 1H), 7.84-7.59 (m, 5H), 7.33 (d, J=8.6 Hz, 2H), 7.17 (t, J=8.8 Hz, 2H), 6.98 (s, 1H), 6.61 (d, J=5.6 Hz, 1H), 4.47 (t, J=5.9 Hz, 2H), 3.66-3.55 (m, 4H), 2.76 (t, J=5.7 Hz, 2H), 2.51-2.48 (m, 4H), 1.55-1.39 (m, 4H).

Example 18 Synthesis of N-(3-fluoro-4-((7-(2-morpholinoethoxy)-1,6-naphthyridin-4-yl)oxy)phenyl)-N-4-fluorophenyl)-N-methylcyclopropyl-1,1-dicarboxamide (14S)

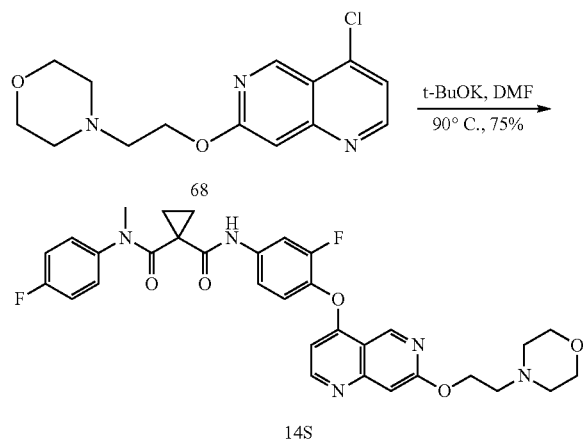

The synthetic route was the same as that of compound 25, except that the starting materials were compound 68 and compound 27. ¹H NMR (DMSO, 300 MHz): δ 10.00 (s, 1H), 9.45 (s, 1H), 8.79 (d, J=5.0 Hz, 1H), 7.60-7.39 (m, 3H), 7.37-7.27 (m, 2H), 7.24 (s, 1H), 7.21-7.05 (m, 2H), 6.46 (d, J=5.1 Hz, 1H), 4.52 (t, J=6.3 Hz, 2H), 3.66-3.51 (m, 4H), 3.25 (s, 3H), 2.77 (t, J=6.0 Hz, 2H), 2.56-2.49 (m, 4H), 1.51-1.38 (m, 2H), 1.30-1.20 (m, 2H).

Example 22 Synthesis of N-(3-fluoro-4-((7-(2-morpholinoethoxy)-1,6-naphthyridin-4-yl)oxy)phenyl)-1-(4-fluorophenyl)-2-oxo-1,2-dihydropyridine-3-carboxamide (15S)

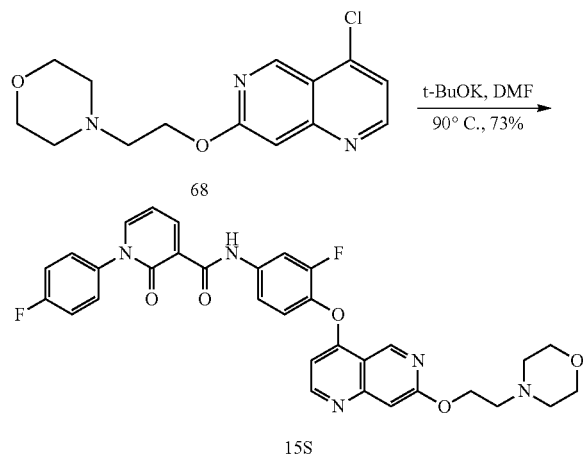

The synthetic route was the same as that of compound 2S, except that the starting materials were compound 68 and compound 36. ¹H NMR (DMSO, 300 MHz): δ 12.18 (s, 1H), 9.52 (s, 1H), 8.83 (d, J=5.3 Hz, 1H), 8.61 (d, J=7.2 Hz, 1H), 8.22-8.06 (m, 2H), 7.71-7.47 (m, 4H), 7.53-7.23 (m, 3H), 6.76 (t, J=7.5 Hz, 1H), 6.61 (d, J=5.1 Hz, 1H), 4.90-4.75 (m, 2H), 4.02-3.76 (m, 4H), 3.69-3.60 (m, 2H), 2.53-2.43 (m, 4H).

Example 23 Synthesis of 1-(3-fluoro-4-((7-(2-morpholinoethoxy)-1,6-naphthyridin-4-yl)oxy)phenyl)-N-(4-fluorophenyl)-2-oxo-1,2-dihydropyridine-3-carboxamide (16S)

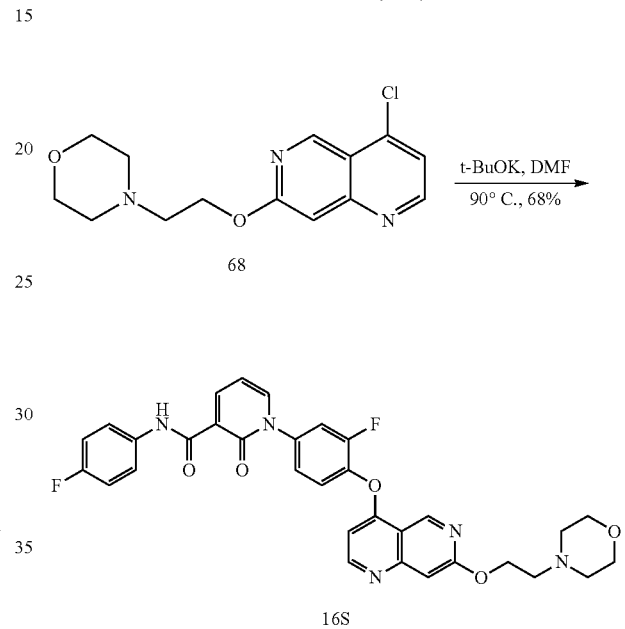

The synthetic route was the same as that of compound 2S, except that the starting materials were compound 68 and compound 42. ¹H NMR (DMSO, 300 MHz): δ 11.65 (s, 1H), 9.46 (s, 1H), 8.74 (s, 2H), 7.74-7.60 (m, 3H), 7.56-7.40 (m, 2H), 7.38-7.30 (m, 1H), 7.28 (s, 1H), 7.02 (t, J=8.7 Hz, 2H), 6.65 (t, J=7.1 Hz, 1H), 6.48 (d, J=5.3 Hz, 1H), 4.58 (t, J=5.3 Hz, 2H), 3.82-3.66 (m, 4H), 2.88 (t, J=5.6 Hz, 2H), 2.71-2.54 (m, 4H).

Example 24 Synthesis of methyl 1-(3-fluoro-4-((7-(2-morpholinoethoxy)-1,6-naphthyridin-4-yl)oxy)phenyl)-2-oxo-1,2-dihydro-pyridine-3-carboxylate (17S)

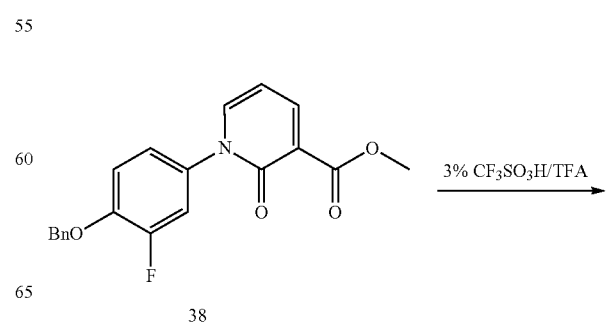

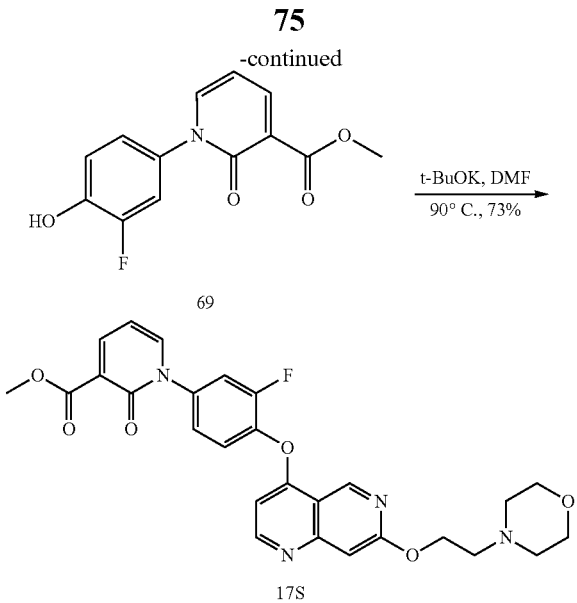

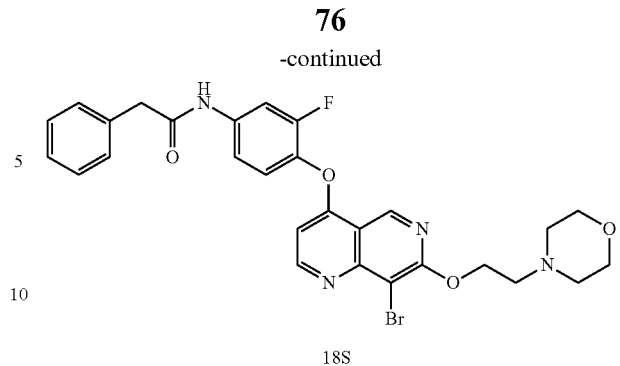

Synthesis of methyl 1-(3-fluoro-4-hydroxyphenyl)-2-oxo-1,2-dihydropyridine-3-carboxylate (69)

3% trifluoromethanesulphonic acid was added to the solution of compound 25 (400 mg, 1.13 mmol) in 3 ml TFA. The mixture was allowed to react with stirring at room temperature and the reaction was monitored by TLC. After the reaction was completed, the resultant was diluted with EA, washed with saturated NH$_4$Cl solution and saturated NaCl, dried over anhydrous Na$_2$SO$_4$ and concentrated under reduced pressure, and the residue was purified by column chromatography to give the title compound. $^1$H NMR (DMSO, 300 MHz): δ 10.31 (s, 1H), 8.11 (d, J=7.1 Hz, 1H), 7.93 (d, J=4.6 Hz, 1H), 7.34 (d, J=11.5 Hz, 1H), 7.05 (s, 2H), 6.39 (t, J=6.3 Hz, 1H), 3.76 (s, 3H).

Synthesis of methyl 1-(3-fluoro-4-((7-(2-morpholinoethoxy)-1,6-naphthyridin-4-yl)oxy)phenyl)-2-oxo-1,2-dihydro Pyridine-3-carboxylate (17S)

The synthetic route was the same as that of compound 2S, except that the starting materials were compound 68 and compound 69. $^1$H NMR (CDCl$_3$, 300 MHz): δ 9.45 (s, 1H), 8.72 (d, J=5.2 Hz, 1H), 8.27 (d, J=4.9 Hz, 1H), 7.61 (d, J=4.7 Hz, 2H), 7.49-7.37 (m, 2H), 7.29 (d, J=9.2 Hz, 1H), 6.47-6.32 (m, 2H), 4.57 (t, J=5.8 Hz, 2H), 3.91 (s, 3H), 3.79-3.65 (m, 4H), 2.88 (t, J=5.7 Hz, 2H), 2.71-2.56 (m, 4H).

Example 25 Synthesis of N-(4-((8-bromo-7-(2-morpholinoethoxy)-1,6-naphthyridin-4-yl)oxy)-3-fluorophenyl)-2-phenyl Acetamide (18S)

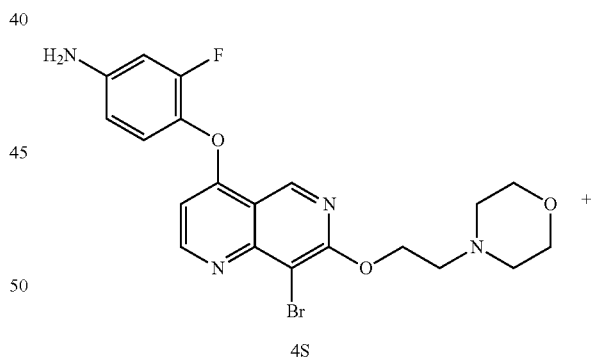

Compound 4S (100 mg, 0.22 mmol) was dissolved in 10 ml THF, 3 eq of DIEA was added thereto and the mixture was cooled to 0° C. 1.5 eq of phenylacetyl chloride was slowly added, reacted therewith for 1 h with stirring at this temperature. After the reaction was completed, the resultant was diluted with EA, washed with saturated NH$_4$Cl solution and saturated NaCl, dried over anhydrous Na$_2$SO$_4$ and concentrated under reduced pressure, and the residue was purified by column chromatography to give the title compound, yield 86%. $^1$H NMR (CDCl$_3$, 300 MHz): δ 10.58 (s, 1H), 9.43 (s, 1H), 8.87 (d, J=5.3 Hz, 1H), 7.92 (d, J=13.3 Hz, 1H), 7.64-7.20 (m, 6H), 6.64 (d, J=5.2 Hz, 1H), 4.67 (t, J=5.7 Hz, 2H), 3.70 (s, 2H), 3.63-3.49 (m, 4H), 2.82 (t, J=6.0 Hz, 2H), 2.60-2.50 (m, 4H).

Example 26 Synthesis of N-(4-((8-bromo-7-(2-morpholinoethoxy)-1,6-naphthyridin-4-yl)oxy)-3-fluorophenyl)-4-oxo-5-phenyl-1,4-dihydropyridine-3-carboxamide (195)

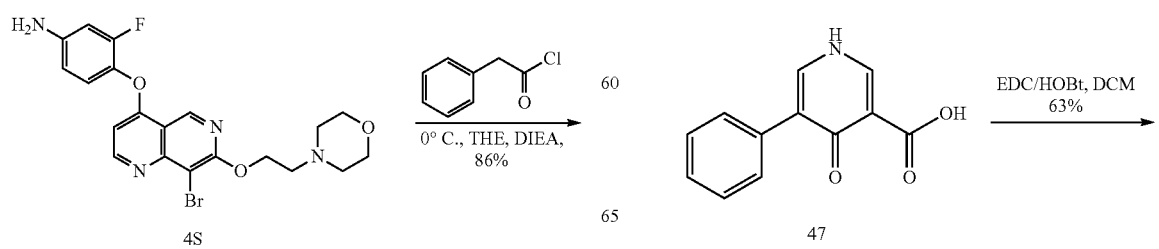

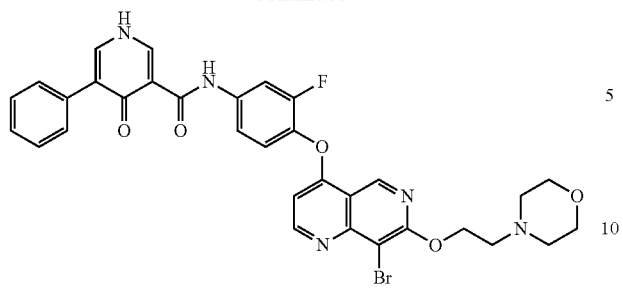

19S

Compound 45 (100 mg, 0.22 mmol) and compound 47 (71 mg, 0.33 mmol) were dissolved in 10 ml of DCM, and HOBt (130 mg, 0.66 mmol) and EDC (89 mg, 0.66 mmol) were added therein at room temperature. The mixture was stirred at room temperature and the reaction was monitored by TLC. After the reaction was completed, the resultant was evaporated to remove most DCM, extracted with EA, then washed with saturated NaHCO$_3$, water (pH=3) and saturated brine, dried over anhydrous Na$_2$SO$_4$ and concentrated to give the crude product, which was further purified by column chromatography to give the title compound, yield 63%. $^1$H NMR (DMSO, 300 MHz): δ 13.60 (s, 1H), 9.44 (s, 1H), 8.89 (s, 1H), 8.65 (s, 1H), 8.26-8.08 (m, 2H), 7.74-7.63 (m, 2H), 7.63-7.30 (m, 5H), 6.69 (d, J=5.4 Hz, 1H), 4.68 (t, J=5.7 Hz, 2H), 3.64-3.53 (m, 4H), 2.81 t, J=5.8 Hz, 2H), 2.60-2.52 (m, 4H).

Example 27 Synthesis of N-(3-fluoro-4-((7-(2-morpholinoethoxy)-1,6-naphthyridin-4-yl)oxy)phenyl)-4-oxo-5-phenyl-1,4-dihydropyridine-3-carboxamide (20S)

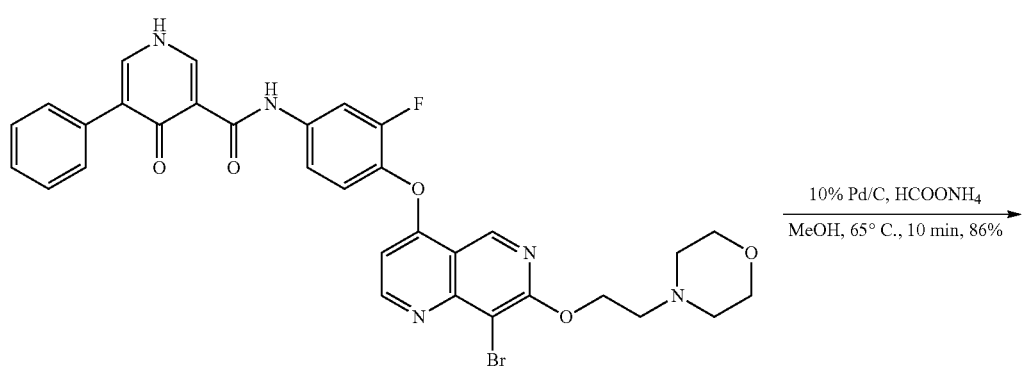

19S

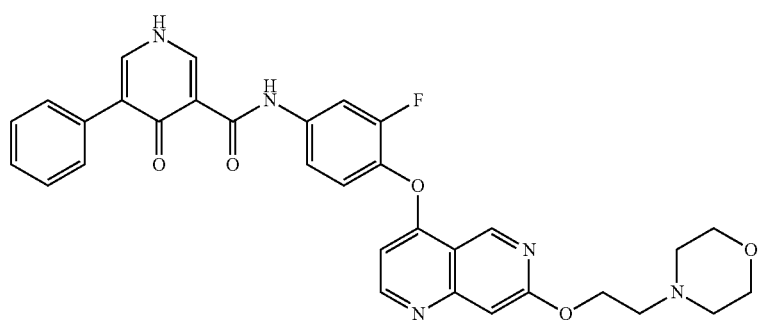

20S

The synthesis route was the same as that of compound 55, except that the starting material was compound 19S. ¹H NMR (DMSO, 300 MHz): δ 13.31 (s, 1H), 9.47 (s, 1H), 8.78 (d, J=5.2 Hz, 1H), 8.65 (s, 1H), 8.17-8.04 (m, 2H), 7.67 (d, J=6.8 Hz, 2H), 7.61-7.53 (m, 2H), 7.50-7.32 (m, 4H), 7.25 (s, 1H), 6.56 (d, J=5.2 Hz, 1H), 4.54 (t, J=5.7 Hz, 2H), 3.65-3.54 (m, 4H), 2.81 (t, J=6.8 Hz, 2H), 2.58-2.52 (m, 4H).

Example 28 Synthesis of N-(4-((8-bromo-7-(2-morpholinoethoxy)-1,6-naphthyridin-4-yl)oxy)-3-fluorophenyl)-5-(4-fluorophenyl)-4-oxo-1,4-dihydropyridine-3-carboxamide (21S)

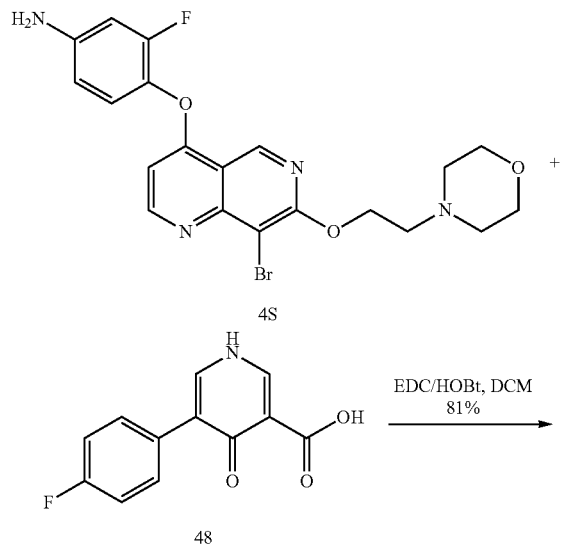

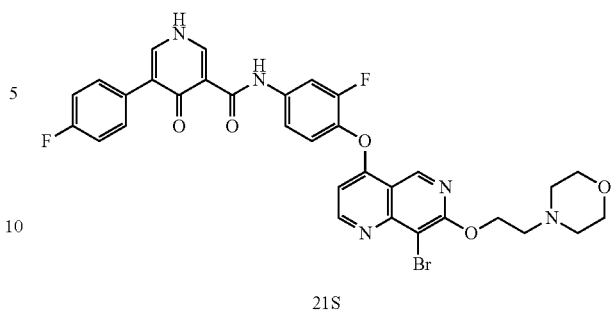

The synthetic route was the same as that of compound 19S, except that the starting materials were compound 4S and compound 48. ¹H NMR (DMSO, 300 MHz): δ13.39 (s, 1H), 9.44 (s, 1H), 8.89 (d, J=5.3 Hz, 1H), 8.65 (s, 1H), 8.18-8.03 (m, 2H), 7.81-7.65 (m, 2H), 7.55 (s, 2H), 7.34-7.20 (m, 2H), 6.68 (d, J=4.3 Hz, 1H), 4.68 (t, J=5.6 Hz, 2H), 3.61-3.54 (m, 4H), 2.81 (t, J=5.7 Hz, 2H), 2.61-2.53 (m, 4H).

Example 29 Synthesis of N-(3-Fluoro-4-((7-(2-morpholinoethoxy)-1,6-naphthyridin-4-yl)oxy)phenyl)-5-(4-fluorophenyl)-4-oxo-1,4-dihydropyridine-3-carboxamide (22S)

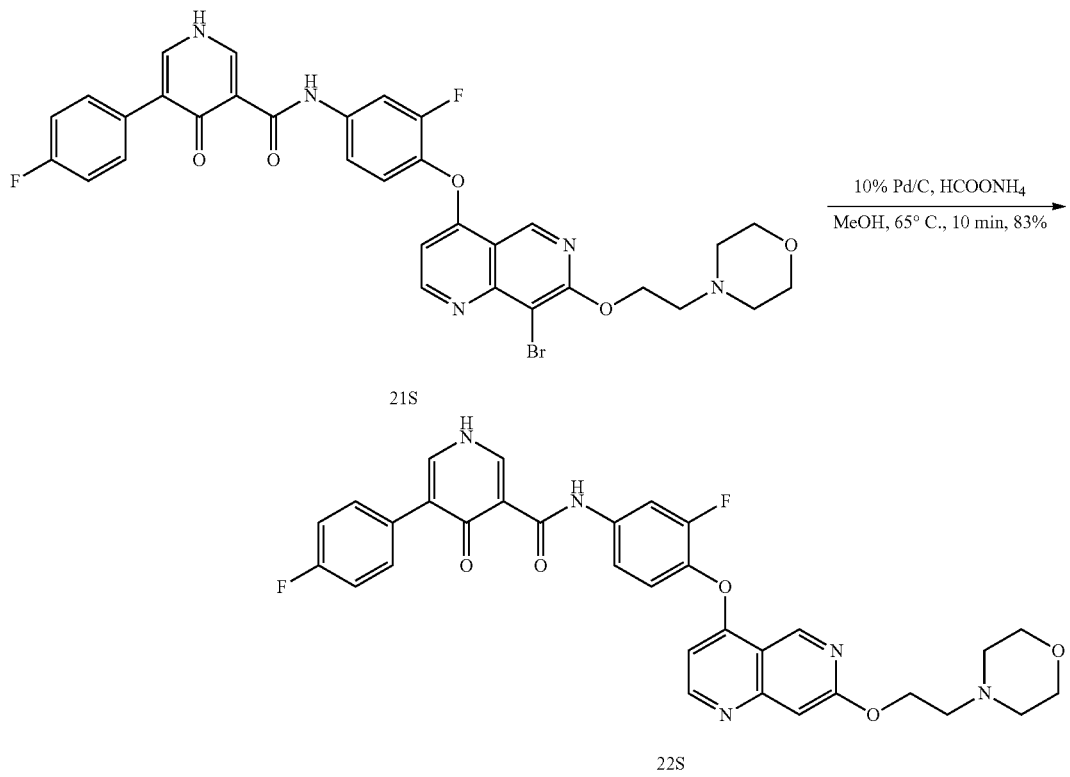

The synthetic route was the same as that of compound 5S, except that the starting material was compound 21S. ¹H NMR (DMSO, 300 MHz): δ 13.26 (s, 1H), 9.46 (s, 1H), 8.78 (d, J=5.3 Hz, 1H), 8.64 (s, 1H), 8.16-8.07 (m, 2H), 7.76-7.67 (m, 3H), 7.55-7.48 (m, 2H), 7.30-7.24 (m, 3H), 6.55 (d, J=5.4 Hz, 1H), 4.54 (t, J=5.6 Hz, 2H), 3.63-3.57 (m, 4H), 2.82 (t, J=7.3 Hz, 2H), 2.61-2.52 (m, 4H).

Example 30 Synthesis of N-(3,4-difluorophenyl)-N-(3-fluoro-4-((7-(2-morpholinoethoxy)-1,6-naphthyridin-4-yl)oxy)phenyl)cyclopropyl-1,1-dicarboxamide (23S)

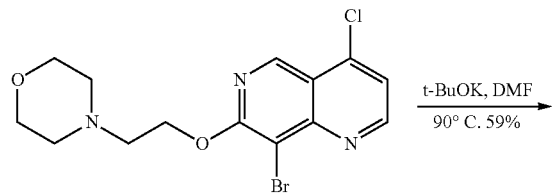

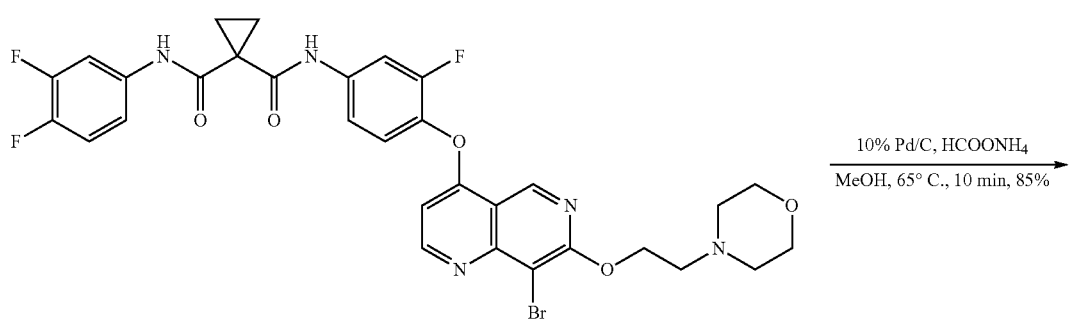

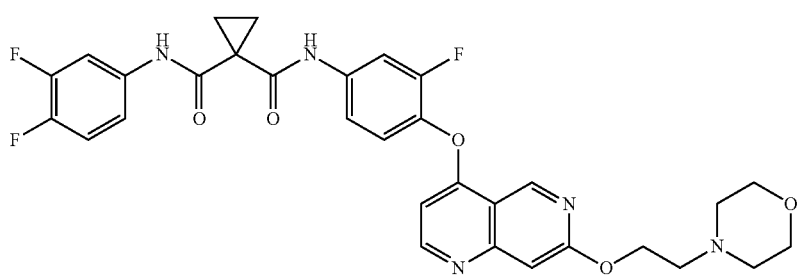

N-(4-((8-bromo-7-(2-morpholinoethoxy)-1,6-naphthyridin-4-yl)oxy)-3-fluorophenyl)-N-(3,4-difluorophenyl)cyclopropyl-1,1-dicarboxamide (70)

The synthetic route was the same as that of compound 2S, except that the starting materials were compound 63 and compound 28. ¹H NMR (DMSO, 300 MHz): δ10.40 (s, 1H), 10.21 (s, 1H), 9.43 (s, 1H), 8.89 (d, J=5.4 Hz, 1H), 7.94 (d, J=13.6 Hz, 1H), 7.89-7.75 (m, 1H), 7.64-7.48 (m, 2H), 7.46-7.32 (m, 2H), 6.62 (d, J=5.3 Hz, 1H), 4.68 (t, J=5.7 Hz, 2H), 3.67-3.52 (m, 4H), 2.83 (t, J=6.0 Hz, 2H), 2.68-2.54 (m, 4H), 1.57-1.41 (m, 4H).

N-(3,4-difluorophenyl)-N-(3-fluoro-4-((7-(2-morpholinoethoxy)-1,6-naphthyridin-4-yl)oxy)phenyl) cyclopropyl-1,1-dicarboxamide (23S)

The synthesis route was the same as that of compound 5S, except that the starting material was compound 70. ¹H NMR (CD3OD, 300 MHz): δ9.48 (d, J=0.6 Hz, 1H), 8.71 (d, J=5.4 Hz, 1H), 7.86 (d, J=12.7 Hz, 1H), 7.71 (dd, J=11.7, 6.3 Hz, 1H), 7.46-7.36 (m, 2H), 7.28-7.15 (m, 3H), 6.52 (d, J=5.4 Hz, 1H), 4.70-4.64 (m, 2H), 3.80-3.71 (m, 4H), 3.08-3.01 (m, 2H), 2.85-2.75 (m, 4H), 1.64 (m, 4H).

Example 31 Synthesis of N-(4-fluoro-3-methoxy)-N-(3-fluoro-4-((7-(2-morpholinoethoxy)-1,6-naphthyridin-4-yl)oxy)phenyl)cyclopropyl-1,1-dicarboxamide (245)

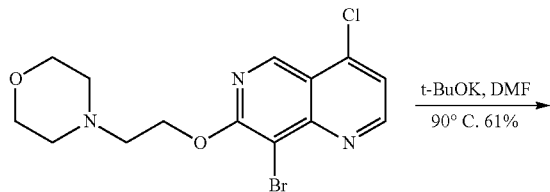

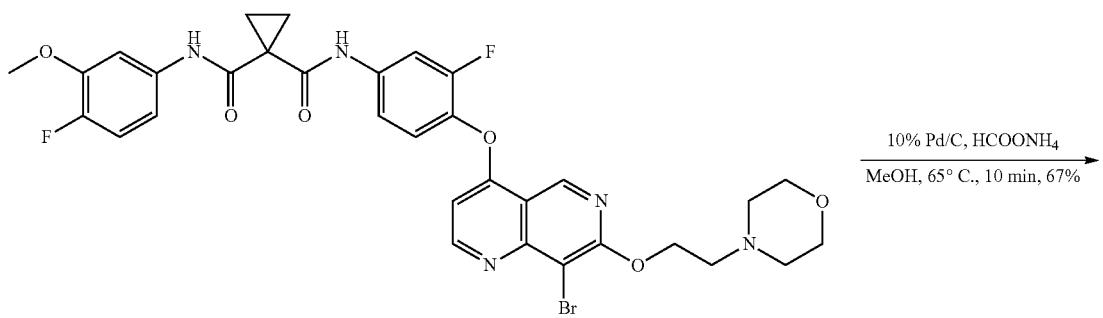

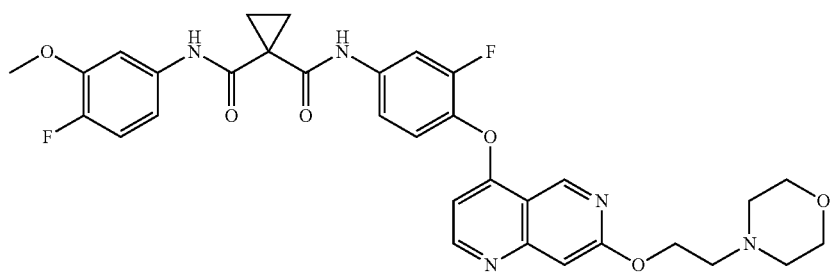

N-(4-((8-bromo-7-(2-morpholinoethoxy)-1,6-naphthyridin-4-yl)oxy)-3-fluorophenyl)-N-(3-methoxy-4-fluorophenyl)cyclopropyl-1,1-dicarboxamide (71)

The synthetic route was the same as that of compound 25, except that the starting materials were compound 63 and compound 29. $^1$H NMR (DMSO, 300 MHz): δ10.40 (s, 1H), 10.00 (s, 1H), 9.43 (s, 1H), 8.88 (d, J=7.4 Hz, 1H), 7.94 (d, J=12.9 Hz, 1H), 7.64-7.50 (m, 3H), 7.25-7.14 (m, 2H), 6.60 (d, J=8.2 Hz, 1H), 4.66 (t, J=6.1 Hz, 2H), 3.81 (s, 3H), 3.64-3.55 (m, 4H), 2.80 (t, J=8.4 Hz, 2H), 2.65-2.55 (m, 4H), 1.54-1.44 (m, 4H).

N-(4-fluoro-3-methoxy)-N-(3-fluoro-4-((7-(2-morpholinoethoxy)-1,6-naphthyridin-4-yl)oxy)phenyl)cyclopropyl-1,1-dicarboxamide (245)

The synthetic route was the same as that of compound 5S, except that the starting material was compound 71. $^1$H NMR (DMSO, 300 MHz): δ9.97 (s, 1H), 9.44 (s, 1H), 9.32 (s, 1H), 8.68 (d, J=5.1 Hz, 1H), 8.30 (s, 1H), 7.80 (t, J=12.8 Hz, 1H), 7.45-7.29 (m, 2H), 7.23-7.19 (m, 1H), 7.06-6.83 (m, 2H), 6.32 (t, J=4.9 Hz, 1H), 4.56 (t, J=5.7 Hz, 2H), 3.89 (s, 3H), 3.79-3.69 (m, 4H), 2.88 (t, J=5.8 Hz, 2H), 2.68-2.57 (m, 4H), 1.83-1.75 (m, 2H), 1.68-1.57 (m, 2H).

Example 32 Synthesis of N-(3-fluoro-4-((7-(2-(pyridin-4-yl)ethoxy)-1,6-naphthyridin-4-yl)oxy)phenyl)-N-(4-fluorophenyl)yclopropyl-1,1-dicarboxamide (25S)

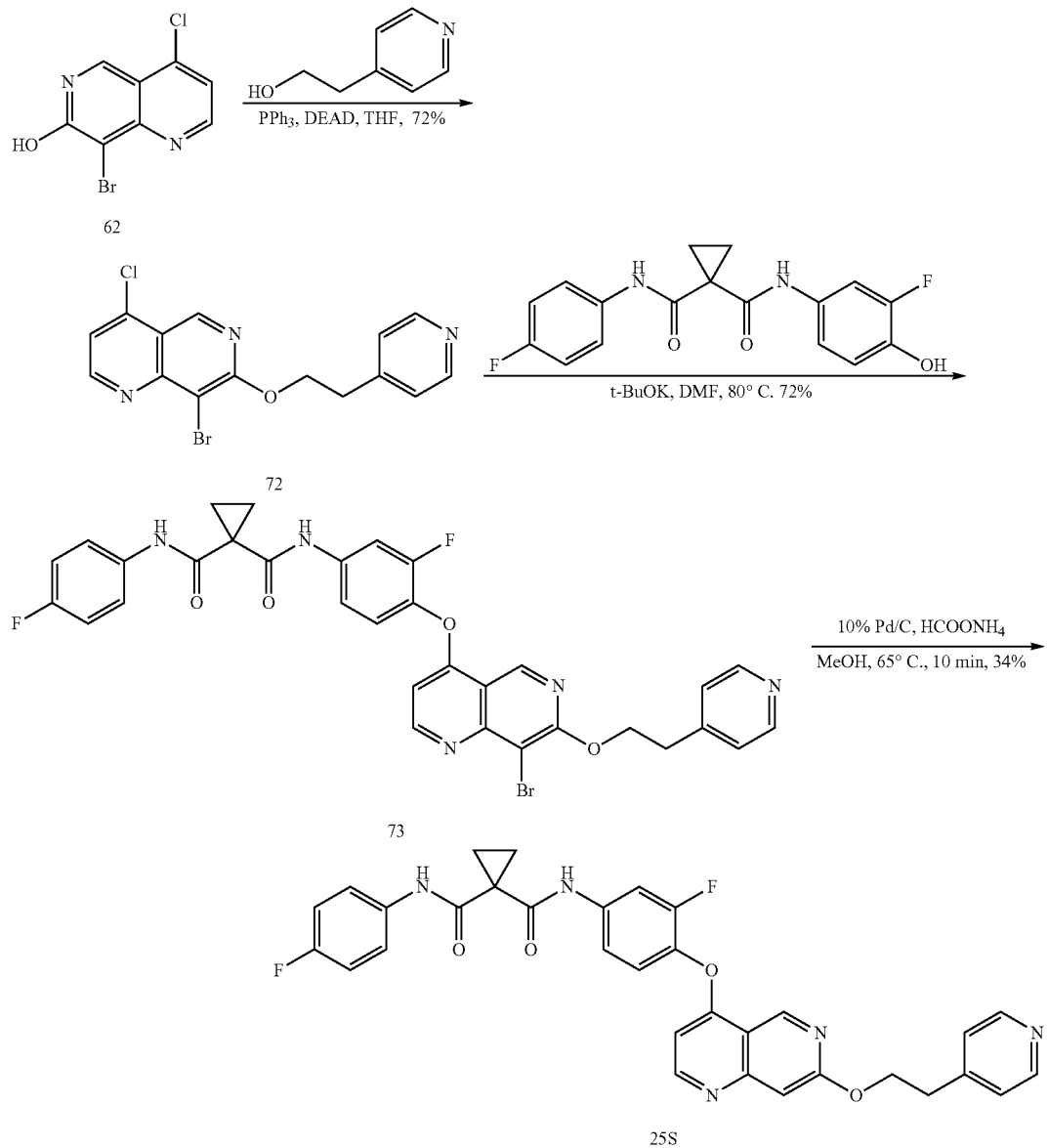

8-bromo-4-chloro-7-(2-(pyridin-4-yl)ethoxy)-1,6-naphthyridine (72)

The synthesis route was the same as that of compound 63, except that the starting materials were compound 62 and 1-(2-hydroxyethyl)pyridine. $^1$H NMR (CDCl$_3$, 300 MHz): δ9.21 (s, 1H), 8.94 (d, J=4.7 Hz, 1H), 8.52 (d, J=5.9 Hz, 2H), 7.40 (d, J=4.7 Hz, 1H), 7.30 (d, J=5.9 Hz, 2H), 4.77 (t, J=6.5 Hz, 2H), 3.18 (t, J=6.5 Hz, 2H).

N-(4-((8-bromo-7-(2-(pyridin-4-yl)ethoxy)-1,6-naphthyridin-4-yl)oxy)-3-fluorophenyl)-N-(4-fluorophenyl)cyclopropyl-1,1-dicarboxamide (73)

The synthetic route was the same as that of compound 25, except that the starting materials were compound 72 and compound 26. $^1$H NMR (DMSO, 300 MHz): δ10.44 (s, 1H), 10.01 (s, 1H), 9.44 (s, 1H), 8.89 (d, J=5.3 Hz, 1H), 8.51 (d, J=7.6 Hz, 2H), 7.94 (d, J=13.9 Hz, 1H), 7.69-7.62 (m, 2H), 7.58-7.48 (m, 2H), 7.49-7.37 (m, 2H), 7.17 (t, J=8.9 Hz, 2H), 6.62 (d, J=6.2 Hz, 1H), 4.80 (t, J=7.2 Hz, 2H), 3.16 (t, J=7.2 Hz, 2H), 1.54-1.43 (m, 4H).

N-(3-fluoro-4-((7-(2-(pyridin-4-yl)ethoxy)-1,6-naphthyridin-4-yl)oxy)phenyl)-N-(4-fluoro phenyl)cyclopropyl-1,1-dicarboxamide (25S)

The synthesis route was the same as that of compound 55, except that the starting material was compound 73. ¹H NMR (CDCl₃, 300 MHz): δ10.19 (s, 1H), 9.44 (s, 1H), 8.68 (d, J=5.2 Hz, 1H), 8.52 (d, J=6.0 Hz, 2H), 8.10 (s, 1H), 7.78 (dd, J=12.1, 2.3 Hz, 1H), 7.48-7.38 (m, 2H), 7.29-7.25 (m, 3H), 7.21 (m, 2H), 7.10-6.99 (m, 2H), 6.33 (d, J=5.4 Hz, 1H), 4.67 (t, J=6.7 Hz, 2H), 3.17 (t, J=6.6 Hz, 2H), 1.86-1.76 (m, 2H), 1.61-1.57 (m, 2H).

Example 33 Synthesis of N-(3-fluoro-4-((7-((1-morpholinopropan-2-yl)oxy)-1,6-naphthyridin-4-yl)oxy)phenyl)-N-(4-fluorophenyl)cyclopropyl-1,1-dicarboxamide (26S)

4-(2-((8-bromo-4-chloro-1,6-naphthyridin-7-yl)oxy)propyl)morpholine (74)

The synthesis route was the same as that of compound 63, except that the starting materials were compound 62 and N-(2-hydroxypropyl)morpholine. ¹H NMR (CDCl₃, 300 MHz): δ9.21 (s, 1H), 8.93 (d, J=4.7 Hz, 1H), 7.38 (d, J=4.7 Hz, 1H), 5.68-5.57 (m, 1H), 3.57 (t, J=4.6 Hz, 4H), 2.65-2.50 (m, 4H), 1.81-1.66 (m, 2H), 1.43 (d, J=6.2 Hz, 3H).

N-(4-((8-bromo-7-((1-morpholinoprop-2-yl)oxy)-1,6-naphthyridin-4-yl)oxy)-3-fluorophenyl)-N-(4-fluorophenyl)cyclopropyl-1,1-dicarboxamide (75)

The synthetic route was the same as that of compound 2S, except that the starting materials were compound 74 and compound 26. ¹H NMR (CDCl₃, 300 MHz): δ110.20 (s, 1H), 9.35 (s, 1H), 8.81 (d, J=5.3 Hz, 1H), 8.00 (s, 1H), 7.78

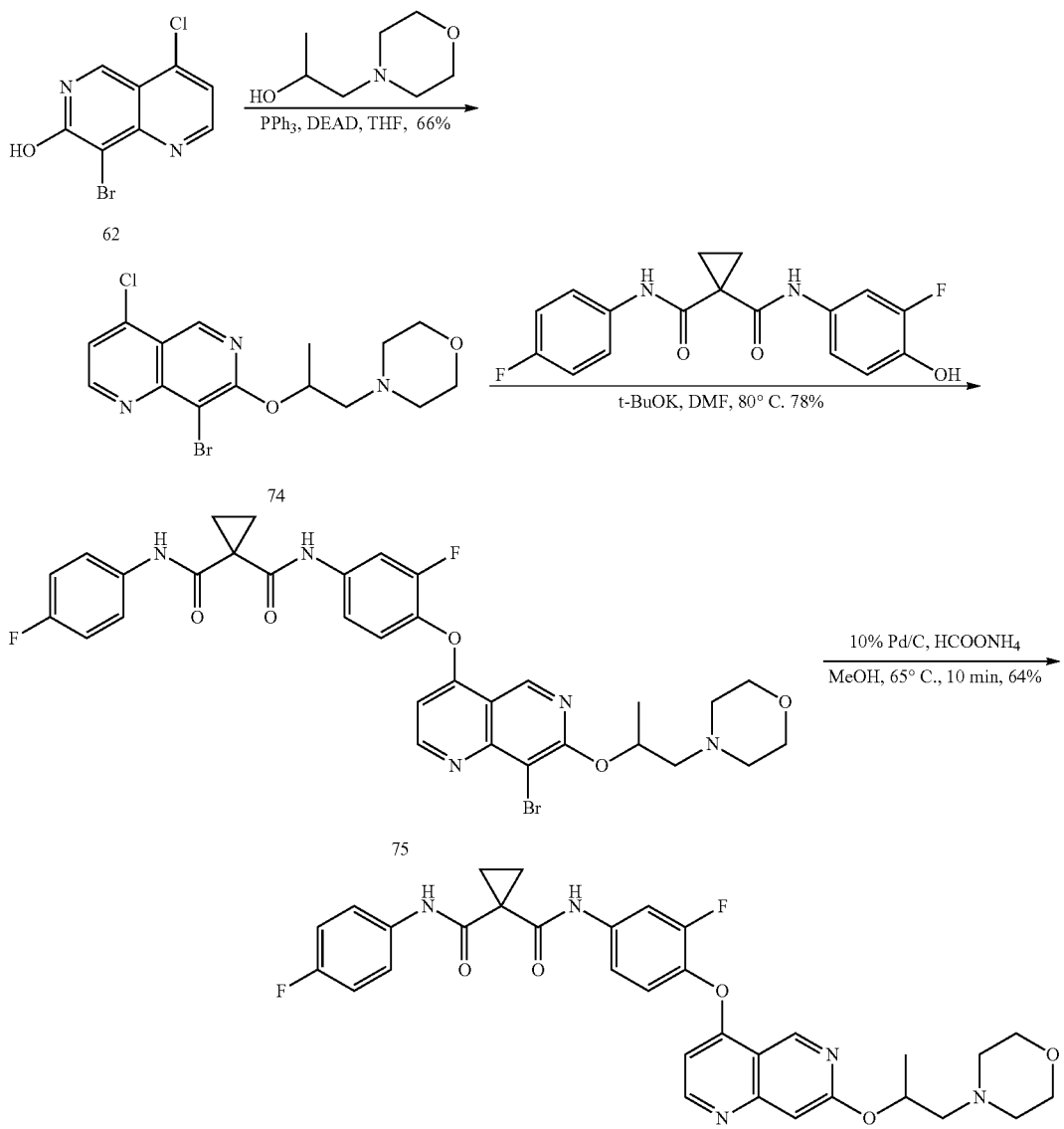

(d, J=12.4 Hz, 1H), 7.48-7.38 (m, 2H), 7.28-7.25 (m), 7.06 (t, J=8.6 Hz, 2H), 6.40 (d, J=5.4 Hz, 1H), 5.72-5.59 (m, 1H), 3.60 (t, J=4.4 Hz, 4H), 2.63-2.53 (m, 4H), 1.86-1.78 (m, 2H), 1.63-1.58 (m, 4H), 1.45 (d, J=6.3 Hz, 3H).

N-(3-fluoro-4-((7-((1-morpholinopropan-2-yl)oxy)-1,6-naphthyridin-4-yl)oxy)phenyl)-N-(4-fluorophenyl)cyclopropyl-1,1-dicarboxamide (26S)

The synthetic route was the same as that of compound 5S, except that the starting material was compound 75. $^1$H NMR (DMSO, 300 MHz): δ10.43 (s, 1H), 10.01 (s, 1H), 9.44 (s, 1H), 8.75 (d, J=5.2 Hz, 1H), 7.93 (dd, J=13.1, 2.3 Hz, 1H), 7.64 (dd, J=9.1, 5.0 Hz, 2H), 7.59-7.45 (m, 2H), 7.22-7.10 (m, 3H), 6.46 (d, J=5.2 Hz, 1H), 5.58-5.46 (m, 1H), 3.55-3.48 (m, 4H), 2.78-2.56 (m, 2H), 2.50-2.43 (m, 4H), 1.52-1.44 (m, 4H), 1.34 (d, J=6.2 Hz, 3H).

Example 34 Synthesis of N-(3-fluoro-4-((7-morpholino-1,6-naphthyridin-4-yl)oxy)phenyl)-N-(4-fluorophenyl)cyclopropyl-1,1-dicarboxamide (27S)

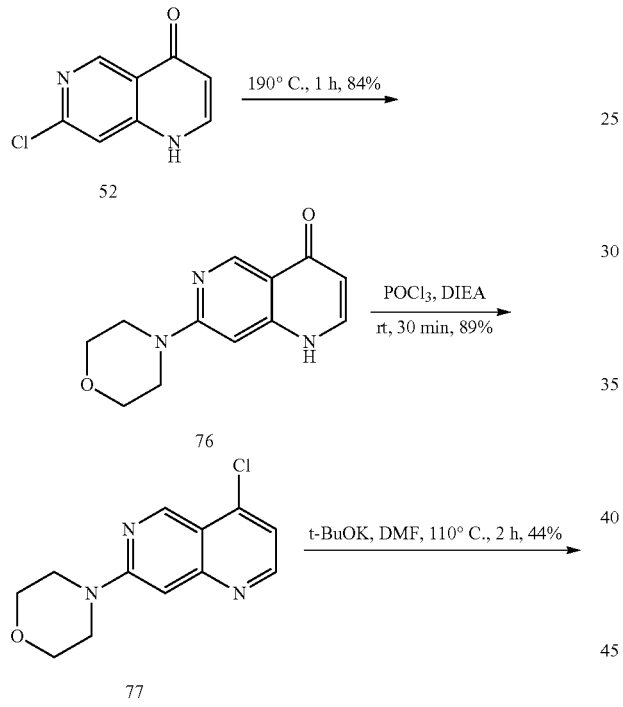

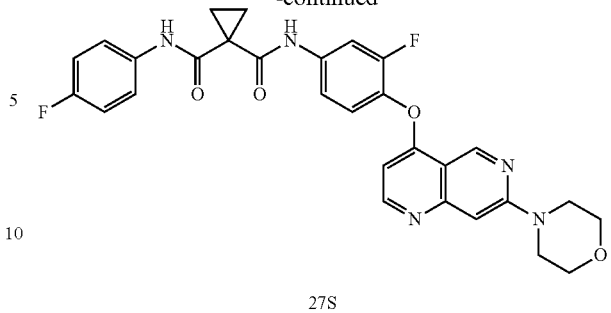

27S 7-morpholino-1,6-naphthyridin-4(1H)-one (76)

The compound 52 (340 mg, 1.89 mmol) was dissolved in morpholine and reacted therewith at 190° C. for 1 h and the reaction was monitored by TLC. After the reaction was completed, the resultant was cooled to room temperature, precipitated by adding ether, filtered and washed with ether to give the crude product. $^1$H NMR (DMSO, 400 MHz): δ 8.83 (s, 1H), 7.74 (d, J=7.6 Hz, 1H), 6.45 (s, 1H), 5.87 (d, J=7.6 Hz, 1H), 3.75-3.65 (m, 4H), 3.54-3.45 (m, 4H).

N-(3-fluoro-4-((7-morpholino-1,6-naphthyridin-4-yl)oxy)phenyl)-N-(4-fluorophenyl)cyclopropyl-1,1-dicarboxamide (27S)

The synthetic route was the same as that of compound 2S, except that the starting material was compound 76. $^1$H NMR (DMSO, 400 MHz): δ 10.54 (s, 1H), 10.02 (s, 1H), 9.55 (s, 1H), 8.84 (d, J=6.0 Hz, 1H), 7.99 (d, J=12.8 Hz, 1H), 7.72-7.62 (m, 2H), 7.62-7.51 (m, 2H), 7.17 (t, J=8.5 Hz, 2H), 7.03 (s, 1H), 6.63 (d, J=7.1 Hz, 1H), 3.84-3.76 (m, 4H), 3.75-3.69 (m, 4H), 1.57-1.43 (m, 4H).

Example 35 Synthesis of N-(3-fluoro-4-((7-(4-morpholinopiperidin-1-yl)-naphthyridin-4-yl)oxy)-3-fluorophenyl)-N-(4-fluorophenyl)cyclopropyl-1,1-dicarboxamide (28S)

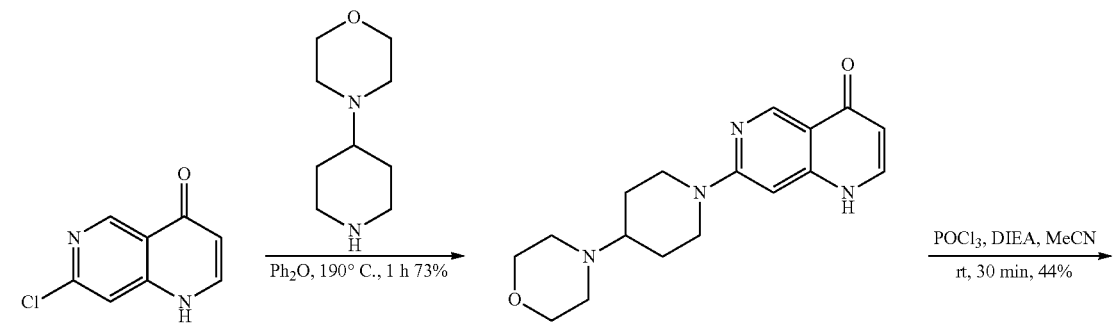

-continued
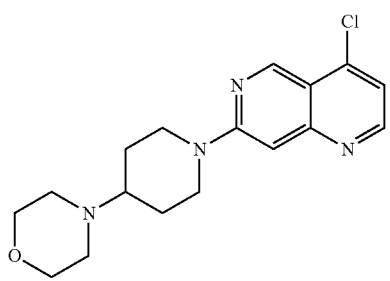
79
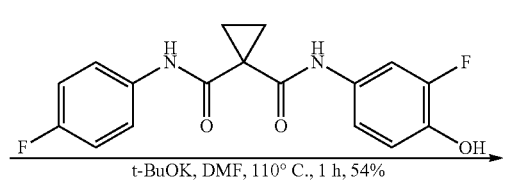
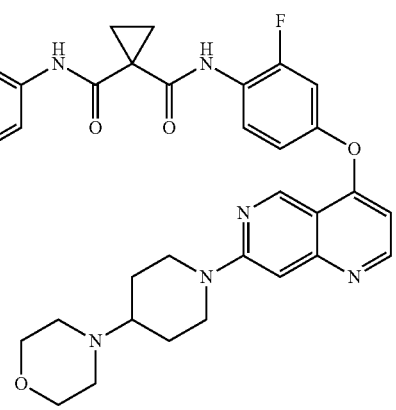
28S
The synthetic route is the same as that of compound 275, except that the starting material was 4-(4-piperidinyl)morpholine. ¹H NMR (CDCl₃, 300 MHz): δ 10.05 (s, 1H), 9.39 (s, 1H), 8.55 (d, J=5.3 Hz, 1H), 8.15 (s, 1H), 7.75 (d, J=12.5 Hz, 1H), 7.43 (dd, J=9.3, 4.4 Hz, 2H), 7.23-7.16 (m, 1H), 7.05 (t, J=8.8 Hz, 2H), 6.96 (s, 1H), 6.17 (d, J=4.7 Hz, 1H), 4.50 (d, J=12.3 Hz, 2H), 3.84-3.63 (m, 4H), 3.04-2.85 (m, 2H), 2.67-2.54 (m, 4H), 2.52-2.41 (m, 1H), 2.04-1.92 (m, 2H), 1.87-1.75 (m, 2H), 1.69-1.54 (m, 4H).
Example 36 Synthesis of (S)—N-(3-fluoro-4-((7-(2-(3-methylmorpholino)ethoxy)-naphthyridin-4-yl)oxy)-3-fluorophenyl)-N-(4-fluorophenyl)cyclopropyl-1,1-dicarboxamide (295)
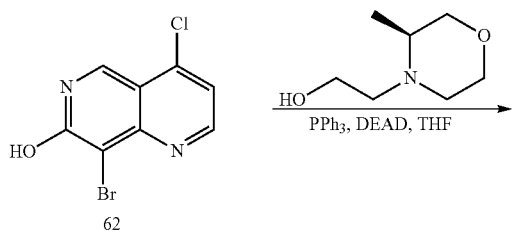
62
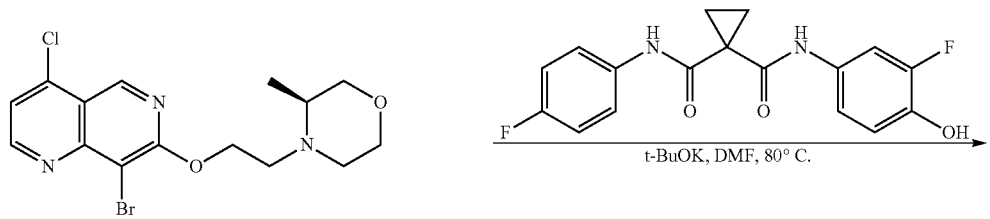
80

-continued

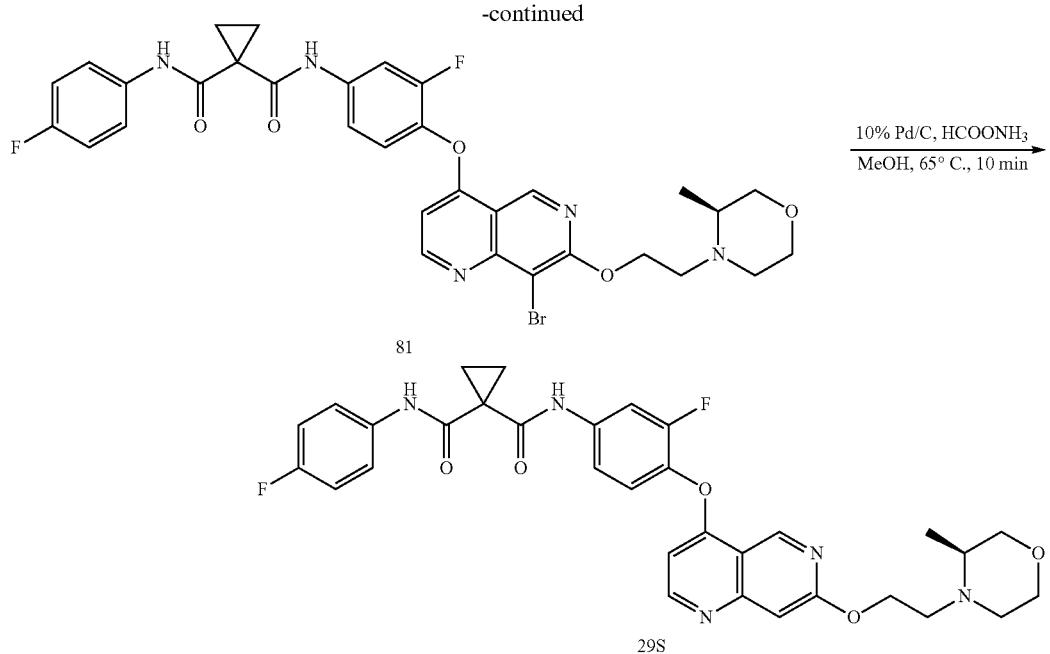

The synthetic route was the same as that of compound 26S, except that the starting materials were compound 62 and (S)-2-(3-methylmorpholino)ethanol. $^1$H NMR (CDCl$_3$, 300 MHz): δ 10.17 (s, 1H), 9.45 (s, 1H), 8.68 (d, J=5.2 Hz, 1H), 8.10 (s, 1H), 7.77 (d, J=12.3 Hz, 1H), 7.43 (dd, J=9.0, 4.8 Hz, 2H), 7.30-7.22 (m, 3H), 7.05 (t, J=8.6 Hz, 2H), 6.32 (d, J=4.9 Hz, 1H), 4.53 (t, J=6.0 Hz, 2H), 3.80 (d, J=11.5 Hz, 1H), 3.72-3.60 (m, 2H), 3.31-3.15 (m, 2H), 2.95-2.74 (m, 2H), 2.65-2.51 (m, 2H), 1.85-1.77 (m, 2H), 1.63-1.56 (m, 2H), 1.04 (d, J=6.3 Hz, 3H).

Example 37 Synthesis of (R)—N-(3-fluoro-4-((7-(2-(3-methylmorpholino)ethoxy)-naphthyridin-4-yl)oxy)-3-fluorophenyl)-N-(4-fluorophenyl)cyclopropyl-1,1-dicarboxamide (30S)

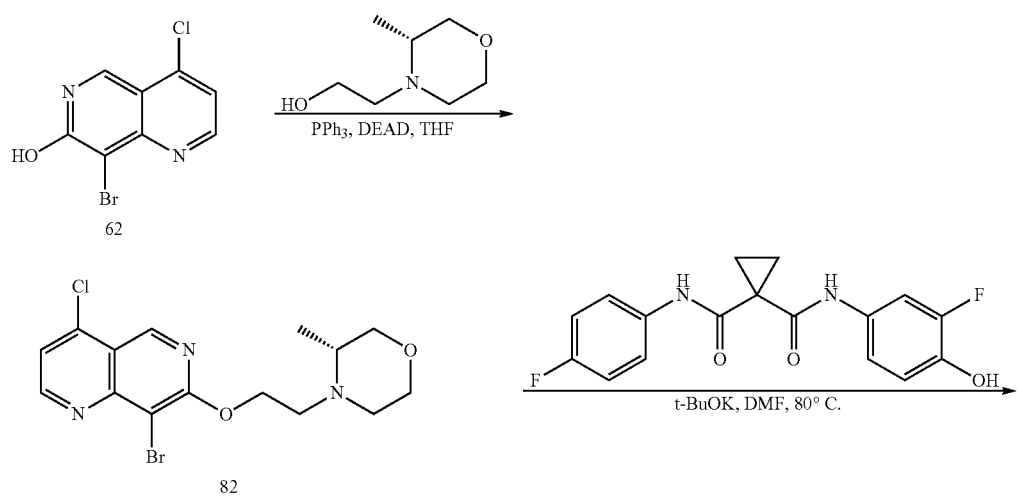

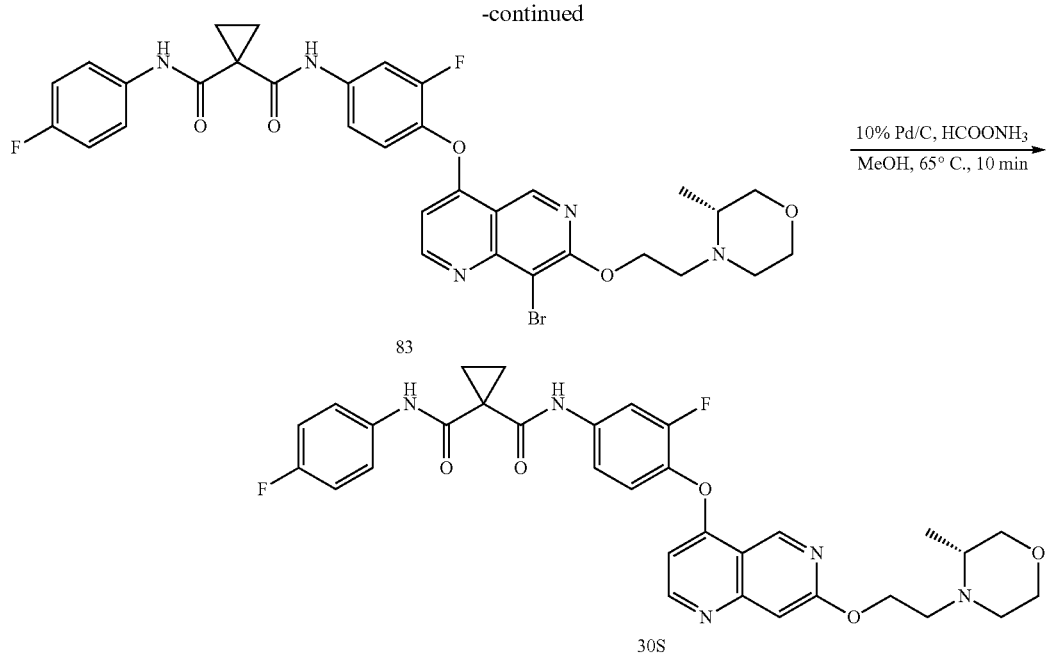
The synthetic route was the same as that of compound 265, except that the starting materials were compound 62 and (R)-2-(3-methylmorpholino)ethanol. $^1$H NMR (CDCl$_3$, 300 MHz): δ 10.19 (s, 1H), 9.45 (s, 1H), 8.68 (d, J=5.2 Hz, 1H), 8.13 (s, 1H), 7.77 (d, J=12.5 Hz, 1H), 7.55-7.35 (m, 2H), 7.27-7.19 (m, 2H), 7.05 (t, J=8.6 Hz, 2H), 6.33 (d, J=5.2 Hz, 1H), 4.55 (t, J=4.5 Hz, 2H), 3.86-3.74 (m, 1H), 3.75-3.60 (m, 2H), 3.37-3.14 (m, 2H), 3.01-2.76 (m, 2H), 2.70-2.51 (m, 2H), 1.87-1.74 (m, 2H), 1.68-1.53 (m, 2H), 1.05 (d, J=6.1 Hz, 3H).
Example 38 Synthesis of N-(4-((7-(2-(1H-imidazol-1-yl)ethoxy)-naphthyridin-4-yl)oxy)-3-fluorophenyl)-N-(4-fluorophenyl)cyclopropyl-1,1-dicarboxamide (31S)
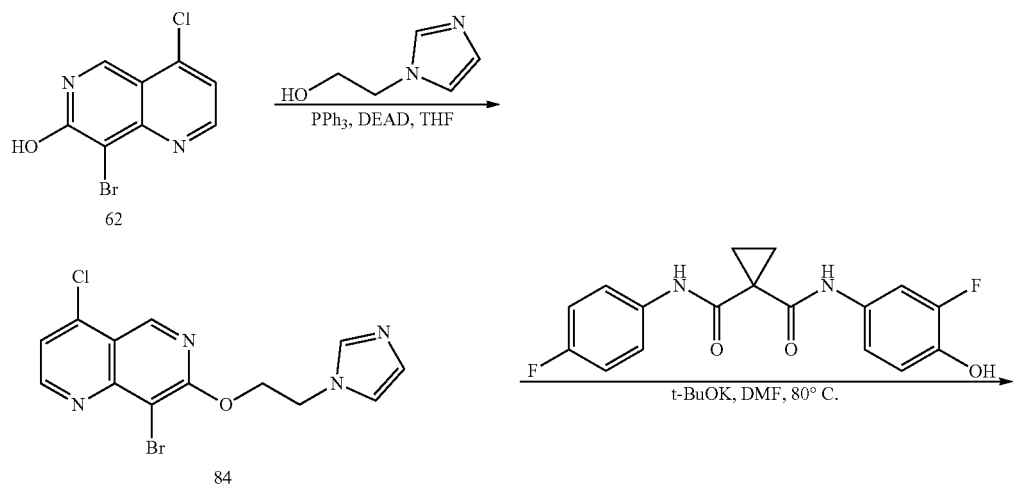

-continued
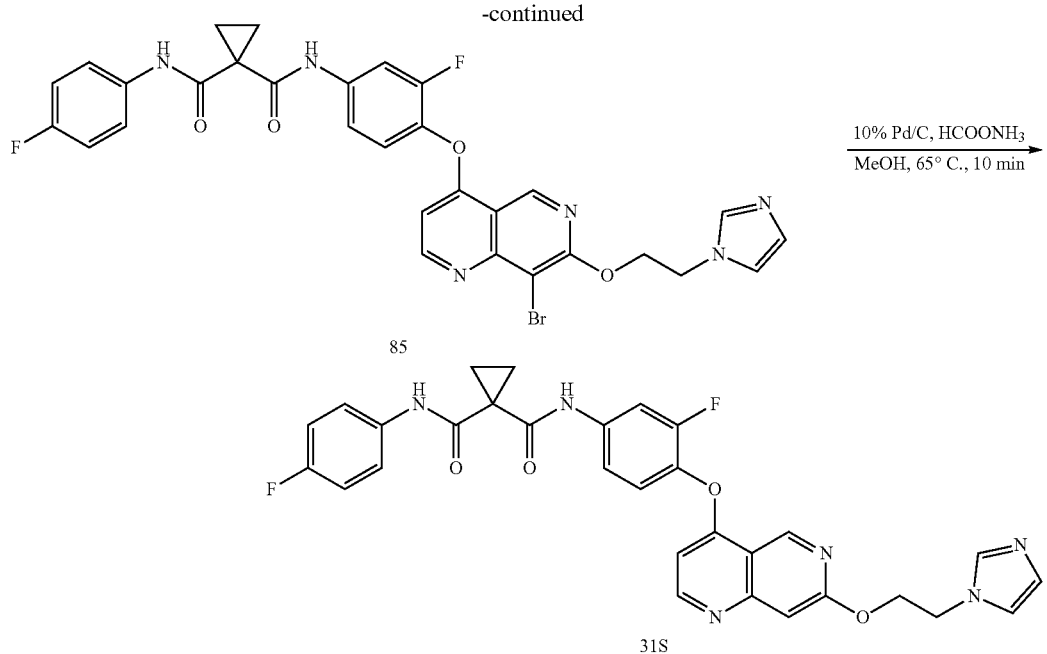
The synthetic route was the same as that of compound 265, except that the starting materials were compound 62 and 2-(1H-imidazol-1-yl)ethanol. $^1$H NMR (CDCl$_3$, 300 MHz): δ 10.40 (s, 1H), 9.41 (s, 1H), 8.68 (d, J=5.3 Hz, 1H), 8.55 (s, 1H), 7.78 (d, J=12.1 Hz, 1H), 7.65 (s, 1H), 7.43 (dd, J=9.0, 4.7 Hz, 2H), 7.33-7.26 (m, 1H), 7.24-7.15 (m, 2H), 7.11-6.97 (m, 4H), 6.34 (d, J=5.2 Hz, 1H), 4.72 (t, J=5.3 Hz, 2H), 4.41 (t, J=5.2 Hz, 2H), 1.86-1.75 (m, 2H), 1.67-1.55 (m, 2H).
Example 39 Synthesis of N-(4-((7-(4-benzylpiperazin-1-yl)-naphthyridin-4-yl)oxy)-3-fluorophenyl)-N-(4-fluorophenyl)cyclopropyl-1,1-dicarboxamide (32S)
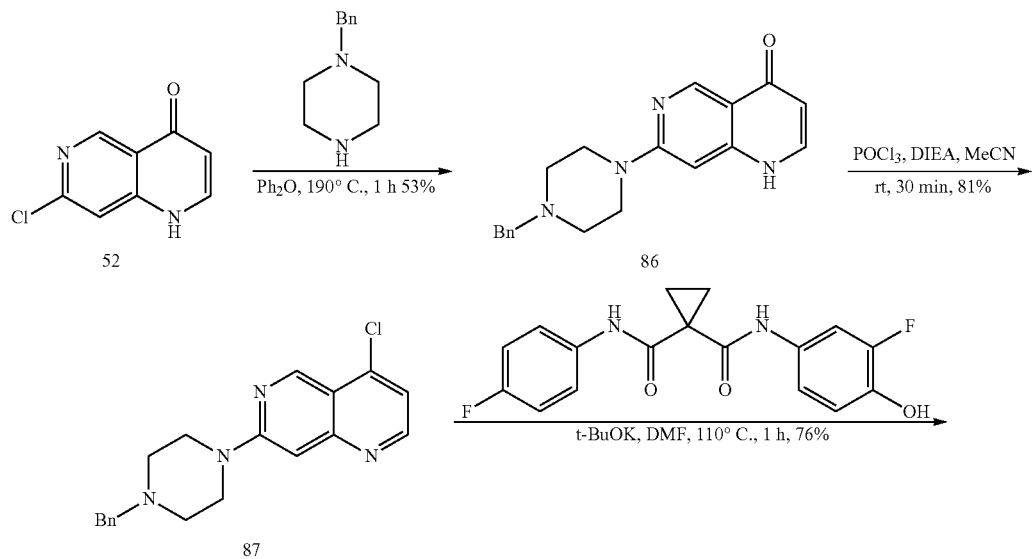

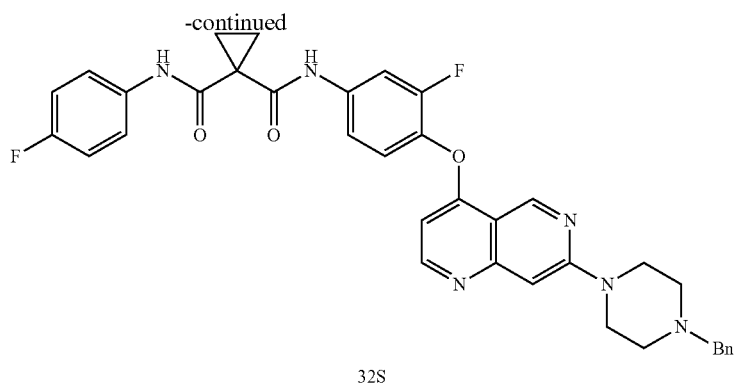

32S

The synthesis route was the same as that of compound 27S. except that the starting material was 4-benzylmorpholine. $^1$H NMR (CDCl$_3$, 300 MHz): δ 10.03 (s, 1H), 9.39 (s, 1H), 8.55 (d, J=5.3 Hz, 1H), 8.18 (s, 1H), 7.74 (d, J=12.1 Hz, 1H), 7.49-7.39 (m, 2H), 7.39-7.26 (m, 5H), 7.23-7.15 (m, 1H), 7.05 (t, J=8.5 Hz, 2H), 6.92 (s, 1H), 6.18 (d, J=5.1 Hz, 1H), 3.74-3.63 (m, 4H), 3.57 (s, 2H), 2.69-2.54 (m, 4H), 1.84-1.75 (m, 2H), 1.61-1.54 (m, 2H).

Example 40 Synthesis of N-(3-fluoro-4-((3-oxo-3,4-dihydropyrido[2,3-b]pyrazin-8-yl)oxy)phenyl)-N-(4-fluorophenyl)cyclopropyl-1,1-dicarboxamide (335)

N-(3-fluoro-4-((2-oxo-1,2-dihydropyrido[2,3-b]pyrazin-8-yl)oxy)phenyl)-N-(4-fluorophenyl)cyclopropyl-1,1-dicarboxamide (34S)

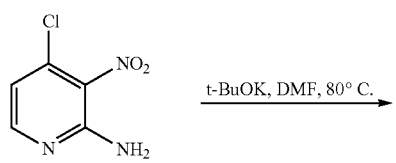

t-BuOK, DMF, 80° C.

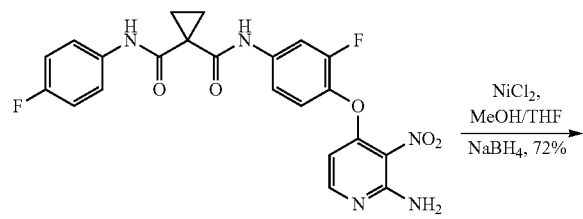

88

NiCl$_2$, MeOH/THF
NaBH$_4$, 72%

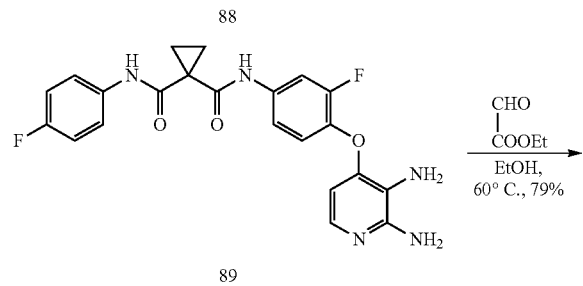

89

CHO
|
COOEt
EtOH,
60° C., 79%

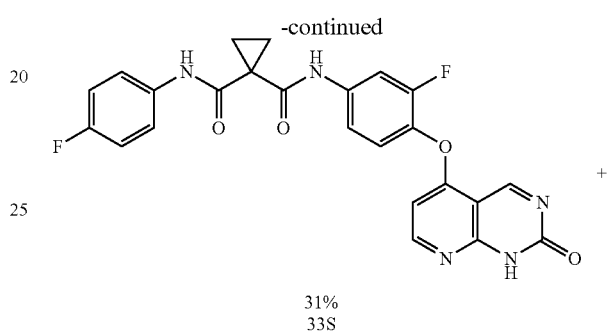

31%
33S

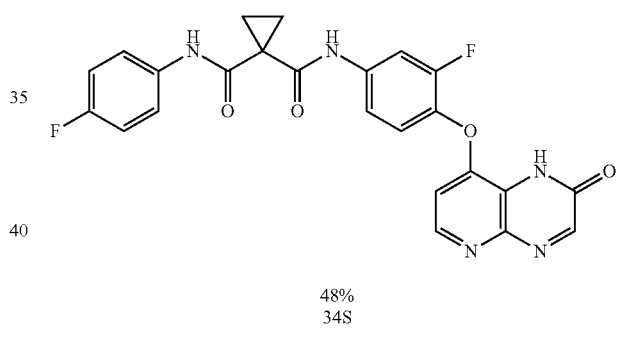

48%
34S

N-(4-((2-amino-3-nitropyridin-4-yl)oxy)-3-fluorophenyl)-N-(4-fluorophenyl)cyclopropyl-1,1-dicarboxamide (88)

2-amino-3-nitro-4-chloropyridine (1 g, 5.8 mmol) was dissolved in anhydrous DMF and 1.1 eq of compound 26 was added therein followed by the addition of 1.1 eq of potassium tert-butoxide. The atmosphere was replaced with N$_2$ three times. The mixture was allowed to react for 1 h with stirring at 80'C and the reaction was monitored by TLC. After the reaction was completed, the resultant was diluted with EA, washed with saturated NH$_4$Cl solution and saturated NaCl, dried over anhydrous Na$_2$SO$_4$ and concentrated under reduced pressure, and the residue was purified by column chromatography to give the title compound, yield 81%. $^1$H NMR (300 MHz, DMSO) δ 10.64 (s, 1H), 9.94 (s, 1H), 8.05 (d, J=5.7 Hz, 1H), 7.97 (t, J=8.6 Hz, 1H), 7.62 (dd, J=9.0, 5.0 Hz, 2H), 7.32 (d, J=11.2 Hz, 1H), 7.25 (s, 2H), 7.18 (t, J=8.9 Hz, 2H), 7.06 (d, J=8.4 Hz, 1H), 6.06 (d, J=5.6 Hz, 1H), 1.58 (t, J=10.6 Hz, 4H).

N-(4-((2,3-diaminopyridin-4-yl)oxy)-3-fluorophenyl)-N-(4-fluorophenyl)cyclopropyl-1,1-dicarboxamide (89)

1 eq of compound 88 was dissolved in 20 ml of THF/MeOH solution (V:V=1:1), and then 4 eq of NiCl$_2$*6H$_2$O was added thereto and 2 eq of NaBH$_4$ was added in portions under stirring at 0° C. The mixture was allowed to react for 10 min with stirring and the reaction was monitored by TLC. After the reaction was completed, the resultant was diluted with EA, washed with saturated NH$_4$Cl solution and saturated NaCl, dried over anhydrous Na$_2$SO$_4$ and concentrated under reduced pressure, and the residue was purified by column chromatography to give the title compound. $^1$H NMR (300 MHz, CD3OD) δ 8.02 (d, J=5.7 Hz, 1H), 7.87 (dd, J=13.2, 2.3 Hz, 1H), 7.68-7.58 (m, 2H), 7.48 (d, J=9.0 Hz, 1H), 7.36 (t, J=9.0 Hz, 1H), 7.24 (s, 1H), 7.20-7.07 (m, 2H), 5.97 (d, J=5.7 Hz, 1H), 1.52-1.40 (m, 4H).

Synthesis of N-(3-fluoro-4-((3-oxo-3,4-dihydropyrido[2,3-b]pyrazin-8-yl)oxy) Phenyl)-N-(4-fluorophenyl)cyclopropyl-1,1-dicarboxamide (33S)

Synthesis of N-(3-fluoro-4-((2-oxo-1,2-dihydropyrido[2,3-b]pyrazin-8-yl)oxy) Phenyl)-N-(4-fluorophenyl)cyclopropyl-1,1-dicarboxamide (34S)

Compound 89 (100 mg, 0.23 mmol) was dissolved in ethanol and 2 eq of ethyl formyl acetate in toluene was added at 60° C. with stirring and the mixture was stirred for another 3 h, and the reaction was monitored by TLC. After the reaction was completed, the resultant was diluted with EA, washed with saturated NH$_4$Cl solution and saturated NaCl, dried over anhydrous Na$_2$SO$_4$ and concentrated under reduced pressure, and the residue was purified by column chromatography to give the title compound, yield, 33S: 31%, 34S: 48%. 33S: $^1$H NMR (DMSO, 300 MHz): δ12.96 (s, 1H), 10.40 (s, 1H), 10.01 (s, 1H), 8.37 (d, J=5.7 Hz, 1H), 8.20 (s, 1H), 7.91 (d, J=13.3 Hz, 1H), 7.65 (dd, J=9.1, 5.1 Hz, 2H), 7.51 (d, J=8.0 Hz, 1H), 7.39 (t, J=9.0 Hz, 1H), 7.16 (t, J=8.9 Hz, 2H), 6.56 (d, J=5.6 Hz, 1H), 1.58-1.36 (m, 4H). 34S: $^1$H NMR (DMSO, 300 MHz): δ12.67 (s, 1H), 10.41 (s, 1H), 10.00 (s, 1H), 8.43 (s, 1H), 8.35 (d, J=5.4 Hz, 1H), 7.89 (d, J=13.7 Hz, 1H), 7.64 (dd, J=8.7, 5.0 Hz, 2H), 7.50 (d, J=9.2 Hz, 1H), 7.40 (t, J=8.9 Hz, 1H), 7.16 (t, J=8.9 Hz, 2H), 6.81 (d, J=5.5 Hz, 1H), 1.49-1.44 (m, 4H).

Example 41 Synthesis of N-(4-((7-((1-ethyl-3-fluoropiperidin-4-yl)amino)-1,6-naphthyridin-4-yl)oxy)-3-fluorophenyl)-2-(4-fluorophenyl)-3-oxo-2,3-dihydropyridazine-4-carboxamide (35S)

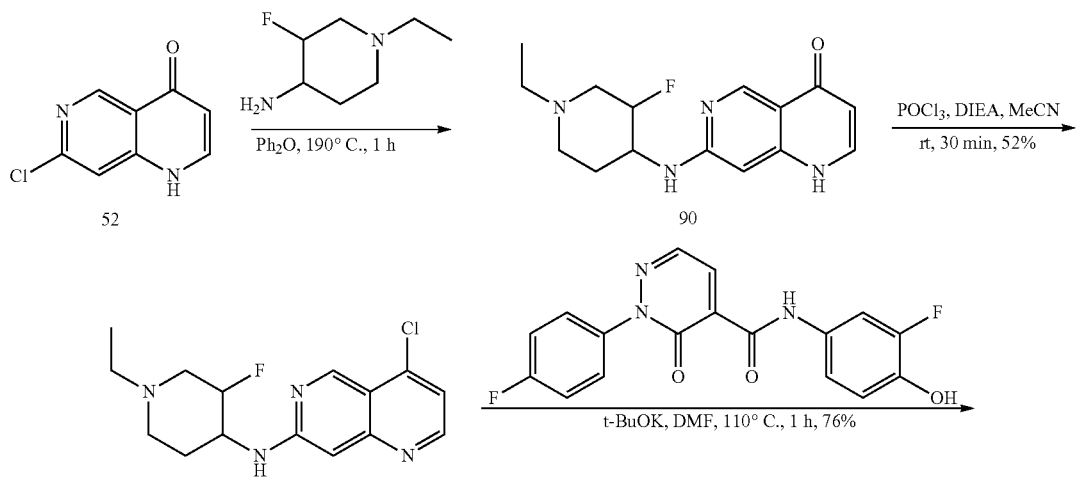

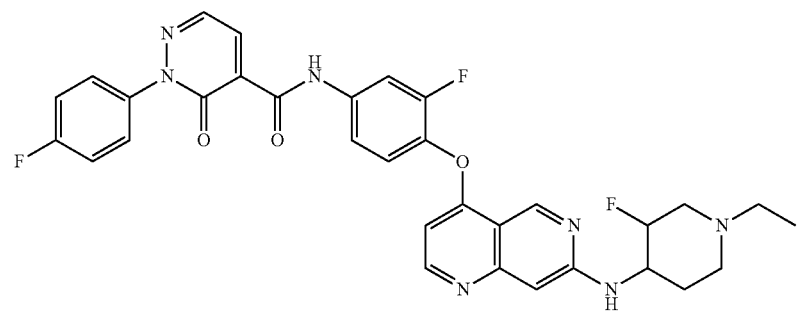

35S

The synthesis route was the same as that of compound 27S, except that the starting material was N-ethyl-4-amino-3-fluoropiperidine. $^1$H NMR (DMSO, 300 MHz): δ9.06 (d, J=15.0 Hz, 1H), 8.93 (s, 1H), 8.82 (d, J=12.5 Hz, 1H), 8.59 (d, J=12.3 Hz, 1H), 7.55 (dd, J=16.0, 3.0 Hz, 1H), 7.50-7.41 (m, 2H), 7.41-7.31 (m, 2H), 7.25 (d, J=14.8 Hz, 1H), 7.16 (s, 1H), 7.12 (dd, J=14.9, 3.0 Hz, 1H), 6.83 (dd, J=14.9, 10.0 Hz, 1H), 5.23-4.91 (m, 1H), 4.06-3.80 (m, 1H), 3.23-2.98 (m, 1H), 2.83-2.69 (m, 1H), 2.57-2.28 (m, 4H), 2.19-2.02 (m, 1H), 1.86-1.68 (m, 1H), 1.09 (t, J=12.6 Hz, 3H).
Example 42 Synthesis of N-(3-fluoro-4-((7-(2-morpholino-2-acetoxy)-1,6-naphthyridin-4-yl)oxy)phenyl)-N-(4-fluorophenyl)cyclopropyl-1,1-dicarboxamide (365)
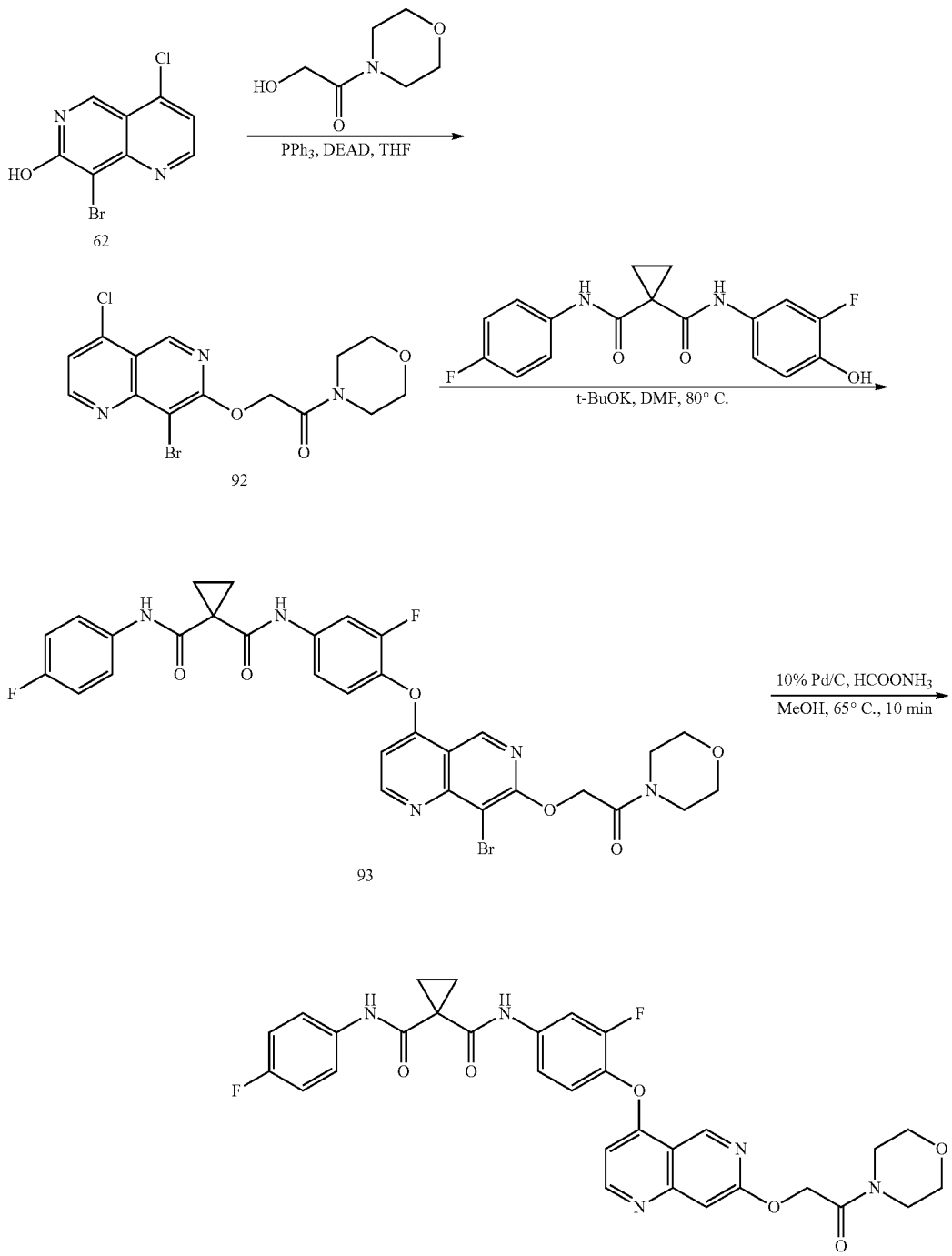

The synthetic route was the same as that of compound 26S, except that the starting materials were compound 62 and 2-hydroxy-1-morpholino-acetamide. 1H NMR (CDCl₃, 300 MHz): δ 10.07 (s, 1H), 9.37 (s, 1H), 8.72 (s, 1H), 8.65 (d, J=5.3 Hz, 1H), 7.62 (d, J=12.0 Hz, 1H), 7.50-7.41 (m, 2H), 7.31 (s, 1H), 7.21-7.14 (m, 1H), 7.13-7.07 (m, 1H), 7.07-7.00 (m, 2H), 6.24 (d, J=5.9 Hz, 1H), 5.18 (s, 2H), 3.79-3.68 (m, 4H), 3.68-3.56 (m, 4H), 1.80-1.72 (m, 2H), 1.62-1.57 (m, 2H).

Example 43 Synthesis of N-(3-fluoro-4-((7-(2-(3-oxomorpholino)ethoxy)-1,6-naphthyridin-4-yl)oxy)phenyl)-N-(4-fluoro Phenyl)cyclopropyl-1,1-dicarboxamide (37S)

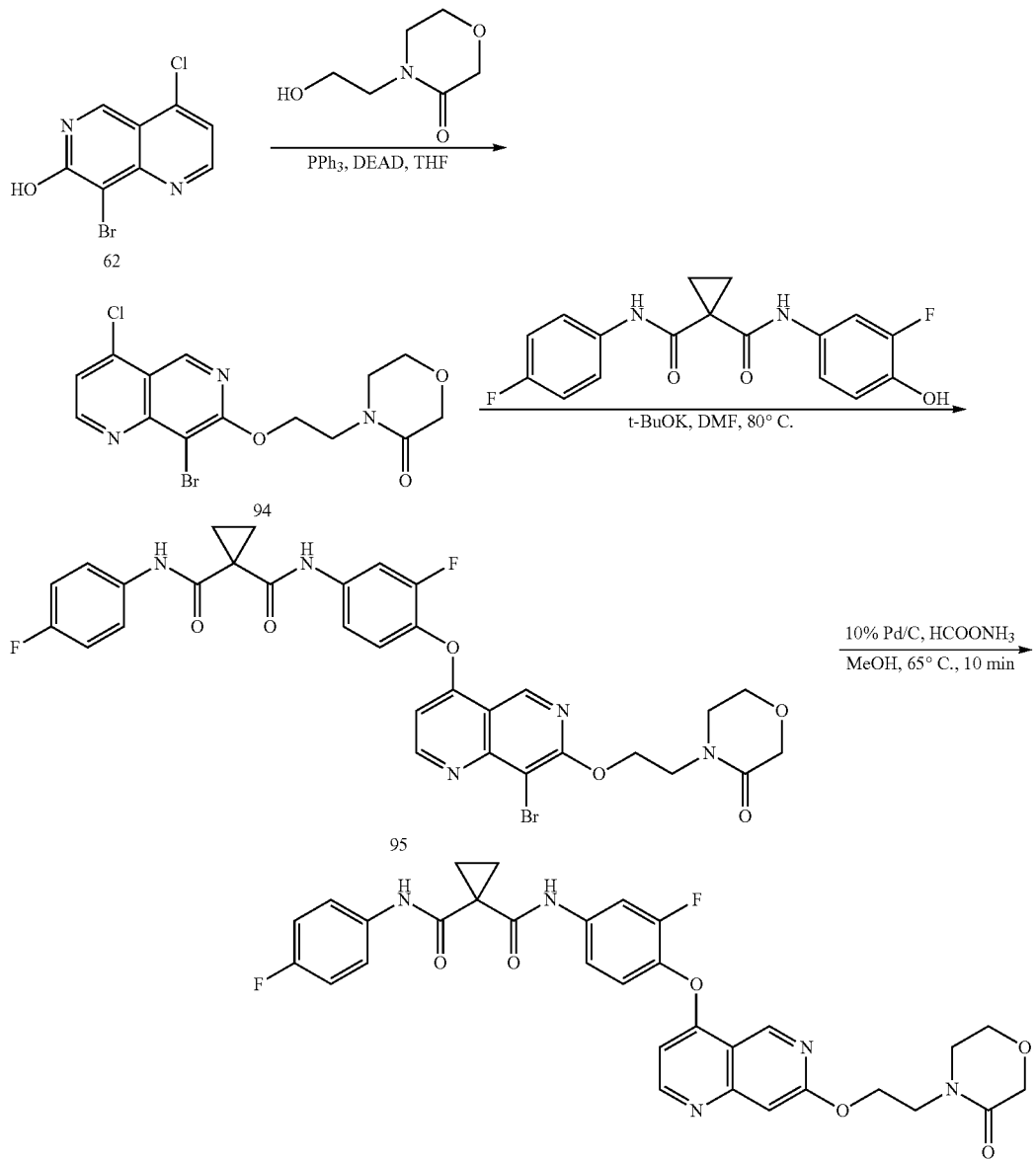

The synthetic route was the same as that of compound 26S, except that the starting materials were compound 62 and 2-hydroxyethyl-2-morpholinone. ¹H NMR (CDCl₃, 300 MHz): δ 10.23 (s, 1H), 9.43 (s, 1H), 8.68 (d, J=5.3 Hz, 1H), 8.26 (s, 1H), 7.78 (d, J=12.0 Hz, 1H), 7.43 (dd, J=8.9, 4.7 Hz, 2H), 7.29 (d, J=8.8 Hz, 1H), 7.24-7.17 (m, 2H), 7.05 (t, J=8.5 Hz, 2H), 6.34 (d, J=5.2 Hz, 1H), 4.63 (t, J=4.9 Hz, 2H), 4.17 (s, 2H), 3.93-3.81 (m, 4H), 3.67-3.55 (m, 2H), 1.86-1.75 (m, 2H), 1.65-1.54 (m, 2H).

Example 44 Synthesis of N-(3-fluoro-4-((7-(1-methyl-1H-pyrazol-4-yl))-1,6-naphthyridin-4-yl)oxy)phenyl)-N-(4-fluorophenyl)cyclopropyl-1,1-dicarboxamide (38S)

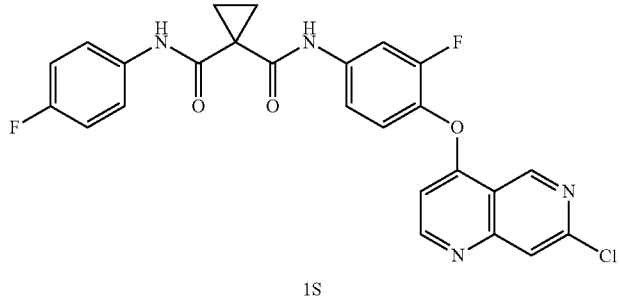
1S

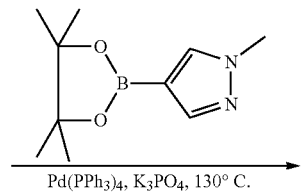

Pd(PPh₃)₄, K₃PO₄, 130° C.

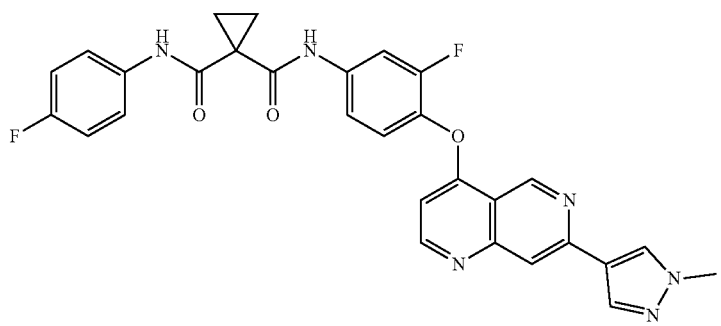
38S

Compound 15 (50 mg, 0.10 mmol) was dissolved in dioxane/water (v:v=3:2), 2 eq of potassium phosphate and 2 eq of 1-methyl-4-(4,4,5,5-tetramethyl-1,3,2-dioxaborolan-2-yl)-1H-pyrazole were then added therein, the mixture was stirred at 130° C. for 3 h under the protection of nitrogen, and the reaction was monitored by TLC. After the reaction was completed, the resultant was diluted with EA, washed with saturated NH₄Cl solution and saturated NaCl, dried over anhydrous Na₂SO₄ and concentrated under reduced pressure, and the residue was purified by column chromatography to give the title compound, yield, 81%. ¹H NMR (CDCl₃, 300 MHz): δ 10.20 (s, 1H), 9.70 (s, 1H), 8.73 (d, J=5.4 Hz, 1H), 8.23 (s, 1H), 8.06 (d, J=8.3 Hz, 2H), 7.96 (s, 1H), 7.78 (d, J=12.0 Hz, 1H), 7.50-7.35 (m, 2H), 7.30-7.26 (m, 1H), 7.04 (t, J=8.6 Hz, 2H), 6.46 (d, J=5.3 Hz, 1H), 3.98 (s, 3H), 1.84-1.78 (m, 2H), 1.63-1.57 (m, 2H).

Example 45 Synthesis of N-(4-((7-(1H-pyrazol-4-yl)-1,6-naphthyridin-4-yl)oxy)-3-fluorophenyl)-N-(4-fluorophenyl)cyclopropyl-1,1-dicarboxamide (39S)

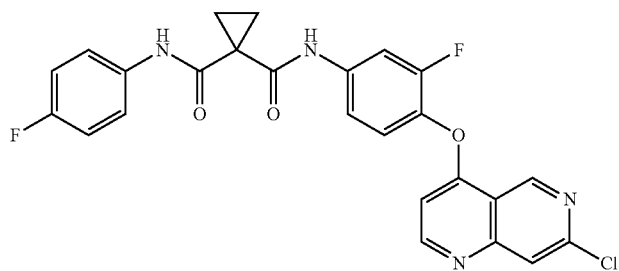
1S

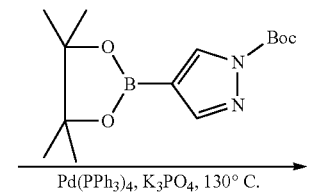

Pd(PPh₃)₄, K₃PO₄, 130° C.

-continued

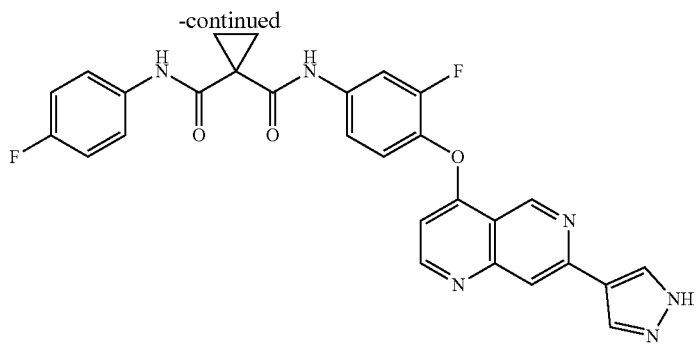

39S

The synthetic route was the same as that of compound 385, except that the starting materials were compound 15S and 1-tert-butoxycarbonyl-4-(4,4,5,5-tetramethyl-1,3,2-dioxaborolan-2-yl)-1H-pyrazole. $^1$H NMR (CDCl$_3$, 300 MHz): δ 9.61 (s, 1H), 8.64 (d, J=5.3 Hz, 1H), 8.14 (s, 1H), 7.93 (s, 1H), 7.69 (d, J=12.0 Hz, 1H), 7.41-7.31 (m, 2H), 7.31-7.20 (m, 2H), 7.20-7.06 (m, 1H), 6.91 (t, J=8.5 Hz, 2H), 6.46 (d, J=5.3 Hz, 1H), 1.69-1.49 (m, 4H).

Example 46 Synthesis of N-(3-fluoro-4-((7-(1-(methylsulfonyl)-1H-pyrazol-4-yl)-1,6-naphthyridin-4-yl)oxy)-phenyl)-N-(4-fluorophenyl)cyclopropyl-1,1-dicarboxamide (405)

Compound 39S was dissolved in tetrahydrofuran, 2 eq of DIEA was added with stirring at room temperature, and 1.1 eq of methanesulfonyl chloride was slowly added dropwise. The mixture was stirred at room temperature for 30 min, and the reaction was monitored by TLC. After the reaction was completed, the resultant was diluted with EA, washed with saturated Na$_2$CO$_3$ solution and saturated NaCl, dried over anhydrous Na$_2$SO$_4$ and concentrated under reduced pressure, and the residue was purified by column chromatography to give the title compound, yield, 68%. $^1$H NMR (CDCl$_3$, 300 MHz): δ 10.25 (s, 1H), 9.77 (s, 1H), 8.93-8.86 (m, 1H), 8.80 (d, J=6.0 Hz, 1H), 8.69 (s, 1H), 8.43 (s, 1H), 8.07 (s, 1H), 7.99 (s, 1H), 7.80 (d, J=11.7 Hz, 1H), 7.45-7.41 (m, 2H), 7.32-7.28 (m, 1H), 7.09-7.00 (m, 2H), 6.55 (d, J=5.5 Hz, 1H), 3.41 (s, 3H), 1.85-1.80 (m, 2H), 1.59-1.57 (m, 2H).

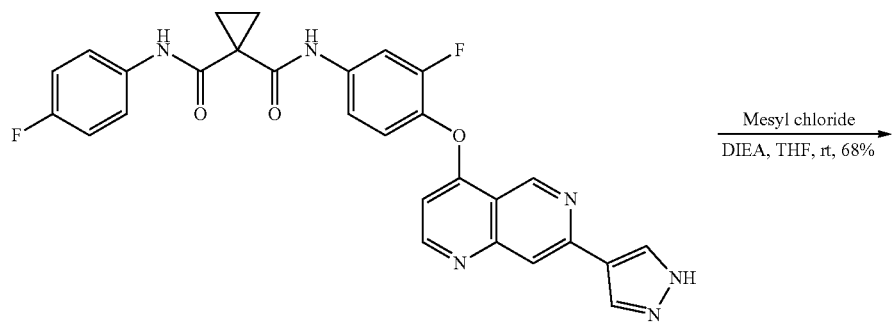

39S

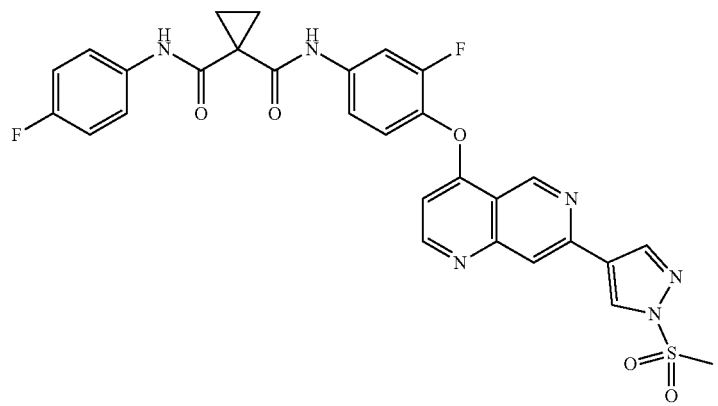

40S

Example 47 Synthesis of N-(3-fluoro-4-((7-(1-(iso-propyl)-1H-pyrazol-4-yl)-1,6-naphthyridin-4-yl)oxy)-phenyl)-N-(4-fluorophenyl)cyclopropyl-1,1-dicarboxamide (41S)

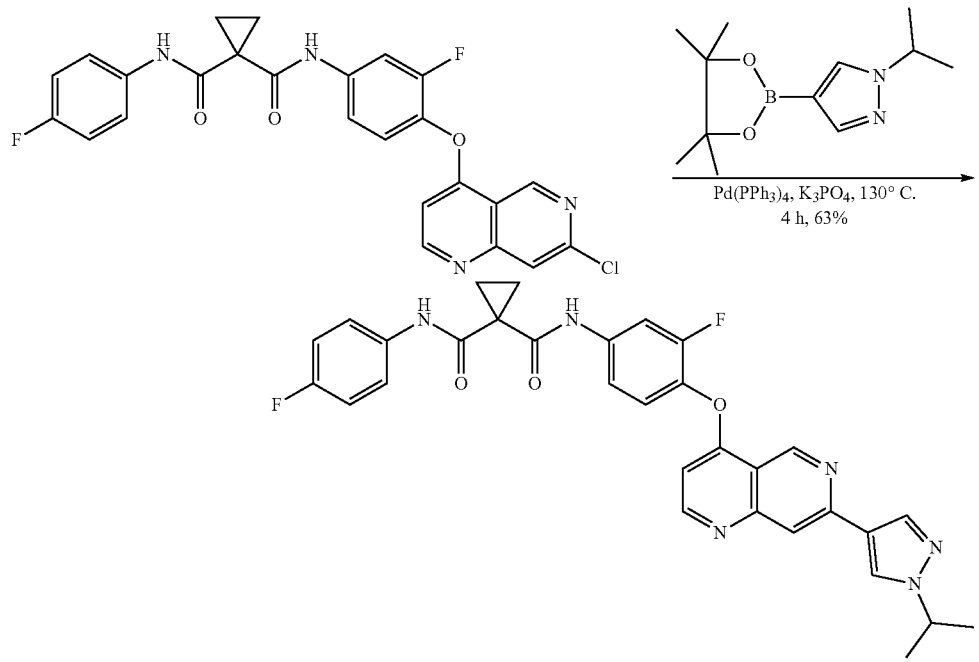

The synthetic route was the same as that of compound 385, except that the starting materials were compound 1S and 1-isopropyl-4-(4,4,5,5-tetramethyl-1,3,2-dioxaborolan-2-yl)-1H-pyrazole. $^1$H NMR (CDCl$_3$, 300 MHz): δ 10.22 (s, 1H), 9.75 (d, J=0.8 Hz, 1H), 8.78 (d, J=5.3 Hz, 1H), 8.18 (s, 2H), 8.13 (s, 1H), 8.02 (d, J=0.8 Hz, 1H), 7.83 (dd, J=12.1, 2.2 Hz, 1H), 7.50-7.43 (m, 2H), 7.33-7.31 (m, 1H), 7.30-7.29 (m, 1H), 7.14-7.05 (m, 2H), 6.50 (dd, J=5.3, 1.2 Hz, 1H), 4.61 (dt, J=13.4, 6.7 Hz, 1H), 1.85 (dd, J=7.9, 4.8 Hz, 2H), 1.65-1.60 (m, 8H).

Example 48 Synthesis of N-(3-fluoro-4-((7-(1-(piperidin-4-yl)-1H-pyrazol-4-yl)-1,6-naphthyridin-4-yl)oxy)-phenyl)-N-(4-fluorophenyl)cyclopropyl-1,1-dicarboxamide (42S)

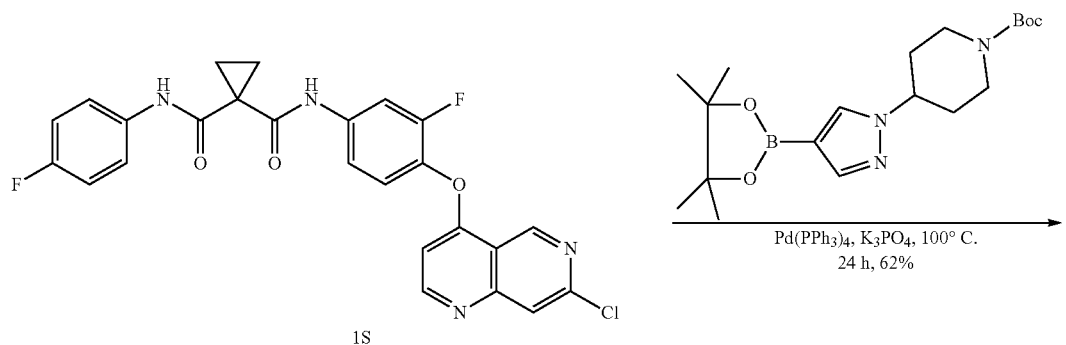

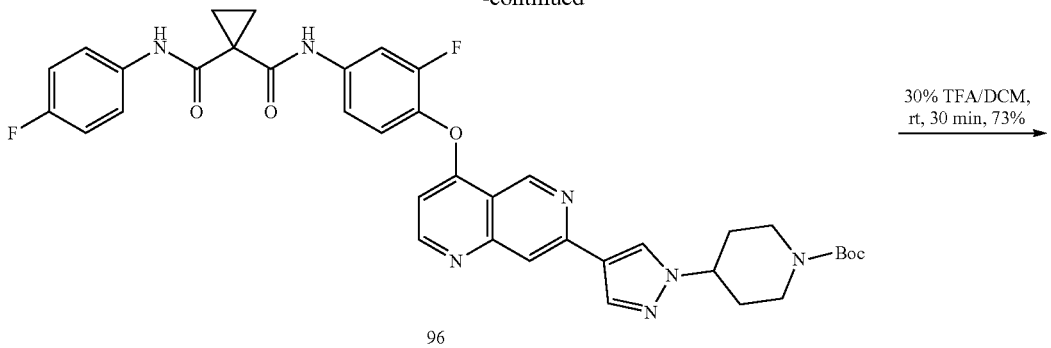

96

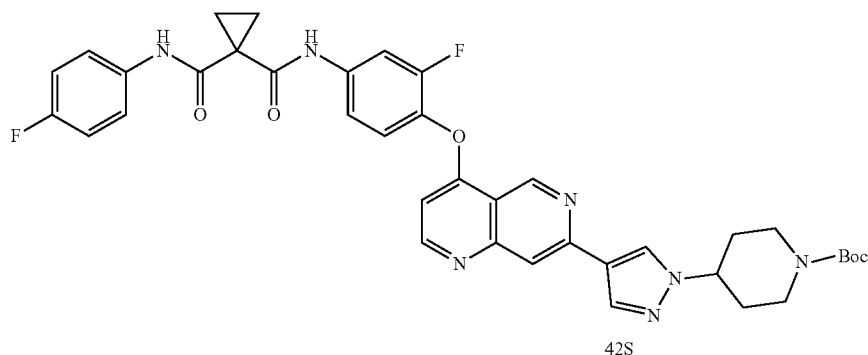

42S

Compound 96 was synthesized in the same manner as compound 385, except that the starting materials were compound 15 and tert-butyl 4-[4-(4,4,5,5-tetramethyl-1,3,2-dioxaborolan-2-yl)-1H-pyrazol-1-yl]piperidinyl-1-carboxylate. ¹H NMR (CDCl₃, 300 MHz): δ 10.21 (s, 1H), 9.70 (s, 1H), 8.74 (d, J=5.3 Hz, 1H), 8.27-8.07 (m, 3H), 7.97 (s, 1H), 7.79 (d, J=12.0 Hz, 1H), 7.43 (dd, J=9.0, 4.8 Hz, 2H), 7.35-7.26 (m, 2H), 7.05 (t, J=8.5 Hz, 1H), 6.46 (d, J=5.2 Hz, 1H), 4.46-4.18 (m, 3H), 3.03-2.82 (m, 2H), 2.30-2.12 (m, 2H), 2.07-1.89 (m, 2H), 1.88-1.76 (m, 2H), 1.66-1.55 (m, 2H), 1.47 (s, 9H).

Compound 96 was dissolved in DCM, 5% TFA was added thereto. The mixture was allowed to react at room temperature for 30 min with stirring, and the reaction was monitored by TLC. After the reaction was completed, the resultant was concentrated, and the residue was purified by column chromatography to give the product 42S. ¹H NMR (DMSO, 300 MHz): δ 9.72 (s, 1H), 8.82 (d, J=5.5 Hz, 1H), 8.45 (s, 1H), 8.25 (s, 1H), 8.08 (s, 1H), 7.88 (d, J=12.5 Hz, 1H), 7.56 (dd, J=9.1, 4.8 Hz, 2H), 7.51-7.35 (m, 2H), 7.07 (t, J=8.8 Hz, 2H), 6.69 (d, J=5.4 Hz, 1H), 4.73-4.60 (m, 1H), 3.68-3.50 (m, 2H), 3.27-3.18 (m, 2H), 2.48-2.22 (m, 4H), 1.69-1.54 (m, 4H).

Example 48 Synthesis of N-(3-fluoro-4-((7-(1-(1-isopropylpiperidin-4-yl)-1H-pyrazol-4-yl)-1,6-naphthyridin-4-yl)oxy)-phenyl)-N-(4-fluorophenyl)cyclopropyl-1,1-dicarboxamide (43S)

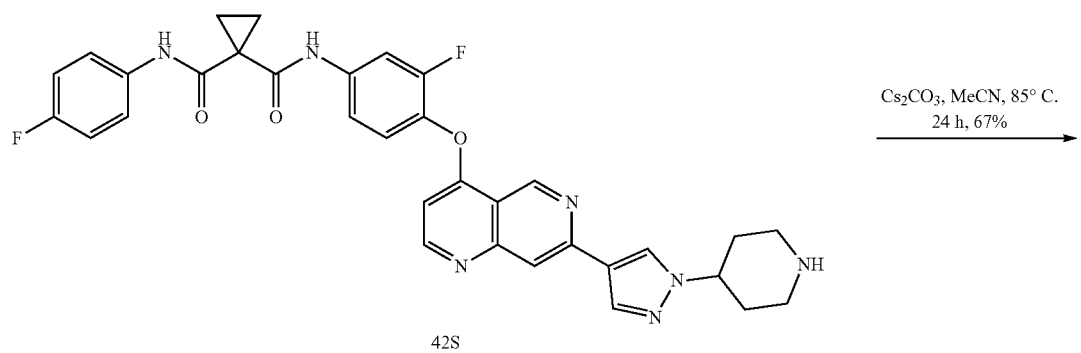

42S

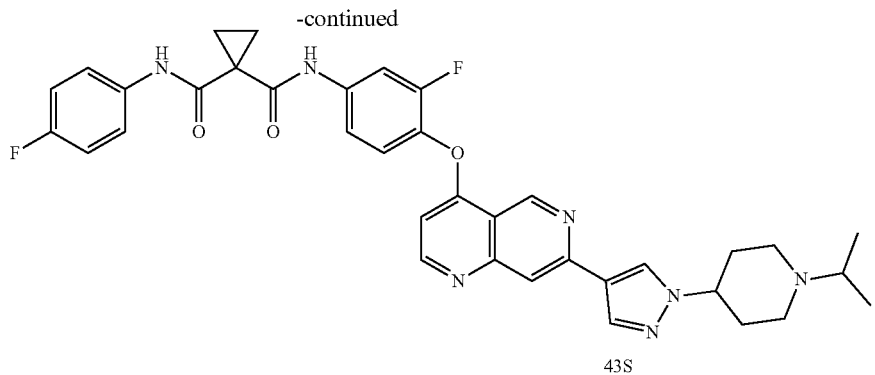

Compound 42S was dissolved in acetonitrile, 2 eq of cesium carbonate was added with stirring at room temperature, and then 2 eq of 2-iodopropane was added dropwise. The mixture was warmed to 85° C., and the reaction was monitored by TLC. After the reaction was completed, the resultant was diluted with EA, washed with saturated Na$_2$CO$_3$ solution and saturated NaCl, dried over anhydrous Na$_2$SO$_4$ and concentrated under reduced pressure, and the residue was purified by column chromatography to give the title compound, yield, 67%. $^1$H NMR (CD$_3$OD, 300 MHz): δ 9.64 (s, 1H), 8.64 (d, J=5.4 Hz, 1H), 8.44 (s, 1H), 8.23 (s, 1H), 8.04 (s, 1H), 7.44-7.36 (m, 2H), 7.18 (t, J=8.7 Hz, 2H), 7.03-6.96 (m, 1H), 6.89-6.81 (m, 2H), 6.25 (d, J=5.2 Hz, 1H), 5.29-5.19 (m, 1H), 4.73-4.59 (m, 1H), 3.67-3.56 (m, 4H), 2.46-2.41 (m, 4H), 1.49 (m, 2H), 1.42-1.39 (m, 8H).

Example 49 Synthesis of N-(4-((7-(3,5-dimethyl-isoxazol-4-yl)-1,6-naphthyridin-4-yl)oxy)-3-fluoro-phenyl)-N-(4-fluorophenyl)cyclopropyl-1,1-dicar-boxamide (45S)

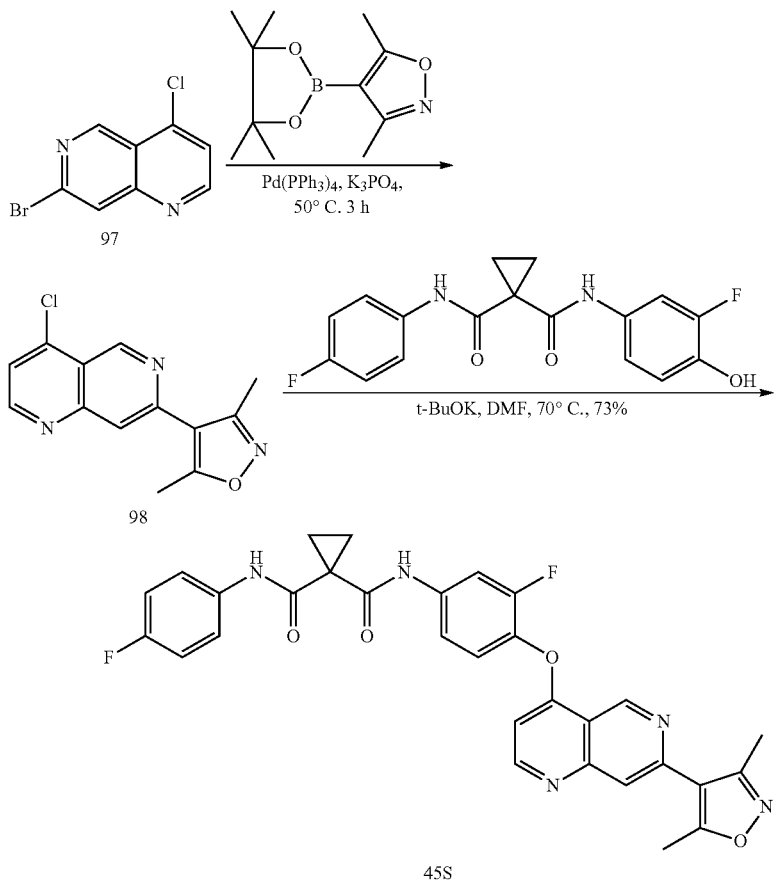

7-bromo-4-chloro-1,6-naphthyridine (97)

Compound 97 was synthesized in the same manner as compound 53, except that the starting material was 2,6-dibromo-4-aminopyridine. $^1$H NMR (300 MHz, CDCl$_3$) δ

9.40 (s, 1H), 8.93 (d, J=4.7 Hz, 1H), 8.16 (s, 1H), 7.57 (d, J=4.7 Hz, 1H). 4-(4-chloro-1,6-naphthyridin-7-yl)-3,5-dimethylisoxazole (98) Compound 97 was synthesized in the same manner as compound 38S, except that the starting material was 3,5-dimethylisoxazole-4-boronic acid pinacol ester, and the reaction temperature was 50° C. $^1$H NMR (400 MHz, DMSO) δ 9.68 (s, 1H), 9.09 (d, J=4.8 Hz, 1H), 8.11 (s, 1H), 7.92 (d, J=4.7 Hz, 1H), 2.67 (s, 3H), 2.47 (s, 3H).

N-(4-((7-(3,5-dimethylisoxazol-4-yl)-1,6-naphthyridin-4-yl)oxy)-3-fluorophenyl)-N-(4-fluorophenyl)cyclopropyl-1,1-dicarboxamide (45S)

Compound 45S was synthesized in the same manner as compound 1S, except that the starting materials were compound 98 and compound 26. $^1$H NMR (300 MHz, CDCl$_3$) δ 10.28 (s, 1H), 9.83 (s, 1H), 8.81 (d, J=5.3 Hz, 1H), 7.99 (s, 1H), 7.88 (s, 1H), 7.81 (d, J=12.4 Hz, 1H), 7.53-7.37 (m, 2H), 7.28 (m, 2H), 7.06 (t, J=8.6 Hz, 2H), 6.56 (d, J=5.2 Hz, 1H), 2.67 (s, 3H), 2.52 (s, 3H), 1.83 (m, 2H), 1.60 (m, 2H).

Example 50 Synthesis of N-(3-fluoro-4-((7-(pyridin-4-yl)-1,6-naphthyridin-4-yl)oxy)-phenyl)-N-(4-fluorophenyl)cyclopropyl-1,1-dicarboxamide (46S)

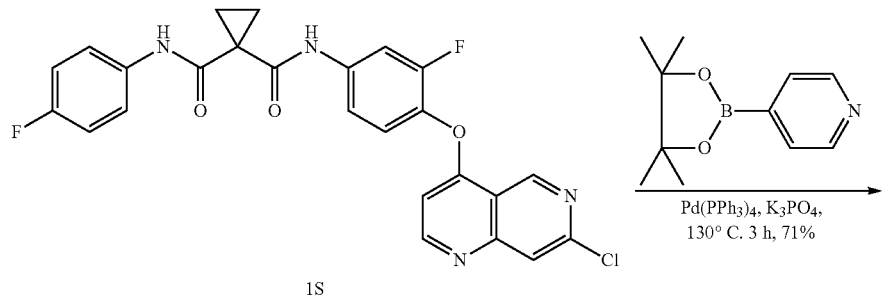

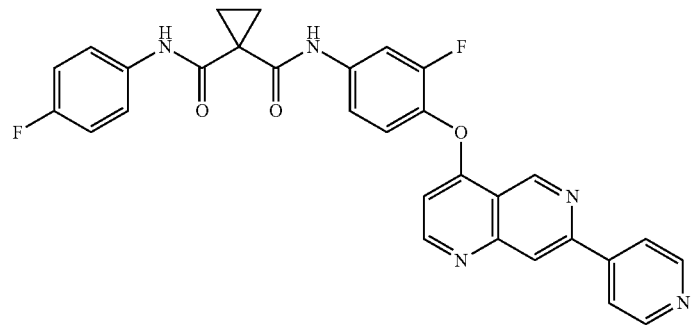

Compound 46S was synthesized in the same manner as compound 38S, except that the starting materials were compound 1S and 4-pyridine boronic acid pinacol ester. 1H NMR (400 MHz, DMSO): δ 10.39 (s, 1H), 9.92 (s, 1H), 8.89 (d, J=5.3 Hz, 1H), 8.82 (s, 2H), 8.44 (s, 1H), 8.14 (d, J=4.5 Hz, 2H), 7.86 (dd, J=12.1, 2.2 Hz, 1H), 7.54-7.43 (m, 2H), 7.39-7.30 (m, 2H), 7.17-7.04 (m, 2H), 6.65 (d, J=5.2 Hz, 1H), 1.93-1.87 (m, 2H), 1.70-1.60 (m, 2H).

Example 51 Synthesis of N-(3-fluoro-4-((7-(pyrimidin-5-yl)-1,6-naphthyridin-4-yl)oxy)-phenyl)-N-(4-fluorophenyl)cyclo Propyl-1,1-dicarboxamide (47S)

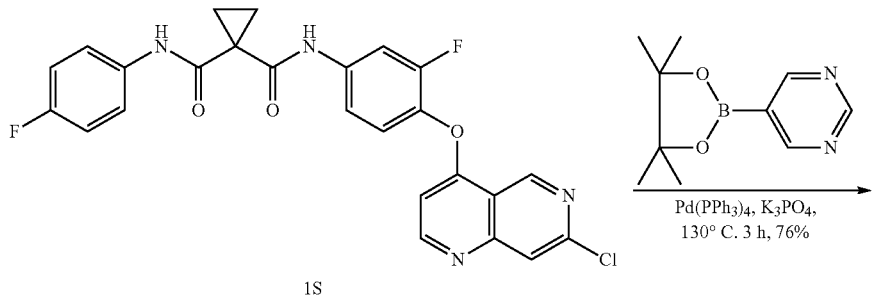

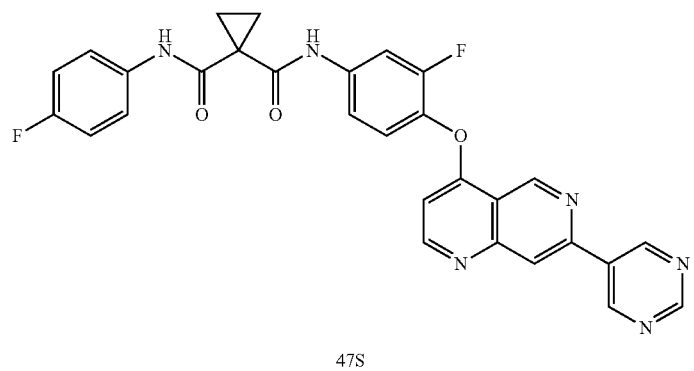

Compound 47S was synthesized in the same manner as compound 38S, except that the starting materials were compound 1S and pyrimidin-5-ylboronic acid pinacol ester. $^1$H NMR (400 MHz, DMSO): δ 10.46 (s, 1H), 10.03 (s, 1H), 9.88 (s, 1H), 9.67 (s, 2H), 9.32 (s, 1H), 8.97 (d, J=5.3 Hz, 1H), 8.75 (s, 1H), 7.96 (d, J=13.5 Hz, 1H), 7.65 (dd, J=9.1, 5.1 Hz, 2H), 7.61-7.51 (m, 2H), 7.17 (t, J=8.9 Hz, 2H), 6.79 (d, J=5.4 Hz, 1H), 1.53-1.44 (m, 4H).

Example 52 Synthesis of N-(3-fluoro-4-((7-(4-nitrophenyl)-1,6-naphthyridin-4-yl)oxy)-phenyl)-N-(4-fluorophenyl)cyclo Propyl-1,1-dicarboxamide (48S)

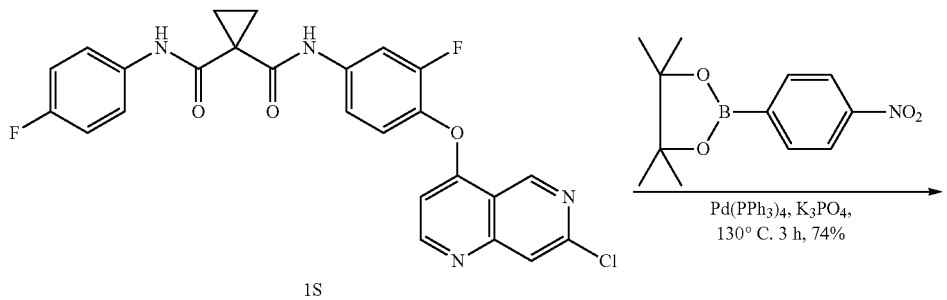

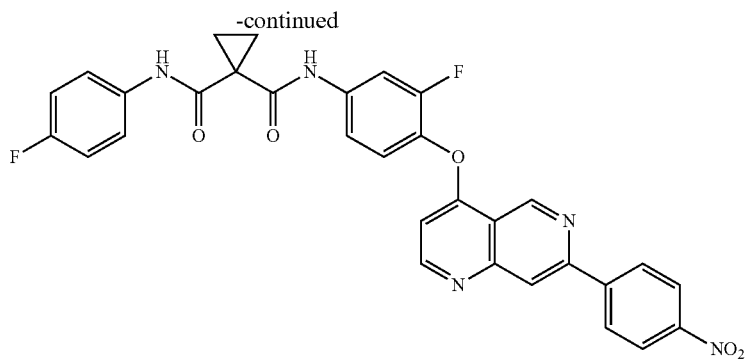

48S

Compound 48S was synthesized in the same manner as compound 385, except that the starting materials were compound 1S and 4-nitrophenylboronic acid pinacol ester. $^1$H NMR (400 MHz, DMSO): δ 10.47 (s, 1H), 10.03 (s, 1H), 9.88 (s, 1H), 8.97 (d, J=5.3 Hz, 1H), 8.69 (s, 1H), 8.62 (s, 1H), 8.60 (s, 1H), 8.41 (s, 1H), 8.39 (s, 1H), 7.97 (d, J=12.7 Hz, 1H), 7.65 (dd, J=9.1, 5.1 Hz, 2H), 7.59-7.54 (m, 2H), 7.17 (t, J=8.9 Hz, 2H), 6.79 (d, J=4.8 Hz, 1H), 1.53-1.44 (m, 4H).

Example 52 Synthesis of N-(3-fluoro-4-((7-(3,4-difluorophenyl)-1,6-naphthyridin-4-yl)oxy)-phenyl)-N-(4-fluorophenyl) Cyclopropyl-1,1-dicarboxamide (49S)

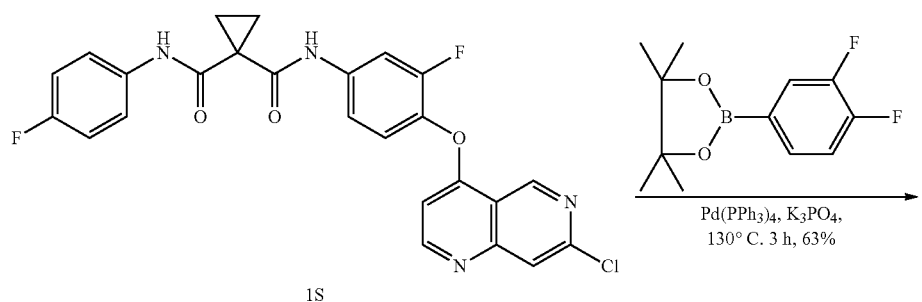

1S

Pd(PPh$_3$)$_4$, K$_3$PO$_4$, 130° C. 3 h, 63%

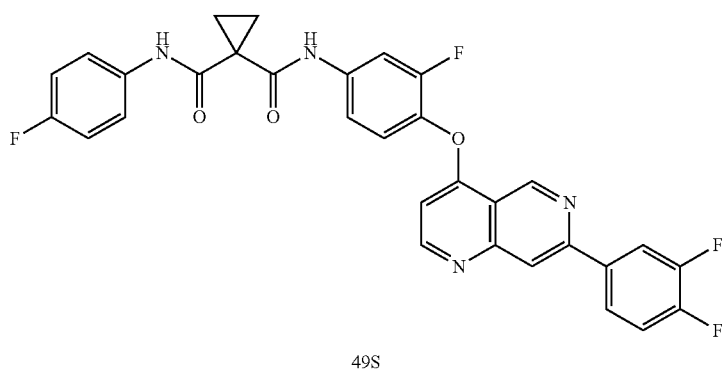

49S

Compound 49S was synthesized in the same manner as compound 385, except that the starting materials were compound 1S and 3,4-difluorophenylboronic acid pinacol ester. $^1$H NMR (400 MHz, DMSO): δ 10.46 (s, 1H), 10.03 (s, 1H), 9.81 (s, 1H), 8.93 (d, J=6.4 Hz, 1H), 8.58 (s, 1H), 8.44-8.34 (m, 1H), 8.23 (s, 1H), 7.96 (d, J=13.4 Hz, 1H), 7.73-7.60 (m, 5H), 7.60-7.48 (m, 3H), 7.17 (t, J=8.7 Hz, 2H), 6.74 (d, J=6.9 Hz, 1H), 1.55-1.41 (m, 4H).

Example 53 Synthesis of N-(3-fluoro-4-((7-(4-morpholinophenyl)-1,6-naphthyridin-4-yl)oxy)-phenyl)-N-(4-fluorophenyl)cyclopropyl-1,1-dicarboxamide (50S)

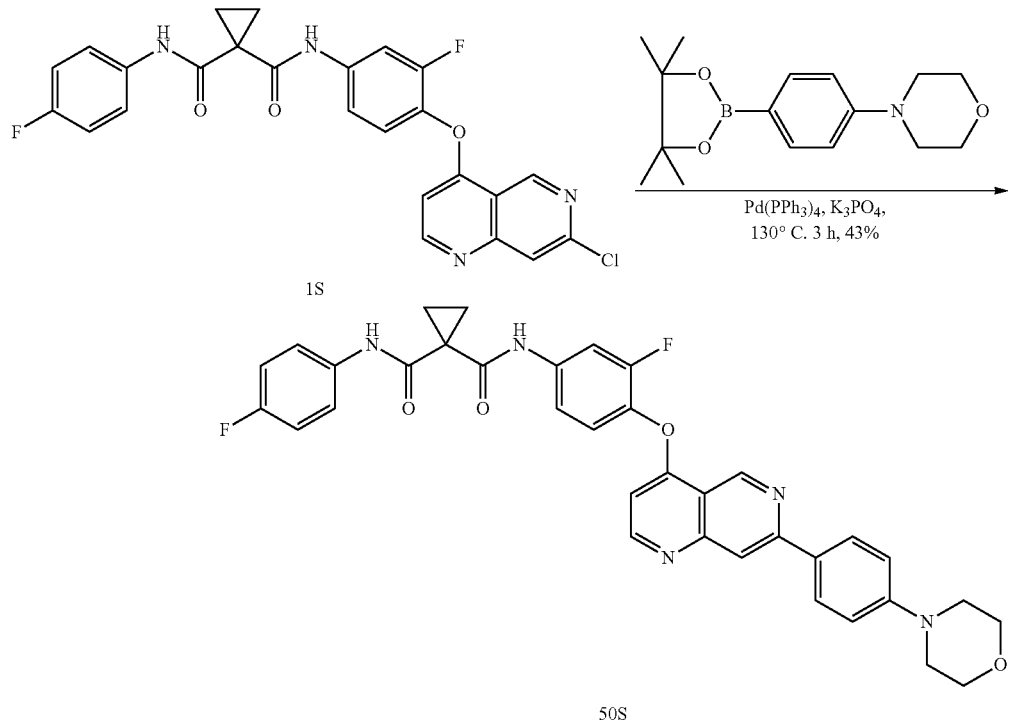

Compound 50S was synthesized in the same manner as compound 38S, except that the starting materials were compound 15S and 4-morpholinophenylboronic acid pinacol ester. $^1$H NMR (400 MHz, DMSO): δ 10.45 (s, 1H), 10.03 (s, 1H), 9.74 (s, 1H), 8.86 (d, J=5.0 Hz, 1H), 8.31 (s, 1H), 8.20 (d, J=8.5 Hz, 2H), 7.95 (d, J=12.9 Hz, 1H), 7.65 (dd, J=9.0, 5.0 Hz, 2H), 7.58-7.50 (m, 2H), 7.16 (t, J=8.9 Hz, 2H), 7.10 (d, J=8.5 Hz, 2H), 6.64 (d, J=4.7 Hz, 1H), 3.86-3.72 (m, 4H), 3.31-3.19 (m, 4H), 1.54-1.42 (m, 4H).

Example 54 Synthesis of N-(4-((7-(isoxazol-4-yl)-1,6-naphthyridin-4-yl)oxy)-3-fluorophenyl)-N-(4-fluorophenyl)cyclopropyl-1,1-dicarboxamide (51S)

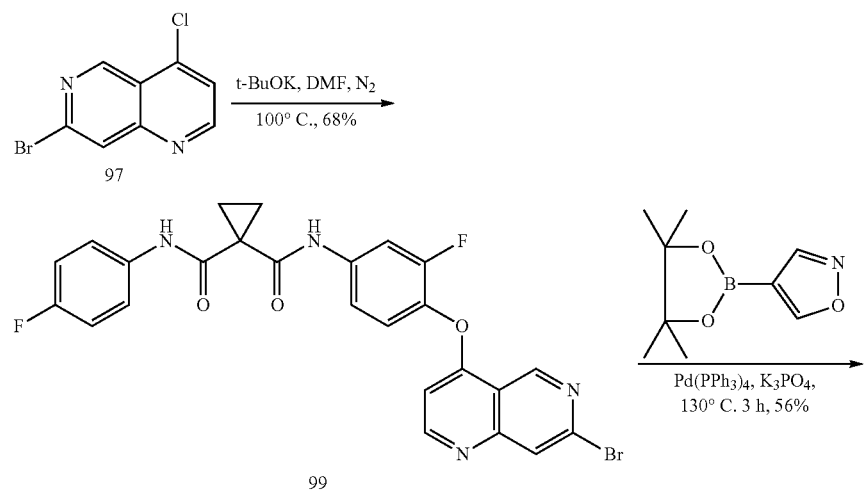

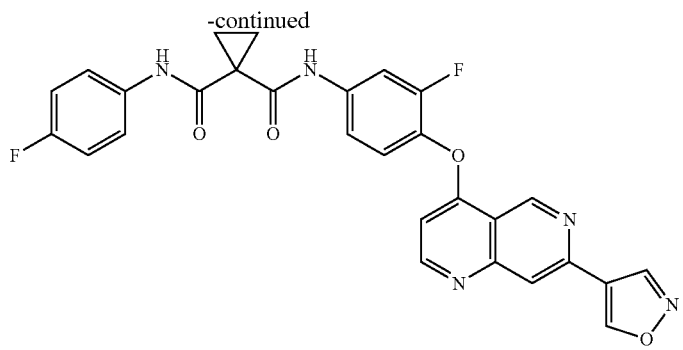

51S

N-(4-((7-bromo-1,6-naphthyridin-4-yl)oxy)-3-fluorophenyl)-N-(4-fluorophenyl)cycloprop yl-1,1-dicarboxamide (99)

Compound 99 was synthesized in the same manner as compound 1S, except that the material required was 4-chloro-7-bromo-1,6-naphthyridine. $^1$H NMR (CDCl$_3$, 300 MHz): δ 10.32 (s, 1H), 9.56 (s, 1H), 8.81 (d, J=5.2 Hz, 1H), 8.14 (s, 1H), 8.01 (s, 1H), 7.82 (d, J=11.6 Hz, 1H), 7.54-7.39 (m, 2H), 7.35-7.27 (m, 1H), 7.07 (t, J=8.4 Hz, 2H), 6.58 (d, J=5.1 Hz, 1H), 1.91-1.79 (m, 2H), 1.35-1.17 (m, 2H).

N-(4-((7-(isoxazol-4-yl)-1,6-naphthyridin-4-yl)oxy)-3-fluorophenyl)-N-(4-fluorophenyl)cyclopropyl-1,1-dicarboxamide (515)

Compound 515 was synthesized in the same manner as compound 385, except that the starting materials were compound 99 and 4-isoxaboronic acid pinacol ester. $^1$H NMR (DMSO, 300 MHz): δ 10.43 (s, 1H), 9.99 (s, 1H), 9.74 (s, 2H), 9.42 (s, 1H), 8.89 (d, J=5.3 Hz, 1H), 8.40 (s, 1H), 7.93 (d, J=12.1 Hz, 1H), 7.65-7.59 (m, 2H), 7.58-7.49 (m, 2H), 7.14 (t, J=8.9 Hz, 2H), 6.69 (d, J=5.4 Hz, 1H), 1.50-1.41 (m, 4H).

Example 55 Synthesis of N-(4-((7-(isothiazol-3-yl)-1,6-naphthyridin-4-yl)oxy)-3-fluorophenyl)-N-(4-fluorophenyl)cyclopropyl-1,1-dicarboxamide (525)

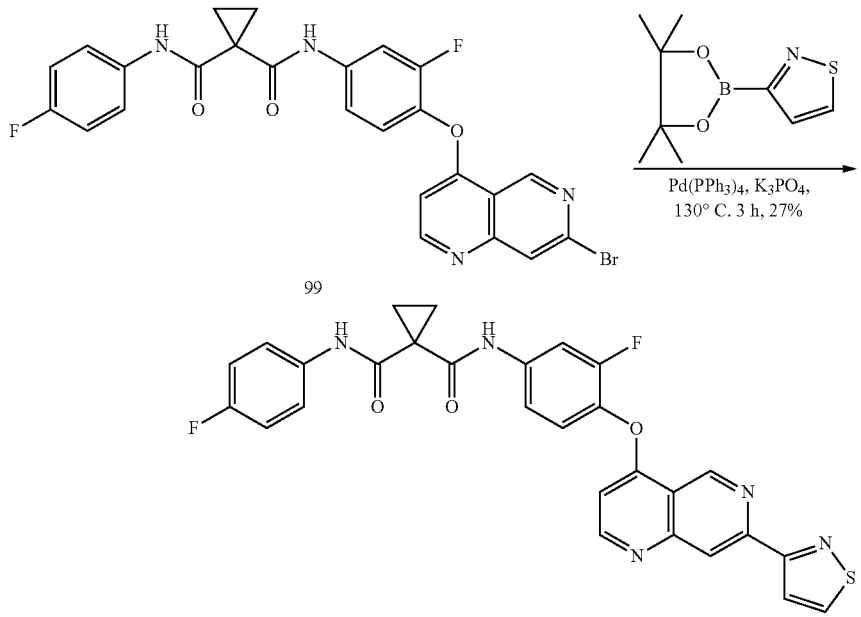

Compound 525 was synthesized in the same manner as compound 385, except that the starting materials were compound 99 and 3-isothiazole boronic acid pinacol ester. $^1$H NMR (DMSO, 300 MHz): δ 10.46 (s, 1H), 10.03 (s, 1H), 9.77 (s, 1H), 8.95 (d, J=5.3 Hz, 1H), 8.72 (d, J=1.7 Hz, 1H), 8.66 (s, 1H), 8.32 (d, J=1.7 Hz, 1H), 7.96 (d, J=13.7 Hz, 1H), 7.66-7.62 (m, 2H), 7.58-7.52 (m, 2H), 7.17 (t, J=8.9 Hz, 2H), 6.77 (d, J=5.0 Hz, 1H), 1.48 (d, J=3.9 Hz, 4H).

Example 56 Synthesis of N-(3-fluoro-4-((7-(1-methyl-1H-pyrazol-4-yl)-1,6-naphthyridin-4-yl)oxy)phenyl)-1-(4-fluorophenyl)-2-oxo-1,2-dihydropyridine-3-carboxamide (535)

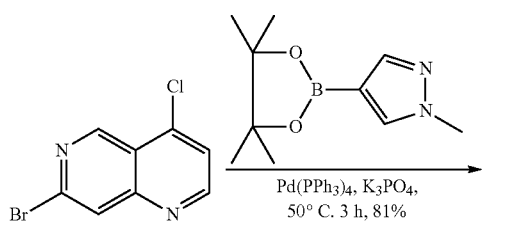

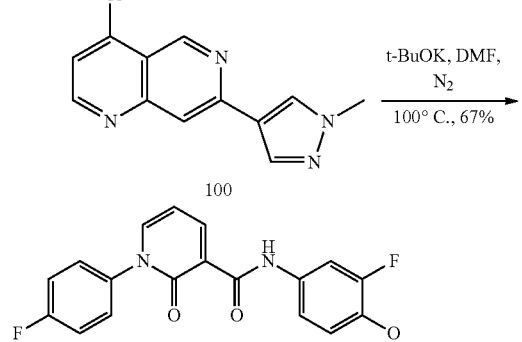

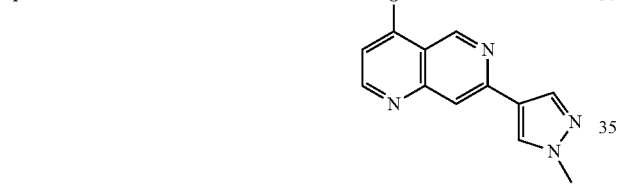

53S

Compound 535 was synthesized in the same manner as compound 45S, except that the material required was 4-chloro-7-bromo-1,6-naphthyridine. ¹H NMR (300 MHz, CDCl₃) δ 9.64 (s, 1H), 9.10 (d, J=15.0 Hz, 1H), 8.38 (d, J=21.8 Hz, 1H), 8.30 (s, 1H), 8.22 (s, 1H), 7.96 (d, J=3.1 Hz, 1H), 7.77 (d, J=3.1 Hz, 1H), 7.61-7.57 (m, 1H), 7.58-7.55 (m, 1H), 7.56-7.52 (m, 1H), 7.45-7.36 (m, 2H), 7.25 (d, J=15.0 Hz, 1H), 7.15 (dd, J=15.0, 3.0 Hz, 1H), 6.86 (dd, J=15.0, 10.1 Hz, 1H), 5.95 (d, J=21.8 Hz, 1H), 3.94 (s, 3H).

Example 57 Synthesis of N-(3-fluoro-4-((7-(1-methyl-1H-pyrazol-4-yl)-1,6-naphthyridin-4-yl)oxy)phenyl)-5-(4-fluorophenyl)-4-oxo-1,4-dihydropyridine-3-carboxamide (54S)

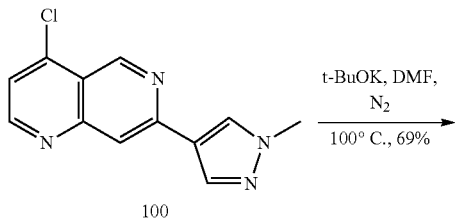

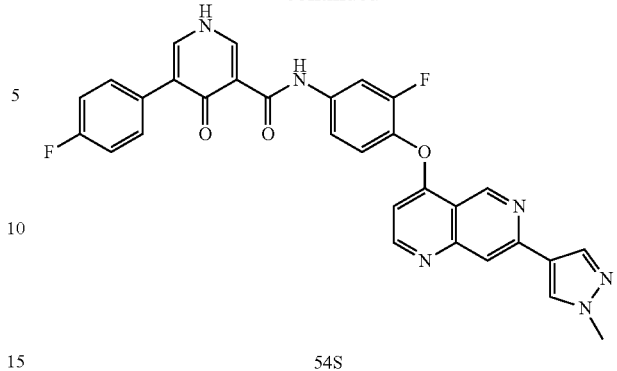

54S

Compound 53S was synthesized in the same manner as compound 45S, except that the material required was 4-chloro-7-bromo-1,6-naphthyridine. ¹H NMR (300 MHz, CDCl₃) δ 9.64 (s, 1H), 9.49 (s, 1H), 9.10 (d, J=15.0 Hz, 1H), 8.30 (s, 1H), 7.96 (d, J=3.1 Hz, 1H), 7.93 (s, 1H), 7.71 (d, J=2.9 Hz, 1H), 7.58 (dd, J=16.0, 3.0 Hz, 1H), 7.32-7.24 (m, 3H), 7.23 (s, 2H), 7.15 (dd, J=15.0, 3.0 Hz, 1H), 6.86 (dd, J=15.0, 10.1 Hz, 1H), 3.94 (s, 3H).

Example 58 Synthesis of N-(4-((3-chloropyrido[2,3-b]pyrazin-8-yl)oxy)-3-fluorophenyl)-N-(4-fluorophenyl)cyclopropyl-1,1-dicarboxamide (555)

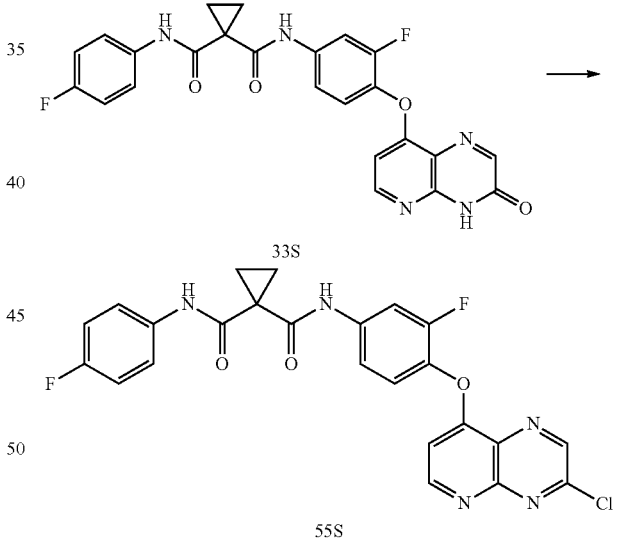

200 mg of compound 335 was dissolved in acetonitrile, 2 eq of DIEA was added thereto, and 0.5 ml of phosphorus oxychloride was added dropwise at room temperature. The mixture was stirred for reaction, and the reaction was monitored by TLC. After the reaction was completed, the resultant was extracted with ethyl acetate, washed with sodium bicarbonate and saturated brine successively, dried over anhydrous sodium sulfate, concentrated and purified by column chromatography to give the final product 55S, yield 80%. ¹H NMR (400 MHz, DMSO): δ 10.43 (s, 1H), 10.01 (s, 1H), 9.14 (s, 1H), 8.96 (d, J=5.1 Hz, 1H), 7.93 (d, J=13.0 Hz, 1H), 7.64 (dd, J=8.8, 5.1 Hz, 2H), 7.54 (d, J=9.1 Hz, 1H), 7.45 (t, J=8.9 Hz, 1H), 7.16 (t, J=8.9 Hz, 2H), 7.03 (d, J=5.2 Hz, 1H), 1.58-1.40 (m, 4H);

Example 59 Synthesis of N-(4-((2-chloropyrido[2,3-b]pyrazin-8-yl)oxy)-3-fluorophenyl)-N-(4-fluorophenyl)cyclopropyl-1,1-dicarboxamide (56S)

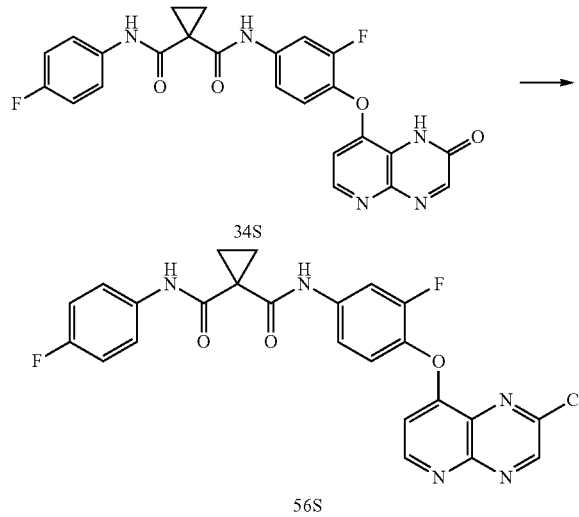

The reaction was operated in the same manner as that for compound 55S, except that the raw material was 34S, yield 83%. ¹H NMR (400 MHz, DMSO): δ 10.44 (s, 1H), 10.01 (s, 1H), 9.24 (s, 1H), 8.96 (d, J=5.3 Hz, 1H), 7.94 (dd, J=13.3, 2.2 Hz, 1H), 7.64 (dd, J=9.1, 5.1 Hz, 2H), 7.54 (d, J=8.9 Hz, 1H), 7.46 (t, J=8.9 Hz, 1H), 7.16 (t, J=8.9 Hz, 2H), 7.03 (d, J=5.2 Hz, 1H), 1.51-1.45 (m, 4H);

Example 60 Synthesis of N-(4-((3-morpholinylpyrido[2,3-b]pyrazin-8-yl)oxy)-3-fluorophenyl)-N-(4-fluorophenyl)cyclopropyl-1,1-dicarboxamide (57S)

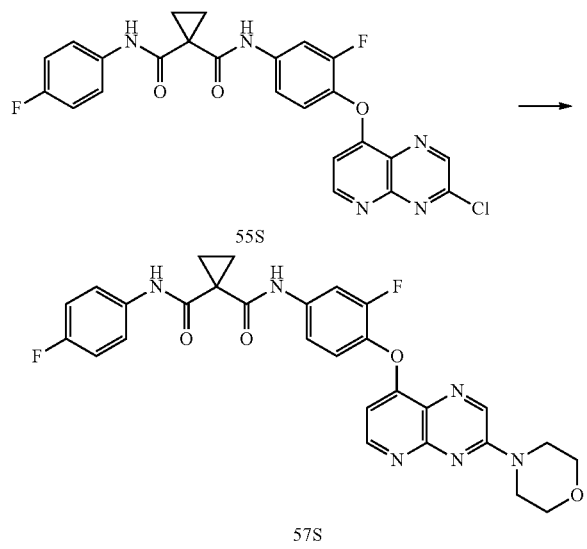

20 mg of compound 55S was dissolved in tetrahydrofuran at room temperature, and 0.5 mL of morpholine was added therein. The mixture was stirred for reaction at room temperature, and the reaction was monitored by TLC. After the reaction was completed, the resultant was extracted with ethyl acetate, washed with sodium bicarbonate and saturated brine, dried over anhydrous sodium sulfate, concentrated and purified by column chromatography to give the title compound, a light yellow solid product, yield 68%. ¹H NMR (400 MHz, DMSO): δ 10.38 (s, 1H), 10.01 (s, 1H), 8.86 (s, 1H), 8.60 (d, J=5.4 Hz, 1H), 7.88 (d, J=13.1 Hz, 1H), 7.64 (dd, J=9.0, 5.0 Hz, 2H), 7.49 (d, J=10.2 Hz, 1H), 7.37 (t, J=9.0 Hz, 1H), 7.16 (t, J=8.9 Hz, 2H), 6.55 (d, J=5.4 Hz, 1H), 3.84 (d, J=4.5 Hz, 4H), 3.77 (d, J=4.6 Hz, 4H), 1.47 (m, J=3.4 Hz, 4H);

Example 61 Synthesis of N-(4-((2-morpholinopyrido[2,3-b]pyrazin-8-yl)oxy)-3-fluorophenyl)-N-(4-fluorophenyl)cyclopropyl-1,1-dicarboxamide (58S)

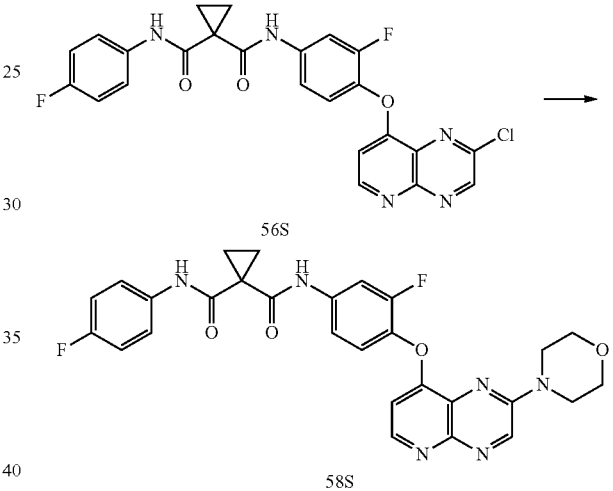

The reaction was operated in the same manner as that for compound 57S, except that the raw material was 56S, yield 74%. ¹H NMR (400 MHz, DMSO): δ10.34 (s, 1H), 10.02 (s, 1H), 9.00 (s, 1H), 8.51 (d, J=5.1 Hz, 1H), 7.86 (dd, J=13.3, 2.2 Hz, 1H), 7.64 (dd, J=9.1, 5.0 Hz, 2H), 7.46 (d, J=8.7 Hz, 1H), 7.32 (t, J=9.0 Hz, 1H), 7.22-7.11 (m, 2H), 6.86 (d, J=5.1 Hz, 1H), 3.8-3.63 (m, 8H), 1.52-1.42 (m, 4H);

Example 62 Synthesis of N-(3-fluoro-4-((3-(4-methylpiperazin-1-yl)pyrido[2,3-b]pyrazin-8-yl)oxy)phenyl)-N-(4-fluorophenyl)cyclopropyl-1,1-dicarboxamide (59S)

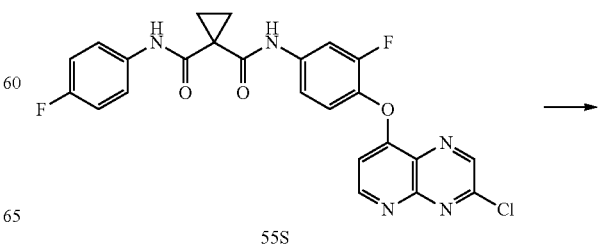

The reaction was operated in the same manner as that for compound 57S, except that the raw materials were compound 55S and N-methylpiperazine, yield 44%. ¹H NMR (400 MHz, DMSO): δ10.39 (s, 1H), 10.02 (s, 1H), 8.87 (s, 1H), 8.58 (d, J=5.3 Hz, 1H), 7.89 (d, J=14.8 Hz, 1H), 7.73-7.57 (m, 2H), 7.49 (d, J=10.1 Hz, 1H), 7.36 (t, J=9.0 Hz, 1H), 7.16 (t, J=8.8 Hz, 2H), 6.53 (d, J=5.3 Hz, 1H), 3.90-3.83 (m, 4H), 2.50-2.43 (m, 4H), 2.26 (s, 3H), 1.51-1.44 (m, 4H);

Example 63 Synthesis of N-(3-fluoro-4-((3-(2-morpholinoethoxy)pyrido[2,3-b]pyrazin-8-yl)oxy)phenyl)-N-(4-fluorophenyl)cyclopropyl-1,1-dicarboxamide (60S)

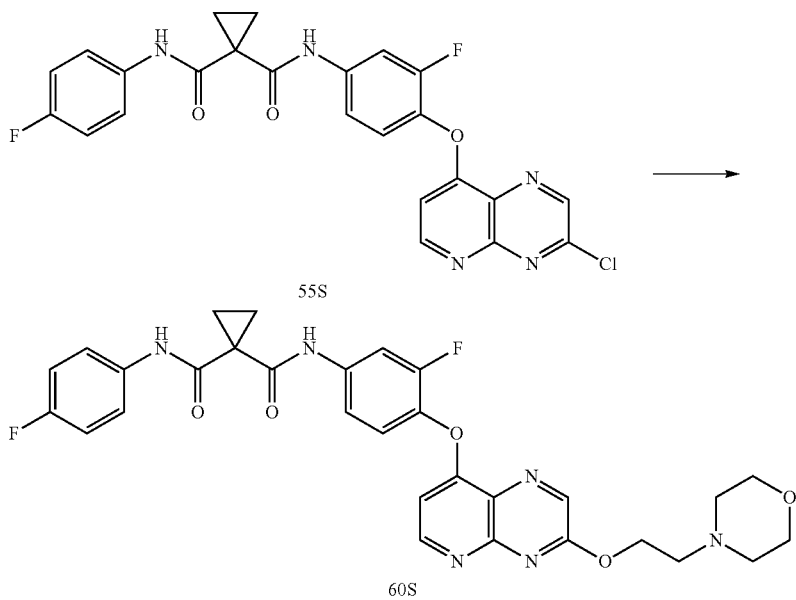

4 eq of 2-morpholine ethanol was added to the tetrahydrofuran solution at room temperature, and 1.5 eq of potassium tert-butoxide was then added. After the mixture was stirred for 10 min, 1 eq of compound 55S was added and then the mixture was stirred for reaction, and the reaction was monitored by TLC. After the reaction was completed, the resultant was extracted with EA, washed with saturated sodium bicarbonate and saturated brine, dried over anhydrous sodium sulfate, and purified by column chromatography to give the product, a light yellow solid, yield 62%. ¹H NMR (400 MHz, DMSO): δ10.41 (s, 1H), 10.01 (s, 1H), 8.76 (d, J=5.5 Hz, 1H), 8.71 (s, 1H), 7.91 (d, J=11.9 Hz, 1H), 7.64 (dd, J=8.8, 5.0 Hz, 2H), 7.51 (d, J=8.6 Hz, 1H), 7.42 (t, J=9.0 Hz, 1H), 7.16 (t, J=9.0 Hz, 2H), 6.79 (d, J=5.2 Hz, 1H), 4.63 (t, J=5.6 Hz, 2H), 3.68-3.49 (m, 4H), 2.81 (t, J=7.3 Hz, 2H), 2.56-2.51 (m, 4H), 1.56-1.39 (m, 4H);

Example 64 Synthesis of N-(3-fluoro-4-((3-(3-morpholinopropoxy)pyrido[2,3-b]pyrazin-8-yl)oxy)phenyl)-N-(4-fluorophenyl)cyclopropyl-1,1-dicarboxamide (61S)

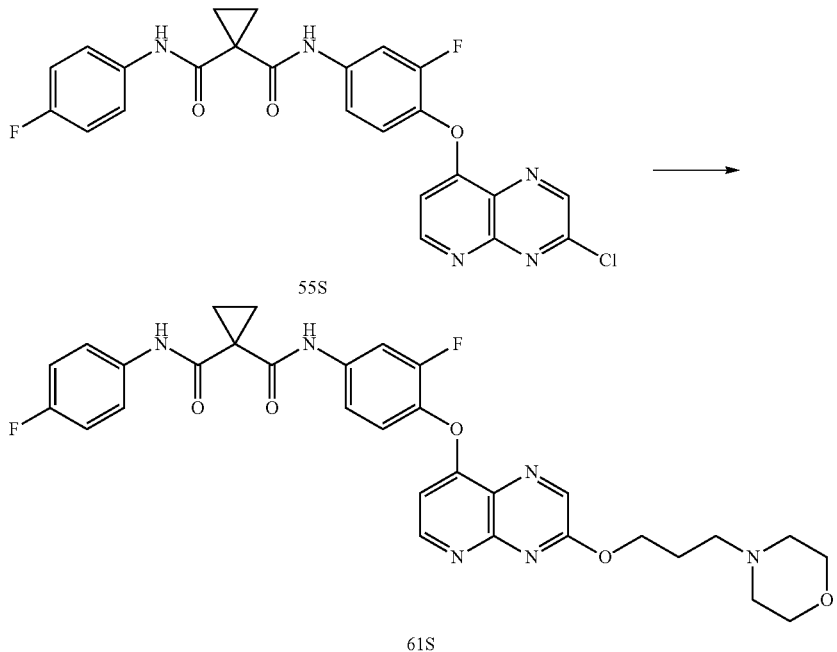

The reaction was operated in the same manner as that for compound 57S, except that the raw materials were compound 55S and 3-morpholine propanol, yield 42%. ¹H NMR (DMSO, 400 MHz): δ10.42 (s, 1H), 10.02 (s, 1H), 8.75 (d, J=5.4 Hz, 1H), 7.93 (d, J=13.4 Hz, 1H), 7.69-7.61 (m, 2H), 7.54 (d, J=8.9 Hz, 1H), 7.45 (t, J=8.9 Hz, 1H), 7.16 (t, J=8.9 Hz, 2H), 6.77 (d, J=5.3 Hz, 1H), 4.58 (t, J=6.4 Hz, 2H), 3.66-3.57 (m, 4H), 2.70-2.53 (m, 4H), 2.49-2.42 (m, 2H), 2.11-1.97 (m, 2H), 1.54-1.41 (m, 4H).

Example 65 Synthesis of N-(3-fluoro-4-((3-((3-(morpholinopropyl)amino)pyrido[2,3-b]pyrazin-8-yl)oxy)phenyl)-N-(4-fluorophenyl)cyclopropyl-1,1-dicarboxamide (62S)

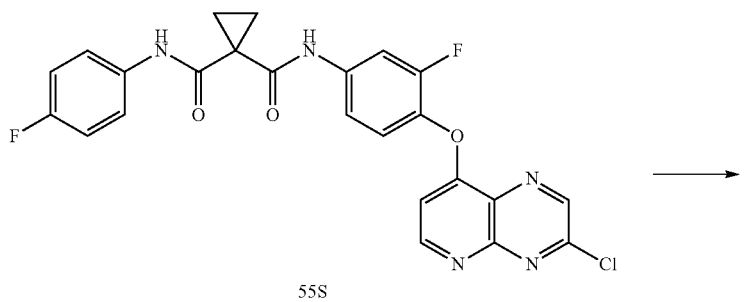

-continued

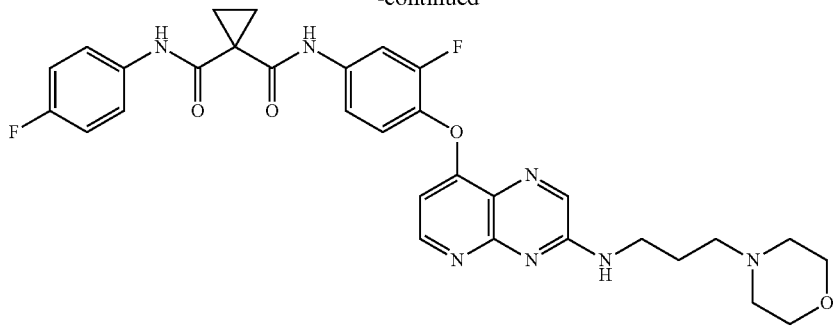

62S 20 mg of compound 55S and 100 µL of N-(3-aminopropyl)morpholine were dissolved in a tetrahydrofuran solution. The mixture was stirred for reaction under an oil bath at 60° C., and the reaction was monitored by TLC. After the reaction was completed, the resultant was extracted with EA, washed with saturated sodium bicarbonate and saturated brine, dried over anhydrous sodium sulfate, and purified by column chromatography to give the product, a white solid, yield 62%. 1H NMR (400 MHz, DMSO): δ10.37 (s, 1H), 10.01 (s, 1H), 8.50 (d, J=5.4 Hz, 1H), 8.33 (s, 1H), 8.11 (t, J=6.2 Hz, 1H), 7.88 (d, J=13.1 Hz, 1H), 7.64 (dd, J=9.0, 5.0 Hz, 2H), 7.48 (d, J=8.8 Hz, 1H), 7.35 (t, J=9.0 Hz, 1H), 7.16 (t, J=8.9 Hz, 2H), 6.46 (d, J=5.2 Hz, 1H), 3.68-3.54 (m, 4H), 3.47-3.42 (m, 2H), 2.44-2.30 (m, 6H), 1.84-1.72 (m, 2H), 1.52-1.39 (m, 4H);

Example 66 Synthesis of N-(3-fluoro-4-((2-((3-morpholinylpropyl)amino)pyrido[2,3-b]pyrazin-8-yl)oxy)phenyl)-N-(4-fluorophenyl)cyclopropyl-1,1-dicarboxamide (63S)

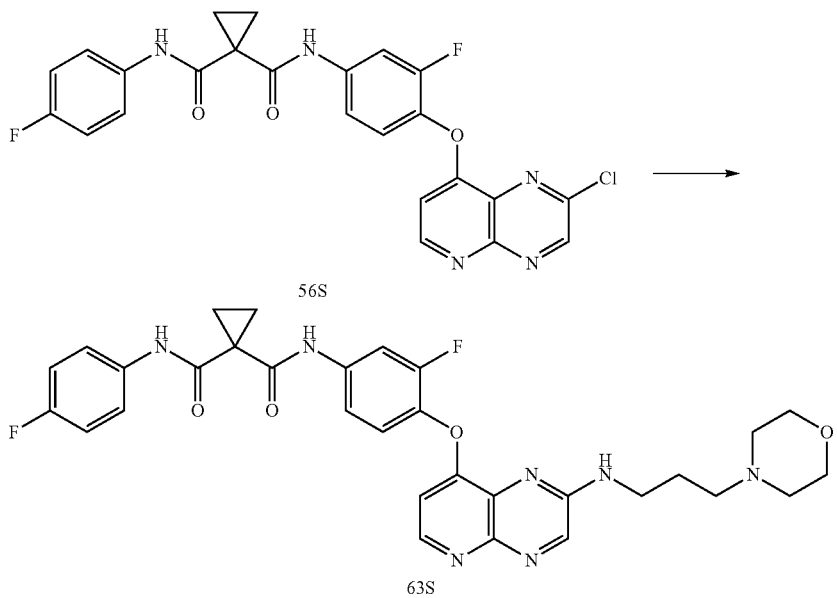

The reaction was operated in the same manner as that for compound 62S, except that the raw materials were compound 56S and N-(3-aminopropyl)morpholine, yield 66%. 1H NMR (DMSO, 400 MHz): δ 10.34 (s, 1H), 10.01 (s, 1H), 8.46 (s, 1H), 8.40 (d, J=5.3 Hz, 1H), 7.98 (t, J=5.5 Hz, 1H), 7.86 (d, J=13.8 Hz, 1H), 7.68-7.58 (m, 2H), 7.44 (d, J=8.1 Hz, 1H), 7.28 (t, J=9.1 Hz, 1H), 7.16 (t, J=8.9 Hz, 2H), 6.81 (d, J=5.0 Hz, 1H), 3.55-3.47 (m, 6H), 2.44-2.25 (m, 6H), 1.76-1.63 (m, 2H), 1.54-1.42 (m, 4H);

Example 67 Synthesis of N-(4-((2-piperazinylpyrido[2,3-b]pyrazin-8-yl)oxy)-3-fluorophenyl)-N-(4-fluorophenyl)cyclopropyl-1,1-dicarboxamide (64S)

Example 68 Synthesis of N-(4-((2-piperazinylpyrido[2,3-b]pyrazin-8-yl)oxy)-3-fluorophenyl)-N-(4-fluorophenyl)cyclopropyl-1,1-dicarboxamide (65S)

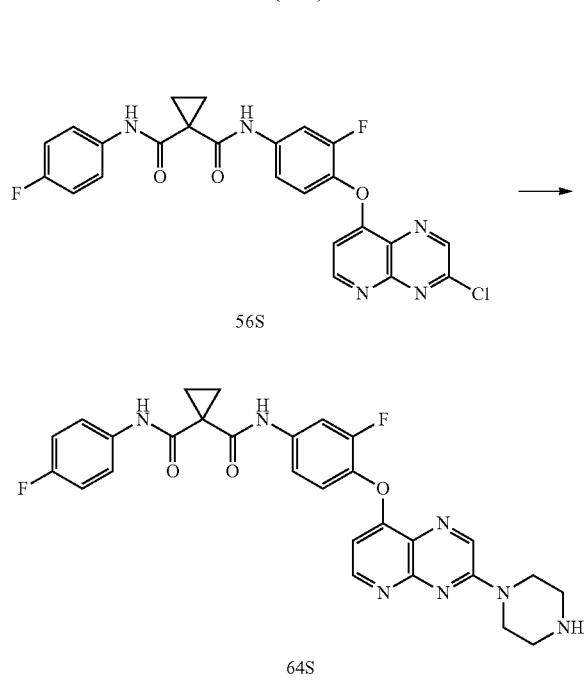

64S

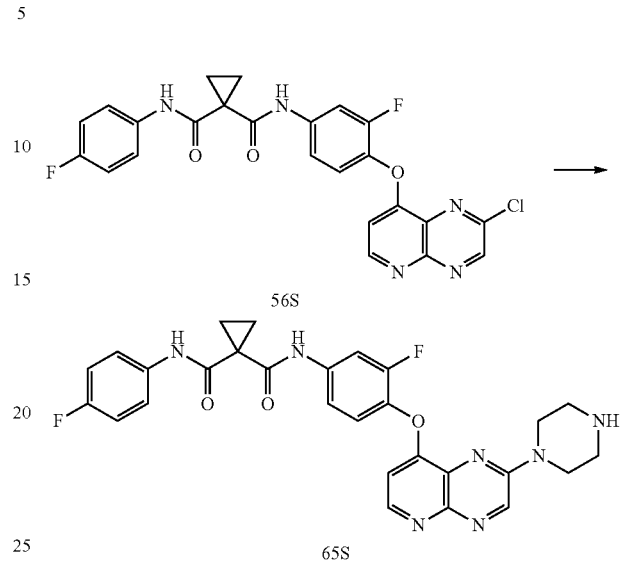

65S

The reaction was operated in the same manner as that for compound 62S, except that the raw materials were compound 56S and piperazine, yield 45%. $^1$H NMR (400 MHz, CDCl$_3$): δ 8.61 (s, 1H), 8.57 (d, J=5.6 Hz, 1H), 7.75 (d, J=12.3 Hz, 1H), 7.49-7.43 (m, 2H), 7.27-7.21 (m, 2H), 7.05-7.00 (m, 2H), 6.46 (d, J=3.4 Hz, 2H), 3.95-3.89 (m, 4H), 3.11-2.95 (m, 4H), 1.71-1.62 (m, 4H);

The reaction was operated in the same manner as that for compound 62S, except that the raw materials were compound 56S and piperazine, yield 48%. $^1$H NMR (400 MHz, DMSO): δ 10.33 (s, 1H), 10.01 (s, 1H), 8.97 (s, 1H), 8.48 (d, J=5.1 Hz, 1H), 7.85 (d, J=13.2 Hz, 1H), 7.64 (dd, J=9.1, 5.1 Hz, 2H), 7.45 (d, J=8.5 Hz, 1H), 7.30 (t, J=9.1 Hz, 1H), 7.15 (t, J=8.9 Hz, 2H), 6.85 (d, J=5.1 Hz, 1H), 3.73-3.63 (m, 4H), 2.86-2.77 (m, 4H), 1.50-1.44 (m, 4H);

Example 69 Synthesis of N-(3-fluoro-4-((2-(2-(4-methylpiperazin-1-yl)ethoxy)pyrido[2,3-b]pyrazin-8-yl)oxy)phenyl)-N-(4-fluorophenyl)cyclopropyl-1,1-dicarboxamide (66S)

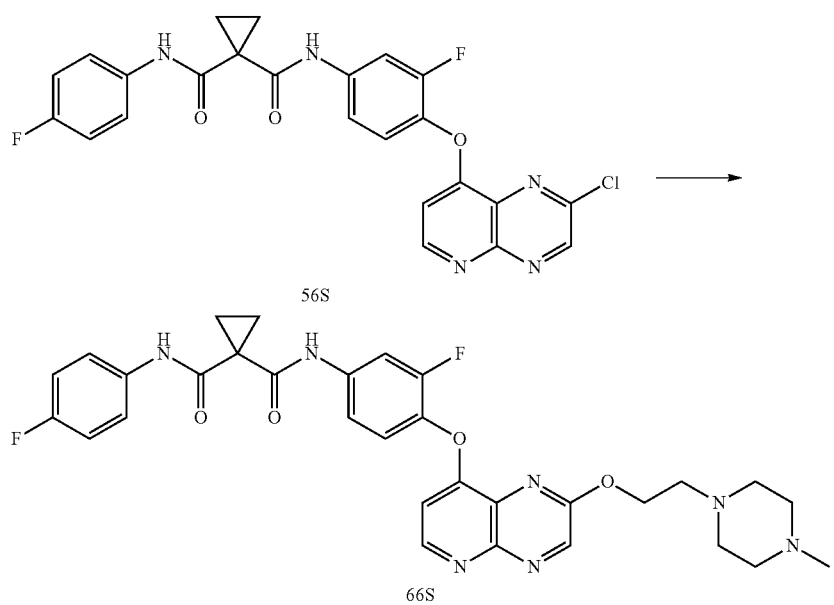

The reaction was operated in the same manner as that for compound 57S, except that the raw materials were compound 56S and 1-hydroxyethyl-4-methylpiperazine, yield 63%. $^1$H NMR (400 MHz, DMSO): δ 10.73 (s, 1H), 10.35 (s, 1H), 9.15 (s, 1H), 9.06 (d, J=5.2 Hz, 1H), 8.23 (d, J=12.9 Hz, 1H), 8.03-7.92 (m, 2H), 7.87-7.79 (m, 1H), 7.69 (t, J=9.0 Hz, 1H), 7.49 (t, J=8.7 Hz, 2H), 7.33 (d, J=5.2 Hz, 1H), 4.84 (t, J=5.4 Hz, 2H), 3.67 (s, 4H), 3.05 (t, J=5.7 Hz, 2H), 2.90-2.76 (m, 7H), 1.90-1.72 (m, 4H).

Example 70 Synthesis of N-(3-Fluoro-4-((2-(2-morpholinoethoxy)pyrido[2,3-b]pyrazin-8-yl)oxy)phenyl)-N-(4-fluorophenyl)cyclopropyl-1,1-dicarboxamide (67S)

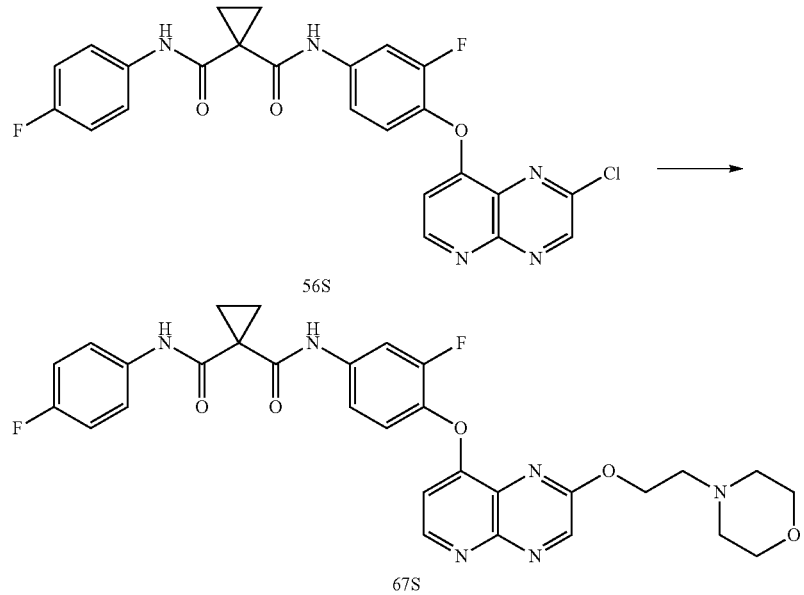

The reaction was operated in the same manner as that for compound 57S, except that the raw materials were compound 56S and 2-morpholine ethanol, yield 68%. $^1$H NMR (400 MHz, DMSO): δ10.40 (s, 1H), 10.02 (s, 1H), 8.84 (s, 1H), 8.75 (d, J=5.0 Hz, 1H), 7.91 (d, J=12.6 Hz, 1H), 7.73-7.60 (m, 2H), 7.50 (d, J=9.5 Hz, 1H), 7.37 (t, J=9.8 Hz, 1H), 7.17 (t, J=9.5 Hz, 2H), 7.01 (d, J=4.3 Hz, 1H), 4.64-4.46 (m, 2H), 3.68-3.46 (m, 4H), 2.84-2.66 (m, 2H), 2.60-2.33 (m, 4H), 1.60-1.41 (m, 4H);

Example 71 Synthesis of N-(3-fluoro-4-((2-(3-morpholinopropoxy)pyrido[2,3-b]pyrazin-8-yl)oxy)phenyl)-N-(4-fluorophenyl)cyclopropyl-1,1-dicarboxamide (68S)

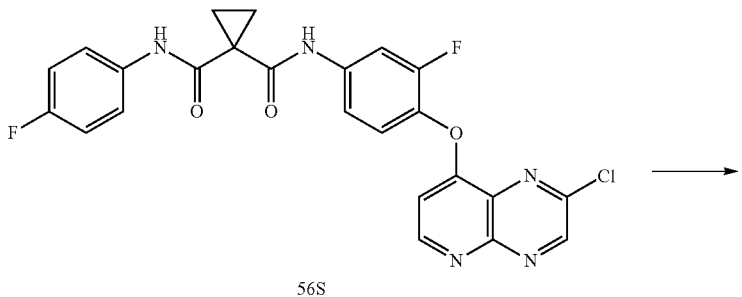

-continued

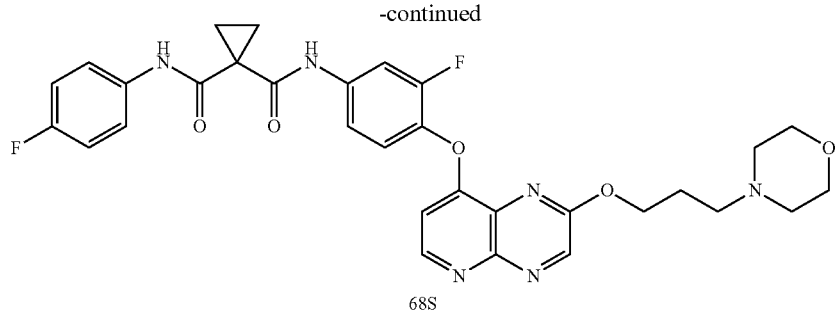

68S

The reaction was operated in the same manner as that for compound 575, except that the raw materials were compound 56S and 3-morpholinopropanol, yield 64%. $^1$H NMR (400 MHz, DMSO): δ10.40 (s, 1H), 10.02 (s, 1H), 8.81 (s, 1H), 8.76-8.64 (m, 1H), 7.91 (d, J=13.0 Hz, 1H), 7.72-7.56 (m, 2H), 7.51 (d, J=8.7 Hz, 1H), 7.39 (t, J=9.1 Hz, 1H), 7.17 (t, J=7.6 Hz, 2H), 6.97 (d, J=4.7 Hz, 1H), 4.48 (t, J=7.1 Hz, 2H), 3.64-3.46 (m, 4H), 2.50-2.26 (m, 6H), 1.98 (t, J=9.1 Hz, 2H), 1.59-1.40 (m, 4H).

Experimental Example

Experimental Example 1: Inhibitory Effect of the Pyrido-azacyclic Compounds on c-Met Kinase Experiment for Preliminarily Evaluating the Inhibitory Effect on the Activity of Receptor Tyrosine Kinase c-Met at Molecular Level 1. Test Method The enzyme substrate Poly (Glu, Tyr)$_4$ 1, which was diluted to 20 μg/ml with K$^+$-free PBS (10 mM sodium phosphate buffer, 150 mM NaCl, pH 7.2-7.4), was coated on ELISA plate in an amount of 125 μL/well and reacted at 37° C. for 12-16 hours. After discarding the liquid in the wells, the plate was washed with T-PBS (0.1% Tween-20 in PBS) in an amount of 200 μL/well three times, each for 5 minutes. The ELISA plate was dried in an oven at 37° C. for 1-2 hours. 50 μl of adenosine triphosphate (ATP) solution diluted with reaction buffer (50 mM 4-hydroxyethylpiperazine ethanesulfonic acid (HEPES) pH 7.4, 50 mM MgCl$_2$, 0.5 mM MnCl$_2$, 0.2 mM Na$_3$VO$_4$, 1 mM dithiothreitol (DTT)) to a final concentration of 5 μM was added to each well. The compounds were diluted to an appropriate concentration with DMSO (1 μL/well) or a solution containing DMSO in a corresponding concentration (negative control well), and then c-Met kinase domain recombinant protein diluted with 49 μL of the reaction buffer was added therein to initiate the reaction, with two ATP-free control wells for each test. The plate was placed in a shaker (100 rpm) at 37° C. for reacting 1 hour, and washed with T-PBS three times. Primary antibody PY99 diluent was added in an amount of 100 μL/well to allow the reaction in a shaker at 37° C. for 0.5 hour, and then the plate was washed with T-PBS three times. Then the secondary antibody horseradish peroxidase labeled goat anti-mouse IgG diluent was added in an amount of 100 μL/well, and the plate was placed in a shaker at 37° C. for reacting 0.5 hour, and then washed with T-PBS three times. 2 mg/ml of o-phenylenediamine (OPD) coloring solution (diluted with 0.1 M citric acid-sodium citrate buffer (pH=5.4) containing 0.03% H$_2$O$_2$) was then added at 100 μL/well and reacted at 25° C. for 1-10 min with light blocked (ultrasound was required to dissolve OPD, the coloring solution was prepared when needed). The reaction was stopped by adding 2 M of H$_2$SO$_4$ in an amount of 50 μL/well, and a wavelength-adjustable microplate reader SPECTRA MAX 190 was read at 490 nm.

The inhibition rate of the sample was calculated by the following equation:

$$\text{Inhibition rate (\%)} = \left(1 - \frac{OD \text{ value of the compound} - OD \text{ value of the } ATP - \text{free control well}}{OD \text{ value of the negative control} - OD \text{ value of the } ATP - \text{free control well}}\right) \times 100\%$$

The thus screened compounds that could effectively inhibit the activity of c-Met kinase (the inhibition rate of the compound on receptor tyrosine kinase c-Met at 10$^{-5}$ M>50%) were prepared into gradient concentrations for IC$_{50}$ evaluation. The IC$_{50}$ value of each compound for inhibiting protein tyrosine kinases at the molecular level was calculated by the four-parameter method and the results were classified according to their concentration ranges and listed in the following Table 1:

TABLE 1

Inhibitory activity of the compounds of the present invention on c-Met kinase and their inhibitory activity on c-Met-mediated EBC-1 cell proliferation

| Cpd. No. | IC$_{50}$ c-Met kinase | EBC-1cells | Cpd No. | IC$_{50}$ c-Met kinase | EBC-1cells |
|---|---|---|---|---|---|
| 1S | D | C | 2S | A | B |
| 3S | A | C | 4S | D | ND |
| 5S | C | ND | 6S | B | ND |
| 7S | A | B | 8S | A | B |
| 9S | A | B | 10S | B | ND |
| 11S | A | C | 12S | A | C |
| 13S | A | C | 14S | C | ND |
| 15S | A | B | 16S | B | ND |
| 17S | A | ND | 18S | C | ND |
| 19S | B | ND | 20S | A | B |
| 21S | B | ND | 22S | A | B |
| 23S | A | C | 24S | A | C |
| 25S | A | C | 26S | B | C |
| 27S | B | ND | 28S | B | ND |
| 29S | B | ND | 30S | B | ND |
| 31S | B | ND | 32S | B | ND |
| 33S | C | ND | 34S | C | ND |
| 35S | B | ND | 36S | B | ND |
| 37S | A | B | 38S | A | A |
| 39S | A | A | 40S | A | B |
| 41S | A | A | 42S | A | A |
| 43S | A | C | 44S | B | C |

TABLE 1-continued

Inhibitory activity of the compounds of the present invention on c-Met kinase and their inhibitory activity on c-Met-mediated EBC-1 cell proliferation

| Cpd. No. | $IC_{50}$ c-Met kinase | $IC_{50}$ EBC-1cells | Cpd. No. | $IC_{50}$ c-Met kinase | $IC_{50}$ EBC-1cells |
|---|---|---|---|---|---|
| 45S | C | D | 46S | A | C |
| 47S | A | B | 48S | B | ND |
| 49S | A | B | 50S | B | ND |
| 51S | A | ND | 52S | C | ND |
| 53S | B | ND | 54S | A | B |
| 55S | B | D | 56S | C | D |
| 57S | B | D | 58S | C | D |
| 59S | A | C | 60S | B | D |
| 61S | B | ND | 62S | B | D |
| 63S | A | D | 64S | A | D |
| 65S | D | D | 66S | S | D |
| 67S | D | D | 68S | D | D |

[a] The tested compounds inhibit the activity of c-Met kinase. A: 1 nM < $IC_{50}$ < 10 nM; B: 10 nM < $IC_{50}$ < 100 nM; C: 100 nM < $IC_{50}$ < 1 μM; D: 1 μM < $IC_{50}$ < 10 μM; ND: Not tested.

Results: it is found that a number of compounds of the present invention show inhibitory activity on c-Met kinase to different degrees, some compounds show very potent inhibitory effect on c-Met kinase at a concentration of 10 nM and the half-inhibitory concentration thereof is 1 nM<$IC_{50}$<10 nM. It is indicated that the compounds of the present invention have a potent effect on c-Met kinase, and thus they are c-Met kinase inhibitors with new structures.

Experimental Example 2: Effect of the Compounds of the Present Invention on the Proliferation Ability of c-Met-Mediated Cell Lines The inhibitory effect of the compounds on the growth of non-small cell cancer EBC-1 cell (a cell line in which Met is continually activated due to the amplification of MET gene, and is a Met-dependent tumor cell line) was measured by sulforhodamine B (SRB) staining assay. A certain amount of EBC-1 cells in their logarithmic growth phase were seeded in 96-well plates at 90 μL per well and cultured overnight, then 10 μL of different concentrations of compounds or solvent control were added thereto, three wells for each concentration. After treated by the compound for 72 hours, the adherent cells were removed of culture medium and fixed with 10% (w/v) trichloroacetic acid (100 μL/well) at 4° C. for 1 hr followed by rinsing with distilled water five times. After drying at room temperature, 100 μL of SRB solution (dissolved in 1% glacial acetic acid at 4 mg/mL) was added to each well to incubate and stain the cells for 15 min at room temperature, then unbound SRB was washed off with 1% glacial acetic acid for five times. After drying at room temperature, 100 μL of 10 mM Tris solution was added to each well. The optical density (OD value) at 515 nm was read on a VERSMax microplate reader. The inhibition rate of the compounds on tumor cell growth was calculated by the following equation: Inhibition rate (%)=(OD of control well-OD of administration well)/OD of control well×100%. The experiment was repeated twice. The $IC_{50}$ data was calculated as a range based on the test results of concentrations set in the initial screening test.

Results: A number of compounds of the invention show significant inhibitory effect on the proliferation of EBC-1 cells with overexpression of c-Met kinase, indicating that the compounds can inhibit the cell proliferation mediated by c-Met activation. The detailed data is listed in the above Table 1, "ND" in the table represents that no relevant test was performed and no relevant data was obtained.

Experimental Example 3: Inhibitory Effect of Compound 7S on Multiple Protein Kinases The test method is the same as Experimental Example 1, and the results are shown in Table 2.

TABLE 2

Inhibition rate of compound 7S on the activity of tyrosine kinase (%)

| Compound No. (1 μM) | c-Met | ALK | FGFR1 | Flt-1 | PDGFR-α | PDGFR-β | RET | EGFR | ErbB4 | c-Src | ABL | EPH-A2 | IGF1R |
|---|---|---|---|---|---|---|---|---|---|---|---|---|---|
| 7S | 100 | 21.7 | 36.3 | 70.3 | 55.6 | 48.7 | 78.2 | 8.6 | 6.6 | 55.9 | 23.3 | 87.9 | 18.1 |
| PF2341066 | 81.6 | 98.2 | / | / | / | / | / | / | / | / | / | / | / |
| AZD4547 | / | / | 100 | / | / | / | / | / | / | / | / | / | / |
| Su11248 | / | / | / | 77.4 | 54.8 | 55.6 | 80.6 | / | / | / | / | / | / |
| BIBW2992 | / | / | / | / | / | / | / | 77.4 | 71.1 | / | / | / | / |
| Dasatinib | / | / | / | / | / | / | / | / | / | 78.9 | 92.4 | 91.6 | / |
| AEW541 | / | / | / | / | / | / | / | / | / | / | / | / | 70.9 |

As can be seen from the above table, compound 7S of the present invention exhibits inhibitory activity on various kinases such as c-Met, Flt-1, PDGFR-α, PDGFR-β, RET, c-Src and EPH-A2, and thus it is a multiple kinase inhibitor with a new structure.

Experimental Example 4: Pharmacokinetic Test of Compound 7S and 8S in Rats

1. Dosing Regimen 14 male Sprague-Dawley rats, weigh 200-220 g, were randomly divided into 4 groups with 4/3 in each group. The rats were intragastrically and intravenously administered with compound 7S and 8S respectively. The compounds were dissolved in normal saline containing 5% of DMSO and solubilized with 5% of tween-80 (Tween 80), and the final concentration of the sample was 1 mg/ml. See Table 3 below for details:

TABLE 3

Dosing regimen for pharmacokinetic test of compound 7S and 8S in rat

| Group | Rat Number | Compound | Administration route | Administration dosage (mg/kg) | Administration volume (ml/kg) |
|---|---|---|---|---|---|
| 1 | 4 | 7S | gavage | 10 | 10 |
| 2 | 3 | 7S | intravenous | 5 | 5 |
| 3 | 4 | 8S | gavage | 10 | 10 |
| 4 | 3 | 8S | intravenous | 5 | 5 |

The rats were fasted 12 h before the test, free drinking water. They were fed 2 h after administration.

2. Time Points for Blood Sampling and Sample Handling:

gavage administration: 0.25 h, 0.5 h, 1.0 h, 2.0 h, 3.0 h, 4.0 h, 6.0 h, 8.0 h and 24 h after administration;

intravenous administration: 5 min, 0.25 h, 0.5 h, 1.0 h, 2.0 h, 4.0 h, 6.0 h, 8.0 h and 24 h after administration;

0.3 ml venous blood was collected from the retrobulbar venous plexus of rats at the above time point, and placed in a heparinized tube and centrifuged at 11000 rpm for 5 min. The plasma was separated and frozen in a refrigerator at −20° C.

3. Sample Testing and Data Analysis

The concentrations of the compounds in rat plasma were measured by LC/MS/MS.

Pharmacokinetic parameters after administration were calculated using the non-compartmental model of the Phoenix 1.3 software (Pharsight, U.S.A.).

Peak concentration $C_{max}$ and peak time $T_{max}$ were the measured values;

The area under the curve of the drug concentration vs. time AUC0-t value: calculated according to trapezoidal rule; $AUC_{0-\infty}=AUC_{0-t}+C_t/k_e$, Ct is the plasma concentration at the last measurable time point, $k_e$ is the elimination rate constant;

Elimination half-life $t_{1/2}=0.693/k_e$;

Average retention time MRT=AUMC/AUC.

Clearance rate $CL=D/AUC_{0-\infty}$;

Volume of distribution at steady state $V_{ss}=CL \times MRT$

Absolute bioavailability F=(AUC gavage×D vein)/(AUC vein×D gavage)×100%

The experimental data are shown in Table 4 and Table 5.

TABLE 4

Pharmacokinetic parameters of compound 7S and 8S (intravenously administered to rat at 5 mg/kg)

| Treatment group | ID | $AUC_{0-t}$ (h*ng/ml) | $AUC_{0-\infty}$ (h*ng/ml) | MRT (h) | $t_{1/2}$ (h) | Cl (l/h/kg) | $V_{ss}$ (l/kg) |
|---|---|---|---|---|---|---|---|
| 7S | mean | 15938 | 15971 | 1.106 | 1.002 | 0.314 | 0.346 |
|    | SD   | 1263  | 1262  | 0.094 | 0.124 | 0.026 | 0.006 |
|    | CV % | 7.9   | 7.9   | 8.5   | 12.4  | 8.2   | 1.8   |
| 8S | mean | 8772  | 8806  | 1.165 | 1.151 | 0.575 | 0.667 |
|    | SD   | 1233  | 1246  | 0.057 | 0.181 | 0.076 | 0.067 |
|    | CV % | 14.1  | 14.1  | 4.9   | 15.7  | 13.2  | 10    |

TABLE 5

Pharmacokinetic parameters of compound 7S and 8S (intragastrically administered to rat at 10 mg/kg)

| Treatment group | ID | $T_{max}$ (h) | $C_{max}$ (ng/ml) | $AUC_{0-t}$ (h*ng/ml) | $AUC_{0-\infty}$ (h*ng/ml) | MRT (h) | $t_{1/2}$ (h) | F % |
|---|---|---|---|---|---|---|---|---|
| 7S | mean | 1.75 | 5446.3 | 16501 | 16652 | 2.653 | 1.66 | 51.8 |
|    | SD   | 0.5  | 1009.7 | 2892  | 2691  | 0.412 | 0.535 | |
|    | CV % | 28.6 | 18.5   | 17.5  | 16.2  | 15.5  | 32.2 | |
| 8S | mean | 1.25 | 2060.5 | 6779  | 6871  | 2.705 | 1.488 | 38.6 |
|    | SD   | 0.5  | 349.8  | 2068  | 2003  | 0.501 | 0.408 | |
|    | CV % | 40   | 17     | 30.5  | 29.1  | 18.5  | 27.5 | |

The results show that compound 7S exhibits good pharmacokinetic properties: bioavailability F=51.8%, mean retention time MRT=2.6 h, half life $t_{1/2}$=1.66 h, and the area under the curve of the drug concentration vs. time AUC=16652 h*ng/ml.

Experimental Example 5: Growth Inhibitory Effect of Compound 7S on Subcutaneous Xenograft Tumor of Human Lung Cancer EBC-1 in Nude Mice Test Method EBC-1 cells were subcutaneously inoculated into the armpit on the right side of the nude mice in an amount of $5 \times 10^6$/mouse respectively to form xenograft tumor, which were then passaged in nude mice for three generations. Tumor tissue that was growing vigorously was cut into about 1.5 mm³ under sterile conditions, and subcutaneously inoculated into the armpit on the right side of the nude mice, and the diameter of the xenograft tumor was measured with a vernier caliper. The diameter of the subcutaneous xenograft tumor in nude mice was measured with a vernier caliper. When the average volume of the tumor grew to about

TABLE 6

Experimental therapeutic effect of compound 7S on subcutaneous xenograft tumor of human lung cancer EBC-1 in nude mice

| Group | Dosage, Administration route | Number of mice $d_0$ $d_{21}$ | | Weight (g) $d_0$ $d_{21}$ | | TV (mm$^3$, mean ± SD) $d_0$ $d_{21}$ | | RTV (mean ± SD) | T/C (%) |
|---|---|---|---|---|---|---|---|---|---|
| Solvent control | 0.2 ml/mouse qd/21 po | 12 | 12 | 17.9 | 22.8 | 126 ± 31 | 1606 ± 362 | 13.18 ± 3.39 | |
| PF2341066 | 50 mg/kg qd/21 po | 6 | 6 | 17.2 | 19.6 | 123 ± 25 | 0 ± 0(6) | 0.00 ± 0.00* | 0.00 |
| 7S | 100 mg/kg qd/21 po | 6 | 6 | 17.4 | 20.7 | 128 ± 39 | 181 ± 156 | 1.26 ± 0.85* | 9.58 |
| | 10 mg/kg qd/21 po | 6 | 6 | 18.2 | 22.0 | 128 ± 34 | 764 ± 258 | 6.09 ± 2.17* | 46.24 |

*p < 0.001, the number within "( )" represents the number of mice whose tumor regressed.

control drug was administered orally once daily for 21 consecutive days; and the solvent control group, in which the solvent was administered in an equal amount. The diameter of xenograft tumor was measured twice a week and the body weight of mice was weighed during the whole experiment. The tumor volume (TV) was calculated by the following equation: TV=½×a×b$^2$, wherein a and b represent the length and width, respectively. The relative tumor volume (RTV) was calculated based on the measured results, and the calculation equation thereof is: RTV=V$_t$/V$_0$, wherein V$_0$ is the tumor volume measured when the mice were divided in different cages and administered (i.e., d$_0$) and V$_t$ is the tumor volume measured each time. The evaluation indexes of antitumor activity were as follows: 1) the relative tumor proliferation rate T/C (%), and the calculation equation thereof is as follows: T/C (%)=(T$_{RTV}$/C$_{RTV}$)×100%, T$_{RTV}$: RTV of the treatment group; C$_{RTV}$: RTV of the negative control group; 2) tumor volume growth inhibition rate GI %, and the calculation equation thereof is as follows: GI %=[1−(TV$_t$−TV$_0$)/(CV$_t$−CV$_0$)]×100%, TV$_t$ is the tumor volume measured each time in the treatment group; TV$_0$ is the tumor volume obtained when the mice were divided in different cages and administered in the treatment group; CV$_t$ is the tumor volume measured each time in the control group; CV$_0$ is the tumor volume obtained when the mice were divided in different cages and administered in the control group; 3) The tumor weight inhibition rate was calculated as follows: Tumor weight inhibition rate %=(W$_C$−W$_T$)/W$_C$×100%, W$_C$: tumor weight in the control group, W$_T$: tumor weight in the treatment group.

Experimental Results:

As shown in FIG. 1 and Table 6, in the 100 mg/kg treatment group, in which compound 75 was orally administered once daily for 21 consecutive days, compound 7S shows significant inhibitory effect on the growth of subcutaneous xenograft tumor of human lung cancer EBC-1 in nude mice, and the T/C percentage is 9.58% at day 21. In the 10 mg/kg treatment group, in which compound 7S was orally administered once daily for 21 consecutive days, the compound 7S shows some inhibitory effect on the growth of subcutaneous xenograft tumor of human lung cancer EBC-1 in nude mice, and the T/C percentage is 46.24% at day 21. In the positive control drug PF2341066 50 mg/kg group, in which the positive control drug was orally administered once daily for 21 consecutive days, the positive control drug shows significant inhibitory effect on the growth of subcutaneous xenograft tumor of human lung cancer EBC-1 in nude mice, the tumors in all the mice completely regressed at day 21, and the T/C percentage is 0.00%. The mice in each administration group were in good condition during the administration, and no mice died.

The invention claimed is:

1. A pyrido-azacyclic compound, a pharmaceutically acceptable salt thereof or a pharmaceutically acceptable solvate thereof, wherein the compound has a structure represented by the following formula I:

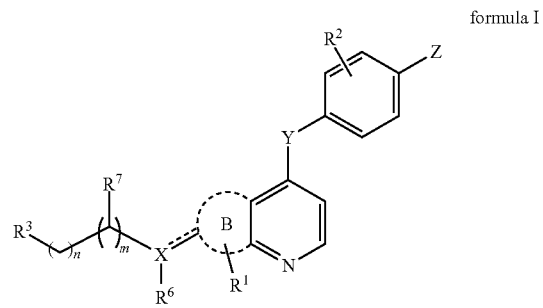

formula I wherein,

⸺ represents a single bond;

R$^1$ and R$^2$ are each independently selected from hydrogen and halogen;

X is absent or is O;

Y is O;

n is 0, 1, 2 or 3; m is 0 or 1;

R$^3$ is absent, or is hydrogen, a substituted or unsubstituted C$_1$-C$_6$ alkyl, a substituted or unsubstituted C$_6$-C$_{10}$ aryl, a substituted or unsubstituted 5- or 6-membered saturated or unsaturated heterocyclic group containing 1 to 2 heteroatoms selected from N, O and S, a substituted or unsubstituted 5- or 6-membered saturated or unsaturated heterocyclic carbonyl group containing 1 to 2 heteroatoms selected from N, O and S,

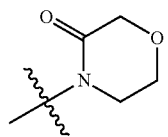 [SMILES: *N1CCOCC1=O]

or a substituted or unsubstituted 5- or 6-membered heteroaromatic ring group containing 1 to 2 heteroatoms selected from N, O and S, wherein, the number of the substituents may be 1 or 2 and the substituents are each independently selected from halogen, —CN, —CF$_3$, —NO$_2$, hydroxyl, C$_1$-C$_6$ alkyl, amino substituted by C$_1$-C$_6$ alkyl, C$_1$-C$_6$ alkoxy, benzyl, C$_1$-C$_6$ alkoxy substituted by halogen, C$_1$-C$_6$ alkylsulfonyl and an unsubstituted or C$_1$-C$_6$ alkyl-substituted 5- or 6-membered saturated or unsaturated heterocyclic group or heteroaromatic ring group containing 1 to 2 heteroatoms selected from N and O;

R$^6$ is absent, or is selected from hydrogen and C$_1$-C$_6$ alkyl;

R$^7$ is absent, or is selected from hydrogen and C$_1$-C$_6$ alkyl;

Z is phenylacetamido or any of the following structures:

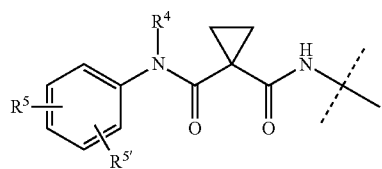

II

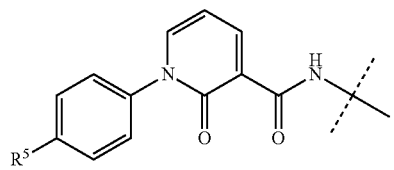

III

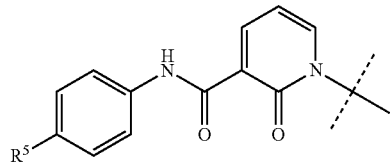

IV

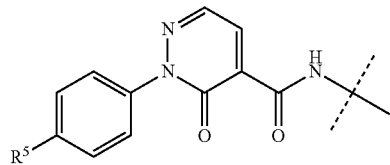

V

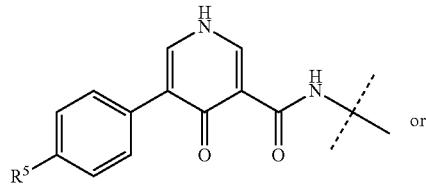

VI or

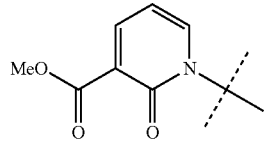

VII in the above formulas II, III, IV, V and VI, R$^4$ is selected from hydrogen, C$_1$-C$_6$ alkyl and C$_5$-C$_{10}$ aryl or heteroaryl; R$^5$ and R$^{5'}$ are each independently selected from hydrogen, halogen and C$_1$-C$_6$ alkoxy;

Ring B forms one structure of the following formulas with pyridine:

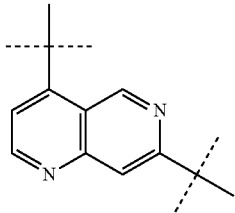

VIII

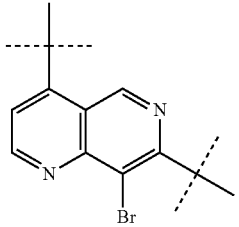

IX

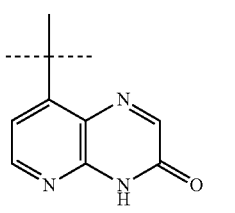

X

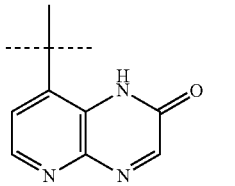

XI

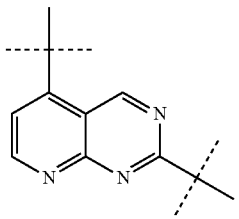

XII

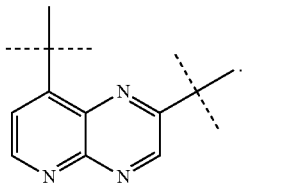

or

XIII

2. The compound, the pharmaceutically acceptable salt thereof or the pharmaceutically acceptable solvate thereof according to claim 1, wherein, R$^1$ and R$^2$ are each independently selected from hydrogen, F, Cl and Br;

X is absent or is O;

Y is O;

n is 0, 1 or 2; m is 0 or 1;

R$^3$ absent, or is hydrogen, a substituted or unsubstituted C$_1$-C$_6$ alkyl, a substituted or unsubstituted C$_6$-C$_{10}$ aryl, a substituted or unsubstituted 5- or 6-membered saturated or unsaturated heterocyclic group containing 1 to 2 heteroatoms selected from N, O and S, a substituted or unsubstituted 5- or 6-membered saturated or unsaturated heterocyclic carbonyl group containing 1 to 2 heteroatoms selected from N, O and S,

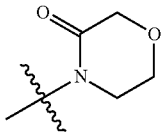

or a substituted or unsubstituted 5- or 6-membered heteroaromatic ring group containing 1 to 2 heteroatoms selected from N and O, wherein, the number of the substituents may be 1 or 2 and the substituents are each independently selected from halogen, —CN, benzyl, —NO$_2$, C$_1$-C$_6$ alkyl, amino substituted by C$_1$-C$_6$ alkyl, C$_1$-C$_6$ alkylsulfonyl and an unsubstituted or C$_1$-C$_6$ alkyl-substituted 5- or 6-membered saturated or unsaturated heterocyclic group containing 1 to 2 heteroatoms selected from N and O;

R$^6$ is absent, or is selected from hydrogen and C$_1$-C$_4$ alkyl;

R$^7$ is absent, or is selected from hydrogen, methyl, ethyl and propyl;

R$^4$ is selected from hydrogen and C$_1$-C$_6$ alkyl; R$^5$ and R$^{5'}$ are each independently selected from hydrogen, F, Cl, Br and C$_1$-C$_4$ alkoxy.

3. The compound, the pharmaceutically acceptable salt thereof or the pharmaceutically acceptable solvate thereof according to claim 1, wherein, R$^1$ is selected from hydrogen, Cl and Br; R$^2$ is selected from hydrogen, F and Cl;

X is absent or is O;

Y is O;

n is 0, 1 or 2; m is 0 or 1;

R$^3$ is absent, or is hydrogen, a substituted or unsubstituted C$_1$-C$_6$ alkyl, a substituted or unsubstituted C$_6$-C$_{10}$ aryl, a substituted or unsubstituted 5- or 6-membered saturated or unsaturated heterocyclic group containing 1 to 2 heteroatoms selected from N, O and S, a substituted or unsubstituted 5- or 6-membered saturated or unsaturated heterocyclic carbonyl group containing 1 to 2 heteroatoms selected from N, O and S,

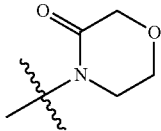

or a substituted or unsubstituted 5- or 6-membered heteroaromatic ring group containing 1 to 2 heteroatoms selected from N and O, wherein, the number of the substituents may be 1 or 2 and the substituents are each independently selected from halogen, —NO$_2$, benzyl, C$_1$-C$_4$ alkyl, amino substituted by C$_1$-C$_4$ alkyl, C$_1$-C$_4$ alkylsulfonyl and an unsubstituted or C$_1$-C$_6$ alkyl-substituted 5- or 6-membered saturated or unsaturated heterocyclic group containing 1 to 2 heteroatoms selected from N and O;

R$^6$ is absent, or is selected from hydrogen and C$_1$-C$_2$ alkyl;

R$^7$ is absent, or is methyl;

R$^4$ is selected from hydrogen and C$_1$-C$_3$ alkyl;

R$^5$ and R$^{5'}$ are each independently selected from hydrogen, F and C$_1$-C$_2$ alkoxy.

4. The compound, the pharmaceutically acceptable salt thereof or the pharmaceutically acceptable solvate thereof according to claim 1, wherein, R$^1$ is hydrogen, Cl or Br; R$^2$ is hydrogen or F;

X is absent or is O;

Y is O;

n is, 1 or 2; m is 0 or 1;

R$_3$ is absent, or is C$_1$-C$_3$ alkyl, a substituted or unsubstituted pyridyl, a substituted or unsubstituted morpholinyl, a substituted or unsubstituted morpholinylcarbonyl,

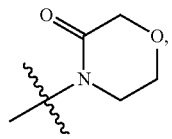 [SMILES: *N1CCOCC1=O]

a substituted or unsubstituted piperidyl, a substituted or unsubstituted imidazolyl, a substituted or unsubstituted piperazinyl, a substituted or unsubstituted oxazolyl, a substituted or unsubstituted isoxazolyl, a substituted or unsubstituted pyrimidinyl, a substituted or unsubstituted thiazolyl, a substituted or unsubstituted isothiazolyl, a substituted or unsubstituted phenyl, or a substituted or unsubstituted pyrazolyl, wherein the number of the substituents may be 1 or 2 and the substituents are each independently selected from F, Cl, Br, —NO$_2$, benzyl, C$_1$-C$_3$ alkyl, amino substituted by C$_1$-C$_3$ alkyl, C$_1$-C$_3$ alkylsulfonyl, unsubstituted or C$_1$-C$_6$ alkyl substituted piperidinyl and morpholinyl;

R$^6$ is absent, or is hydrogen or methyl;

R$^7$ is absent, or is methyl;

Z is phenylacetamido or any of the following structures:

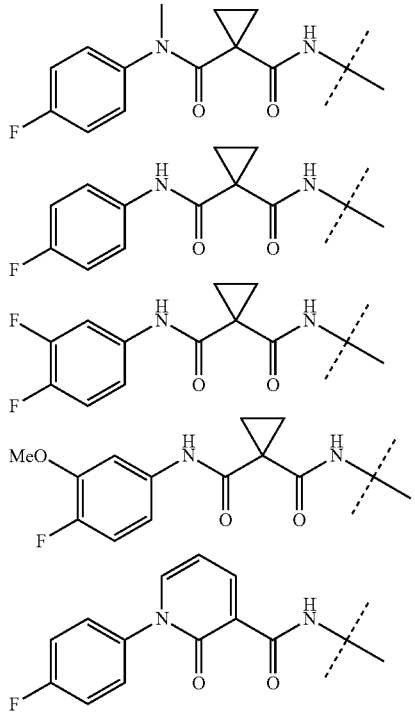

153

-continued

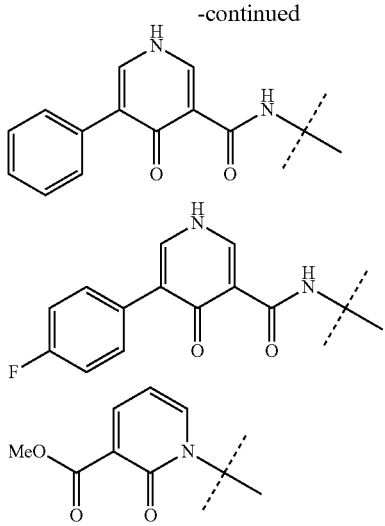

154

-continued

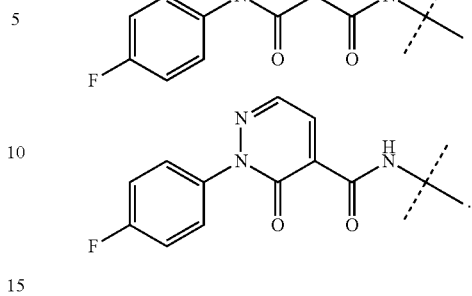

5. A compound, a pharmaceutically acceptable salt or a pharmaceutically acceptable solvate thereof, wherein, the compound is selected from the group consisting of the following compounds:

| Cpd. No. | Name | Structure |
|---|---|---|
| 1S | N-(4-((7-chloro-1,6-naphthyridin-4-yl)oxy)-3-fluorophenyl)-N-(4-fluorophenyl)cyclopropyl-1,1-dicarboxamide | 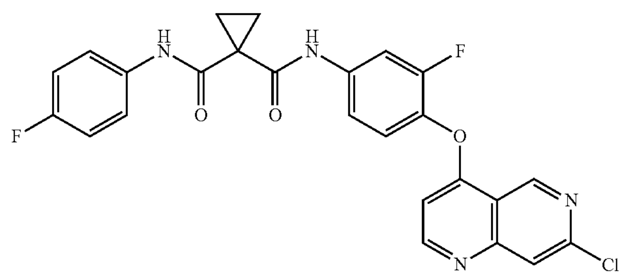 [SMILES: O=C(Nc1ccc(F)cc1)C1(C(=O)Nc2ccc(Oc3ccnc4cc(Cl)ncc34)c(F)c2)CC1] |
| 2S | N-(4-((7-(dimethylamino)-1,6-naphthyridin-4-yl)oxy)-3-fluorophenyl)-N-(4-fluorophenyl)cyclopropyl-1,1-dicarboxamide | 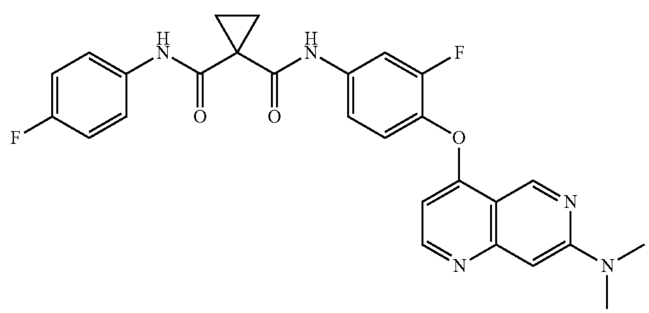 [SMILES: CN(C)c1cc2nccc(Oc3ccc(NC(=O)C4(C(=O)Nc5ccc(F)cc5)CC4)cc3F)c2cn1] |
| 3S | N-(4-((7-methoxy-1,6-naphthyridin-4-yl)oxy)-3-fluorophenyl)-N-(4-fluorophenyl)cyclopropyl-1,1-dicarboxamide | 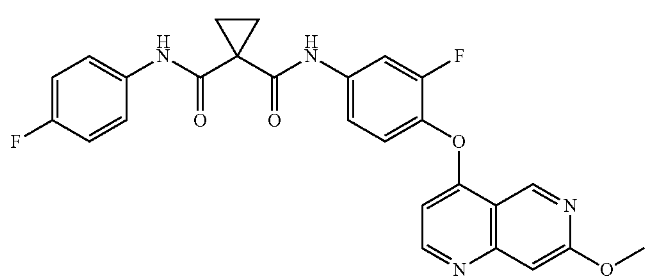 [SMILES: COc1cc2nccc(Oc3ccc(NC(=O)C4(C(=O)Nc5ccc(F)cc5)CC4)cc3F)c2cn1] |

| Cpd. No. | Name | Structure |
|---|---|---|
| 6S | N-(4-((8-bromo-7-(2-morpholinoethoxy)-1,6-naphthyridin-4-yl)oxy)-3-fluorophenyl)-N-(4-fluorophenyl)cyclopropyl-1,1-dicarboxamide | 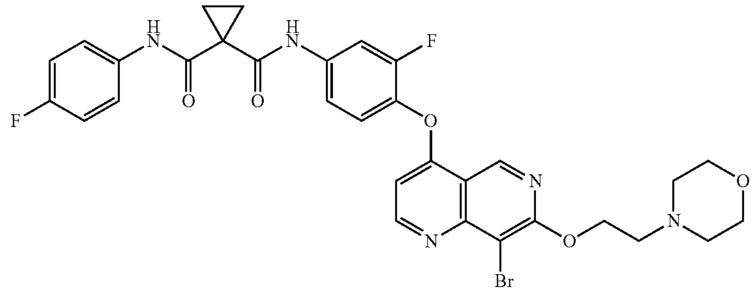 [SMILES: O=C(Nc1ccc(F)cc1)C1(C(=O)Nc2ccc(Oc3ccnc4c(Br)c(OCCN5CCOCC5)ncc34)c(F)c2)CC1] |
| 7S | N-(3-fluoro-4-((7-(2-morpholinoethoxy)-1,6-naphthyridin-4-yl)oxy)phenyl)-N-(4-fluorophenyl)cyclopropyl-1,1-dicarboxamide | 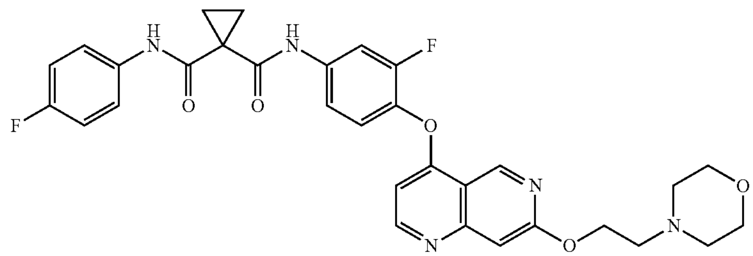 [SMILES: O=C(Nc1ccc(F)cc1)C1(C(=O)Nc2ccc(Oc3ccnc4cc(OCCN5CCOCC5)ncc34)c(F)c2)CC1] |
| 8S | N-(3-fluoro-4-((7-(2-morpholinopropoxy)-1,6-naphthyridin-4-yl)oxy)phenyl)-N-(4-fluorophenyl)cyclopropyl-1,1-dicarboxamide | 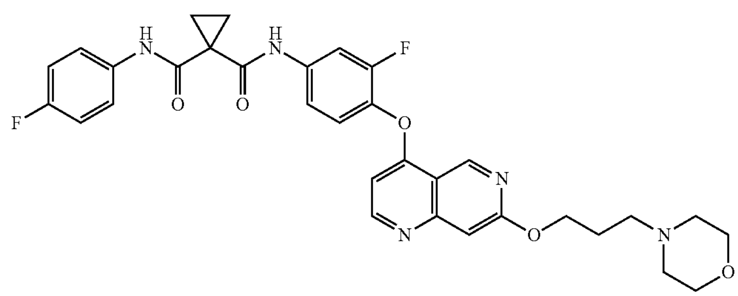 [SMILES: O=C(Nc1ccc(F)cc1)C1(C(=O)Nc2ccc(Oc3ccnc4cc(OCCCN5CCOCC5)ncc34)c(F)c2)CC1] |
| 9S | N-(3-fluoro-4-((7-((1-methylpiperidin-4-yl)methoxy)-1,6-naphthyridin-4-yl)oxy)phenyl)-N-(4-fluorophenyl)cyclopropyl-1,1-dicarboxamide | 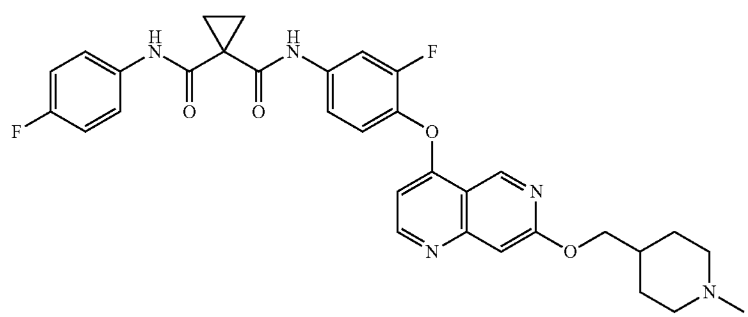 [SMILES: CN1CCC(COc2cc3nccc(Oc4ccc(NC(=O)C5(C(=O)Nc6ccc(F)cc6)CC5)cc4F)c3cn2)CC1] |
| 10S | N-(4-((8-bromo-7-(2-(4-methylpiperazin-1-yl)ethoxy)-1,6-naphthyridin-4-yl)oxy)-3-fluorophenyl)-N-(4-fluorophenyl)cyclopropyl-1,1-dicarboxamide | 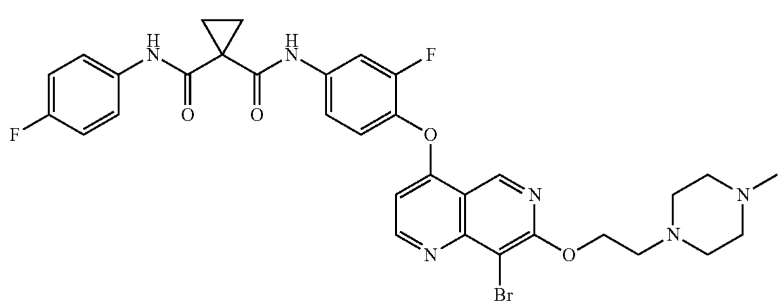 [SMILES: CN1CCN(CCOc2ncc3c(Oc4ccc(NC(=O)C5(C(=O)Nc6ccc(F)cc6)CC5)cc4F)ccnc3c2Br)CC1] |

-continued

| Cpd. No. | Name | Structure |
|---|---|---|
| 11S | N-(3-fluoro-4-((7-(2-(4-methylpiperazin-1-yl)ethoxy)-1,6-naphthyridin-4-yl)oxy)phenyl)-N-(4-fluorophenyl)cyclopropyl-1,1-dicarboxamide | 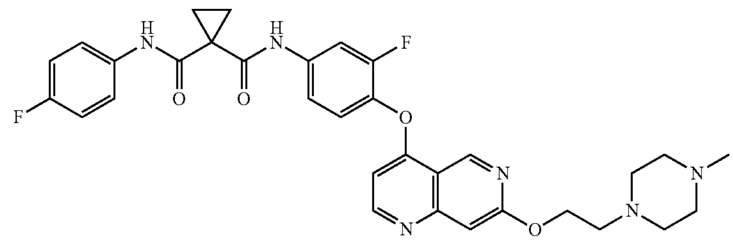 [SMILES: CN1CCN(CCOc2cc3nccc(Oc4ccc(NC(=O)C5(C(=O)Nc6ccc(F)cc6)CC5)cc4F)c3cn2)CC1] |
| 12S | N-(4-fluorophenyl)-N-(4-((7-(2-morpholinoethoxy)-1,6-naphthyridin-4-yl)oxy)phenyl)cyclopropyl-1,1-dicarboxamide | 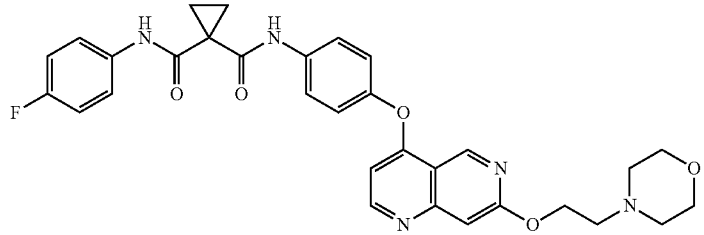 [SMILES: O=C(Nc1ccc(F)cc1)C1(C(=O)Nc2ccc(Oc3ccnc4cc(OCCN5CCOCC5)ncc34)cc2)CC1] |
| 13S | N-(4-fluorophenyl)-N-(4-((7-(2-morpholinoethoxy)-1,6-naphthyridin-4-yl)amino)phenyl)cyclopropyl-1,1-dicarboxamide | 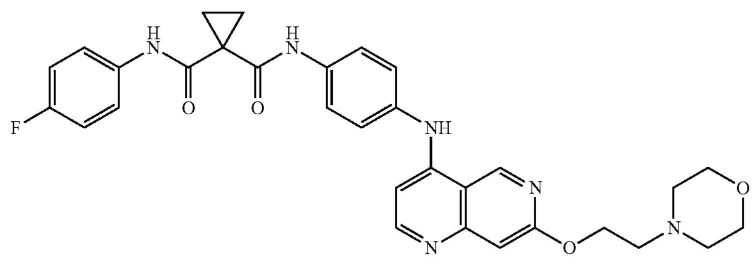 [SMILES: O=C(Nc1ccc(F)cc1)C1(C(=O)Nc2ccc(Nc3ccnc4cc(OCCN5CCOCC5)ncc34)cc2)CC1] |
| 14S | N-(3-fluoro-4-((7-(2-morpholinoethoxy)-1,6-naphthyridin-4-yl)oxy)phenyl)-N-(4-fluorophenyl)-N-methylcyclopropyl-1,1-dicarboxamide | 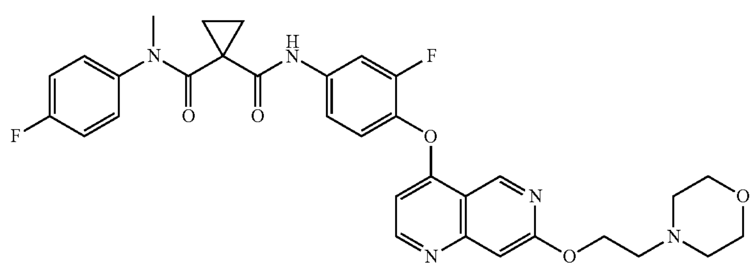 [SMILES: CN(C(=O)C1(C(=O)Nc2ccc(Oc3ccnc4cc(OCCN5CCOCC5)ncc34)c(F)c2)CC1)c1ccc(F)cc1] |
| 15S | N-(3-fluoro-4-((7-(2-morpholinoethoxy)-1,6-naphthyridin-4-yl)oxy)phenyl)-1-(4-fluorophenyl)-2-oxo-1,2-dihydropyridine-3-carboxamide | 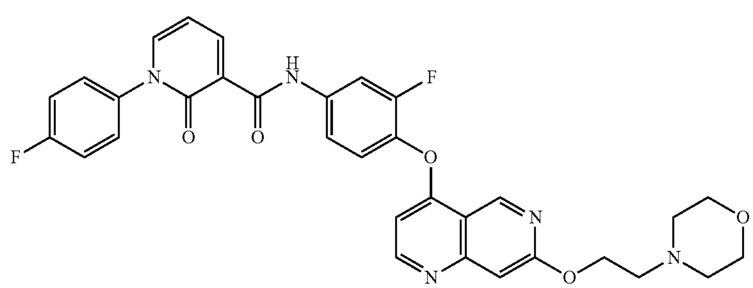 [SMILES: O=C(Nc1ccc(Oc2ccnc3cc(OCCN4CCOCC4)ncc23)c(F)c1)c1cccn(-c2ccc(F)cc2)c1=O] |
| 16S | 1-(3-fluoro-4-((7-(2-morpholinoethoxy)-1,6-naphthyridin-4-yl)oxy)phenyl)-N-(4-fluorophenyl)-2-oxo-1,2-dihydropyridine-3-carboxamide | 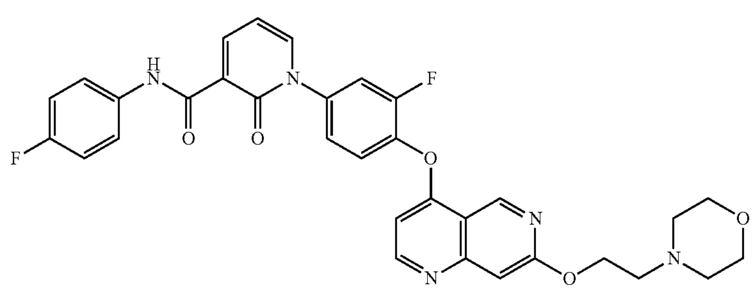 [SMILES: O=C(Nc1ccc(F)cc1)c1cccn(-c2ccc(Oc3ccnc4cc(OCCN5CCOCC5)ncc34)c(F)c2)c1=O] |

| Cpd. No. | Name | Structure |
|---|---|---|
| 17S | methyl 1-(3-fluoro-4-((7-(2-morpholinoethoxy)-1,6-naphthyridin-4-yl)oxy)phenyl)-2-oxo-1,2-dihydropyridine-3-carboxylate | 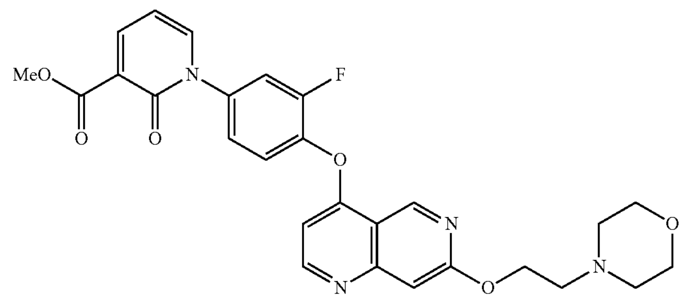 [SMILES: COC(=O)c1cccn(-c2ccc(Oc3ccnc4cc(OCCN5CCOCC5)ncc34)c(F)c2)c1=O] |
| 18S | N-(4-((8-bromo-7-(2-morpholinoethoxy)-1,6-naphthyridin-4-yl)oxy)-3-fluorophenyl)-2-phenylacetamide | 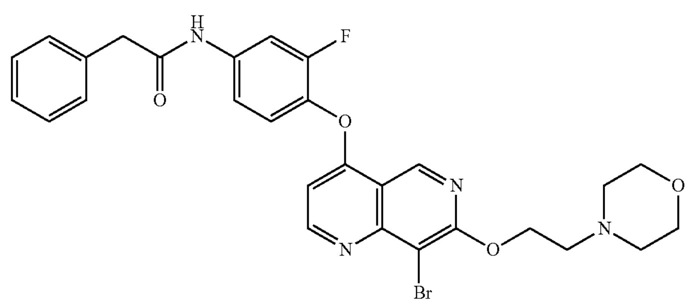 [SMILES: O=C(Cc1ccccc1)Nc1ccc(Oc2ccnc3c(Br)c(OCCN4CCOCC4)ncc23)c(F)c1] |
| 19S | N-(4-((8-bromo-7-(2-morpholinoethoxy)-1,6-naphthyridin-4-yl)oxy)-3-fluorophenyl)-4-oxo-5-phenyl-1,4-dihydropyridine-3-carboxamide | 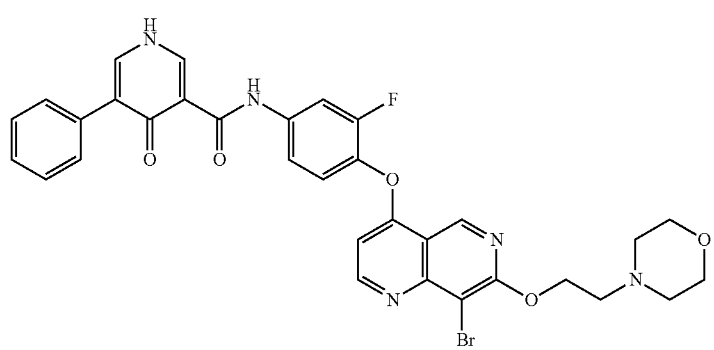 [SMILES: O=C(Nc1ccc(Oc2ccnc3c(Br)c(OCCN4CCOCC4)ncc23)c(F)c1)c1c[nH]cc(-c2ccccc2)c1=O] |
| 20S | N-(3-fluoro-4-((7-(2-morpholinoethoxy)-1,6-naphthyridin-4-yl)oxy)phenyl)-4-oxo-5-phenyl-1,4-dihydropyridine-3-carboxamide | 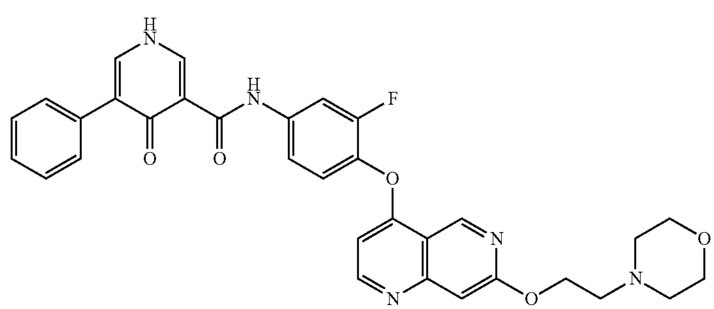 [SMILES: O=C(Nc1ccc(Oc2ccnc3cc(OCCN4CCOCC4)ncc23)c(F)c1)c1c[nH]cc(-c2ccccc2)c1=O] |

-continued

| Cpd. No. | Name | Structure |
|---|---|---|
| 21S | N-(4-((8-bromo-7-(2-morpholinoethoxy)-1,6-naphthyridin-4-yl)oxy)-3-fluorophenyl)-5-(4-fluorophenyl)-4-oxo-1,4-dihydropyridine-3-carboxamide | 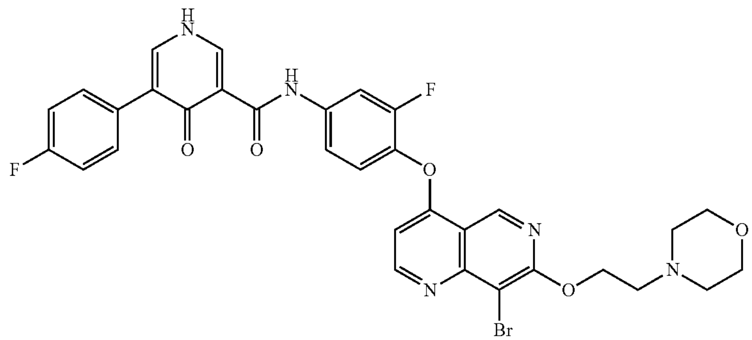 [SMILES: O=C(Nc1ccc(Oc2ccnc3c(Br)c(OCCN4CCOCC4)ncc23)c(F)c1)c1c[nH]cc(-c2ccc(F)cc2)c1=O] |
| 22S | N-(3-fluoro-4-((7-(2-morpholinoethoxy)-1,6-naphthyridin-4-yl)oxy)phenyl)-5-(4-fluorophenyl)-4-oxo-1,4-dihydropyridine-3-carboxamide | 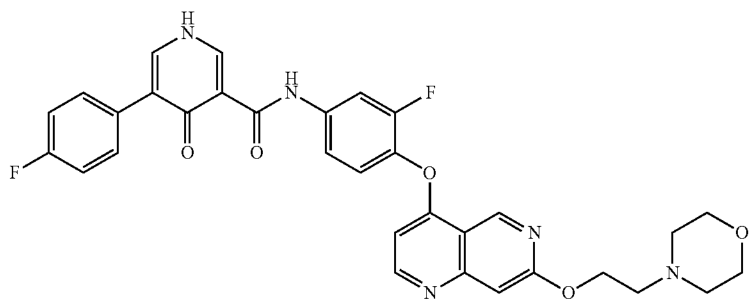 [SMILES: O=C(Nc1ccc(Oc2ccnc3cc(OCCN4CCOCC4)ncc23)c(F)c1)c1c[nH]cc(-c2ccc(F)cc2)c1=O] |
| 23S | N-(3,4-difluorophenyl)-N-(3-fluoro-4-((7-(2-morpholinoethoxy)-1,6-naphthyridin-4-yl)oxy)phenyl)cyclopropyl-1,1-dicarboxamide | 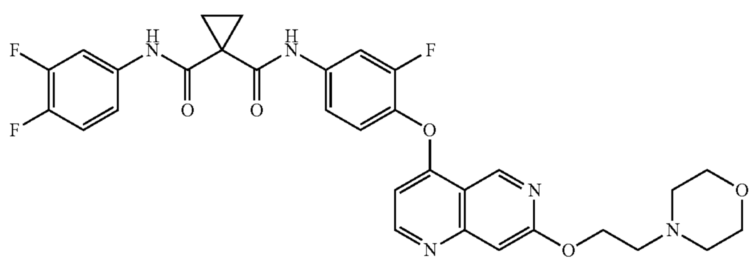 [SMILES: O=C(Nc1ccc(F)c(F)c1)C1(C(=O)Nc2ccc(Oc3ccnc4cc(OCCN5CCOCC5)ncc34)c(F)c2)CC1] |
| 24S | N-(4-fluoro-3-methoxyphenyl)-N-(3-fluoro-4-((7-(2-morpholinoethoxy)-1,6-naphthyridin-4-yl)oxy)phenyl)cyclopropyl-1,1-dicarboxamide | 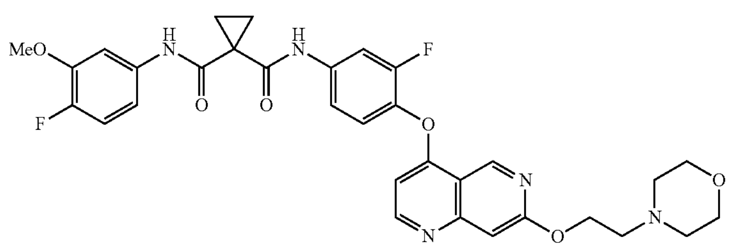 [SMILES: COc1cc(NC(=O)C2(C(=O)Nc3ccc(Oc4ccnc5cc(OCCN6CCOCC6)ncc45)c(F)c3)CC2)ccc1F] |
| 25S | N-(3-fluoro-4-((7-(2-(pyridin-4-yl)ethoxy)-1,6-naphthyridin-4-yl)oxy)phenyl)-N-(4-fluorophenyl)cyclopropyl-1,1-dicarboxamide | 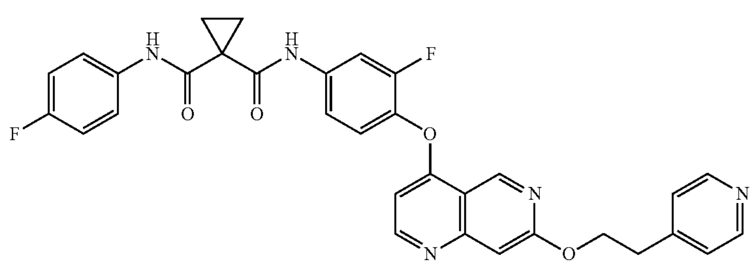 [SMILES: O=C(Nc1ccc(F)cc1)C1(C(=O)Nc2ccc(Oc3ccnc4cc(OCCc5ccncc5)ncc34)c(F)c2)CC1] |

| Cpd. No. | Name | Structure |
|---|---|---|
| 26S | N-(3-fluoro-4-((7-((1-morpholinopropan-2-yl)oxy)-1,6-naphthyridin-4-yl)oxy)phenyl)-N-(4-fluorophenyl)cyclopropyl-1,1-dicarboxamide | 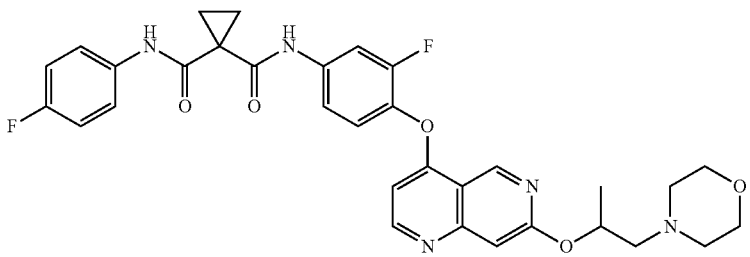 |
| 27S | N-(3-fluoro-4-((7-morpholino-1,6-naphthyridin-4-yl)oxy)phenyl)-N-(4-fluorophenyl)cyclopropyl-1,1-dicarboxamide | 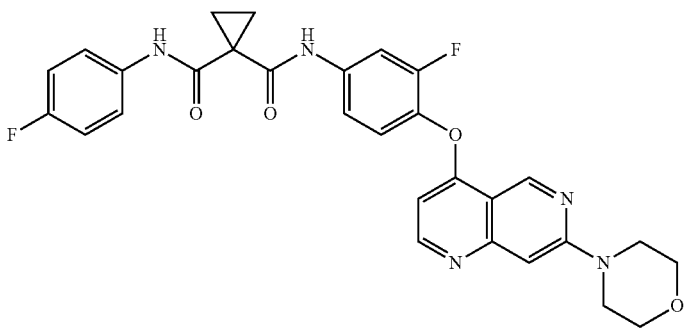 [SMILES: O=C(Nc1ccc(F)cc1)C1(C(=O)Nc2ccc(Oc3ccnc4cc(N5CCOCC5)ncc34)c(F)c2)CC1] |
| 28S | N-(3-fluoro-4-((7-(4-morpholinopiperidin-1-yl)-naphthyridin-4-yl)oxy)phenyl)-N-(4-fluorophenyl)cyclopropyl-1,1-dicarboxamide | 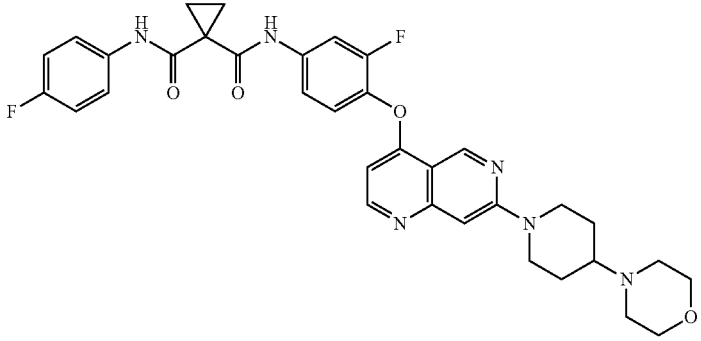 [SMILES: O=C(Nc1ccc(F)cc1)C1(C(=O)Nc2ccc(Oc3ccnc4cc(N5CCC(N6CCOCC6)CC5)ncc34)c(F)c2)CC1] |
| 29S | (S)-N-(3-fluoro-4-((7-(2-(3-methylmorpholino)ethoxy)-naphthyridin-4-yl)oxy)phenyl)-N-(4-fluorophenyl)cyclopropyl-1,1-dicarboxamide | 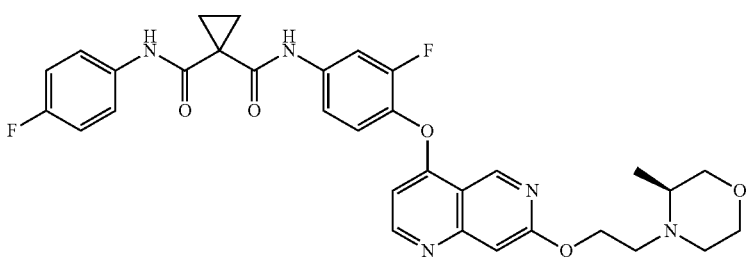 [SMILES: C[C@H]1COCCN1CCOc1cc2nccc(Oc3ccc(NC(=O)C4(C(=O)Nc5ccc(F)cc5)CC4)cc3F)c2cn1] |
| 30S | (R)-N-(3-fluoro-4-((7-(2-(3-methylmorpholino)ethoxy)-naphthyridin-4-yl)oxy)phenyl)-N-(4-fluorophenyl)cyclopropyl-1,1-dicarboxamide | 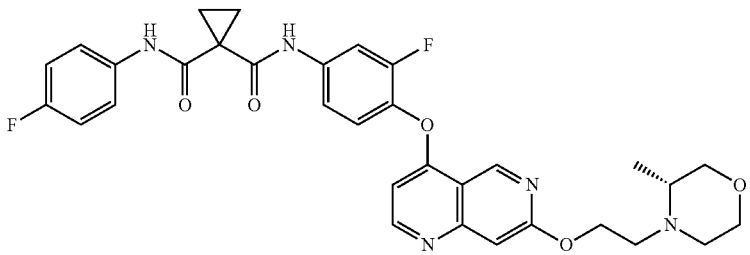 [SMILES: C[C@@H]1COCCN1CCOc1cc2nccc(Oc3ccc(NC(=O)C4(C(=O)Nc5ccc(F)cc5)CC4)cc3F)c2cn1] |

| Cpd. No. | Name | Structure |
|---|---|---|
| 31S | N-(4-((7-(2-(1H-imidazol-1-yl)ethoxy)-naphthyridin-4-yl)oxy)-3-fluorophenyl)-N-(4-fluorophenyl)cyclopropyl-1,1-dicarboxamide | 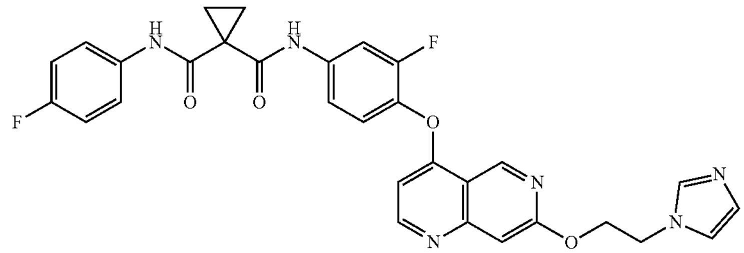 [SMILES: O=C(Nc1ccc(F)cc1)C1(C(=O)Nc2ccc(Oc3ccnc4cc(OCCn5ccnc5)ncc34)c(F)c2)CC1] |
| 32S | N-(4-((7-(4-benzylpiperazin-1-yl)-naphthyridin-4-yl)oxy)-3-fluorophenyl)-N-(4-fluorophenyl)cyclopropyl-1,1-dicarboxamide | 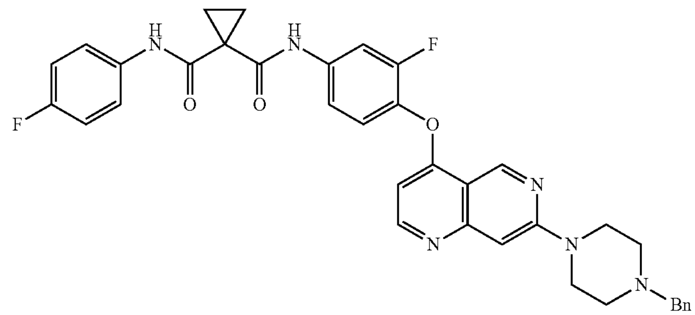 [SMILES: O=C(Nc1ccc(F)cc1)C1(C(=O)Nc2ccc(Oc3ccnc4cc(N5CCN(Cc6ccccc6)CC5)ncc34)c(F)c2)CC1] |
| 33S | N-(3-fluoro-4-((3-oxo-3,4-dihydropyrido[2,3-b]pyrazin-8-yl)oxy)phenyl)-N-(4-fluorophenyl)cyclopropyl-1,1-dicarboxamide | 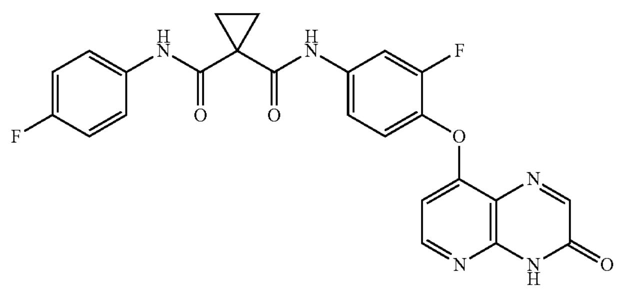 [SMILES: O=C(Nc1ccc(F)cc1)C1(C(=O)Nc2ccc(Oc3ccnc4[nH]c(=O)cnc34)c(F)c2)CC1] |
| 34S | N-(3-fluoro-4-((2-oxo-1,2-dihydropyrido[2,3-b]pyrazin-8-yl)oxy)phenyl)-N-(4-fluorophenyl)cyclopropyl-1,1-dicarboxamide | 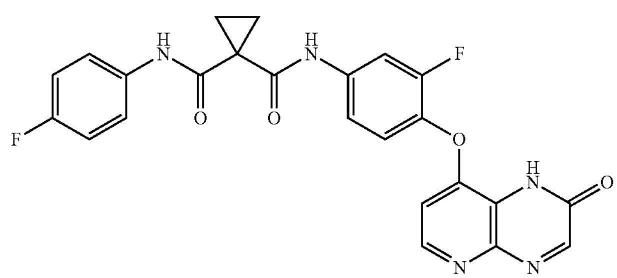 [SMILES: O=C(Nc1ccc(F)cc1)C1(C(=O)Nc2ccc(Oc3ccnc4ncc(=O)[nH]c34)c(F)c2)CC1] |
| 35S | N-(4-((7-((1-ethyl-3-fluoropiperidin-4-yl)amino)-1,6-naphthyridin-4-yl)oxy)-3-fluorophenyl)-2-(4-fluorophenyl)-3-oxo-2,3-dihydropyridazine-4-carboxamide | 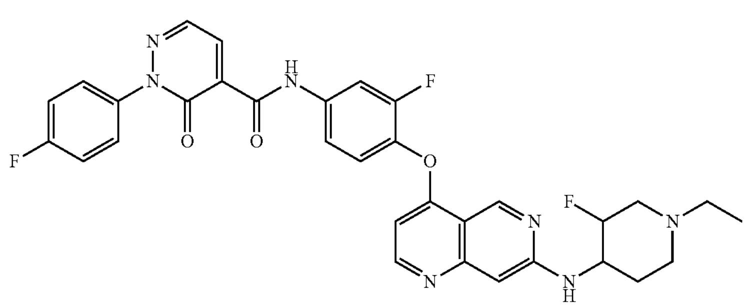 [SMILES: CCN1CCC(Nc2cc3nccc(Oc4ccc(NC(=O)c5ccnn(-c6ccc(F)cc6)c5=O)cc4F)c3cn2)C(F)C1] |

| Cpd. No. | Name | Structure |
|---|---|---|
| 36S | N-(3-fluoro-4-((7-(2-morpholino-2-acetoxy)-1,6-naphthyridin-4-yl)oxy)phenyl)-N-(4-fluorophenyl)cyclopropyl-1,1-dicarboxamide | 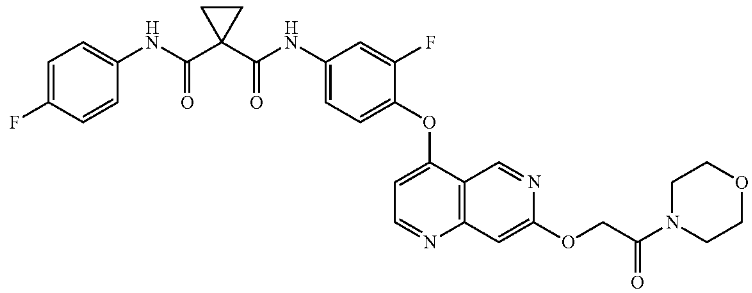 [SMILES: O=C(COc1cc2nccc(Oc3ccc(NC(=O)C4(C(=O)Nc5ccc(F)cc5)CC4)cc3F)c2cn1)N1CCOCC1] |
| 37S | N-(3-fluoro-4-((7-(2-(3-oxomorpholino)ethoxy)-1,6-naphthyridin-4-yl)oxy)phenyl)-N-(4-fluorophenyl)cyclopropyl-1,1-dicarboxamide | 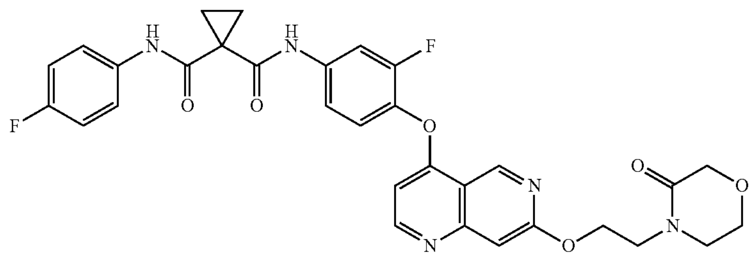 [SMILES: O=C1COCCN1CCOc1cc2nccc(Oc3ccc(NC(=O)C4(C(=O)Nc5ccc(F)cc5)CC4)cc3F)c2cn1] |
| 38S | N-(3-fluoro-4-((7-(1-methyl-1H-pyrazol-4-yl)-1,6-naphthyridin-4-yl)oxy)phenyl)-N-(4-fluorophenyl)cyclopropyl-1,1-dicarboxamide | 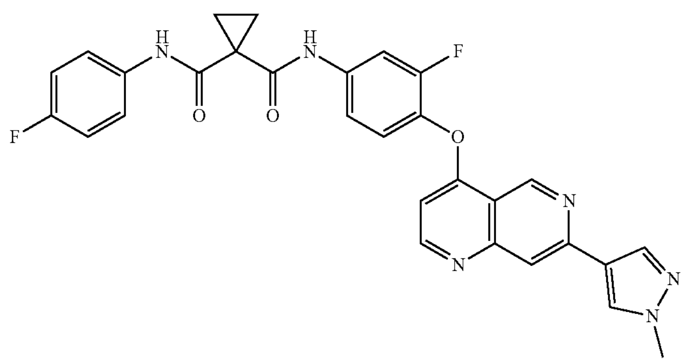 [SMILES: Cn1cc(-c2cc3nccc(Oc4ccc(NC(=O)C5(C(=O)Nc6ccc(F)cc6)CC5)cc4F)c3cn2)cn1] |
| 39S | N-(4-((7-(1H-pyrazol-4-yl)-1,6-naphthyridin-4-yl)oxy)-3-fluorophenyl)-N-(4-fluorophenyl)cyclopropyl-1,1-dicarboxamide | 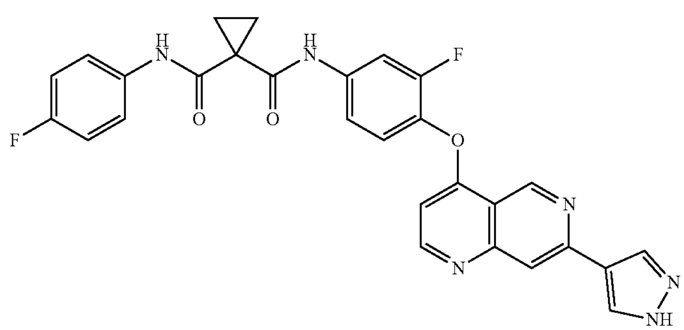 [SMILES: O=C(Nc1ccc(F)cc1)C1(C(=O)Nc2ccc(Oc3ccnc4cc(-c5cn[nH]c5)ncc34)c(F)c2)CC1] |

-continued

| Cpd. No. | Name | Structure |
|---|---|---|
| 40S | N-(3-fluoro-4-((7-(1-(methylsulfonyl)-1H-pyrazol-4-yl)-1,6-naphthyridin-4-yl)oxy)phenyl)-N-(4-fluorophenyl)cyclopropyl-1,1-dicarboxamide | 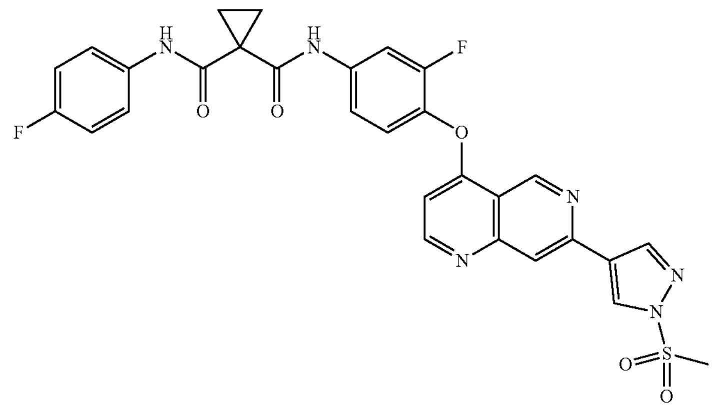 [SMILES: CS(=O)(=O)n1cc(-c2cc3nccc(Oc4ccc(NC(=O)C5(C(=O)Nc6ccc(F)cc6)CC5)cc4F)c3cn2)cn1] |
| 41S | N-(3-fluoro-4-((7-(1-isopropyl-1H-pyrazol-4-yl)-1,6-naphthyridin-4-yl)oxy)phenyl)-N-(4-fluorophenyl)cyclopropyl-1,1-dicarboxamide | 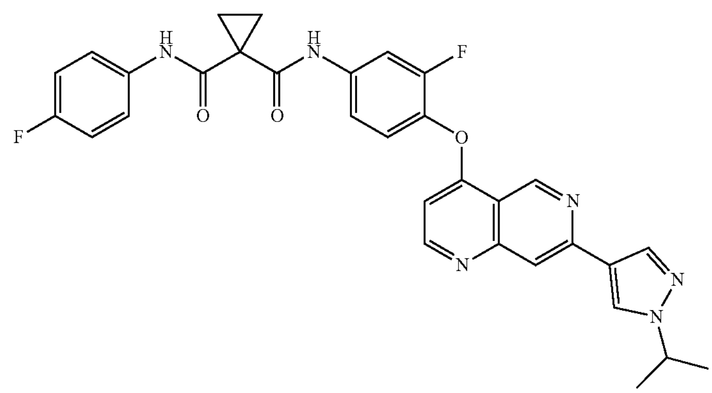 [SMILES: CC(C)n1cc(-c2cc3nccc(Oc4ccc(NC(=O)C5(C(=O)Nc6ccc(F)cc6)CC5)cc4F)c3cn2)cn1] |
| 42S | N-(3-fluoro-4-((7-(1-(piperidin-4-yl)-1H-pyrazol-4-yl)-1,6-naphthyridin-4-yl)oxy)phenyl)-N-(4-fluorophenyl)cyclopropyl-1,1-dicarboxamide | 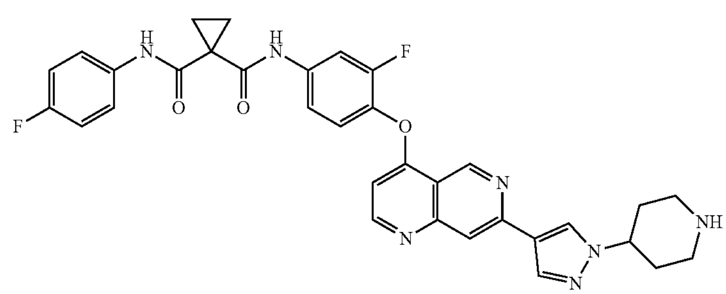 [SMILES: O=C(Nc1ccc(F)cc1)C1(C(=O)Nc2ccc(Oc3ccnc4cc(-c5cnn(C6CCNCC6)c5)ncc34)c(F)c2)CC1] |
| 43S | N-(3-fluoro-4-((7-(1-(1-isopropylpiperidin-4-yl)-1H-pyrazol-4-yl)-1,6-naphthyridin-4-yl)oxy)phenyl)-N-(4-fluorophenyl)cyclopropyl-1,1-dicarboxamide | 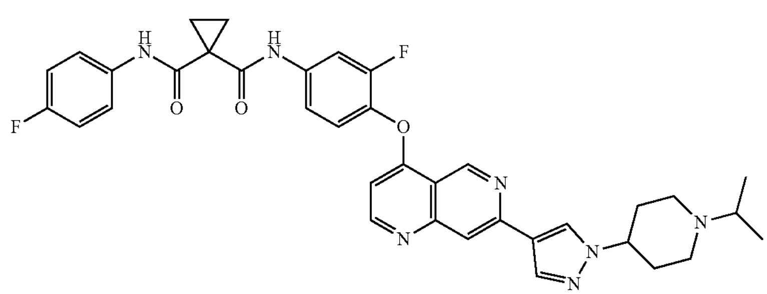 [SMILES: CC(C)N1CCC(n2cc(-c3cc4nccc(Oc5ccc(NC(=O)C6(C(=O)Nc7ccc(F)cc7)CC6)cc5F)c4cn3)cn2)CC1] |

-continued

| Cpd. No. | Name | Structure |
|---|---|---|
| 44S | N-(4-((7-((1H-imidazol-1-yl)methyl)-1,6-naphthyridin-4-yl)oxy)-3-fluorophenyl)-N-(4-fluorophenyl)cyclopropyl-1,1-dicarboxamide | 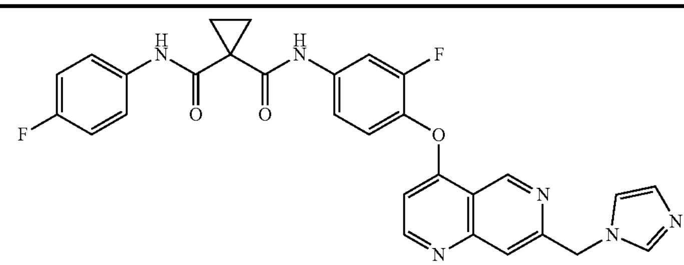 |
| 45S | N-(4-((7-(3,5-dimethylisoxazol-4-yl)-1,6-naphthyridin-4-yl)oxy)-3-fluorophenyl)-N-(4-fluorophenyl)cyclopropyl-1,1-dicarboxamide | 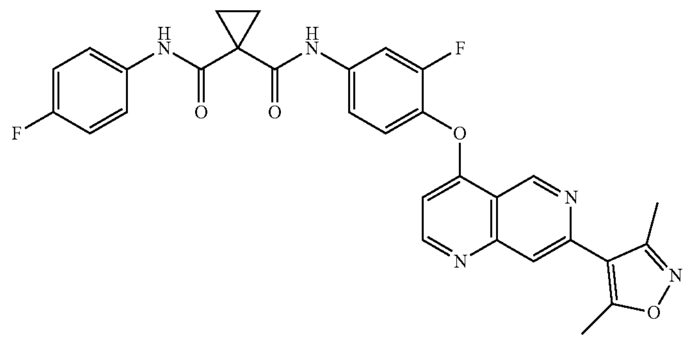 [SMILES: Cc1noc(C)c1-c1cc2nccc(Oc3ccc(NC(=O)C4(C(=O)Nc5ccc(F)cc5)CC4)cc3F)c2cn1] |
| 46S | N-(3-fluoro-4-((7-(pyridin-4-yl)-1,6-naphthyridin-4-yl)oxy)phenyl)-N-(4-fluorophenyl)cyclopropyl-1,1-dicarboxamide | 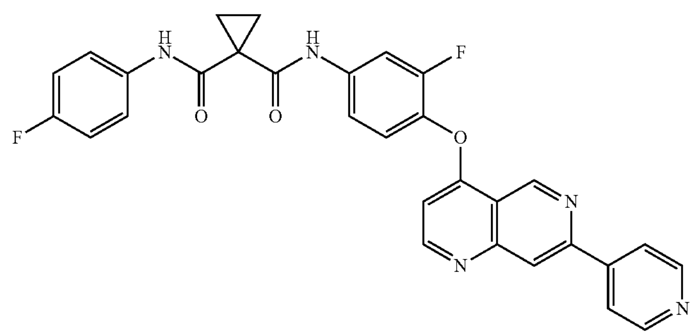 [SMILES: O=C(Nc1ccc(F)cc1)C1(C(=O)Nc2ccc(Oc3ccnc4cc(-c5ccncc5)ncc34)c(F)c2)CC1] |
| 47S | N-(3-fluoro-4-((7-(pyrimidin-5-yl)-1,6-naphthyridin-4-yl)oxy)phenyl)-N-(4-fluorophenyl)cyclopropyl-1,1-dicarboxamide | 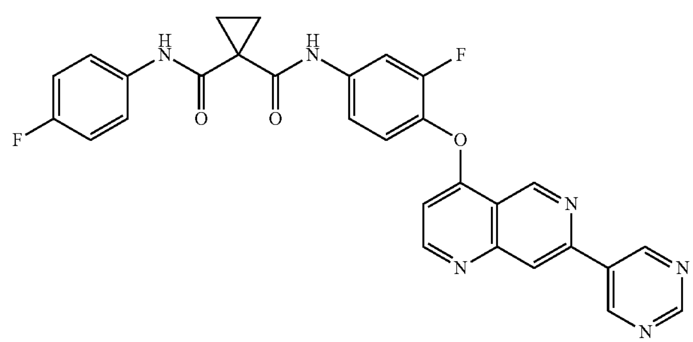 [SMILES: O=C(Nc1ccc(F)cc1)C1(C(=O)Nc2ccc(Oc3ccnc4cc(-c5cncnc5)ncc34)c(F)c2)CC1] |
| 48S | N-(3-fluoro-4-((7-(4-nitrophenyl)-1,6-naphthyridin-4-yl)oxy)phenyl)-N-(4-fluorophenyl)cyclopropyl-1,1-dicarboxamide | 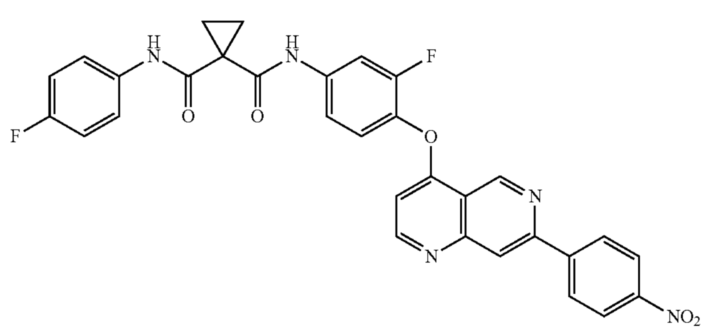 [SMILES: O=C(Nc1ccc(F)cc1)C1(C(=O)Nc2ccc(Oc3ccnc4cc(-c5ccc([N+](=O)[O-])cc5)ncc34)c(F)c2)CC1] |

| Cpd. No. | Name | Structure |
|---|---|---|
| 49S | N-(3-fluoro-4-((7-(3,4-difluorophenyl)-1,6-naphthyridin-4-yl)oxy)phenyl)-N-(4-fluorophenyl)cyclopropyl-1,1-dicarboxamide | 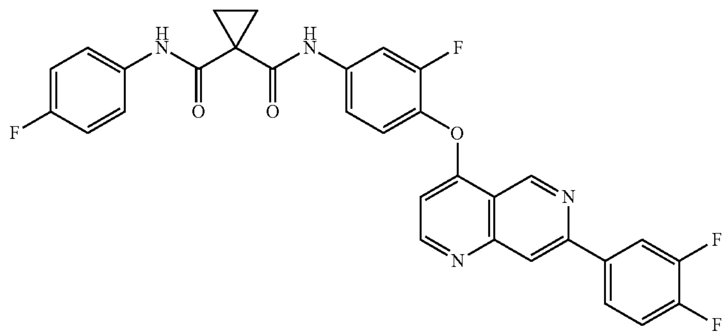 [SMILES: O=C(Nc1ccc(F)cc1)C1(C(=O)Nc2ccc(Oc3ccnc4cc(-c5ccc(F)c(F)c5)ncc34)c(F)c2)CC1] |
| 50S | N-(3-fluoro-4-((7-(4-morpholinophenyl)-1,6-naphthyridin-4-yl)oxy)phenyl)-N-(4-fluorophenyl)cyclopropyl-1,1-dicarboxamide | 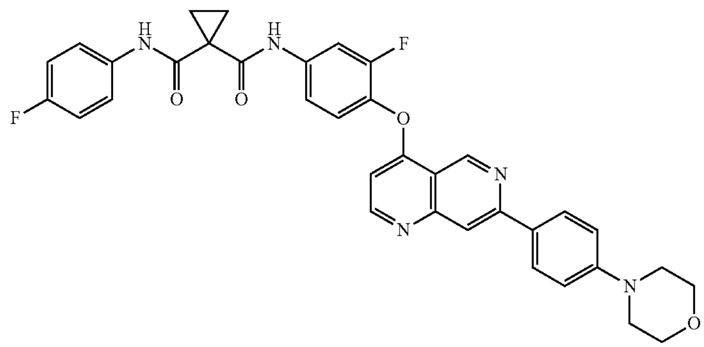 [SMILES: O=C(Nc1ccc(F)cc1)C1(C(=O)Nc2ccc(Oc3ccnc4cc(-c5ccc(N6CCOCC6)cc5)ncc34)c(F)c2)CC1] |
| 51S | N-4-((7-(isoxazol-4-yl)-1,6-naphthyridin-4-yl)oxy)-3-fluorophenyl)-N-(4-fluorophenyl)cyclopropyl-1,1-dicarboxamide | 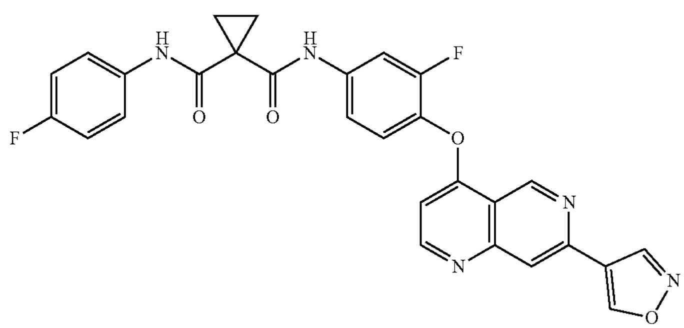 [SMILES: O=C(Nc1ccc(F)cc1)C1(C(=O)Nc2ccc(Oc3ccnc4cc(-c5cnoc5)ncc34)c(F)c2)CC1] |
| 52S | N-4-((7-(isothiazol-3-yl)-1,6-naphthyridin-4-yl)oxy)-3-fluorophenyl)-N-(4-fluorophenyl)cyclopropyl-1,1-dicarboxamide | 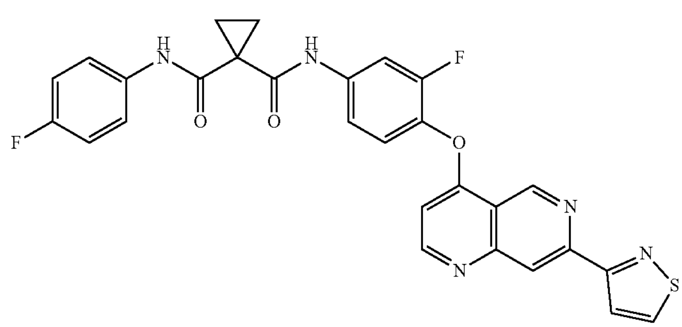 [SMILES: O=C(Nc1ccc(F)cc1)C1(C(=O)Nc2ccc(Oc3ccnc4cc(-c5ccsn5)ncc34)c(F)c2)CC1] |

| Cpd. No. | Name | Structure |
|---|---|---|
| 53S | N-(3-fluoro-4-((7-(1-methyl-1H-pyrazol-4-yl)-1,6-naphthyridin-4-yl)oxy)phenyl)-1-(4-fluorophenyl)-2-oxo-1,2-dihydropyridine-3-carboxamide | 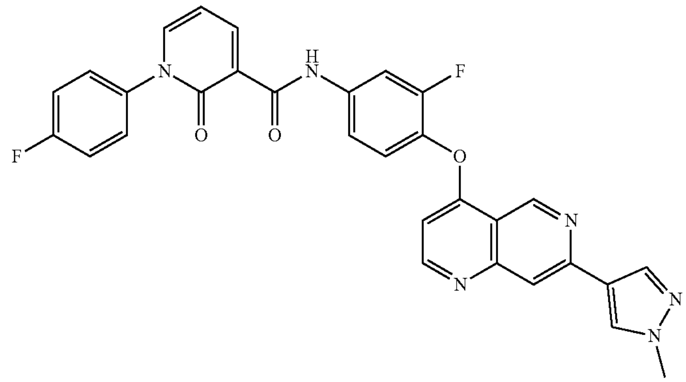 [SMILES: Cn1cc(-c2cc3nccc(Oc4ccc(NC(=O)c5cccn(-c6ccc(F)cc6)c5=O)cc4F)c3cn2)cn1] |
| 54S | N-(3-fluoro-4-((7-(1-methyl-1H-pyrazol-4-yl)-1,6-naphthyridin-4-yl)oxy)phenyl)-5-(4-fluorophenyl)-4-oxo-1,4-dihydropyridine-3-carboxamide | 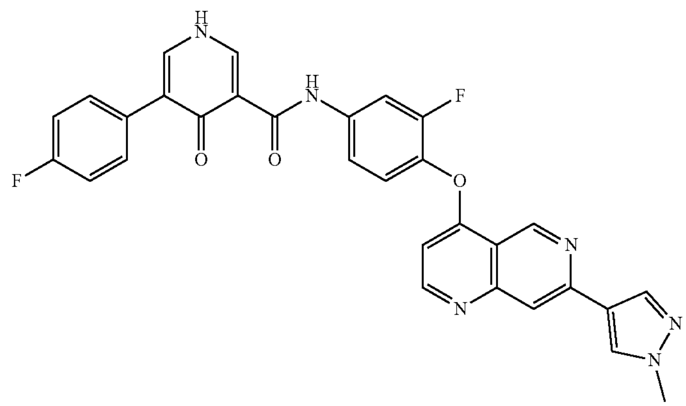 [SMILES: Cn1cc(-c2cc3nccc(Oc4ccc(NC(=O)c5c[nH]cc(-c6ccc(F)cc6)c5=O)cc4F)c3cn2)cn1] |
| 55S | N-(4-((3-chloropyrido[2,3-b]pyrazin-8-yl)oxy)-3-fluorophenyl)-N-(4-fluorophenyl)cyclopropyl-1,1-dicarboxamide | 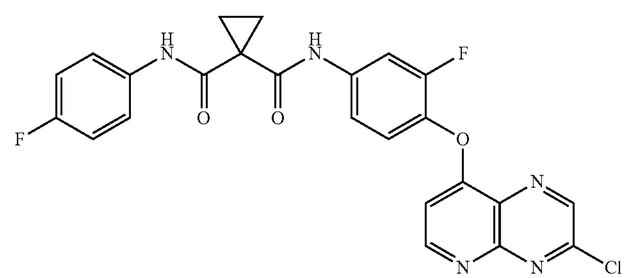 [SMILES: O=C(Nc1ccc(F)cc1)C1(C(=O)Nc2ccc(Oc3ccnc4nc(Cl)cnc34)c(F)c2)CC1] |
| 56S | N-(4-(2-chloropyrido[2,3-b]pyrazin-8-yl)oxy)-3-fluorophenyl)-N-(4-fluorophenyl)cyclopropyl-1,1-dicarboxamide | 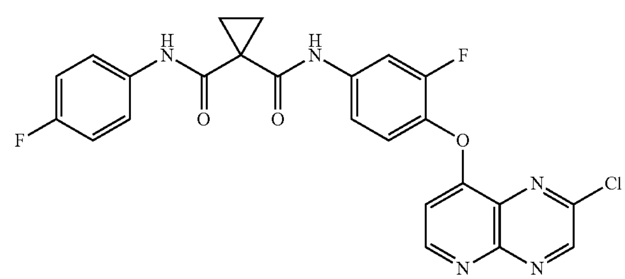 [SMILES: O=C(Nc1ccc(F)cc1)C1(C(=O)Nc2ccc(Oc3ccnc4ncc(Cl)nc34)c(F)c2)CC1] |

| Cpd. No. | Name | Structure |
|---|---|---|
| 57S | N-4-((3-morpholinopyrido[2,3-b]pyrazin-8-yl)oxy)-3-fluorophenyl)-N-(4-fluorophenyl)cyclopropyl-1,1-dicarboxamide | 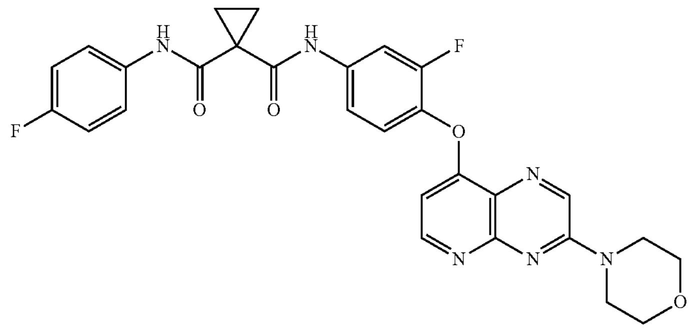 [SMILES: O=C(Nc1ccc(F)cc1)C1(C(=O)Nc2ccc(Oc3ccnc4nc(N5CCOCC5)cnc34)c(F)c2)CC1] |
| 58S | N-4-((2-morpholinopyrido[2,3-b]pyrazin-8-yl)oxy)-3-fluorophenyl)-N-(4-fluorophenyl)cyclopropyl-1,1-dicarboxamide | 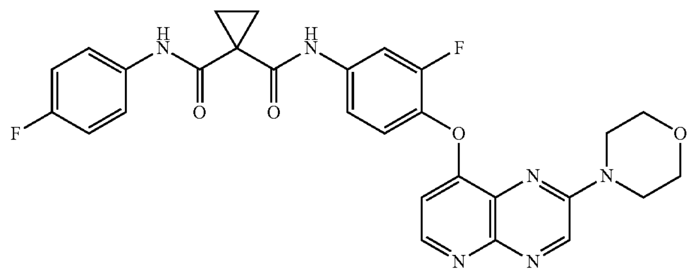 [SMILES: O=C(Nc1ccc(F)cc1)C1(C(=O)Nc2ccc(Oc3ccnc4ncc(N5CCOCC5)nc34)c(F)c2)CC1] |
| 59S | N-(3-fluoro-4-((3-(4-methylpiperazin-1-yl)pyrido[2,3-b]pyrazin-8-yl)oxy)phenyl)-N-(4-fluorophenyl)cyclopropyl-1,1-dicarboxamide | 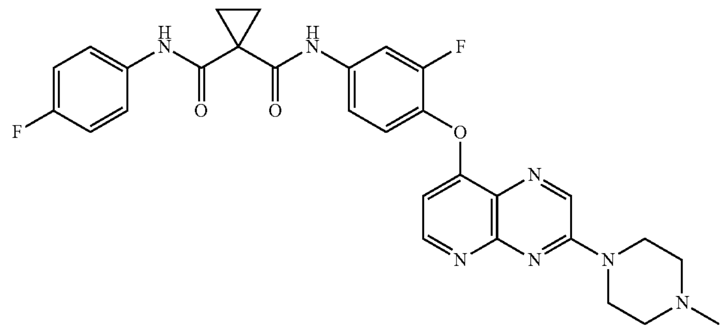 [SMILES: CN1CCN(c2cnc3c(Oc4ccc(NC(=O)C5(C(=O)Nc6ccc(F)cc6)CC5)cc4F)ccnc3n2)CC1] |
| 60S | N-(3-fluoro-4-((3-(2-morpholinoethoxy)pyrido[2,3-b]pyrazin-8-yl)oxy)phenyl)-N-(4-fluorophenyl)cyclopropyl-1,1-dicarboxamide | 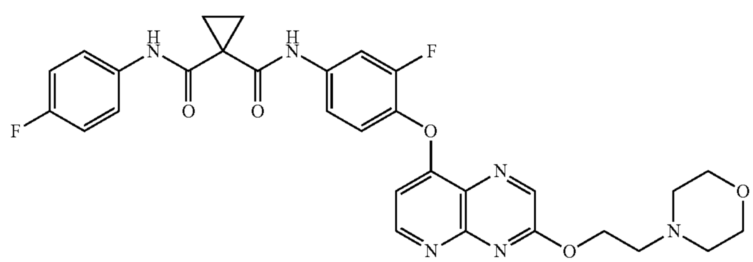 [SMILES: O=C(Nc1ccc(F)cc1)C1(C(=O)Nc2ccc(Oc3ccnc4nc(OCCN5CCOCC5)cnc34)c(F)c2)CC1] |
| 61S | N-(3-fluoro-4-((3-(2-morpholinopropoxy)pyrido[2,3-b]pyrazin-8-yl)oxy)phenyl)-N-(4-fluorophenyl)cyclopropyl-1,1-dicarboxamide | 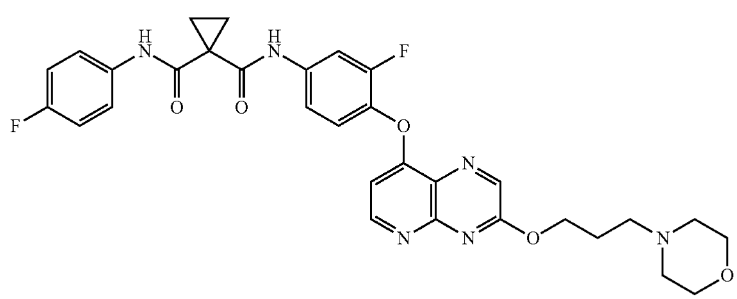 [SMILES: O=C(Nc1ccc(F)cc1)C1(C(=O)Nc2ccc(Oc3ccnc4nc(OCCCN5CCOCC5)cnc34)c(F)c2)CC1] |

| Cpd. No. | Name | Structure |
|---|---|---|
| 62S | N-(3-fluoro-4-((3-((3-morpholinopropyl)amino)pyrido[2,3-b]pyrazin-8-yl)oxy)phenyl)-N-(4-fluorophenyl)cyclopropyl-1,1-dicarboxamide | 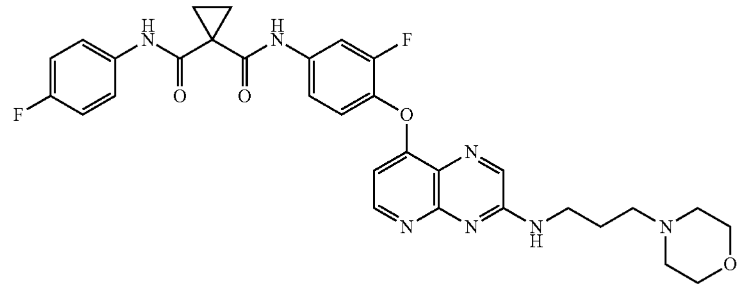 [SMILES: O=C(Nc1ccc(F)cc1)C1(C(=O)Nc2ccc(Oc3ccnc4nc(NCCCN5CCOCC5)cnc34)c(F)c2)CC1] |
| 63S | N-(3-fluoro-4-((2-((3-morpholinopropyl)amino)pyrido[2,3-b]pyrazin-8-yl)oxy)phenyl)-N-(4-fluorophenyl)cyclopropyl-1,1-dicarboxamide | 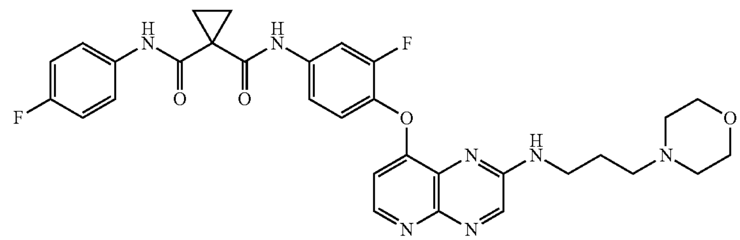 [SMILES: O=C(Nc1ccc(F)cc1)C1(C(=O)Nc2ccc(Oc3ccnc4ncc(NCCCN5CCOCC5)nc34)c(F)c2)CC1] |
| 64S | N-(4-((3-piperazinyl-pyrido[2,3-b]pyrazin-8-yl)oxy)-3-fluorophenyl)-N-(4-fluorophenyl)cyclopropyl-1,1-dicarboxamide | 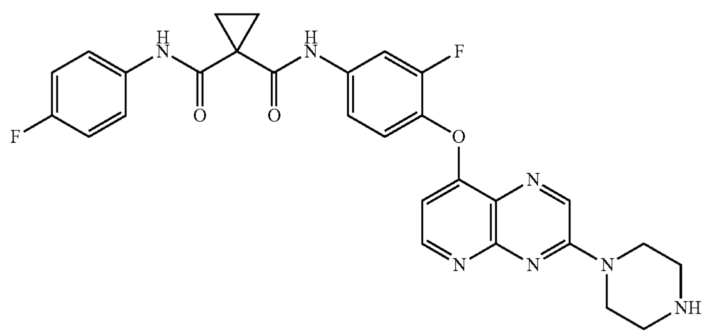 [SMILES: O=C(Nc1ccc(F)cc1)C1(C(=O)Nc2ccc(Oc3ccnc4nc(N5CCNCC5)cnc34)c(F)c2)CC1] |
| 65S | N-(4-((2-piperazinyl-pyrido[2,3-b]pyrazin-8-yl)oxy)-3-fluorophenyl)-N-(4-fluorophenyl)cyclopropyl-1,1-dicarboxamide | 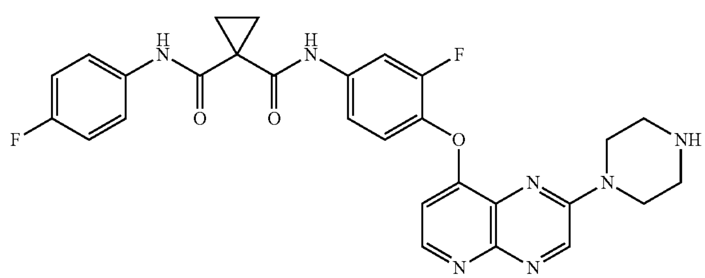 [SMILES: O=C(Nc1ccc(F)cc1)C1(C(=O)Nc2ccc(Oc3ccnc4ncc(N5CCNCC5)nc34)c(F)c2)CC1] |
| 66S | N-(3-fluoro-4-((2-(2-(4-methylpiperazin-1-yl)ethoxy)pyrido[2,3-b]pyrazin-8-yl)oxy)phenyl)-N-(4-fluorophenyl)cyclopropyl-1,1-dicarboxamide | 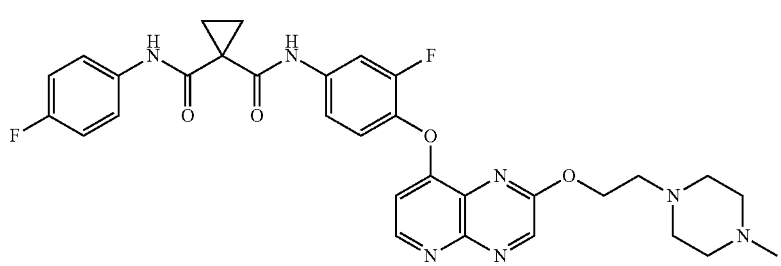 [SMILES: CN1CCN(CCOc2cnc3nccc(Oc4ccc(NC(=O)C5(C(=O)Nc6ccc(F)cc6)CC5)cc4F)c3n2)CC1] |

| Cpd. No. | Name | Structure |
|---|---|---|
| 67S | N-(3-fluoro-4-((2-(2-morpholinoethoxy)pyrido[2,3-b]pyrazin-8-yl)oxy)phenyl)-N-(4-fluorophenyl)cyclopropyl-1,1-dicarboxamide | 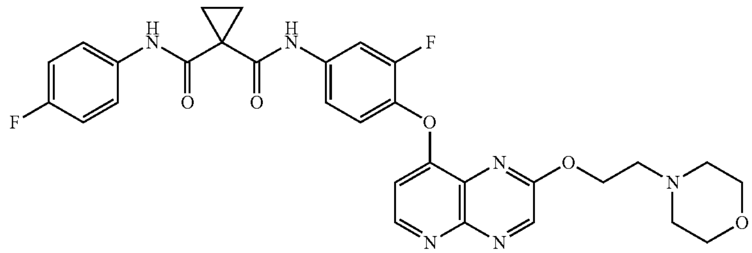 |
| 68S | N-(3-fluoro-4-((2-(3-morpholinopropoxy)pyrido[2,3-b]pyrazin-8-yl)oxy)phenyl)-N-(4-fluorophenyl)cyclopropyl-1,1-dicarboxamide | 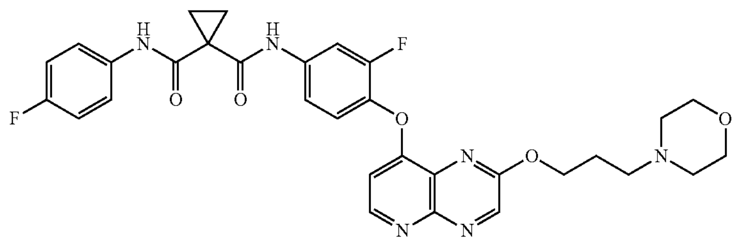 |

6. A composition comprising a therapeutically effective amount of one or more selected from the compound, the pharmaceutically acceptable salt thereof or the pharmaceutically acceptable solvate thereof according to claim 1.

7. A method for treating a disease selected from the group consisting of lung cancer, medullary thyroid tumor, glioblastoma, stomach cancer, renal cell cancer, breast cancer, ovarian cancer, prostate cancer and colorectal cancer, wherein the method comprises:
  administering to a subject an effective amount of the compound, the pharmaceutically acceptable salt or the pharmaceutically acceptable solvate thereof according to claim 1, or the composition of claim 6.

\* \* \* \* \*